(12) United States Patent
Xiao

(10) Patent No.: US 8,273,855 B2
(45) Date of Patent: Sep. 25, 2012

(54) NOGO, CASPR, F3 NB-3 USEFUL IN THE TREATMENT OF INJURY AND DISEASE TO THE CENTRAL NERVOUS SYSTEM

(75) Inventor: Zhi-Cheng Xiao, Singapore (SG)

(73) Assignee: Jiangsu Novavac Bio-Tec Co., Ltd., Su Zhou (CN)

( * ) Notice: Subject to any disclaimer, the term of this patent is extended or adjusted under 35 U.S.C. 154(b) by 1403 days.

(21) Appl. No.: 11/767,595

(22) Filed: Jun. 25, 2007

(65) Prior Publication Data

US 2010/0015099 A1 Jan. 21, 2010

Related U.S. Application Data

(63) Continuation of application No. 10/537,757, filed as application No. PCT/GB03/05329 on Dec. 5, 2003, now abandoned.

(60) Provisional application No. 60/431,549, filed on Dec. 6, 2002, provisional application No. 60/480,138, filed on Jun. 20, 2003.

(51) Int. Cl.
*C07K 14/00* (2006.01)
*A61K 38/00* (2006.01)
*A61P 25/00* (2006.01)

(52) U.S. Cl. ........................ 530/350; 514/17.7

(58) Field of Classification Search .................. None
See application file for complete search history.

(56) References Cited

U.S. PATENT DOCUMENTS 6,465,210 B1 10/2002 Peles
7,745,391 B2 * 6/2010 Mintz et al. .................. 514/19.3

FOREIGN PATENT DOCUMENTS

WO WO 00/05364 2/2000
WO WO 01/36631 5/2001

OTHER PUBLICATIONS

Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Shimoda et al. Cell Adhesion Migration 3:64-70, 2009.*
Lee et al Gene 245: 253-266, 2000.*
Bhat, M.A., et al., "Axon-glia interactions and the domain organization of myelinated axons requires neurexin IV/Caspr/Paranodin", Neuron, 30: 369-383 (2001).
Hauben, E., et al., "Vaccination with a Nogo-A-derived peptide after incomplete spinal-cord injury promotes recovery . . . ", PNAS USA, 98: 15173-15178 (2001).
Woolf, C.J., "No Nogo: now where to go?", Neuron, 38: 153-156 (2003).
Nie, D-Y et al., "Nogo-A at CNS paranodes is a ligand of Caspr: possible regulation of K+ channel localization", EMBO Journal, 22: 5666-5678 (2003).
Wang, X et al., "Localization of Nogo-A and Nogo-66 Receptor Proteins at Sites of Axon-Myelin and Synaptic Contact", Journal of Neuroscience, 22: 5505-5515 (2002).
Mingorance, A. et al., "Regulation of Nogo and Nogo receptor during the development of the entorhino-hippocampal pathway and after adult hippocampal lesions", Mol. Cell Neurosc, 26: 34-49 (2004).
Teng, F. et al., "Inter- and intracellular interactions of Nogo: new findings and hypothesis", J. Neurochem, 89: 801-806 (2004).
Rios, J. et al., "Contactin-Associated Protein (Caspr) and Contactin Form a Complex That is Targeted to the Paranodal Junctions during Myelination", Journal of Neuroscience, 20: 8354-8364 (2000).
Karnezis et al., "The neurite outgrowth inhibitor Nogo A is involved in autoimmune-mediated demyelination", Nature Neuroscience, 7: 736-744 (2004).

* cited by examiner

*Primary Examiner* — Daniel E Kolker
*Assistant Examiner* — Aditi Dutt
(74) *Attorney, Agent, or Firm* — Patrick J. Hagan; Dann, Dorfman, Herrell and Skillman, PC

(57) ABSTRACT

The application provides materials and methods for promoting myelination of neuronal axons in the CNS. These derive from the findings first that the molecules Nogo and Caspr interact with one another during establishment and maintenance of the axoglial junction, and secondly that the molecules F3 and NB-3 are capable of promoting oligodendrocyte maturation via interaction with Notch. The materials and methods provided may be used in the treatment of CNS damage, in particular the treatment of spinal cord injury, multiple sclerosis, epilepsy and stroke.

4 Claims, 42 Drawing Sheets

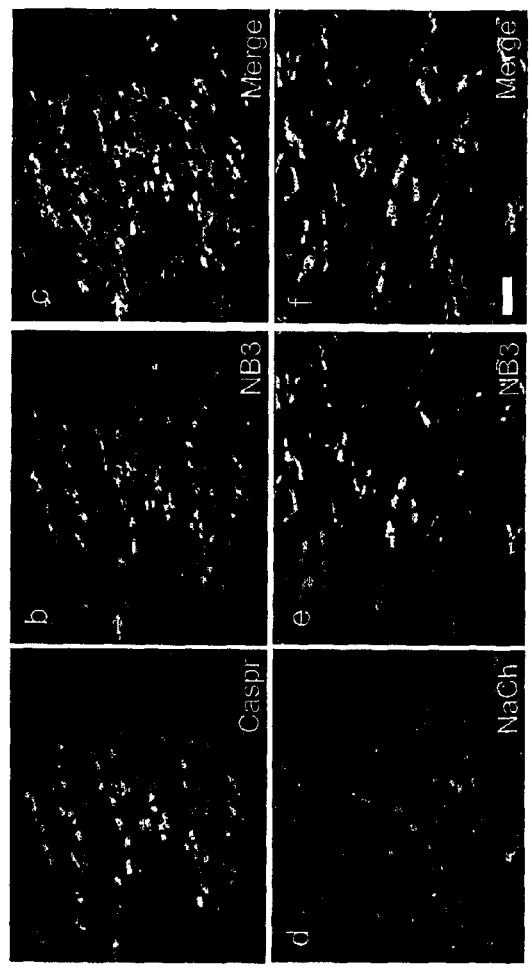
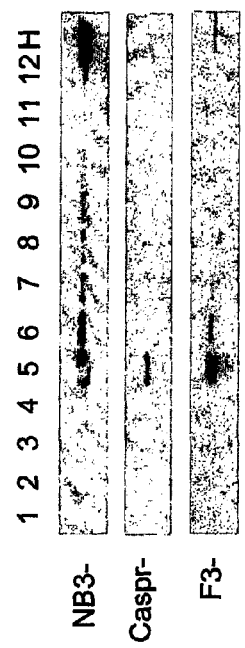
Figure 22B
Figure 22C c h i

SEQUENCE LISTING

<160> NUMBER OF SEQ ID NOS: 33

<210> SEQ ID NO 1
<211> LENGTH: 1192
<212> TYPE: PRT

<213> ORGANISM: Homo sapiens

<400> SEQUENCE: 1

Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro
                20                  25                  30

Asp Glu Glu Glu Glu Glu Glu Glu Glu Asp Glu Asp Glu Asp
            35                  40                  45

Leu Glu Glu Leu Glu Val Leu Glu Arg Lys Pro Ala Ala Gly Leu Ser
        50                  55                  60

Ala Ala Pro Val Pro Thr Ala Pro Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
            100                 105                 110

Val Ser Ser Thr Val Pro Ala Pro Ser Pro Leu Ser Ala Ala Ala Val
            115                 120                 125

Ser Pro Ser Lys Leu Pro Glu Asp Asp Glu Pro Pro Ala Arg Pro Pro
    130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Ser Thr Pro Ala Ala Pro
            165                 170                 175

Lys Arg Arg Gly Ser Ser Gly Ser Val Asp Glu Thr Leu Phe Ala Leu
            180                 185                 190

Pro Ala Ala Ser Glu Pro Val Ile Arg Ser Ser Ala Glu Asn Met Asp
        195                 200                 205

Leu Lys Glu Gln Pro Gly Asn Thr Ile Ser Ala Gly Gln Glu Asp Phe
    210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
            260                 265                 270

Ser Lys Glu Val Ser Glu Lys Ala Lys Thr Leu Leu Ile Asp Arg Asp
    275                 280                 285

Leu Thr Glu Phe Ser Glu Leu Glu Tyr Ser Glu Met Gly Ser Ser Phe
    290                 295                 300

Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Lys Leu Val Ser
                325                 330                 335

Asn Asn Ile Leu His Asn Gln Gln Glu Leu Pro Thr Ala Leu Thr Lys
            340                 345                 350

Leu Val Lys Glu Asp Glu Val Val Ser Ser Glu Lys Ala Lys Asp Ser
    355                 360                 365

Phe Asn Glu Lys Arg Val Ala Val Glu Ala Pro Met Arg Glu Glu Tyr
    370                 375                 380

Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu

```
                    405                 410                 415
Glu Ser Lys Val Asp Lys Lys Cys Phe Ala Asp Ser Leu Glu Gln Thr
                420                 425                 430

Asn His Glu Lys Asp Ser Glu Ser Ser Asn Asp Asp Thr Ser Phe Pro
            435                 440                 445

Ser Thr Pro Glu Gly Ile Lys Asp Arg Pro Gly Ala Tyr Ile Thr Cys
        450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys Lys
                485                 490                 495

Ile Glu Glu Lys Lys Ala Gln Ile Val Thr Glu Lys Asn Thr Ser Thr
                500                 505                 510

Lys Thr Ser Asn Pro Phe Leu Val Ala Ala Gln Asp Ser Glu Thr Asp
            515                 520                 525

Tyr Val Thr Thr Asp Asn Leu Thr Lys Val Thr Glu Glu Val Val Ala
        530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
                565                 570                 575

Met Asp Leu Val Gln Thr Ser Glu Val Met Gln Glu Ser Leu Tyr Pro
                580                 585                 590

Ala Ala Gln Leu Cys Pro Ser Phe Glu Glu Ser Glu Ala Thr Pro Ser
            595                 600                 605

Pro Val Leu Pro Asp Ile Val Met Glu Ala Pro Leu Asn Ser Ala Val
        610                 615                 620

Pro Ser Ala Gly Ala Ser Val Ile Gln Pro Ser Ser Pro Leu Glu
625                 630                 635                 640

Ala Ser Ser Val Asn Tyr Glu Ser Ile Lys His Glu Pro Glu Asn Pro
                645                 650                 655

Pro Pro Tyr Glu Glu Ala Met Ser Val Ser Leu Lys Lys Val Ser Gly
                660                 665                 670

Ile Lys Glu Glu Ile Lys Glu Pro Glu Asn Ile Asn Ala Ala Leu Gln
            675                 680                 685

Glu Thr Glu Ala Pro Tyr Ile Ser Ile Ala Cys Asp Leu Ile Lys Glu
        690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
                725                 730                 735

Asp Ser Ser Pro Asp Ser Glu Pro Val Asp Leu Phe Ser Asp Asp Ser
            740                 745                 750

Ile Pro Asp Val Pro Gln Lys Gln Asp Glu Thr Val Met Leu Val Lys
        755                 760                 765

Glu Ser Leu Thr Glu Thr Ser Phe Glu Ser Met Ile Glu Tyr Glu Asn
770                 775                 780

Lys Glu Lys Leu Ser Ala Leu Pro Pro Glu Gly Gly Lys Pro Tyr Leu
785                 790                 795                 800

Glu Ser Phe Lys Leu Ser Leu Asp Asn Thr Lys Asp Thr Leu Leu Pro
                805                 810                 815

Asp Glu Val Ser Thr Leu Ser Lys Lys Glu Lys Ile Pro Leu Gln Met
            820                 825                 830
```

-continued

Glu Glu Leu Ser Thr Ala Val Tyr Ser Asn Asp Asp Leu Phe Ile Ser
        835                 840                 845

Lys Glu Ala Gln Ile Arg Glu Thr Glu Thr Phe Ser Asp Ser Ser Pro
    850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
            885                 890                 895

Lys Ser Glu Ile Ala Asn Ala Pro Asp Gly Ala Gly Ser Leu Pro Cys
        900                 905                 910

Thr Glu Leu Pro His Asp Leu Ser Leu Lys Asn Ile Gln Pro Lys Val
        915                 920                 925

Glu Glu Lys Ile Ser Phe Ser Asp Asp Phe Ser Lys Asn Gly Ser Ala
    930                 935                 940

Thr Ser Lys Val Leu Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
            965                 970                 975

Ala Glu Lys Lys Leu Pro Ser Asp Thr Glu Lys Glu Asp Arg Ser Pro
    980                 985                 990

Ser Ala Ile Phe Ser Ala Glu Leu Ser Lys Thr Ser Val Val Asp Leu
    995                 1000                1005

Leu Tyr Trp Arg Asp Ile Lys Lys Thr Gly Val Val Phe Gly Ala
    1010                1015                1020

Ser Leu Phe Leu Leu Leu Ser Leu Thr Val Phe Ser Ile Val Ser
    1025                1030                1035

Val Thr Ala Tyr Ile Ala Leu Ala Leu Leu Ser Val Thr Ile Ser
    1040                1045                1050

Phe Arg Ile Tyr Lys Gly Val Ile Gln Ala Ile Gln Lys Ser Asp
    1055                1060                1065

Glu Gly His Pro Phe Arg Ala Tyr Leu Glu Ser Glu Val Ala Ile
    1070                1075                1080

Ser Glu Glu Leu Val Gln Lys Tyr Ser Asn Ser Ala Leu Gly His
    1085                1090                1095

Val Asn Cys Thr Ile Lys Glu Leu Arg Arg Leu Phe Leu Val Asp
    1100                1105                1110

Asp Leu Val Asp Ser Leu Lys Phe Ala Val Leu Met Trp Val Phe
    1115                1120                1125

Thr Tyr Val Gly Ala Leu Phe Asn Gly Leu Thr Leu Leu Ile Leu
    1130                1135                1140

Ala Leu Ile Ser Leu Phe Ser Val Pro Val Ile Tyr Glu Arg His
    1145                1150                1155

Gln Ala Gln Ile Asp His Tyr Leu Gly Leu Ala Asn Lys Asn Val
    1160                1165                1170

Lys Asp Ala Met Ala Lys Ile Gln Ala Lys Ile Pro Gly Leu Lys
    1175                1180                1185

Arg Lys Ala Glu
    1190

<210> SEQ ID NO 2
<211> LENGTH: 373
<212> TYPE: PRT
<213> ORGANISM: Homo sapiens

<400> SEQUENCE: 2

```
Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro Glu
            20                  25                  30

Asp Glu Glu Glu Glu Glu Glu Glu Glu Asp Glu Asp Glu Asp
        35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Gly Ala Pro Leu Met Asp
65                  70                  75                  80

Phe Gly Asn Asp Phe Val Pro Pro Ala Pro Arg Gly Pro Leu Pro Ala
            85                  90                  95

Ala Pro Pro Val Ala Pro Glu Arg Gln Pro Ser Trp Asp Pro Ser Pro
        100                 105                 110

Val Ser Ser Thr Val Pro Ala Pro Ser Pro Leu Ser Ala Ala Ala Val
        115                 120                 125

Ser Pro Ser Lys Leu Pro Glu Asp Asp Glu Pro Pro Ala Arg Pro Pro
    130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
            165                 170                 175

Lys Arg Arg Gly Ser Ser Gly Ser Val Val Asp Leu Leu Tyr Trp
                180                 185                 190

Arg Asp Ile Lys Lys Thr Gly Val Val Phe Gly Ala Ser Leu Phe Leu
            195                 200                 205

Leu Leu Ser Leu Thr Val Phe Ser Ile Val Ser Val Thr Ala Tyr Ile
    210                 215                 220

Ala Leu Ala Leu Leu Ser Val Thr Ile Ser Phe Arg Ile Tyr Lys Gly
225                 230                 235                 240

Val Ile Gln Ala Ile Gln Lys Ser Asp Glu Gly His Pro Phe Arg Ala
            245                 250                 255

Tyr Leu Glu Ser Glu Val Ala Ile Ser Glu Glu Leu Val Gln Lys Tyr
    260                 265                 270

Ser Asn Ser Ala Leu Gly His Val Asn Cys Thr Ile Lys Glu Leu Arg
    275                 280                 285

Arg Leu Phe Leu Val Asp Asp Leu Val Asp Ser Leu Lys Phe Ala Val
    290                 295                 300

Leu Met Trp Val Phe Thr Tyr Val Gly Ala Leu Phe Asn Gly Leu Thr
305                 310                 315                 320

Leu Leu Ile Leu Ala Leu Ile Ser Leu Phe Ser Val Pro Val Ile Tyr
            325                 330                 335

Glu Arg His Gln Ala Gln Ile Asp His Tyr Leu Gly Leu Ala Asn Lys
    340                 345                 350

Asn Val Lys Asp Ala Met Ala Lys Ile Gln Ala Lys Ile Pro Gly Leu
        355                 360                 365

Lys Arg Lys Ala Glu
    370

<210> SEQ ID NO 3
<211> LENGTH: 199
<212> TYPE: PRT
<213> ORGANISM: Homo sapiens

<400> SEQUENCE: 3
```

```
Met Asp Gly Gln Lys Lys Asn Trp Lys Asp Lys Val Val Asp Leu Leu
1               5                   10                  15

Tyr Trp Arg Asp Ile Lys Lys Thr Gly Val Val Phe Gly Ala Ser Leu
            20                  25                  30

Phe Leu Leu Leu Ser Leu Thr Val Phe Ser Ile Val Ser Val Thr Ala
                35                  40                  45

Tyr Ile Ala Leu Ala Leu Leu Ser Val Thr Ile Ser Phe Arg Ile Tyr
    50                  55                  60

Lys Gly Val Ile Gln Ala Ile Gln Lys Ser Asp Glu Gly His Pro Phe
65                  70                  75                  80

Arg Ala Tyr Leu Glu Ser Glu Val Ala Ile Ser Glu Glu Leu Val Gln
                85                  90                  95

Lys Tyr Ser Asn Ser Ala Leu Gly His Val Asn Cys Thr Ile Lys Glu
            100                 105                 110

Leu Arg Arg Leu Phe Leu Val Asp Asp Leu Val Asp Ser Leu Lys Phe
        115                 120                 125

Ala Val Leu Met Trp Val Phe Thr Tyr Val Gly Ala Leu Phe Asn Gly
130                 135                 140

Leu Thr Leu Leu Ile Leu Ala Leu Ile Ser Leu Phe Ser Val Pro Val
145                 150                 155                 160

Ile Tyr Glu Arg His Gln Ala Gln Ile Asp His Tyr Leu Gly Leu Ala
            165                 170                 175

Asn Lys Asn Val Lys Asp Ala Met Ala Lys Ile Gln Ala Lys Ile Pro
        180                 185                 190

Gly Leu Lys Arg Lys Ala Glu
        195
```

<210> SEQ ID NO 4
<211> LENGTH: 1384
<212> TYPE: PRT
<213> ORGANISM: Homo sapiens

<400> SEQUENCE: 4

```
Met Met His Leu Arg Leu Phe Cys Ile Leu Leu Ala Ala Val Ser Gly
1               5                   10                  15

Ala Glu Gly Trp Gly Tyr Tyr Gly Cys Asp Glu Glu Leu Val Gly Pro
            20                  25                  30

Leu Tyr Ala Arg Ser Leu Gly Ala Ser Ser Tyr Tyr Ser Leu Leu Thr
        35                  40                  45

Ala Pro Arg Phe Ala Arg Leu His Gly Ile Ser Gly Trp Ser Pro Arg
    50                  55                  60

Ile Gly Asp Pro Asn Pro Trp Leu Gln Ile Asp Leu Met Lys Lys His
65                  70                  75                  80

Arg Ile Arg Ala Val Ala Thr Gln Gly Ser Phe Asn Ser Trp Asp Trp
                85                  90                  95

Val Thr Arg Tyr Met Leu Leu Tyr Gly Asp Arg Val Asp Ser Trp Thr
            100                 105                 110

Pro Phe Tyr Gln Arg Gly His Asn Ser Thr Phe Phe Gly Asn Val Asn
        115                 120                 125

Glu Ser Ala Val Val Arg His Asp Leu His Phe His Phe Thr Ala Arg
130                 135                 140

Tyr Ile Arg Ile Val Pro Leu Ala Trp Asn Pro Arg Gly Lys Ile Gly
145                 150                 155                 160

Leu Arg Leu Gly Leu Tyr Gly Cys Pro Tyr Lys Ala Asp Ile Leu Tyr
            165                 170                 175
```

```
Phe Asp Gly Asp Asp Ala Ile Ser Tyr Arg Phe Pro Arg Gly Val Ser
                180                 185                 190

Arg Ser Leu Trp Asp Val Phe Ala Phe Ser Phe Lys Thr Glu Glu Lys
            195                 200                 205

Asp Gly Leu Leu Leu His Ala Glu Gly Ala Gln Gly Asp Tyr Val Thr
        210                 215                 220

Leu Glu Leu Glu Gly Ala His Leu Leu Leu His Met Ser Leu Gly Ser
225                 230                 235                 240

Ser Pro Ile Gln Pro Arg Pro Gly His Thr Thr Val Ser Ala Gly Gly
                245                 250                 255

Val Leu Asn Asp Gln His Trp His Tyr Val Arg Val Asp Arg Phe Gly
            260                 265                 270

Arg Asp Val Asn Phe Thr Leu Asp Gly Tyr Val Gln Arg Phe Ile Leu
        275                 280                 285

Asn Gly Asp Phe Glu Arg Leu Asn Leu Asp Thr Glu Met Phe Ile Gly
        290                 295                 300

Gly Leu Val Gly Ala Ala Arg Lys Asn Leu Ala Tyr Arg His Asn Phe
305                 310                 315                 320

Arg Gly Cys Ile Glu Asn Val Ile Phe Asn Arg Val Asn Ile Ala Asp
                325                 330                 335

Leu Ala Val Arg Arg His Ser Arg Ile Thr Phe Glu Gly Lys Val Ala
            340                 345                 350

Phe Arg Cys Leu Asp Pro Val Pro His Pro Ile Asn Phe Gly Gly Pro
        355                 360                 365

His Asn Phe Val Gln Val Pro Gly Phe Pro Arg Arg Gly Arg Leu Ala
        370                 375                 380

Val Ser Phe Arg Phe Arg Thr Trp Asp Leu Thr Gly Leu Leu Leu Phe
385                 390                 395                 400

Ser Arg Leu Gly Asp Gly Leu Gly His Val Glu Leu Thr Leu Ser Glu
                405                 410                 415

Gly Gln Val Asn Val Ser Ile Ala Gln Ser Gly Arg Lys Lys Leu Gln
            420                 425                 430

Phe Ala Ala Gly Tyr Arg Leu Asn Asp Gly Phe Trp His Glu Val Asn
        435                 440                 445

Phe Val Ala Gln Glu Asn His Ala Val Ile Ser Ile Asp Asp Val Glu
        450                 455                 460

Gly Ala Glu Val Arg Val Ser Tyr Pro Leu Leu Ile Arg Thr Gly Thr
465                 470                 475                 480

Ser Tyr Phe Phe Gly Gly Cys Pro Lys Pro Ala Ser Arg Trp Asp Cys
                485                 490                 495

His Ser Asn Gln Thr Ala Phe His Gly Cys Met Glu Leu Leu Lys Val
            500                 505                 510

Asp Gly Gln Leu Val Asn Leu Thr Leu Val Glu Gly Arg Arg Leu Gly
        515                 520                 525

Phe Tyr Ala Glu Val Leu Phe Asp Thr Cys Gly Ile Thr Asp Arg Cys
        530                 535                 540

Ser Pro Asn Met Cys Glu His Asp Gly Arg Cys Tyr Gln Ser Trp Asp
545                 550                 555                 560

Asp Phe Ile Cys Tyr Cys Glu Leu Thr Gly Tyr Lys Gly Glu Thr Cys
                565                 570                 575

His Thr Pro Leu Tyr Lys Glu Ser Cys Glu Ala Tyr Arg Leu Ser Gly
            580                 585                 590

Lys Thr Ser Gly Asn Phe Thr Ile Asp Pro Asp Gly Ser Gly Pro Leu
        595                 600                 605
```

-continued

Lys Pro Phe Val Val Tyr Cys Asp Ile Arg Glu Asn Arg Ala Trp Thr
610                 615                 620

Val Val Arg His Asp Arg Leu Trp Thr Thr Arg Val Thr Gly Ser Ser
625                 630                 635                 640

Met Glu Arg Pro Phe Leu Gly Ala Ile Gln Tyr Trp Asn Ala Ser Trp
            645                 650                 655

Glu Glu Val Ser Ala Leu Ala Asn Ala Ser Gln His Cys Glu Gln Trp
            660                 665                 670

Ile Glu Phe Ser Cys Tyr Asn Ser Arg Leu Leu Asn Thr Ala Gly Gly
            675                 680                 685

Tyr Pro Tyr Ser Phe Trp Ile Gly Arg Asn Glu Glu Gln His Phe Tyr
    690                 695                 700

Trp Gly Gly Ser Gln Pro Gly Ile Gln Arg Cys Ala Cys Gly Leu Asp
705                 710                 715                 720

Arg Ser Cys Val Asp Pro Ala Leu Tyr Cys Asn Cys Asp Ala Asp Gln
                725                 730                 735

Pro Gln Trp Arg Thr Asp Lys Gly Leu Leu Thr Phe Val Asp His Leu
            740                 745                 750

Pro Val Thr Gln Val Val Ile Gly Asp Thr Asn Arg Ser Thr Ser Glu
            755                 760                 765

Ala Gln Phe Phe Leu Arg Pro Leu Arg Cys Tyr Gly Asp Arg Asn Ser
770                 775                 780

Trp Asn Thr Ile Ser Phe His Thr Gly Ala Ala Leu Arg Phe Pro Pro
785                 790                 795                 800

Ile Arg Ala Asn His Ser Leu Asp Val Ser Phe Tyr Phe Arg Thr Ser
                805                 810                 815

Ala Pro Ser Gly Val Phe Leu Glu Asn Met Gly Gly Pro Tyr Cys Gln
            820                 825                 830

Trp Arg Arg Pro Tyr Val Arg Val Glu Leu Asn Thr Ser Arg Asp Val
            835                 840                 845

Val Phe Ala Phe Asp Val Gly Asn Gly Asp Glu Asn Leu Thr Val His
850                 855                 860

Ser Asp Asp Phe Glu Phe Asn Asp Glu Trp His Leu Val Arg Ala
865                 870                 875                 880

Glu Ile Asn Val Lys Gln Ala Arg Leu Arg Val Asp His Arg Pro Trp
            885                 890                 895

Val Leu Arg Pro Met Pro Leu Gln Thr Tyr Ile Trp Met Glu Tyr Asp
            900                 905                 910

Gln Pro Leu Tyr Val Gly Ser Ala Glu Leu Lys Arg Arg Pro Phe Val
    915                 920                 925

Gly Cys Leu Arg Ala Met Arg Leu Asn Gly Val Thr Leu Asn Leu Glu
    930                 935                 940

Gly Arg Ala Asn Ala Ser Glu Gly Thr Ser Pro Asn Cys Thr Gly His
945                 950                 955                 960

Cys Ala His Pro Arg Leu Pro Cys Phe His Gly Gly Arg Cys Val Glu
            965                 970                 975

Arg Tyr Ser Tyr Tyr Thr Cys Asp Cys Asp Leu Thr Ala Phe Asp Gly
            980                 985                 990

Pro Tyr Cys Asn His Asp Ile Gly Phe Phe Glu Pro Gly Thr Trp
        995                 1000                1005

Met Arg Tyr Asn Leu Gln Ser Ala Leu Arg Ser Ala Ala Arg Glu
    1010                1015                1020

Phe Ser His Met Leu Ser Arg Pro Val Pro Gly Tyr Glu Pro Gly 1025                1030                1035

Tyr Ile Pro Gly Tyr Asp Thr Pro Gly Tyr Val Pro Gly Tyr His
    1040                1045                1050

Gly Pro Gly Tyr Arg Leu Pro Asp Tyr Pro Arg Pro Gly Arg Pro
    1055                1060                1065

Val Pro Gly Tyr Arg Gly Pro Val Tyr Asn Val Thr Gly Glu Glu
    1070                1075                1080

Val Ser Phe Ser Phe Ser Thr Ser Ser Ala Pro Ala Val Leu Leu
    1085                1090                1095

Tyr Val Ser Ser Phe Val Arg Asp Tyr Met Ala Val Leu Ile Lys
    1100                1105                1110

Asp Asp Gly Thr Leu Gln Leu Arg Tyr Gln Leu Gly Thr Ser Pro
    1115                1120                1125

Tyr Val Tyr Gln Leu Thr Thr Arg Pro Val Thr Asp Gly Gln Pro
    1130                1135                1140

His Ser Ile Asn Ile Thr Arg Val Tyr Arg Asn Leu Phe Ile Gln
    1145                1150                1155

Val Asp Tyr Phe Pro Leu Thr Glu Gln Lys Phe Ser Leu Leu Val
    1160                1165                1170

Asp Ser Gln Leu Asp Ser Pro Lys Ala Leu Tyr Leu Gly Arg Val
    1175                1180                1185

Met Glu Thr Gly Val Ile Asp Pro Glu Ile Gln Arg Tyr Asn Thr
    1190                1195                1200

Pro Gly Phe Ser Gly Cys Leu Ser Gly Val Arg Phe Asn Asn Val
    1205                1210                1215

Ala Pro Leu Lys Thr His Phe Arg Thr Pro Arg Pro Met Thr Ala
    1220                1225                1230

Glu Leu Ala Glu Ala Leu Arg Val Gln Gly Glu Leu Ser Glu Ser
    1235                1240                1245

Asn Cys Gly Ala Met Pro Arg Leu Val Ser Glu Val Pro Pro Glu
    1250                1255                1260

Leu Asp Pro Trp Tyr Leu Pro Pro Asp Phe Pro Tyr Tyr His Asp
    1265                1270                1275

Glu Gly Trp Val Ala Ile Leu Leu Gly Phe Leu Val Ala Phe Leu
    1280                1285                1290

Leu Leu Gly Leu Val Gly Met Leu Val Leu Phe Tyr Leu Gln Asn
    1295                1300                1305

His Arg Tyr Lys Gly Ser Tyr His Thr Asn Glu Pro Lys Ala Ala
    1310                1315                1320

His Glu Tyr His Pro Gly Ser Lys Pro Pro Leu Pro Thr Ser Gly
    1325                1330                1335

Pro Ala Gln Val Pro Thr Pro Thr Ala Ala Pro Asn Gln Ala Pro
    1340                1345                1350

Ala Ser Ala Pro Ala Pro Ala Pro Thr Pro Ala Pro Ala Pro Gly
    1355                1360                1365

Pro Arg Asp Gln Asn Leu Pro Gln Ile Leu Glu Glu Ser Arg Ser
    1370                1375                1380

Glu

<210> SEQ ID NO 5
<211> LENGTH: 65
<212> TYPE: PRT
<213> ORGANISM: Homo sapiens

<400> SEQUENCE: 5

```
Arg Ile Tyr Lys Gly Val Ile Gln Ala Ile Gln Lys Ser Asp Glu Gly
1               5                   10                  15

His Pro Phe Arg Ala Tyr Leu Glu Ser Glu Val Ala Ile Ser Glu Glu
            20                  25                  30

Leu Val Gln Lys Tyr Ser Asn Ser Ala Leu Gly His Val Asn Cys Thr
        35                  40                  45

Ile Lys Glu Leu Arg Arg Leu Phe Leu Val Asp Leu Val Asp Ser Leu
    50                  55                  60

Lys
65

<210> SEQ ID NO 6
<211> LENGTH: 31
<212> TYPE: DNA
<213> ORGANISM: Artificial sequence
<220> FEATURE:
<223> OTHER INFORMATION: Primer

<400> SEQUENCE: 6
agtcggatcc acaaaatcat cgmtaymagg g                                    31

<210> SEQ ID NO 7
<211> LENGTH: 38
<212> TYPE: DNA
<213> ORGANISM: Artificial sequence
<220> FEATURE:
<223> OTHER INFORMATION: Primer

<400> SEQUENCE: 7
actcgaattc agacctggac tcctcctcca rgatctgg                             38

<210> SEQ ID NO 8
<211> LENGTH: 66
<212> TYPE: PRT
<213> ORGANISM: Unknown
<220> FEATURE:
<223> OTHER INFORMATION: Sequence source uncertain

<400> SEQUENCE: 8

Lys Leu Ser Asp Val Leu Asp Val Leu Phe Leu Arg Arg Leu Glu
1               5                   10                  15

Lys Ile Thr Cys Asn Val His Gly Leu Ala Ser Asn Ser Tyr Lys Gln
            20                  25                  30

Val Leu Glu Glu Ser Ile Ala Val Glu Ser Glu Leu Tyr Ala Arg Phe
        35                  40                  45

Pro His Gly Glu Asp Ser Lys Gln Ile Ala Gln Ile Val Gly Lys Tyr
    50                  55                  60

Ile Arg
65

<210> SEQ ID NO 9
<211> LENGTH: 27
<212> TYPE: DNA
<213> ORGANISM: Artificial sequence
<220> FEATURE:
<223> OTHER INFORMATION: Primer

<400> SEQUENCE: 9
ctgaattctt aggatataca agggtgt                                         27

<210> SEQ ID NO 10
<211> LENGTH: 29
```

<210> SEQ ID NO 11
<211> LENGTH: 27
<212> TYPE: DNA
<213> ORGANISM: Artificial sequence
<220> FEATURE:
<223> OTHER INFORMATION: Primer

<400> SEQUENCE: 10
gctaagcttt cacttcagag aatcaacta          29

<210> SEQ ID NO 11
<211> LENGTH: 27
<212> TYPE: DNA
<213> ORGANISM: Artificial sequence
<220> FEATURE:
<223> OTHER INFORMATION: Primer

<400> SEQUENCE: 11
aggaattcta gatgagaccc tttttgc          27

<210> SEQ ID NO 12
<211> LENGTH: 33
<212> TYPE: DNA
<213> ORGANISM: Artificial sequence
<220> FEATURE:
<223> OTHER INFORMATION: Primer

<400> SEQUENCE: 12
cccaagcttt caattaaaac tgtcttttgc ttt          33

<210> SEQ ID NO 13
<211> LENGTH: 1018
<212> TYPE: PRT
<213> ORGANISM: Homo sapiens

<400> SEQUENCE: 13

Met Lys Met Trp Leu Leu Val Ser His Leu Val Ile Ile Ser Ile Thr
1               5                   10                  15

Thr Cys Leu Ala Glu Phe Thr Trp Tyr Arg Arg Tyr Gly His Gly Val
            20                  25                  30

Ser Glu Glu Asp Lys Gly Phe Gly Pro Ile Phe Glu Glu Gln Pro Ile
        35                  40                  45

Asn Thr Ile Tyr Pro Glu Glu Ser Leu Glu Gly Lys Val Ser Leu Asn
    50                  55                  60

Cys Arg Ala Arg Ala Ser Pro Phe Pro Val Tyr Lys Trp Arg Met Asn
65                  70                  75                  80

Asn Gly Asp Val Asp Leu Thr Ser Asp Arg Tyr Ser Met Val Gly Gly
                85                  90                  95

Asn Leu Val Ile Asn Asn Pro Asp Lys Gln Lys Asp Ala Gly Ile Tyr
            100                 105                 110

Tyr Cys Leu Ala Ser Asn Asn Tyr Gly Met Val Arg Ser Thr Glu Ala
        115                 120                 125

Thr Leu Ser Phe Gly Tyr Leu Asp Pro Phe Pro Glu Glu Arg Pro
    130                 135                 140

Glu Val Arg Val Lys Glu Gly Lys Gly Met Val Leu Leu Cys Asp Pro
145                 150                 155                 160

Pro Tyr His Phe Pro Asp Asp Leu Ser Tyr Arg Trp Leu Leu Asn Glu
                165                 170                 175

Phe Pro Val Phe Ile Thr Met Asp Lys Arg Arg Phe Val Ser Gln Thr
            180                 185                 190

Asn Gly Asn Leu Tyr Ile Ala Asn Val Glu Ala Ser Asp Lys Gly Asn
        195                 200                 205

```
Tyr Ser Cys Phe Val Ser Ser Pro Ser Ile Thr Lys Ser Val Phe Ser
    210                 215                 220

Lys Phe Ile Pro Leu Ile Pro Ile Pro Glu Arg Thr Thr Lys Pro Tyr
225                 230                 235                 240

Pro Ala Asp Ile Val Val Gln Phe Lys Asp Val Tyr Ala Leu Met Gly
                245                 250                 255

Gln Asn Val Thr Leu Glu Cys Phe Ala Leu Gly Asn Pro Val Pro Asp
            260                 265                 270

Ile Arg Trp Arg Lys Val Leu Glu Pro Met Pro Ser Thr Ala Glu Ile
        275                 280                 285

Ser Thr Ser Gly Ala Val Leu Lys Ile Phe Asn Ile Gln Leu Glu Asp
    290                 295                 300

Glu Gly Ile Tyr Glu Cys Glu Ala Glu Asn Ile Arg Gly Lys Asp Lys
305                 310                 315                 320

His Gln Ala Arg Ile Tyr Val Gln Ala Phe Pro Glu Trp Val Glu His
                325                 330                 335

Ile Asn Asp Thr Glu Val Asp Ile Gly Ser Asp Leu Tyr Trp Pro Cys
            340                 345                 350

Val Ala Thr Gly Lys Pro Ile Pro Thr Ile Arg Trp Leu Lys Asn Gly
        355                 360                 365

Tyr Ala Tyr His Lys Gly Glu Leu Arg Leu Tyr Asp Val Thr Phe Glu
    370                 375                 380

Asn Ala Gly Met Tyr Gln Cys Ile Ala Glu Asn Thr Tyr Gly Ala Ile
385                 390                 395                 400

Tyr Ala Asn Ala Glu Leu Lys Ile Leu Ala Leu Ala Pro Thr Phe Glu
                405                 410                 415

Met Asn Pro Met Lys Lys Ile Leu Ala Ala Lys Gly Gly Arg Val
            420                 425                 430

Ile Ile Glu Cys Lys Pro Lys Ala Ala Pro Lys Pro Lys Phe Ser Trp
        435                 440                 445

Ser Lys Gly Thr Glu Trp Leu Val Asn Ser Ser Arg Ile Leu Ile Trp
    450                 455                 460

Glu Asp Gly Ser Leu Glu Ile Asn Asn Ile Thr Arg Asn Asp Gly Gly
465                 470                 475                 480

Ile Tyr Thr Cys Phe Ala Glu Asn Asn Arg Gly Lys Ala Asn Ser Thr
                485                 490                 495

Gly Thr Leu Val Ile Thr Asp Pro Thr Arg Ile Ile Leu Ala Pro Ile
            500                 505                 510

Asn Ala Asp Ile Thr Val Gly Glu Asn Ala Thr Met Gln Cys Ala Ala
        515                 520                 525

Ser Phe Asp Pro Ala Leu Asp Leu Thr Phe Val Trp Ser Phe Asn Gly
    530                 535                 540

Tyr Val Ile Asp Phe Asn Lys Glu Asn Ile His Tyr Gln Arg Asn Phe
545                 550                 555                 560

Met Leu Asp Ser Asn Gly Glu Leu Leu Ile Arg Asn Ala Gln Leu Lys
                565                 570                 575

His Ala Gly Arg Tyr Thr Cys Thr Ala Gln Thr Ile Val Asp Asn Ser
            580                 585                 590

Ser Ala Ser Ala Asp Leu Val Val Arg Gly Pro Pro Gly Pro Pro Gly
        595                 600                 605

Gly Leu Arg Ile Glu Asp Ile Arg Ala Thr Ser Val Ala Leu Thr Trp
    610                 615                 620

Ser Arg Gly Ser Asp Asn His Ser Pro Ile Ser Lys Tyr Thr Ile Gln
625                 630                 635                 640
```

```
Thr Lys Thr Ile Leu Ser Asp Asp Trp Lys Asp Ala Lys Thr Asp Pro
            645                 650                 655

Pro Ile Ile Glu Gly Asn Met Glu Ala Ala Arg Ala Val Asp Leu Ile
        660                 665                 670

Pro Trp Met Glu Tyr Glu Phe Arg Val Val Ala Thr Asn Thr Leu Gly
    675                 680                 685

Arg Gly Glu Pro Ser Ile Pro Ser Asn Arg Ile Lys Thr Asp Gly Ala
690                 695                 700

Ala Pro Asn Val Ala Pro Ser Asp Val Gly Gly Gly Gly Arg Asn
705                 710                 715                 720

Arg Glu Leu Thr Ile Thr Trp Ala Pro Leu Ser Arg Glu Tyr His Tyr
                725                 730                 735

Gly Asn Asn Phe Gly Tyr Ile Val Ala Phe Lys Pro Phe Asp Gly Glu
            740                 745                 750

Glu Trp Lys Lys Val Thr Val Thr Asn Pro Asp Thr Gly Arg Tyr Val
        755                 760                 765

His Lys Asp Glu Thr Met Ser Pro Ser Thr Ala Phe Gln Val Lys Val
    770                 775                 780

Lys Ala Phe Asn Asn Lys Gly Asp Gly Pro Tyr Ser Leu Leu Ala Val
785                 790                 795                 800

Ile Asn Ser Ala Gln Asp Ala Pro Ser Glu Ala Pro Thr Glu Val Gly
                805                 810                 815

Val Lys Val Leu Ser Ser Ser Glu Ile Ser Val His Trp Glu His Val
            820                 825                 830

Leu Glu Lys Ile Val Glu Ser Tyr Gln Ile Arg Tyr Trp Ala Ala His
        835                 840                 845

Asp Lys Glu Glu Ala Ala Asn Arg Val Gln Val Thr Ser Gln Glu Tyr
    850                 855                 860

Ser Ala Arg Leu Glu Asn Leu Leu Pro Asp Thr Gln Tyr Phe Ile Glu
865                 870                 875                 880

Val Gly Ala Cys Asn Ser Ala Gly Cys Gly Pro Pro Ser Asp Met Ile
                885                 890                 895

Glu Ala Phe Thr Lys Lys Ala Pro Pro Ser Gln Pro Pro Arg Ile Ile
            900                 905                 910

Ser Ser Val Arg Ser Gly Ser Arg Tyr Ile Ile Thr Trp Asp His Val
        915                 920                 925

Val Ala Leu Ser Asn Glu Ser Thr Val Thr Gly Tyr Lys Val Leu Tyr
    930                 935                 940

Arg Pro Asp Gly Gln His Asp Gly Lys Leu Tyr Ser Thr His Lys His
945                 950                 955                 960

Ser Ile Glu Val Pro Ile Pro Arg Asp Gly Glu Tyr Val Val Glu Val
                965                 970                 975

Arg Ala His Ser Asp Gly Gly Asp Gly Val Val Ser Gln Val Lys Ile
            980                 985                 990

Ser Gly Ala Pro Thr Leu Ser Pro  Ser Leu Leu Gly Leu  Leu Leu Pro
        995                 1000                1005

Ala Phe  Gly Ile Leu Val Tyr  Leu Glu Phe
    1010                1015

<210> SEQ ID NO 14
<211> LENGTH: 1028
<212> TYPE: PRT
<213> ORGANISM: Homo sapiens

<400> SEQUENCE: 14
```

-continued

```
Met Arg Leu Leu Trp Lys Leu Val Ile Leu Pro Leu Ile Asn Ser
1               5                   10                  15

Ser Ala Gly Asp Gly Leu Leu Ser Arg Pro Ile Phe Thr Gln Glu Pro
            20                  25                  30

His Asp Val Ile Phe Pro Leu Asp Leu Ser Lys Ser Glu Val Ile Leu
            35                  40                  45

Asn Cys Ala Ala Asn Gly Tyr Pro Ser Pro His Tyr Arg Trp Lys Gln
50                  55                  60

Asn Gly Thr Asp Ile Asp Phe Thr Met Ser Tyr His Tyr Arg Leu Asp
65                  70                  75                  80

Gly Gly Ser Leu Ala Ile Asn Ser Pro His Thr Asp Gln Asp Ile Gly
                85                  90                  95

Met Tyr Gln Cys Leu Ala Thr Asn Leu Leu Gly Thr Ile Leu Ser Arg
            100                 105                 110

Lys Ala Lys Leu Gln Phe Ala Tyr Ile Glu Asp Phe Glu Thr Lys Thr
            115                 120                 125

Arg Ser Thr Val Ser Val Arg Glu Gly Gln Gly Val Val Leu Leu Cys
            130                 135                 140

Gly Pro Pro His Phe Gly Asp Leu Ser Tyr Ala Trp Thr Phe Asn
145                 150                 155                 160

Asp Asn Pro Leu Tyr Val Gln Glu Asp Asn Arg Arg Phe Val Ser Gln
                165                 170                 175

Glu Thr Gly Asn Leu Tyr Ile Ala Lys Val Glu Pro Ser Asp Val Gly
            180                 185                 190

Asn Tyr Thr Cys Phe Ile Thr Asn Lys Glu Ala Gln Arg Ser Val Gln
            195                 200                 205

Gly Pro Pro Thr Pro Leu Val Gln Arg Thr Asp Gly Val Met Gly Glu
            210                 215                 220

Tyr Glu Pro Lys Ile Glu Val Arg Phe Pro Glu Thr Ile Gln Ala Ala
225                 230                 235                 240

Lys Asp Ser Ser Val Lys Leu Glu Cys Phe Ala Leu Gly Asn Pro Val
                245                 250                 255

Pro Asp Ile Ser Trp Arg Arg Leu Asp Gly Ser Pro Leu Pro Gly Lys
            260                 265                 270

Val Lys Tyr Ser Lys Ser Gln Ala Ile Leu Glu Ile Pro Asn Phe Gln
            275                 280                 285

Gln Glu Asp Glu Gly Phe Tyr Glu Cys Ile Ala Ser Asn Leu Arg Gly
            290                 295                 300

Arg Asn Leu Ala Lys Gly Gln Leu Ile Phe Tyr Ala Pro Pro Glu Trp
305                 310                 315                 320

Glu Gln Lys Ile Gln Asn Thr His Leu Ser Ile Tyr Asp Asn Leu Leu
            325                 330                 335

Trp Glu Cys Lys Ala Ser Gly Lys Pro Asn Pro Trp Tyr Thr Trp Leu
            340                 345                 350

Lys Asn Gly Glu Arg Leu Asn Pro Glu Glu Arg Ile Gln Ile Glu Asn
            355                 360                 365

Gly Thr Leu Ile Ile Thr Met Leu Asn Val Ser Asp Ser Gly Val Tyr
370                 375                 380

Gln Cys Ala Ala Glu Asn Lys Tyr Gln Ile Ile Tyr Ala Asn Ala Glu
385                 390                 395                 400

Leu Arg Val Leu Ala Ser Ala Pro Asp Phe Ser Lys Ser Pro Val Lys
            405                 410                 415

Lys Lys Ser Phe Val Gln Val Gly Gly Asp Ile Val Ile Gly Cys Lys
```

-continued

```
                420                 425                 430
Pro Asn Ala Phe Pro Arg Ala Ile Ser Trp Lys Arg Gly Thr Glu
            435                 440                 445
Thr Leu Arg Gln Ser Lys Arg Ile Phe Leu Leu Glu Asp Gly Ser Leu
        450                 455                 460
Lys Ile Tyr Asn Ile Thr Arg Ser Asp Ala Gly Ser Tyr Thr Cys Ile
465                 470                 475                 480
Ala Thr Asn Gln Phe Gly Thr Ala Lys Asn Thr Gly Ser Leu Ile Val
                485                 490                 495
Lys Glu Arg Thr Val Ile Thr Val Pro Pro Ser Lys Met Asp Val Thr
            500                 505                 510
Val Gly Glu Ser Ile Val Leu Pro Cys Gln Val Ser His Asp Pro Ser
            515                 520                 525
Ile Glu Val Val Phe Val Trp Phe Phe Asn Gly Asp Val Ile Asp Leu
        530                 535                 540
Lys Lys Gly Val Ala His Phe Glu Arg Ile Gly Gly Glu Ser Val Gly
545                 550                 555                 560
Asp Leu Met Ile Arg Asn Ile Gln Leu His His Ser Gly Lys Tyr Leu
                565                 570                 575
Cys Thr Val Gln Thr Thr Leu Glu Ser Leu Ser Ala Val Ala Asp Ile
            580                 585                 590
Ile Val Arg Gly Pro Pro Gly Pro Pro Glu Asp Val Gln Val Glu Asp
            595                 600                 605
Ile Ser Ser Thr Thr Ser Gln Leu Ser Trp Arg Ala Gly Pro Asp Asn
        610                 615                 620
Asn Ser Pro Ile Gln Ile Phe Thr Ile Gln Thr Arg Thr Pro Phe Ser
625                 630                 635                 640
Val Gly Trp Gln Ala Val Ala Thr Val Pro Glu Ile Leu Asn Gly Lys
                645                 650                 655
Thr Tyr Asn Ala Thr Val Val Gly Leu Ser Pro Trp Val Glu Tyr Glu
            660                 665                 670
Phe Arg Val Val Ala Gly Asn Ser Ile Gly Ile Gly Glu Pro Ser Glu
            675                 680                 685
Pro Ser Glu Leu Leu Arg Thr Lys Ala Ser Val Pro Val Val Ala Pro
        690                 695                 700
Val Asn Ile His Gly Gly Gly Gly Ser Arg Ser Glu Leu Val Ile Thr
705                 710                 715                 720
Trp Glu Ser Ile Pro Glu Glu Leu Gln Asn Gly Glu Gly Phe Gly Tyr
                725                 730                 735
Ile Ile Met Phe Arg Pro Val Gly Ser Thr Thr Trp Ser Lys Glu Lys
            740                 745                 750
Val Ser Ser Val Glu Ser Ser Arg Phe Val Tyr Arg Asn Glu Ser Ile
            755                 760                 765
Ile Pro Leu Ser Pro Phe Glu Val Lys Val Gly Val Tyr Asn Asn Glu
        770                 775                 780
Gly Glu Gly Ser Leu Ser Thr Val Thr Ile Val Tyr Ser Gly Glu Asp
785                 790                 795                 800
Glu Pro Gln Leu Ala Pro Arg Gly Thr Ser Leu Gln Ser Phe Ser Ala
                805                 810                 815
Ser Glu Met Glu Val Ser Trp Asn Ala Ile Ala Trp Asn Arg Asn Thr
            820                 825                 830
Gly Arg Val Leu Gly Tyr Glu Val Leu Tyr Trp Thr Asp Asp Ser Lys
            835                 840                 845
```

```
Glu Ser Met Ile Gly Lys Ile Arg Val Ser Gly Asn Val Thr Thr Lys
        850                 855                 860

Asn Ile Thr Gly Leu Lys Ala Asn Thr Ile Tyr Phe Ala Ser Val Arg
865                 870                 875                 880

Ala Tyr Asn Thr Ala Gly Thr Gly Pro Ser Pro Pro Val Asn Val
                885                 890                 895

Thr Thr Lys Lys Ser Pro Pro Ser Gln Pro Pro Ala Asn Ile Ala Trp
            900                 905                 910

Lys Leu Thr Asn Ser Lys Leu Cys Leu Asn Trp Glu His Val Lys Thr
            915                 920                 925

Met Glu Asn Glu Ser Glu Val Leu Gly Tyr Lys Ile Leu Tyr Arg Gln
        930                 935                 940

Asn Arg Gln Ser Lys Thr His Ile Leu Glu Thr Asn Asn Thr Ser Ala
945                 950                 955                 960

Glu Leu Leu Val Pro Phe Glu Asp Tyr Leu Ile Glu Ile Arg Thr
                965                 970                 975

Val Ser Asp Gly Gly Asp Gly Ser Ser Glu Glu Ile Arg Ile Pro
                980                 985                 990

Lys Met Ser Ser Leu Ser Ser Arg  Gly Ile Gln Phe Leu  Glu Pro Ser
            995                 1000                1005

Thr His  Phe Leu Ser Ile Val  Ile Val Ile Phe His  Cys Phe Ala
    1010                1015                1020

Ile Gln  Pro Leu Ile
    1025

<210> SEQ ID NO 15
<211> LENGTH: 2556
<212> TYPE: PRT
<213> ORGANISM: Homo sapiens
<220> FEATURE:
<221> NAME/KEY: MISC_FEATURE
<222> LOCATION: (891)..(891)
<223> OTHER INFORMATION: Xaa is uncertain

<400> SEQUENCE: 15

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175
```

```
Gln Asp Val Asn Glu Cys Gly Gln Lys Pro Arg Leu Cys Arg His Gly
        180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
            245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Pro Cys Pro Pro Glu Trp Thr
        275                 280                 285

Gly Gln Tyr Cys Thr Glu Asp Val Asp Glu Cys Gln Leu Met Pro Asn
        290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
        370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
450                 455                 460

Ala Thr Cys Leu Asp Gln Ile Gly Glu Phe Gln Cys Met Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
```

-continued

```
            595                 600                 605
Ser Gln Pro Cys Arg Leu Arg Gly Thr Cys Gln Asp Pro Asp Asn Ala
610                 615                 620

Tyr Leu Cys Phe Cys Leu Lys Gly Thr Gly Pro Asn Cys Glu Ile
625                 630                 635                 640

Asn Leu Asp Asp Cys Ala Ser Ser Pro Cys Asp Ser Gly Thr Cys Leu
            645                 650                 655

Asp Lys Ile Asp Gly Tyr Glu Cys Ala Cys Glu Pro Gly Tyr Thr Gly
                660                 665                 670

Ser Met Cys Asn Ser Asn Ile Asp Glu Cys Ala Gly Asn Pro Cys His
            675                 680                 685

Asn Gly Gly Thr Cys Glu Asp Gly Ile Asn Gly Phe Thr Cys Arg Cys
690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
            725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
            755                 760                 765

Lys Asp Met Thr Ser Gly Ile Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Lys Gly Thr Cys Ile Asp Asp Val Ala Gly Tyr Lys Cys Asn
            805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
            835                 840                 845

Asp Tyr Glu Ser Phe Ser Cys Val Cys Pro Thr Ala Gly Ala Lys Gly
850                 855                 860

Gln Thr Cys Glu Val Asp Ile Asn Glu Cys Val Leu Ser Pro Cys Arg
865                 870                 875                 880

His Gly Ala Ser Cys Gln Asn Thr His Gly Xaa Tyr Arg Cys His Cys
            885                 890                 895

Gln Ala Gly Tyr Ser Gly Arg Asn Cys Glu Thr Asp Ile Asp Asp Cys
            900                 905                 910

Arg Pro Asn Pro Cys His Asn Gly Gly Ser Cys Thr Asp Gly Ile Asn
            915                 920                 925

Thr Ala Phe Cys Asp Cys Leu Pro Gly Phe Arg Gly Thr Phe Cys Glu
930                 935                 940

Glu Asp Ile Asn Glu Cys Ala Ser Asp Pro Cys Arg Asn Gly Ala Asn
945                 950                 955                 960

Cys Thr Asp Cys Val Asp Ser Tyr Thr Cys Thr Cys Pro Ala Gly Phe
            965                 970                 975

Ser Gly Ile His Cys Glu Asn Asn Thr Pro Asp Cys Thr Glu Ser Ser
            980                 985                 990

Cys Phe Asn Gly Gly Thr Cys Val Asp Gly Ile Asn Ser Phe Thr Cys
            995                 1000                1005

Leu Cys Pro Pro Gly Phe Thr Gly Ser Tyr Cys Gln His Val Val
    1010                1015                1020
```

```
Asn Glu Cys Asp Ser Arg Pro Cys Leu Leu Gly Gly Thr Cys Gln
1025                1030                1035

Asp Gly Arg Gly Leu His Arg Cys Thr Cys Pro Gln Gly Tyr Thr
1040                1045                1050

Gly Pro Asn Cys Gln Asn Leu Val His Trp Cys Asp Ser Ser Pro
1055                1060                1065

Cys Lys Asn Gly Gly Lys Cys Trp Gln Thr His Thr Gln Tyr Arg
1070                1075                1080

Cys Glu Cys Pro Ser Gly Trp Thr Gly Leu Tyr Cys Asp Val Pro
1085                1090                1095

Ser Val Ser Cys Glu Val Ala Ala Gln Arg Gln Gly Val Asp Val
1100                1105                1110

Ala Arg Leu Cys Gln His Gly Gly Leu Cys Val Asp Ala Gly Asn
1115                1120                1125

Thr His His Cys Arg Cys Gln Ala Gly Tyr Thr Gly Ser Tyr Cys
1130                1135                1140

Glu Asp Leu Val Asp Glu Cys Ser Pro Ser Pro Cys Gln Asn Gly
1145                1150                1155

Ala Thr Cys Thr Asp Tyr Leu Gly Gly Tyr Ser Cys Lys Cys Val
1160                1165                1170

Ala Gly Tyr His Gly Val Asn Cys Ser Glu Glu Ile Asp Glu Cys
1175                1180                1185

Leu Ser His Pro Cys Gln Asn Gly Gly Thr Cys Leu Asp Leu Pro
1190                1195                1200

Asn Thr Tyr Lys Cys Ser Cys Pro Arg Gly Thr Gln Gly Val His
1205                1210                1215

Cys Glu Ile Asn Val Asp Asp Cys Asn Pro Pro Val Asp Pro Val
1220                1225                1230

Ser Arg Ser Pro Lys Cys Phe Asn Asn Gly Thr Cys Val Asp Gln
1235                1240                1245

Val Gly Gly Tyr Ser Cys Thr Cys Pro Pro Gly Phe Val Gly Glu
1250                1255                1260

Arg Cys Glu Gly Asp Val Asn Glu Cys Leu Ser Asn Pro Cys Asp
1265                1270                1275

Ala Arg Gly Thr Gln Asn Cys Val Gln Arg Val Asn Asp Phe His
1280                1285                1290

Cys Glu Cys Arg Ala Gly His Thr Gly Arg Arg Cys Glu Ser Val
1295                1300                1305

Ile Asn Gly Cys Lys Gly Lys Pro Cys Lys Asn Gly Gly Thr Cys
1310                1315                1320

Ala Val Ala Ser Asn Thr Ala Arg Gly Phe Ile Cys Lys Cys Pro
1325                1330                1335

Ala Gly Phe Glu Gly Ala Thr Cys Glu Asn Asp Ala Arg Thr Cys
1340                1345                1350

Gly Ser Leu Arg Cys Leu Asn Gly Gly Thr Cys Ile Ser Gly Pro
1355                1360                1365

Arg Ser Pro Thr Cys Leu Cys Leu Gly Pro Phe Thr Gly Pro Glu
1370                1375                1380

Cys Gln Phe Pro Ala Ser Ser Pro Cys Leu Gly Gly Asn Pro Cys
1385                1390                1395

Tyr Asn Gln Gly Thr Cys Glu Pro Thr Ser Glu Ser Pro Phe Tyr
1400                1405                1410

Arg Cys Leu Cys Pro Ala Lys Phe Asn Gly Leu Leu Cys His Ile
1415                1420                1425
```

-continued

```
Leu Asp Tyr Ser Phe Gly Gly Ala Gly Arg Asp Ile Pro Pro
    1430            1435                1440

Pro Leu Ile Glu Glu Ala Cys Glu Leu Pro Glu Cys Gln Glu Asp
    1445            1450                1455

Ala Gly Asn Lys Val Cys Ser Leu Gln Cys Asn Asn His Ala Cys
    1460            1465                1470

Gly Trp Asp Gly Gly Asp Cys Ser Leu Asn Phe Asn Asp Pro Trp
    1475            1480                1485

Lys Asn Cys Thr Gln Ser Leu Gln Cys Trp Lys Tyr Phe Ser Asp
    1490            1495                1500

Gly His Cys Asp Ser Gln Cys Asn Ser Ala Gly Cys Leu Phe Asp
    1505            1510                1515

Gly Phe Asp Cys Gln Arg Ala Glu Gly Gln Cys Asn Pro Leu Tyr
    1520            1525                1530

Asp Gln Tyr Cys Lys Asp His Phe Ser Asp Gly His Cys Asp Gln
    1535            1540                1545

Gly Cys Asn Ser Ala Glu Cys Glu Trp Asp Gly Leu Asp Cys Ala
    1550            1555                1560

Glu His Val Pro Glu Arg Leu Ala Ala Gly Thr Leu Val Val Val
    1565            1570                1575

Val Leu Met Pro Pro Glu Gln Leu Arg Asn Ser Ser Phe His Phe
    1580            1585                1590

Leu Arg Glu Leu Ser Arg Val Leu His Thr Asn Val Val Phe Lys
    1595            1600                1605

Arg Asp Ala His Gly Gln Gln Met Ile Phe Pro Tyr Tyr Gly Arg
    1610            1615                1620

Glu Glu Glu Leu Arg Lys His Pro Ile Lys Arg Ala Ala Glu Gly
    1625            1630                1635

Trp Ala Ala Pro Asp Ala Leu Leu Gly Gln Val Lys Ala Ser Leu
    1640            1645                1650

Leu Pro Gly Gly Ser Glu Gly Gly Arg Arg Arg Glu Leu Asp
    1655            1660                1665

Pro Met Asp Val Arg Gly Ser Ile Val Tyr Leu Glu Ile Asp Asn
    1670            1675                1680

Arg Gln Cys Val Gln Ala Ser Ser Gln Cys Phe Gln Ser Ala Thr
    1685            1690                1695

Asp Val Ala Ala Phe Leu Gly Ala Leu Ala Ser Leu Gly Ser Leu
    1700            1705                1710

Asn Ile Pro Tyr Lys Ile Glu Ala Val Gln Ser Glu Thr Val Glu
    1715            1720                1725

Pro Pro Pro Pro Ala Gln Leu His Phe Met Tyr Val Ala Ala Ala
    1730            1735                1740

Ala Phe Val Leu Leu Phe Phe Val Gly Cys Gly Val Leu Leu Ser
    1745            1750                1755

Arg Lys Arg Arg Arg Gln His Gly Gln Leu Trp Phe Pro Glu Gly
    1760            1765                1770

Phe Lys Val Ser Glu Ala Ser Lys Lys Lys Arg Arg Glu Pro Leu
    1775            1780                1785

Gly Glu Asp Ser Val Gly Leu Lys Pro Leu Lys Asn Ala Ser Asp
    1790            1795                1800

Gly Ala Leu Met Asp Asp Asn Gln Asn Glu Trp Gly Asp Glu Asp
    1805            1810                1815

Leu Glu Thr Lys Lys Phe Arg Phe Glu Glu Pro Val Val Leu Pro
```

-continued

```
           1820                1825                1830

Asp Leu Asp Asp Gln Thr Asp His Arg Gln Trp Thr Gln Gln His
        1835                1840                1845

Leu Asp Ala Ala Asp Leu Arg Met Ser Ala Met Ala Pro Thr Pro
        1850                1855                1860

Pro Gln Gly Glu Val Asp Ala Asp Cys Met Asp Val Asn Val Arg
        1865                1870                1875

Gly Pro Asp Gly Phe Thr Pro Leu Met Ile Ala Ser Cys Ser Gly
        1880                1885                1890

Gly Gly Leu Glu Thr Gly Asn Ser Glu Glu Glu Asp Ala Pro
        1895                1900                1905

Ala Val Ile Ser Asp Phe Ile Tyr Gln Gly Ala Ser Leu His Asn
        1910                1915                1920

Gln Thr Asp Arg Thr Gly Glu Thr Ala Leu His Leu Ala Ala Arg
        1925                1930                1935

Tyr Ser Arg Ser Asp Ala Ala Lys Arg Leu Leu Glu Ala Ser Ala
        1940                1945                1950

Asp Ala Asn Ile Gln Asp Asn Met Gly Arg Thr Pro Leu His Ala
        1955                1960                1965

Ala Val Ser Ala Asp Ala Gln Gly Val Phe Gln Ile Leu Ile Arg
        1970                1975                1980

Asn Arg Ala Thr Asp Leu Asp Ala Arg Met His Asp Gly Thr Thr
        1985                1990                1995

Pro Leu Ile Leu Ala Ala Arg Leu Ala Val Glu Gly Met Leu Glu
        2000                2005                2010

Asp Leu Ile Asn Ser His Ala Asp Val Asn Ala Val Asp Asp Leu
        2015                2020                2025

Gly Lys Ser Ala Leu His Trp Ala Ala Ala Val Asn Asn Val Asp
        2030                2035                2040

Ala Ala Val Val Leu Leu Lys Asn Gly Ala Asn Lys Asp Met Gln
        2045                2050                2055

Asn Asn Arg Glu Glu Thr Pro Leu Phe Leu Ala Ala Arg Glu Gly
        2060                2065                2070

Ser Tyr Glu Thr Ala Lys Val Leu Leu Asp His Phe Ala Asn Arg
        2075                2080                2085

Asp Ile Thr Asp His Met Asp Arg Leu Pro Arg Asp Ile Ala Gln
        2090                2095                2100

Glu Arg Met His His Asp Ile Val Arg Leu Leu Asp Glu Tyr Asn
        2105                2110                2115

Leu Val Arg Ser Pro Gln Leu His Gly Ala Pro Leu Gly Gly Thr
        2120                2125                2130

Pro Thr Leu Ser Pro Pro Leu Cys Ser Pro Asn Gly Tyr Leu Gly
        2135                2140                2145

Ser Leu Lys Pro Gly Val Gln Gly Lys Lys Val Arg Lys Pro Ser
        2150                2155                2160

Ser Lys Gly Leu Ala Cys Gly Ser Lys Glu Ala Lys Asp Leu Lys
        2165                2170                2175

Ala Arg Arg Lys Lys Ser Gln Asp Gly Lys Gly Cys Leu Leu Asp
        2180                2185                2190

Ser Ser Gly Met Leu Ser Pro Val Asp Ser Leu Glu Ser Pro His
        2195                2200                2205

Gly Tyr Leu Ser Asp Val Ala Ser Pro Pro Leu Leu Pro Ser Pro
        2210                2215                2220
```

```
Phe Gln Gln Ser Pro Ser Val Pro Leu Asn His Leu Pro Gly Met
    2225                2230                    2235

Pro Asp Thr His Leu Gly Ile Gly His Leu Asn Val Ala Ala Lys
    2240                2245                    2250

Pro Glu Met Ala Ala Leu Gly Gly Gly Gly Arg Leu Ala Phe Glu
    2255                2260                    2265

Thr Gly Pro Pro Arg Leu Ser His Leu Pro Val Ala Ser Gly Thr
    2270                2275                    2280

Ser Thr Val Leu Gly Ser Ser Gly Gly Ala Leu Asn Phe Thr
    2285                2290                    2295

Val Gly Gly Ser Thr Ser Leu Asn Gly Gln Cys Glu Trp Leu Ser
    2300                2305                    2310

Arg Leu Gln Ser Gly Met Val Pro Asn Gln Tyr Asn Pro Leu Arg
    2315                2320                    2325

Gly Ser Val Ala Pro Gly Pro Leu Ser Thr Gln Ala Pro Ser Leu
    2330                2335                    2340

Gln His Gly Met Val Gly Pro Leu His Ser Ser Leu Ala Ala Ser
    2345                2350                    2355

Ala Leu Ser Gln Met Met Ser Tyr Gln Gly Leu Pro Ser Thr Arg
    2360                2365                    2370

Leu Ala Thr Gln Pro His Leu Val Gln Thr Gln Val Gln Pro
    2375                2380                    2385

Gln Asn Leu Gln Met Gln Gln Gln Asn Leu Gln Pro Ala Asn Ile
    2390                2395                    2400

Gln Gln Gln Gln Ser Leu Gln Pro Pro Pro Pro Pro Gln Pro
    2405                2410                    2415

His Leu Gly Val Ser Ser Ala Ala Ser Gly His Leu Gly Arg Ser
    2420                2425                    2430

Phe Leu Ser Gly Glu Pro Ser Gln Ala Asp Val Gln Pro Leu Gly
    2435                2440                    2445

Pro Ser Ser Leu Ala Val His Thr Ile Leu Pro Gln Glu Ser Pro
    2450                2455                    2460

Ala Leu Pro Thr Ser Leu Pro Ser Ser Leu Val Pro Pro Val Thr
    2465                2470                    2475

Ala Ala Gln Phe Leu Thr Pro Pro Ser Gln His Ser Tyr Ser Ser
    2480                2485                    2490

Pro Val Asp Asn Thr Pro Ser His Gln Leu Gln Val Pro Glu His
    2495                2500                    2505

Pro Phe Leu Thr Pro Ser Pro Glu Ser Pro Asp Gln Trp Ser Ser
    2510                2515                    2520

Ser Ser Pro His Ser Asn Val Ser Asp Trp Ser Glu Gly Val Ser
    2525                2530                    2535

Ser Pro Pro Thr Ser Met Gln Ser Gln Ile Ala Arg Ile Pro Glu
    2540                2545                    2550

Ala Phe Lys
    2555

<210> SEQ ID NO 16
<211> LENGTH: 2471
<212> TYPE: PRT
<213> ORGANISM: Homo sapiens

<400> SEQUENCE: 16

Met Pro Ala Leu Arg Pro Ala Leu Leu Trp Ala Leu Leu Ala Leu Trp
1               5                   10                  15
```

```
Leu Cys Cys Ala Ala Pro Ala His Ala Leu Gln Cys Arg Asp Gly Tyr
            20              25              30

Glu Pro Cys Val Asn Glu Gly Met Cys Val Thr Tyr His Asn Gly Thr
        35              40              45

Gly Tyr Cys Lys Cys Pro Glu Gly Phe Leu Gly Glu Tyr Cys Gln His
    50              55              60

Arg Asp Pro Cys Glu Lys Asn Arg Cys Gln Asn Gly Gly Thr Cys Val
65              70              75              80

Ala Gln Ala Met Leu Gly Lys Ala Thr Cys Arg Cys Ala Ser Gly Phe
                85              90              95

Thr Gly Glu Asp Cys Gln Tyr Ser Thr Ser His Pro Cys Phe Val Ser
            100             105             110

Arg Pro Cys Leu Asn Gly Gly Thr Cys His Met Leu Ser Arg Asp Thr
        115             120             125

Tyr Glu Cys Thr Cys Gln Val Gly Phe Thr Gly Lys Glu Cys Gln Trp
    130             135             140

Thr Asp Ala Cys Leu Ser His Pro Cys Ala Asn Gly Ser Thr Cys Thr
145             150             155             160

Thr Val Ala Asn Gln Phe Ser Cys Lys Cys Leu Thr Gly Phe Thr Gly
                165             170             175

Gln Lys Cys Glu Thr Asp Val Asn Glu Cys Asp Ile Pro Gly His Cys
            180             185             190

Gln His Gly Gly Thr Cys Leu Asn Leu Pro Gly Ser Tyr Gln Cys Gln
        195             200             205

Cys Pro Gln Gly Phe Thr Gly Gln Tyr Cys Asp Ser Leu Tyr Val Pro
    210             215             220

Cys Ala Pro Ser Pro Cys Val Asn Gly Gly Thr Cys Arg Gln Thr Gly
225             230             235             240

Asp Phe Thr Phe Glu Cys Asn Cys Leu Pro Gly Phe Glu Gly Ser Thr
                245             250             255

Cys Glu Arg Asn Ile Asp Asp Cys Pro Asn His Arg Cys Gln Asn Gly
            260             265             270

Gly Val Cys Val Asp Gly Val Asn Thr Tyr Asn Cys Arg Cys Pro Pro
        275             280             285

Gln Trp Thr Gly Gln Phe Cys Thr Glu Asp Val Asp Glu Cys Leu Leu
    290             295             300

Gln Pro Asn Ala Cys Gln Asn Gly Gly Thr Cys Ala Asn Arg Asn Gly
305             310             315             320

Gly Tyr Gly Cys Val Cys Val Asn Gly Trp Ser Gly Asp Asp Cys Ser
                325             330             335

Glu Asn Ile Asp Asp Cys Ala Phe Ala Ser Cys Thr Pro Gly Ser Thr
            340             345             350

Cys Ile Asp Arg Val Ala Ser Phe Ser Cys Met Cys Pro Glu Gly Lys
        355             360             365

Ala Gly Leu Leu Cys His Leu Asp Asp Ala Cys Ile Ser Asn Pro Cys
    370             375             380

His Lys Gly Ala Leu Cys Asp Thr Asn Pro Leu Asn Gly Gln Tyr Ile
385             390             395             400

Cys Thr Cys Pro Gln Gly Tyr Lys Gly Ala Asp Cys Thr Glu Asp Val
                405             410             415

Asp Glu Cys Ala Met Ala Asn Ser Asn Pro Cys Glu His Ala Gly Lys
            420             425             430

Cys Val Asn Thr Asp Gly Ala Phe His Cys Glu Cys Leu Lys Gly Tyr
        435             440             445
```

```
Ala Gly Pro Arg Cys Glu Met Asp Ile Asn Glu Cys His Ser Asp Pro
    450                 455                 460
Cys Gln Asn Asp Ala Thr Cys Leu Asp Lys Ile Gly Phe Thr Cys
465                 470                 475                 480
Leu Cys Met Pro Gly Phe Lys Gly Val His Cys Glu Leu Glu Ile Asn
                485                 490                 495
Glu Cys Gln Ser Asn Pro Cys Val Asn Asn Gly Gln Cys Val Asp Lys
            500                 505                 510
Val Asn Arg Phe Gln Cys Leu Cys Pro Pro Gly Phe Thr Gly Pro Val
            515                 520                 525
Cys Gln Ile Asp Ile Asp Asp Cys Ser Ser Thr Pro Cys Leu Asn Gly
        530                 535                 540
Ala Lys Cys Ile Asp His Pro Asn Gly Tyr Glu Cys Gln Cys Ala Thr
545                 550                 555                 560
Gly Phe Thr Gly Val Leu Cys Glu Glu Asn Ile Asp Asn Cys Asp Pro
                565                 570                 575
Asp Pro Cys His His Gly Gln Cys Gln Asp Gly Ile Asp Ser Tyr Thr
            580                 585                 590
Cys Ile Cys Asn Pro Gly Tyr Met Gly Ala Ile Cys Ser Asp Gln Ile
        595                 600                 605
Asp Glu Cys Tyr Ser Ser Pro Cys Leu Asn Asp Gly Arg Cys Ile Asp
        610                 615                 620
Leu Val Asn Gly Tyr Gln Cys Asn Cys Gln Pro Gly Thr Ser Gly Val
625                 630                 635                 640
Asn Cys Glu Ile Asn Phe Asp Asp Cys Ala Ser Asn Pro Cys Ile His
                645                 650                 655
Gly Ile Cys Met Asp Gly Ile Asn Arg Tyr Ser Cys Val Cys Ser Pro
            660                 665                 670
Gly Phe Thr Gly Gln Arg Cys Asn Ile Asp Ile Asp Glu Cys Ala Ser
            675                 680                 685
Asn Pro Cys Arg Lys Gly Ala Thr Cys Ile Asn Gly Val Asn Gly Phe
        690                 695                 700
Arg Cys Ile Cys Pro Glu Gly Pro His His Pro Ser Cys Tyr Ser Gln
705                 710                 715                 720
Val Asn Glu Cys Leu Ser Asn Pro Cys Ile His Gly Asn Cys Thr Gly
                725                 730                 735
Gly Leu Ser Gly Tyr Lys Cys Leu Cys Asp Ala Gly Trp Val Gly Ile
                740                 745                 750
Asn Cys Glu Val Asp Lys Asn Glu Cys Leu Ser Asn Pro Cys Gln Asn
        755                 760                 765
Gly Gly Thr Cys Asp Asn Leu Val Asn Gly Tyr Arg Cys Thr Cys Lys
        770                 775                 780
Lys Gly Phe Lys Gly Tyr Asn Cys Gln Val Asn Ile Asp Glu Cys Ala
785                 790                 795                 800
Ser Asn Pro Cys Leu Asn Gln Gly Thr Cys Phe Asp Asp Ile Ser Gly
            805                 810                 815
Tyr Thr Cys His Cys Val Leu Pro Tyr Thr Gly Lys Asn Cys Gln Thr
        820                 825                 830
Val Leu Ala Pro Cys Ser Pro Asn Pro Cys Glu Asn Ala Ala Val Cys
        835                 840                 845
Lys Glu Ser Pro Asn Phe Glu Ser Tyr Thr Cys Leu Cys Ala Pro Gly
850                 855                 860
Trp Gln Gly Gln Arg Cys Thr Ile Asp Ile Asp Glu Cys Ile Ser Lys
```

```
                865                 870                 875                 880
Pro Cys Met Asn His Gly Leu Cys His Asn Thr Gln Gly Ser Tyr Met
                    885                 890                 895
Cys Glu Cys Pro Pro Gly Phe Ser Gly Met Asp Cys Glu Glu Asp Ile
                900                 905                 910
Asp Asp Cys Leu Ala Asn Pro Cys Gln Asn Gly Gly Ser Cys Met Asp
                915                 920                 925
Gly Val Asn Thr Phe Ser Cys Leu Cys Leu Pro Gly Phe Thr Gly Asp
            930                 935                 940
Lys Cys Gln Thr Asp Met Asn Glu Cys Leu Ser Glu Pro Cys Lys Asn
945                 950                 955                 960
Gly Gly Thr Cys Ser Asp Tyr Val Asn Ser Tyr Thr Cys Lys Cys Gln
                965                 970                 975
Ala Gly Phe Asp Gly Val His Cys Glu Asn Asn Ile Asn Glu Cys Thr
            980                 985                 990
Glu Ser Ser Cys Phe Asn Gly Gly Thr Cys Val Asp Gly Ile Asn Ser
            995                 1000                1005
Phe Ser Cys Leu Cys Pro Val Gly Phe Thr Gly Ser Phe Cys Leu
        1010                1015                1020
His Glu Ile Asn Glu Cys Ser Ser His Pro Cys Leu Asn Glu Gly
        1025                1030                1035
Thr Cys Val Asp Gly Leu Gly Thr Tyr Arg Cys Ser Cys Pro Leu
        1040                1045                1050
Gly Tyr Thr Gly Lys Asn Cys Gln Thr Leu Val Asn Leu Cys Ser
        1055                1060                1065
Arg Ser Pro Cys Lys Asn Lys Gly Thr Cys Val Gln Lys Lys Ala
        1070                1075                1080
Glu Ser Gln Cys Leu Cys Pro Ser Gly Trp Ala Gly Ala Tyr Cys
        1085                1090                1095
Asp Val Pro Asn Val Ser Cys Asp Ile Ala Ala Ser Arg Arg Gly
        1100                1105                1110
Val Leu Val Glu His Leu Cys Gln His Ser Gly Val Cys Ile Asn
        1115                1120                1125
Ala Gly Asn Thr His Tyr Cys Gln Cys Pro Leu Gly Tyr Thr Gly
        1130                1135                1140
Ser Tyr Cys Glu Glu Gln Leu Asp Glu Cys Ala Ser Asn Pro Cys
        1145                1150                1155
Gln His Gly Ala Thr Cys Ser Asp Phe Ile Gly Gly Tyr Arg Cys
        1160                1165                1170
Glu Cys Val Pro Gly Tyr Gln Gly Val Asn Cys Glu Tyr Glu Val
        1175                1180                1185
Asp Glu Cys Gln Asn Gln Pro Cys Gln Asn Gly Gly Thr Cys Ile
        1190                1195                1200
Asp Leu Val Asn His Phe Lys Cys Ser Cys Pro Pro Gly Thr Arg
        1205                1210                1215
Gly Leu Leu Cys Glu Glu Asn Ile Asp Asp Cys Ala Arg Gly Pro
        1220                1225                1230
His Cys Leu Asn Gly Gly Gln Cys Met Asp Arg Ile Gly Gly Tyr
        1235                1240                1245
Ser Cys Arg Cys Leu Pro Gly Phe Ala Gly Glu Arg Cys Glu Gly
        1250                1255                1260
Asp Ile Asn Glu Cys Leu Ser Asn Pro Cys Ser Ser Glu Gly Ser
        1265                1270                1275
```

```
Leu Asp Cys Ile Gln Leu Thr Asn Asp Tyr Leu Cys Val Cys Arg
    1280                1285                1290

Ser Ala Phe Thr Gly Arg His Cys Glu Thr Phe Val Asp Val Cys
    1295                1300                1305

Pro Gln Met Pro Cys Leu Asn Gly Gly Thr Cys Ala Val Ala Ser
    1310                1315                1320

Asn Met Pro Asp Gly Phe Ile Cys Arg Cys Pro Pro Gly Phe Ser
    1325                1330                1335

Gly Ala Arg Cys Gln Ser Ser Cys Gly Gln Val Lys Cys Arg Lys
    1340                1345                1350

Gly Glu Gln Cys Val His Thr Ala Ser Gly Pro Arg Cys Phe Cys
    1355                1360                1365

Pro Ser Pro Arg Asp Cys Glu Ser Gly Cys Ala Ser Ser Pro Cys
    1370                1375                1380

Gln His Gly Gly Ser Cys His Pro Gln Arg Gln Pro Pro Tyr Tyr
    1385                1390                1395

Ser Cys Gln Cys Ala Pro Pro Phe Ser Gly Ser Arg Cys Glu Leu
    1400                1405                1410

Tyr Thr Ala Pro Pro Ser Thr Pro Pro Ala Thr Cys Leu Ser Gln
    1415                1420                1425

Tyr Cys Ala Asp Lys Ala Arg Asp Gly Val Cys Asp Glu Ala Cys
    1430                1435                1440

Asn Ser His Ala Cys Gln Trp Asp Gly Gly Asp Cys Ser Leu Thr
    1445                1450                1455

Met Glu Asn Pro Trp Ala Asn Cys Ser Ser Pro Leu Pro Cys Trp
    1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
    1490                1495                1500

Lys Tyr Asp Lys Tyr Cys Ala Asp His Phe Lys Asp Asn His Cys
    1505                1510                1515

Asn Gln Gly Cys Asn Ser Glu Glu Cys Gly Trp Asp Gly Leu Asp
    1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
    1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
    1580                1585                1590

Gly Glu Lys Ser Ala Ala Met Lys Lys Gln Arg Met Thr Arg Arg
    1595                1600                1605

Ser Leu Pro Gly Glu Gln Glu Gln Glu Val Ala Gly Ser Lys Val
    1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Ala Leu Leu Ala Ser His
    1640                1645                1650

Ala Ile Gln Gly Thr Leu Ser Tyr Pro Leu Val Ser Val Val Ser
    1655                1660                1665

Glu Ser Leu Thr Pro Glu Arg Thr Gln Leu Leu Tyr Leu Leu Ala
    1670                1675                1680
```

```
Val Ala Val Val Ile Ile Leu Phe Ile Ile Leu Leu Gly Val Ile
    1685                1690                1695
Met Ala Lys Arg Lys Arg Lys His Gly Ser Leu Trp Leu Pro Glu
    1700                1705                1710
Gly Phe Thr Leu Arg Arg Asp Ala Ser Asn His Lys Arg Arg Glu
    1715                1720                1725
Pro Val Gly Gln Asp Ala Val Gly Leu Lys Asn Leu Ser Val Gln
    1730                1735                1740
Val Ser Glu Ala Asn Leu Ile Gly Thr Gly Thr Ser Glu His Trp
    1745                1750                1755
Val Asp Asp Glu Gly Pro Gln Pro Lys Lys Val Lys Ala Glu Asp
    1760                1765                1770
Glu Ala Leu Leu Ser Glu Glu Asp Asp Pro Ile Asp Arg Arg Pro
    1775                1780                1785
Trp Thr Gln Gln His Leu Glu Ala Ala Asp Ile Arg Arg Thr Pro
    1790                1795                1800
Ser Leu Ala Leu Thr Pro Pro Gln Ala Glu Gln Glu Val Asp Val
    1805                1810                1815
Leu Asp Val Asn Val Arg Gly Pro Asp Gly Cys Thr Pro Leu Met
    1820                1825                1830
Leu Ala Ser Leu Arg Gly Gly Ser Ser Asp Leu Ser Asp Glu Asp
    1835                1840                1845
Glu Asp Ala Glu Asp Ser Ser Ala Asn Ile Ile Thr Asp Leu Val
    1850                1855                1860
Tyr Gln Gly Ala Ser Leu Gln Ala Gln Thr Asp Arg Thr Gly Glu
    1865                1870                1875
Met Ala Leu His Leu Ala Ala Arg Tyr Ser Arg Ala Asp Ala Ala
    1880                1885                1890
Lys Arg Leu Leu Asp Ala Gly Ala Asp Ala Asn Ala Gln Asp Asn
    1895                1900                1905
Met Gly Arg Cys Pro Leu His Ala Ala Val Ala Ala Asp Ala Gln
    1910                1915                1920
Gly Val Phe Gln Ile Leu Ile Arg Asn Arg Val Thr Asp Leu Asp
    1925                1930                1935
Ala Arg Met Asn Asp Gly Thr Thr Pro Leu Ile Leu Ala Ala Arg
    1940                1945                1950
Leu Ala Val Glu Gly Met Val Ala Glu Leu Ile Asn Cys Gln Ala
    1955                1960                1965
Asp Val Asn Ala Val Asp Asp His Gly Lys Ser Ala Leu His Trp
    1970                1975                1980
Ala Ala Ala Val Asn Asn Val Glu Ala Thr Leu Leu Leu Leu Lys
    1985                1990                1995
Asn Gly Ala Asn Arg Asp Met Gln Asp Asn Lys Glu Glu Thr Pro
    2000                2005                2010
Leu Phe Leu Ala Ala Arg Glu Gly Ser Tyr Glu Ala Ala Lys Ile
    2015                2020                2025
Leu Leu Asp His Phe Ala Asn Arg Asp Ile Thr Asp His Met Asp
    2030                2035                2040
Arg Leu Pro Arg Asp Val Ala Arg Asp Arg Met His His Asp Ile
    2045                2050                2055
Val Arg Leu Leu Asp Glu Tyr Asn Val Thr Pro Ser Pro Pro Gly
    2060                2065                2070
Thr Val Leu Thr Ser Ala Leu Ser Pro Val Ile Cys Gly Pro Asn
```

```
              2075                2080                2085

Arg Ser Phe Leu Ser Leu Lys His Thr Pro Met Gly Lys Lys Ser
    2090                2095                2100

Arg Arg Pro Ser Ala Lys Ser Thr Met Pro Thr Ser Leu Pro Asn
    2105                2110                2115

Leu Ala Lys Glu Ala Lys Asp Ala Lys Gly Ser Arg Arg Lys Lys
    2120                2125                2130

Ser Leu Ser Glu Lys Val Gln Leu Ser Glu Ser Ser Val Thr Leu
    2135                2140                2145

Ser Pro Val Asp Ser Leu Glu Ser Pro His Thr Tyr Val Ser Asp
    2150                2155                2160

Thr Thr Ser Ser Pro Met Ile Thr Ser Pro Gly Ile Leu Gln Ala
    2165                2170                2175

Ser Pro Asn Pro Met Leu Ala Thr Ala Ala Pro Pro Ala Pro Val
    2180                2185                2190

His Ala Gln His Ala Leu Ser Phe Ser Asn Leu His Glu Met Gln
    2195                2200                2205

Pro Leu Ala His Gly Ala Ser Thr Val Leu Pro Ser Val Ser Gln
    2210                2215                2220

Leu Leu Ser His His His Ile Val Ser Pro Gly Ser Gly Ser Ala
    2225                2230                2235

Gly Ser Leu Ser Arg Leu His Pro Val Pro Val Pro Ala Asp Trp
    2240                2245                2250

Met Asn Arg Met Glu Val Asn Glu Thr Gln Tyr Asn Glu Met Phe
    2255                2260                2265

Gly Met Val Leu Ala Pro Ala Glu Gly Thr His Pro Gly Ile Ala
    2270                2275                2280

Pro Gln Ser Arg Pro Pro Glu Gly Lys His Ile Thr Thr Pro Arg
    2285                2290                2295

Glu Pro Leu Pro Pro Ile Val Thr Phe Gln Leu Ile Pro Lys Gly
    2300                2305                2310

Ser Ile Ala Gln Pro Ala Gly Ala Pro Gln Pro Gln Ser Thr Cys
    2315                2320                2325

Pro Pro Ala Val Ala Gly Pro Leu Pro Thr Met Tyr Gln Ile Pro
    2330                2335                2340

Glu Met Ala Arg Leu Pro Ser Val Ala Phe Pro Thr Ala Met Met
    2345                2350                2355

Pro Gln Gln Asp Gly Gln Val Ala Gln Thr Ile Leu Pro Ala Tyr
    2360                2365                2370

His Pro Phe Pro Ala Ser Val Gly Lys Tyr Pro Thr Pro Pro Ser
    2375                2380                2385

Gln His Ser Tyr Ala Ser Ser Asn Ala Ala Glu Arg Thr Pro Ser
    2390                2395                2400

His Ser Gly His Leu Gln Gly Glu His Pro Tyr Leu Thr Pro Ser
    2405                2410                2415

Pro Glu Ser Pro Asp Gln Trp Ser Ser Ser Ser Pro His Ser Ala
    2420                2425                2430

Ser Asp Trp Ser Asp Val Thr Thr Ser Pro Thr Pro Gly Gly Ala
    2435                2440                2445

Gly Gly Gly Gln Arg Gly Pro Gly Thr His Met Ser Glu Pro Pro
    2450                2455                2460

His Asn Asn Met Gln Val Tyr Ala
    2465                2470
```

<210> SEQ ID NO 17
<211> LENGTH: 17
<212> TYPE: PRT
<213> ORGANISM: Homo sapiens

<400> SEQUENCE: 17

Cys Ile Ser Cys Gly Ala Pro Asp Lys Tyr Glu Ser Arg Glu Val Ser
1               5                   10                  15

Thr

<210> SEQ ID NO 18
<211> LENGTH: 33
<212> TYPE: DNA
<213> ORGANISM: Artificial sequence
<220> FEATURE:
<223> OTHER INFORMATION: Primer

<400> SEQUENCE: 18
tccggatccc atggagccac aggatgtcat ttt                            33

<210> SEQ ID NO 19
<211> LENGTH: 35
<212> TYPE: DNA
<213> ORGANISM: Artificial sequence
<220> FEATURE:
<223> OTHER INFORMATION: Primer

<400> SEQUENCE: 19
tccggatccg tcgactggca catattcccc catga                          35

<210> SEQ ID NO 20
<211> LENGTH: 27
<212> TYPE: DNA
<213> ORGANISM: Artificial sequence
<220> FEATURE:
<223> OTHER INFORMATION: Primer

<400> SEQUENCE: 20
ggtggaattc taatgccacg gctcctg                                   27

<210> SEQ ID NO 21
<211> LENGTH: 26
<212> TYPE: DNA
<213> ORGANISM: Artificial sequence
<220> FEATURE:
<223> OTHER INFORMATION: Primer

<400> SEQUENCE: 21
ttgaagttcc tcatccgtgt tgattt                                    26

<210> SEQ ID NO 22
<211> LENGTH: 27
<212> TYPE: DNA
<213> ORGANISM: Artificial sequence
<220> FEATURE:
<223> OTHER INFORMATION: Primer

<400> SEQUENCE: 22
tgtggaattc tatgtgatct gggtgcc                                   27

<210> SEQ ID NO 23
<211> LENGTH: 27
<212> TYPE: DNA
<213> ORGANISM: Artificial sequence
<220> FEATURE:
<223> OTHER INFORMATION: Primer

```
<400> SEQUENCE: 23
cgtcaagttc gtcatcgatg tcactct                                       27

<210> SEQ ID NO 24
<211> LENGTH: 27
<212> TYPE: DNA
<213> ORGANISM: Artificial sequence
<220> FEATURE:
<223> OTHER INFORMATION: Primer

<400> SEQUENCE: 24
cttggaattc tatgtgctac cagcccc                                       27

<210> SEQ ID NO 25
<211> LENGTH: 26
<212> TYPE: DNA
<213> ORGANISM: Artificial sequence
<220> FEATURE:
<223> OTHER INFORMATION: Primer

<400> SEQUENCE: 25
ttgaagcttg ccattgatga ctgact                                        26

<210> SEQ ID NO 26
<211> LENGTH: 27
<212> TYPE: DNA
<213> ORGANISM: Artificial sequence
<220> FEATURE:
<223> OTHER INFORMATION: Primer

<400> SEQUENCE: 26
actggaattc tatgccatcc cccctt                                        27

<210> SEQ ID NO 27
<211> LENGTH: 27
<212> TYPE: DNA
<213> ORGANISM: Artificial sequence
<220> FEATURE:
<223> OTHER INFORMATION: Primer

<400> SEQUENCE: 27
aaggaagctt ctgcgagggc agcggag                                       27

<210> SEQ ID NO 28
<211> LENGTH: 18
<212> TYPE: DNA
<213> ORGANISM: Artificial sequence
<220> FEATURE:
<223> OTHER INFORMATION: Primer

<400> SEQUENCE: 28
atcctggcca cggtcatc                                                 18

<210> SEQ ID NO 29
<211> LENGTH: 21
<212> TYPE: DNA
<213> ORGANISM: Artificial sequence
<220> FEATURE:
<223> OTHER INFORMATION: Primer

<400> SEQUENCE: 29
cacaccagta ctccccatcg t                                             21

<210> SEQ ID NO 30
<211> LENGTH: 24
```

```
<212> TYPE: DNA
<213> ORGANISM: Artificial sequence
<220> FEATURE:
<223> OTHER INFORMATION: Taqman probe

<400> SEQUENCE: 30
cagctggaac tccctgcagt gacg                                            24

<210> SEQ ID NO 31
<211> LENGTH: 22
<212> TYPE: DNA
<213> ORGANISM: Artificial sequence
<220> FEATURE:
<223> OTHER INFORMATION: Primer

<400> SEQUENCE: 31
aggccaacat caagctcatt ct                                              22

<210> SEQ ID NO 32
<211> LENGTH: 21
<212> TYPE: DNA
<213> ORGANISM: Artificial sequence
<220> FEATURE:
<223> OTHER INFORMATION: Primer

<400> SEQUENCE: 32
cgggatgtcc tagccatttt c                                               21

<210> SEQ ID NO 33
<211> LENGTH: 24
<212> TYPE: DNA
<213> ORGANISM: Artificial sequence
<220> FEATURE:
<223> OTHER INFORMATION: Taqman probe

<400> SEQUENCE: 33
ccaaacaatg acacaccgc tcca                                             24
```

NOGO, CASPR, F3 NB-3 USEFUL IN THE TREATMENT OF INJURY AND DISEASE TO THE CENTRAL NERVOUS SYSTEM

CROSS-REFERENCE TO RELATED APPLICATIONS

This application is the continuation of U.S. patent application Ser. No. 10/537,757, filed Jun. 6, 2005, now abandoned, which is the U.S. national stage of PCT/GB2003/005329, filed Dec. 5, 2003, which claims priority from U.S. Provisional Application Nos. 60/431,549, filed Dec. 6, 2002 and 60/480,138, filed Jun. 20, 2003. The disclosures of the aforesaid applications are incorporated by reference in their entireties in the present application.

FIELD OF THE INVENTION

The present invention relates to novel methods and materials for treating injury and disease of the central nervous system (CNS). Particularly, but not exclusively, the invention provides methods and materials for spinal cord regeneration and remyelination following spinal cord injury (SCI), stroke, or disease such as multiple sclerosis (MS) and epilepsy.

BACKGROUND TO THE INVENTION

Over 250,000 people in the United States, and several million worldwide, are permanently disabled due to a past spinal cord injury (chronic SCI), and about 12,000 people are newly injured (acute SCI) in the United States each year. Additionally, paralysis due to SCI is predominantly a condition of the young: 60% of spinal cord injuries occur before age 30, and the most frequent incidence is at age 19. Most injuries are caused by motor vehicle, sports or work-related accidents, or by violence. Estimated costs of care for SCI patients in the United States alone exceed $9 billion per year and over $1.5 million per patient lifetime.

Following trauma to the adult central nervous system (CNS) of mammals, injured neurons do not regenerate their transected axons. Currently, the mainstay of treatment in spinal cord injury is still rehabilitation. There is little one can do to address the primary injury. After spinal injury, three major classes of damage have been identified:

1. Neuronal cell death. The death of nerve cells due to injury presents a difficult problem because nerve cells lose the ability to undergo cell division as they mature into the highly specialized cells that make up our nervous systems. Some cells die during the traumatic insult, others die in the hours, days or even weeks following injury. Regardless of when the cell death occurs, functional connections cannot be established if the nerve cells no longer exist. Death of glia, also interferes with nerve function. The first therapeutic goal is to preserve as many cells as possible, also known as neuroprotection. Even with neuroprotective drugs or therapies, some nerve cell death is still likely in SCI. Therefore, replacement of nerve cells may be required.
2. Disruption of nerve pathways. The long axons in the ascending and descending tracts of the spinal cord undergo Wallerian degeneration after injury. Axonal regeneration must occur to re-establish neuronal circuits.
3. Demyelination. Myelin sheaths insulate the long, thin axons to facilitate nerve impulse transmission. In some types of SCI, as well as stroke and epilepsy, the nerve cells and axons may not be lost or interrupted; neuronal dysfunction may be due to loss of the myelin sheath. This type of damage may be the most amendable to treatment because rewiring of complex circuits may not be necessary and remyelination of axons is known to be possible.

Possible Therapies

1. Replacement of Nerve Cells

Mature nerve cells cannot divide to heal a wound. Replacement of lost nerve cells would require transplantation into the site of injury with the hope that grafted nerve cells would mature and integrate into the host nervous system. Use of human fetal tissue has shown promise in some studies, however, it presents ethical and technological considerations regarding donor tissues and important questions about immune rejection of transplanted cells. Very recently, scientists have discovered the presence of adult neural stem cells that can be stimulated to divide and develop into neurons and glia. This exciting finding has opened up new possibilities for cell therapy.

2. Regeneration of Damaged Axons

Neurons in both the central (CNS) and peripheral (PNS) nervous systems are intimately associated with glia. After injury, CNS glia largely inhibit regeneration, whilst in the PNS, the Schwann cells facilitate regeneration. The cells are seeded in specially designed "guidance channels" that have been shown to promote the regeneration of nerve fibres in severed rat spinal cords. Schwann cells and neurons produce growth factors. By introducing these factors into injury sites, alone or in combination with grafts, these have shown that they can stimulate additional spinal cord regeneration. Schwann cells can be genetically engineered to produce growth factors, and these also improve regeneration. Some improvement in hind limb motor function have been observed after grafting, however, the results are not reliable enough yet to justify clinical trials of these procedures. Two exciting new studies show that olfactory ensheathing glia can "usher" long nerve fiber growth into surviving spinal cord regions beyond the site of SCI, after these fibers exit a Schwann cell bridge or grow past the site of injury. These promising studies give hope that successful restoration of function after SCI, stroke or epilepsy may occur one day.

3. Remyelination of Axons

Schwann cells are the cells in peripheral nerves that form myelin sheaths. They are not usually found in the brain or spinal cord where oligodendrocytes are responsible for myelin production. Researchers have shown that Schwann cells grafted into the brain can myelinate central axons. When the loss of myelin is an important part of an injury, implanting Schwann cells could stimulate remyelination and perhaps restore function. A multi-center clinical trial has been initiated at other research centers to study a drug (4-AP) that appears to temporally restore signal transmission through demyelinated nerve fibers.

CNS Myelin and its Major Inhibitory Effects During Axonal Regeneration

An important barrier to regeneration is the axon growth inhibitory activity that is in CNS myelin and that is also associated with the plasma membrane of oligodendrocytes, the cells that synthesize myelin in the CNS. The growth inhibitory properties of CNS myelin have been demonstrated in a number of different laboratories by a wide variety of techniques, including plating neurons on myelin substrates or cryostat sections of white matter, and observations of axon contact with mature oligodendrocytes. Therefore, it is well documented that adult neurons cannot extend neurites over CNS myelin in vitro. It has also been well documented that removing myelin in vivo improves the success of regenerative growth over the native terrain of the CNS. Regeneration occurs after irradiation of newborn rats, a procedure that kills oligodendrocytes and prevents the appearance of myelin proteins. After such a procedure in rats and combined with a corticospinal trait lesion, some corticospinal axons regrow long distances beyond the lesions. Also, in a chick model of spinal cord repair, the onset of myelination correlates with a loss of its regenerative ability of cut axons. The removal of myelin with anti-galactocerebroside and complement in the embryonic chick spinal cord extends the permissive period for axonal regeneration. Known inhibitory molecules in myelin include myelin associated glycoprotein (MAG), tenascin-R (TN-R), arretin, and chondroitin-sulphate proteoglycans (CSPGs). Recently, three groups reported the identification in rats and humans of a gene, Nogo, which encodes an inhibitory myelin protein (GrandPre et al, 2000; Prinjha et al, 2000; Chen et al, 2000). Immunization against myelin has been found to allow extensive axon regeneration after injury,—this demonstrates the enormous potential value of overcoming myelin inhibition. These experiments demonstrate a good correlation between inhibitory factors in myelin and the failure of axons to regenerate in the CNS.

Multiple Sclerosis

MS is a degenerative central nervous system disorder involving decreased nerve function associated with the formation of scars on the insulating sheath known as myelin around nerve cells.

The cause of MS is not known. However, many researchers believe it may be an autoimmune disease, perhaps triggered by a viral infection. There is no definitive clinical test for the diagnosis of MS. However, an MRI (Magnetic Resonance Imaging) can show areas in the brain where myelin has been damaged.

MS affects approximately 250,000-300,000 people in the US. It predominantly afflicts women, Caucasians, and people from temperate climates. Generally, the onset of MS is diagnosed in people ages 20-40.

It is now well accepted that MS lesions contain substantial numbers of premyelinating oligodendrocytes, indicating that:
  The potential for repair is not limited by the loss of these cells;
  Interactions between oligodendrocytes and their surrounding environment may determine the outcome of the repair process.

FIRST ASPECT OF THE INVENTION

Background to First Aspect of the Invention

Nogo-A has been extensively studied in the context of CNS regeneration and is a pivotal factor in the inhibition of axonal regeneration after injury (Woolf, 2003). The three major molecules responsible for the growth inhibitory property of CNS myelin—Nogo-A, myelin-associated glycoprotein (MAG) and oligodendrocyte myelin glycoprotein (OMgp) appear to bind to the same glycosylphosphatidyl inositol (GPI)-anchored Nogo-66 receptor (NgR) on the surface of axons (Woolf, 2003). Understanding of the molecular interactions involved in inhibiting neuronal regeneration has led to the exciting possibility that the CNS environment can be manipulated to enhance neuronal regeneration. Apart from these findings, however, other paradigms for Nogo-A action in the CNS have yet to be determined. For example, the localization of the presence of Nogo-A at synapses (Wang et al, 2002) is suggestive of a possible role in modulating synaptic plasticity.

Nogo is expressed in three isoforms, Nogo-A, B and C, all of which share the same C-terminus with two transmembrane domains and an extracellular 66 amino acid loop (Nogo-66) (GrandPre et al, 2000; Fournier et al, 2001). Nogo-A has a large cytoplasmic N-terminal domain (Nogo-N) not found in Nogo-B or Nogo-C (GrandPre et al, 2000; Prinjha et al, 2000; Brittis et al, 2001). Nogo-66 and Nogo-N of Nogo-A have independent inhibitory activity (Fournier et al, 2001; GrandPre et al, 2000). The Nogo-66 loop on the oligodendrocyte surface binds to the Nogo-66 receptor (NgR), which mediates axonal growth retardation (Fournier et al, 2001). In contrast, no receptor or interacting protein for Nogo-N has been recognized so far. Nogo-A is expressed in the brain of the early embryonic CNS, but there is little or no detectable NgR expression in early embryonic neurons (Wang et al, 2002). Nogo-A therefore may have NgR independent functions during embryonic stages. Neuronal regeneration phenotypes in the absence of Nogo-A in knockout mice were not particularly clear, and the exact role of Nogo-A in the CNS remains to be further investigated (Woolf, 2003). In the adult, although Nogo-A has been localized to oligodendrocytes and NgR to mature axons, the exact distribution pattern and relationship between these two molecules along myelinated axons have not been defined in detail. Knowledge of Nogo-A and NgR distribution at the interface between neurons and oligodendrocytes will be important in understanding their roles in CNS development.

The establishment and maintenance of the molecular architecture of axonal domains is critical to ensure rapid saltatory conduction of nerve impulses (Pedraza et al, 2001). During myelination, there is a complex, yet precise and efficient, process that ensures the clustering of specific ion channels and other protein molecules to distinct segments along the axon (Dupree et al, 1999; Rasband et al, 2000; 2001a). The Nodes of Ranvier are enriched in $Na^+$ channels whilst $K^+$ channels are excluded from this location and instead occupy juxtaparanodal regions. However, during the early stages of both developmental myelination and remyelination, $K^+$ channel clusters are transiently located at the paranodal between the nodes and juxtaparanodes region (Rasband et al, 1998; Vabnick et al, 1999). This is where the glial cytoplasmic loops come into contact with the axolemma. Adhesion molecules, such as F3/Contactin, neurofascin 155, and Caspr (Paranodin), are located at the paranodes (Einheber et al, 1997; Menegoz et al, 1997; Tait et al, 2000; Kazarinova-Noyes et al, 2001). Studies on dysmyelinating mouse mutants deficient in myelin-related and axonal proteins, such as ceramide galactosyl transferase (CGT) (Ishibashi et al, 2002; Popko B, 2000), F3/Contactin (Boyle et al, 2001), or Caspr (Bhat et al, 2001), have shown that clustering of axonal domain constituents and the exact localization of ion channels, particularly $K^+$ channels, are dependent on communication between axons and oligodendroglia. However, the molecular mechanisms that regulate the accumulation of $K^+$ channels into compact zones are not entirely clear.

Contactin-associated protein (Caspr) is a transmembrane protein with an extracellular domain that contains a series of laminin G-like domains and EGF repeats (Peles et al, 1997), as well as a cytoplasmic segment with potential binding sites for SH3-containing proteins and 4.1 family proteins (Gollan et al, 2002). Caspr exists in a complex with F3/Contactin, the GPI-anchored molecule (Peles et al, 1997). During myelination, the interaction of Caspr with F3/Contactin is required for the proper transport of Caspr and $Na^+$ channels to the cell surface (Faivre-Sarrailh et al, 2000; Kazarinova-Noyes et al, 2001). Moreover, this complex constitutes an essential scaffold to maintain the architecture of the axoglial apparatus (Bhat et al, 2001; Boyle et al, 2001). Although neurofascin 155 (NF155) interacts in trans with the Caspr/F3 complex (Charles et al, 2002), the functional consequence of this interaction is still unclear. Judging from Caspr's multiple domain structure, there may exist other glial components that interact with this molecule during myelination.

Summary of the First Aspect of the Invention

The inventor explored whether Nogo-A could have a role in the axoglial junction during the period of myelination—in particular, if Nogo-A participates in molecular interactions between axons and oligodendrocytes. He has determined that Nogo-A can be found localized specifically to paranodes, where it interacts with the paranodal junction protein, Caspr. The inventor has also determined that both Nogo-A and Caspr associate with the voltage-gated $K^+$ channel Kv1.1. Furthermore, the co-localization patterns of Nogo-A/Kv1.1 and Caspr/Kv1.1 during development are closely related. The inventor therefore believes that the interaction of Nogo-A with Caspr plays a role in regulating the location of $K^+$ channels along the axon during the early period of myelination.

Specifically, the work carried out by the inventor has shown that oligodendrocyte Nogo-A is clustered at specific axoglial junctions, where it interacts directly via its extracellular Nogo-66 loop with axonal Caspr, and indirectly with $K^+$ channel proteins. This represents the first NgR-independent Nogo-66 interaction described to date, and has significant implications for the role of Nogo-A in the formation and maintenance of axoglial junction architecture.

Thus, at its most general, the present invention provides materials and methods arising from the determination that Nogo-A and Caspr interact and play a role in myelination. This has important implications particularly in the field of spinal cord injury or other diseases that result in damage to the myelin sheaths.

The invention provides a composition comprising Nogo and Caspr, or mimetics thereof, or a substance capable of promoting interaction between Nogo and Caspr, in combination with a suitable carrier.

Preferably the composition comprises a complex between Nogo and Caspr, or a mimetic of said complex.

The Nogo molecule present in the composition is preferably Nogo-A or a portion or domain thereof. Preferably it comprises Nogo-66, which is found in all three known isoforms of Nogo (A, B and C). It may further comprise other domains of those isoforms; alternatively the Nogo-66 domain may be present in the absence of further portions of Nogo proteins.

The Caspr molecule of the composition is preferably Caspr1 or a portion or domain thereof.

A substance capable of promoting interaction between Nogo and Caspr may be of any molecular type, including, but not limited to a protein, peptide, or small molecule.

Typically, the substance capable of promoting such interaction will bind to one or both of Nogo and Caspr. For example, it may bind to both proteins, e.g. at the interface between Nogo and Caspr. Alternatively it may bind to only one of Nogo and Caspr, possibly stabilising the conformation of that protein in the complex and so promoting association and/or inhibiting dissociation of the complex.

As an example, the substance capable of promoting interaction between Nogo and Caspr may be an antibody, such as an antibody capable of binding to both Nogo and Caspr, e.g. a bispecific antibody.

The composition may be a pharmaceutical composition, in which case the carrier will be of a pharmaceutically acceptable type. Preferably the pharmaceutical composition is formulated for injection in vivo, more preferably for injection directly into the CNS. Specifically, there is provided a pharmaceutical composition comprising Nogo-A and Caspr.

The invention further provides a composition as described above for use in a method of medical treatment, and particularly for use in the treatment of injury to, or disease of, the CNS, such as spinal cord injury (SCI), multiple sclerosis (MS), epilepsy or stroke.

The invention further provides the use of Nogo in the preparation of a medicament for the treatment of injury to, or disease of, the CNS, wherein the medicament is for administration in combination with Caspr or a mimetic thereof.

Likewise, the invention provides the use of Caspr in the preparation of a medicament for the treatment of injury to, or disease of, the CNS, wherein the medicament is for administration in combination with Nogo or a mimetic thereof.

Thus the medicament may comprise both Nogo and Caspr or mimetics thereof (i.e. it may be a pharmaceutical composition as described above). The invention accordingly provides a method of manufacturing a pharmaceutical composition comprising admixing Nogo and Caspr or mimetics thereof, with a pharmaceutically acceptable carrier. Alternatively the two components may be administered separately.

Also provided is the use of a substance capable of promoting interaction between Nogo and Caspr, as herein described, in the preparation of a medicament for the treatment of injury or disease to the CNS.

The invention also provides a method of stimulating myelination of a neuron, specifically a neural axon, comprising contacting a neuron or an oligodendrocyte with a composition as described above. This may be performed in vivo, e.g. as a therapeutic method as elsewhere described in this specification, or in vitro.

Also provided is a method of treating a subject having disease of or injury to the central nervous system, comprising administering to the subject one or more pharmaceutical compositions comprising Nogo and Caspr as described above. Specifically, there is provided a method of treating a patient with disease or injury to the CNS, e.g. SCI, MS, epilepsy or stroke, comprising administering to the patient a complex comprising Nogo-A and Caspr.

All therapeutic methods described are considered particularly appropriate for the treatment of spinal cord injury (SCI), multiple sclerosis (MS) or stroke.

The invention further provides a method of screening for a substance capable of modulating (preferably promoting) interaction between Nogo and Caspr, the method comprising contacting Nogo and Caspr with a candidate substance, and determining the interaction between Nogo and Caspr.

The method may further comprise contacting Nogo and Caspr in the absence of said candidate substance under otherwise analogous conditions, and determining the interaction between Nogo and Caspr.

Preferably the method comprises contacting a complex between Nogo and Caspr with the candidate substance; the complex is preferably formed before it is contacted with the candidate substance.

The method may be performed by any appropriate method. The skilled person will be well aware of many suitable assay formats, and will be well capable of designing a suitable protocol.

One or both of Nogo and caspr may be present in, or on, a cell. The gene from which the protein is expressed may be endogenous to the cell in question, or it may be present on a vector introduced into the cell. The protein is preferably expressed on the surface of the cell.

Additionally or alternatively, one or both of Nogo and Caspr may be immobilised on a solid support. One or both may comprise a detectable label as described in more detail below.

The invention further provides a method of manufacturing a pharmaceutical formulation comprising, having identified a substance capable of modulating interaction between Nogo and Caspr by a screening method described herein, the further step of formulating said substance with a pharmaceutically acceptable carrier. The method may comprise the further step of optimising said identified substance for administration in vivo prior to formulation.

Cells

The term oligodendrocyte is used herein to refer to oligodendroglial cells capable of laying down a myelin sheath around a neuronal axon in the central nervous system (CNS).

Protein Sequences

The term "Nogo" is used to encompass all isoforms of the Nogo protein, including Nogo-A, B and C, as well as portions and isolated domains thereof, including the Nogo-66 domain, as well as mutants and variants thereof having greater than 80%, 85%, 90%, 95%, 96%, 97%, 98% or 99% identity to the sequences given below. Orthologous proteins from other mammalian species are also included. Preferably the Nogo protein has the ability to bind to a Caspr protein, particularly Caspr-1. Nogo-A is particularly preferred.

The term "Caspr" is used to encompass all isoforms of the Nogo protein, including Caspr-1,2, 3 and 4. Caspr-1 is particularly preferred. The term is also intended to encompass isolated domains of such Caspr proteins such as the extracellular domain, as well as mutants and variants thereof having greater than 80%, 85%, 90%, 95%, 96%, 97%, 98% or 99% identity to the sequences given below. Orthologous proteins from other mammalian species are also included. The Caspr protein preferably has the ability to bind to a Nogo protein, particularly Nogo-A. It may also have the ability to bind to at least one subunit of a voltage-gated potassium channel, in particular Kv1.1 and/or Kv1.2.

The amino acid sequences of Nogo and Caspr proteins are shown below, along with their GenBank accession numbers;

```
Nogo-A                    gi: 9408096 (CAB99248)
   1  medldqsplv sssdspprpq-
        pafkyqfvre pedeeeeeee eeedededle elevlerkpa
  61  aglsaapvpt apaagaplmd fgndfvp-
        pap rgplpaappv aperqpswdp spvsstvpap
 121  splsaaavsp sklpeddepp arppppp-
        pas vspqaepvwt ppapapaapp stpaapkrrg
 181  ssgsvdetlf alpaasepvi rssaenm-
        dlk eqpgntisag qedfpsvlle taaslpslsp
 241  lsaasfkehe ylgnlstvlp tegtlqen-
        vs easkevseka ktllidrdlt efseleysem
 301  gssfsvspka esavivanpr eei-
        ivknkde eeklvsnnil hnqqelptal tklvkedevv
 361  ssekakdsfn ekrvaveapm reeyadfk-
        pf ervwevkdsk edsdmlaagg kiesnleskv
 421  dkkcfadsle qtnhekdses snddtsfp-
        st pegikdrpga yitcapfnpa atesiatnif
 481  pllgdptsen ktdekkieek ka-
        qivteknt stktsnpflv aaqdsetdyv ttdnltkvte
 541  evvanmpegl tpdlvqeace selnevt-
        gtk iayetkmdlv qtsevmqesl ypaaqlcpsf
 601  eeseatpspv lpdivmeapl nsavpsa-
        gas viqpsssple assvnyesik hepenpppye
 661  eamsvslkkv sgikeeikep eni-
        naalqet eapyisiacd liketklsae papdfsdyse
 721  makveqpvpd hselvedssp d-
        sepvdlfsd dsipdvpqkq detvmlvkes ltetafesmi
 781  eyenkeklsa lppeggkpyl es-
        fklsldnt kdtllpdevs tlskkekipl qmeelstavy
 841  snddlfiske aqiretetfs dsspiei-
        ide fptlissktd sfsklareyt dlevshksei
 901  anapdgagsl pctelphdls lkniqp-
        kvee kisfsddfsk ngsatskvll lppdvsalat
 961  qaeiesivkp kvlvkeaekk lps-
        dtekedr spsaifsael sktsvvdlly wrdikktgvv
1021  fgaslfllls ltvfsivsvt ayiala-
        llsv tisfriykgv iqaiqksdeg hpfraylese
1081  vaiseelvqk ysnsalghvn ctikelr-
        rlf lvddlvdslk favlmwvfty vgalfngltl
1141  lilalislfs vpviyerhqa qidhyiglan knvkdamaki qakipglkrk ae Nogo-B                    gi: 9408098 (CAB99249)
   1  medldqsplv sssdspprpq-
        pafkyqfvre pedeeeeeee eeedededle elevlerkpa
  61  aglsaapvpt apaagaplmd fgndfvp-
        pap rgplpaappv aperqpswdp spvsstvpap
 121  splsaaavsp sklpeddepp arppppp-
        pas vspqaepvwt ppapapaapp stpaapkrrg
 181  ssgsvvvdll ywrdikktgv vf-
        gaslflll sltvfsivsv tayialalls vtisfriykg
 241  viqaiqksde ghpfrayles evai-
        seelvq kysnsalghv nctikelrrl flvddlvdsl
 301  kfavlmwvft yvgalfnglt llilalis-
        lf svpviyerhq aqidhylgla nknvkdamak
 361  iqakipglkr kae Nogo-C                    gi: 9408100 (CAB99250)
   1  mdgqkknwkd kvvdllywrd ikktgvvf-
        ga slflllsltv fsivsvtayi alallsvtis
  61  friykgviqa iqksdeghpf ray-
        lesevai seelvqkysn salghvncti kelrrlflvd
```

-continued
```
121    dlvdslkfav lmwvftyvga lfngltl-
       lil alislfsvpv iyerhqaqid hylglanknv
181    kdamakiqak ipglkrkae Caspr1                          gi: 4505463 (NP003623)
  1    mmhlrlfcil laavsgaeg-
       w gyygcdeelv gplyarslga ssyyslltap rfarlhgisg
 61    wsprigdpnp wlqidlmkkh rira-
       vatqgs fnswdwvtry mllygdrvds wtpfyqrghn
121    stffgnvnes avvrhdlhfh-
       ftaryirivp lawnprgkig lrlglygcpy kadilyfdgd
181    daisyrfprg vsrslwdvfa fsfk-
       teekdg lllhaegaqg dyvtlelega hlllhmslgs
241    spiqprpght tvsaggvlnd qh-
       whyvrvdr fgrdvnftld gyvqrfilng dferlnldte
301    mfigglvgaa rknlayrhnf rgcienv-
       ifn rvniadlavr rhsritfegk vafrcldpvp
361    hpinfggphn fvqvpgfprr grlavsfr-
       fr twdltglllf srlgdglghv eltlaegqvn
421    vsiaqsgrkk lqfaagyrln dgfwhevn-
       fv aqenhavisi ddvegaevrv sypllirtgt
481    syffggcpkp asrwdchsnq tafhgc-
       mell kvdgqlvnlt lvegrrlgfy aevlfdtcgi
541    tdrcspnmce hdgrcyqswd dfi-
       cyceltg ykgetchtpl ykesceayrl sgktsgnfti
601    dpdgsgplkp fvvycdiren rawtv-
       vrhdr lwttrvtgss merpflgaiq ywnaaweevs
661    alanasqhce qwiefscyns rllntag-
       gyp ysfwigrnee qhfywggsqp giqrcacgld
721    rscvdpalyc ncdadqpqwr tdkgllt-
       fvd hlpvtqvvig dtnrstseaq fflrplrcyg
781    drnswntisf htgaalrfpp iranhsld-
       vs fyfrtsapsg vflenmggpy cqwrrpyvrv
841    elntsrdvvf afdvgngden ltvhsd-
       dfef nddewhlvra einvkqarlr vdhrpwvlrp
901    mplqtyiwme ydqplyvg-
       sa elkrrpfvgc lramrlngvt lnlegranas egtspnctgh
961    cahprlpcfh ggrcverysy ytcdcdl-
       taf dgpycnhdig gffepgtwmr ynlqsalrsa
1022   arefshmlsr pvpgyepgyi pgydt-
       pgyvp gyhgpgyrlp dyprpgrpvp gyrgpvynvt
1081   geevsfsfst ssapavllyv ssfvrdy-
       mav likddgtlql ryqlgtspyv yqlttrpvtd
1141   gqphsinitr vyrnlfiqvd yfplte-
       qkfs llvdsqldsp kalylgrvme tgvidpeiqr
1201   yntpgfsgcl sgvrfnnvap lkthfrt-
       prp mtaelaealr vqgelsesnc gamprlvsev
1261   ppeldpwylp pdfpyyhdeg wvaillg-
       flv aflllglvgm lvlfylqnhr ykgsyhtnep
1321   kaaheyhpgs kpplptsg-
       pa qvptptaapn qapasapapa ptpapapgpr dqnlpqilee
1381   srse
```

Nogo-66 extends from amino acids 823 to 888 of Nogo-A and has the following sequence:

```
Nogo-66
RIYKGVIQ AIQKSDEGHP FRAYLESEVA ISEELVQKYS

NSALGHVNCT IKELRRLFLV DLVDSLK
```

Assay Methods

As described above, the skilled person is well aware of numerous assay formats which may be appropriate for determining interaction between Nogo and Caspr, and identifying substances which modulate, preferably promote, such interaction.

For example, interaction between the two proteins may be studied in vitro by labelling one with a detectable label and bringing it into contact with the other which has been immobilised on a solid support. Suitable detectable labels, especially for petidyl substances, include $^{35}$S-methionine which may be incorporated into recombinantly produced peptides and polypeptides. Alternatively the complex formed on the solid support may be detected by labelling with an antibody directed against an epitope present on the protein which is not immobilised on the solid support. If no suitable antibody is available, a recombinantly-produced peptide or polypeptide may be expressed as a fusion protein containing an epitope against which a suitable antibody is available.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to affect the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

An assay according to the present invention may also take the form of a cell-based assay in which at least one of the two proteins is expressed by, preferably on the surface of, a suitable cell. The assay may utilise a cell line, such as a yeast strain or mammalian cell line, in which the relevant polypeptides or peptides are expressed from one or more vectors introduced into the cell.

Modulators of Nogo-Caspr interaction identified by the methods described may be further modified to increase their suitability for in vivo administration.

Formulations

The compositions of the invention may be prepared as pharmaceutical formulations comprising at least one active compound, as defined above, together with one or more other pharmaceutically acceptable ingredients well known to those skilled in the art, including, but not limited to, pharmaceutically acceptable carriers, adjuvants, excipients, buffers, preservatives and stabilisers. The formulation may further comprise other active agents.

Thus, the present invention further provides a method of making a pharmaceutical composition as previously defined, the method comprising admixing at least one active agent as described herein together with one or more pharmaceutically acceptable ingredients well known to those skilled in the art, e.g., carriers, adjuvants, excipients, etc.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example Remington's Pharmaceutical Sciences, 20th Edition, 2000, pub. Lippincott, Williams & Wilkins; and Handbook of Pharmaceutical Excipients, 2nd edition, 1994.

Formulations may suitably be injectable formulations, e.g. in the form of aqueous, isotonic, pyrogen-free, sterile solutions, in which the active compound is dissolved. Such liquids may additional contain other pharmaceutically acceptable ingredients, such as anti-oxidants, buffers, preservatives, stabilisers, bacteriostats, suspending agents, thickening agents, and solutes which render the formulation isotonic with the blood or cerebrospinal fluid. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Administration

Administration of the compositions of the invention will generally be by injection, preferably directly into the CNS. Injection may be directly into the site of damage. Alternatively, injection may be into the cerebro-spinal fluid, typically near the site of disease or injury.

Sequence Identity

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Percent (%) amino acid similarity is defined in the same way as identity, with the exception that residues scoring a positive value in the BLOSUM62 matrix are counted. Thus, residues which are non-identical but which have similar properties (e.g. as a result of conservative substitutions) are also counted.

In a similar manner, percent (%) nucleic acid sequence identity with respect to a reference nucleic acid is defined as the percentage of nucleotide residues in a candidate sequence that are identical with the nucleotide residues in the reference nucleic acid sequence. The identity values used herein may be generated by the BLASTN module of WU-BLAST-2 set to the default parameters, with overlap span and overlap fraction set to 1 and 0.125, respectively.

The Subject

The subject to which the compositions and/or treatments of the invention will be administered will be a mammal, preferably an experimental animal such as a rodent (e.g. a rabbit, rat or mouse), dog, cat, monkey or ape, or a farm animal such as a cow, horse, sheep, pig or goat. More preferably, the subject is human.

Generally, the subject will have CNS damage, caused by disease or injury, e.g. a head injury. More preferably, however, the damage is to the spinal cord, e.g. SCI. In experimental animals, the damage may be experimental. The CNS damage may also result from a disease or disorder, e.g. stroke, epilepsy or a neurodegenerative condition, learning memory-related condition and/or dementia such as Alzheimer's disease or Parkinson's disease.

The treatments of the invention will generally be intended for use in conjunction with other therapies, such as surgery and/or rehabilitation.

Mimetics

Non-peptide "small molecules" are often preferred to peptides or polypeptides for in vivo pharmaceutical use. Accordingly, mimetics of Caspr and/or Nogo may be designed, especially for pharmaceutical use. Typically a Nogo mimetic of the present invention will be capable of binding to a Caspr molecule to mimic the effects of Nogo binding to that molecule. Likewise a Caspr mimetic will be capable of binding to a Nogo molecule to mimic the effects of Caspr binding to that molecule.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. Alanine scans of peptide are commonly used to refine such peptide motifs. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

In the present case, peptide mapping studies may be used to identify the minimal portion of one protein required to interact with the other. This peptide may then be used as a lead compound for mimetic design, as described above.

Antibodies

As antibodies can be modified in a number of ways, the term "antibody" should be construed as covering any specific binding substance having an binding domain with the required specificity. Thus, this term covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444-6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al, Embo Journal, 10, 3655-3659, (1991).

It may be desirable to "humanise" non-human (e.g. murine) antibodies to provide antibodies having the antigen binding properties of the non-human antibody, while minimising the immunogenic response of the antibodies, e.g. when they are used in human therapy. Thus, humanised antibodies comprise framework regions derived from human immunoglobulins (acceptor antibody) in which residues from one or more complementary determining regions (CDR's) are replaced by residues from CDR's of a non-human species (donor antibody) such as mouse, rat or rabbit antibody having the desired properties, e.g. specificity, affinity or capacity. Some of the framework residues of the human antibody may also be replaced by corresponding non-human residues, or by residues not present in either donor or acceptor antibodies. These modifications are made to the further refine and optimise the properties of the antibody.

Specific embodiments of the first aspect of the present invention will now be illustrated, by way of example, with reference to the accompanying figures. Further embodiments will be apparent to those skilled in the art. All documents mentioned in this text are incorporated herein by reference.

Gold particles are indicated with arrows. Bars: 5 µm for Aa-i, 10 µm for Aj, 200 nm for Ba, d and e, 100 nm for Bb, c, d' and e'.

Figure 2:
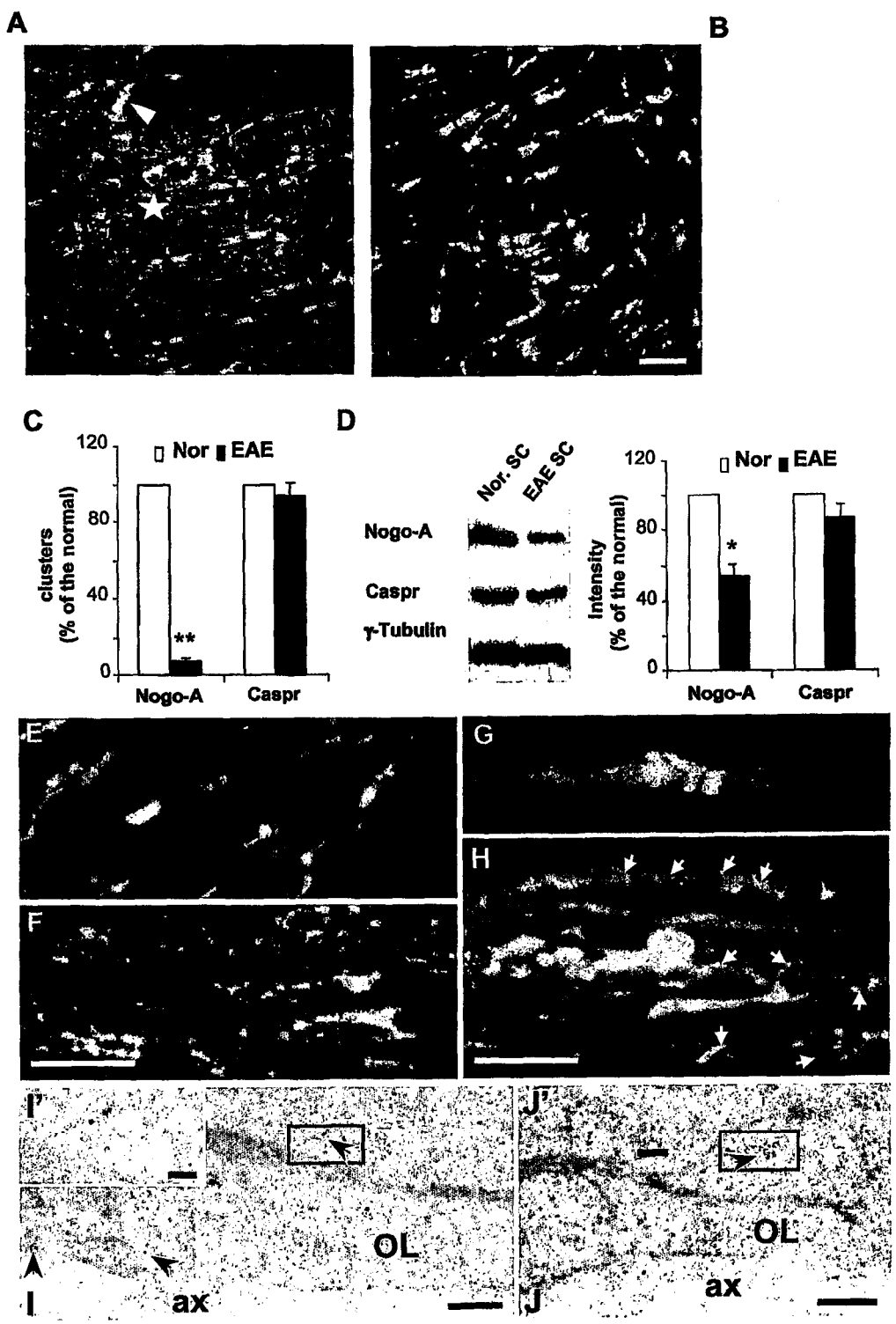

FIG. 2. Expression and localization of Nogo-A in the CNS myelinated axons from EAE rats and CGT$^{-/-}$ mice.
A and B. Spinal cord sections from EAE rats were double immunostained for Nogo-A (green, A), Caspr (green, B) and Kv1.1 (red, A and B). The star marks a Nogo-A positive cell body, and the arrowhead indicates an undisrupted paranodal Nogo-A labeling.
C. Numbers of Nogo-A and Caspr clusters in several microscopic fields of both normal and EAE rat spinal cord sections were counted. Values are given as mean±SEM from at least 3 independent experiments. Nogo-A clusters were dramatically reduced in EAE compared to normal rats. The double asterisks (**) indicates a significance level of $P<0.01$. D. Western blotting result showing that Nogo-A was significantly downregulated in spinal cord of EAE animals, but Caspr expression was only affected slightly. The single asterisk represents a significance level of $P<0.05$. E, F, G, and H. Spinal cord sections from wild type and CGT$^{-/-}$ mice were double-labeled for Nogo-A (green) and PAN Na$^+$ channel. In wild-type (P16), Nogo-A clusters at paranodes and PAN Na$^+$ channels congregated at the nodes of Ranvier (E). In CGT$^{-/-}$ mice (P16), Nogo-A segregation at paranodes and PAN Na$^+$ channel clustering were hardly detected (F). Nogo-A labeling appears to be loosely spiraled around the axon in CGT$^{-/-}$ mice (P21; H), but clusters specifically into the paranodal region in wild type mice (P21; G). Bars: 10 µm for A-B and 5 µm for E-H. I and J. Immunogold labeling of Nogo-A in longitudinal sections of paranodes from P16 CGT$^{-/-}$ mice spinal cord demonstrated that gold particles were visible in the abnormally reversed loops. Panels I' and J' are high magnification of the boxed areas in I and J, respectively. Arrows indicate the gold particles. Stars indicate the reversed papanodal loops. ax: axon. OL: oligodendrocyte. Bars: 200 nm for I and J, 50 nm for I' and J'.

FIG. 3. Caspr Associates with Nogo-A In Vitro.
A. NgR distributes diffusely along the myelinated axon. (a) Tissue lysates from various regions of the CNS of adult rats were subjected to Western blot using antibodies against NgR and γ-tubulin. (b) Brainstems from postnatal day 1-30 (P1-P30) rats were subjected to Western blot using antibodies against NgR and γ-tubulin. Adult hippocampus (c-e) and brainstem (f-h) sections were double stained for NgR (green, c and f), MAP2 (red, d) and Kv1.1 (red, g). e and h represent merged images of c, d, and f, g, respectively. Scale bars for c to h: 10 µm.
B. Nogo-A associates with Caspr/F3. (a) Detergent lysates of brain membrane fractions from adult mice were immunoprecipitated with Caspr, Nogo-A, and NB3 antibodies as well as non-immune IgG. The immunoprecipitates and detergent extracts from brain (Brain) together with the protein-A beads (Beads) were subjected to Western blot using antibodies against Caspr, Nogo-A, F3, and NB3. (b) Membrane fractions of Nogo-A/Caspr/F3-, Nogo-A/F3- and Nogo-A-transfected CHO cells were immunoprecipitated with antibodies to caspr and Nogo-A as well as non-immune IgG. The immunoprecipitates and brain extracts (Brain) were subjected to Western blot analysis using antibodies against Nogo-A, Caspr and F3. (c) Detergent lysates of membrane fractions from P15 rat cerebral cortex were loaded onto a linear sucrose gradient. Twelve gradient fractions were collected, subjected to SDS-PAGE and analyzed for the distribution of Nogo-A, Caspr and F3 by Western blotting. Fraction 1 is the lowest density fraction recovered from the top of gradient. The last lane that is labeled "total" indicates the levels in homogenates before loading onto the sucrose gradient.

Figure 4:
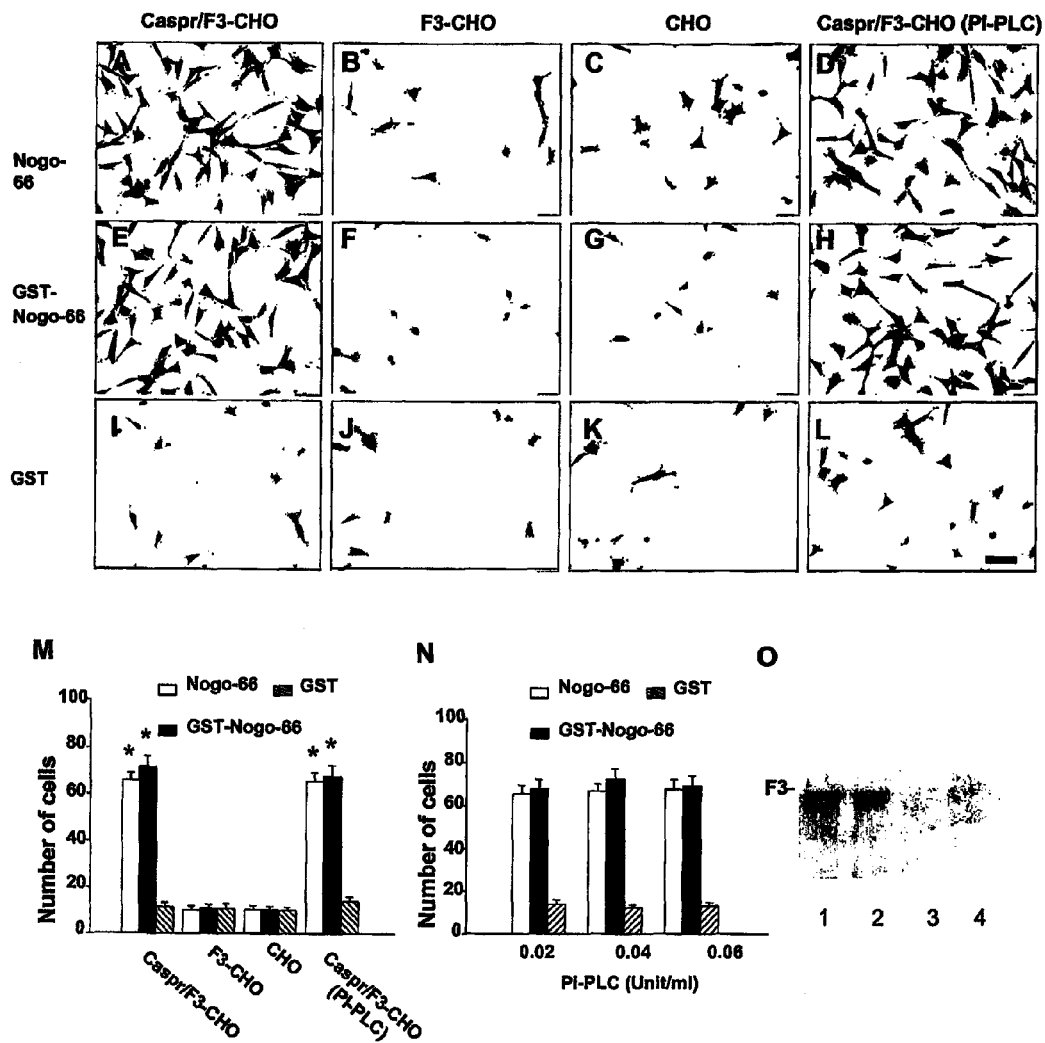

FIG. 4. Caspr expressing cells adhere to Nogo-66.
A to L. Caspr/F3-(A, E and I), F3-(B, F and J), and mock-(C, G and K), as well as PI-PLC treated Caspr/F3-(D, H and L) CHO cells were plated onto substrates coated with Nogo-66 peptide, recombinant GST-Nogo-66 protein, and GST, respectively. Scale bar: 8 µm. M to N. Quantification of cells adherence to various substrates. Caspr/F3-CHO cells (in the presence or absence of PI-PLC treatment), but neither F3-nor wild type CHO cells, bound to Nogo-66 peptide and GST-Nogo-66. Bars represent the number of adherent cells (expressed as mean±SEM) from at least 3 independent experiments (M). O. At the end of cell adhesion assay after PI-PLC treatment, Caspr/F3-CHO and F3-CHO cells and their culture supernatant were collected, and subjected to Western blotting analysis after normalizing for total protein to detect F3/Contactin. 1, mouse brain; 2, F3-CHO cell lysate; 3, Caspr/F3-CHO cell lysate after PI-PLC treatment; 4, Caspr/F3-CHO cell medium after PI-PLC treatment. The asterisk (*) indicate a significance level of $P<0.05$. Caspr/F3-CHO cells adhered to Nogo-66 and GST-Nogo-66 with equal efficiency after treatment with increasing concentrations of PI-PLC (0.02, 0.04 and 0.06 U/ml) (N).

Figure 5:
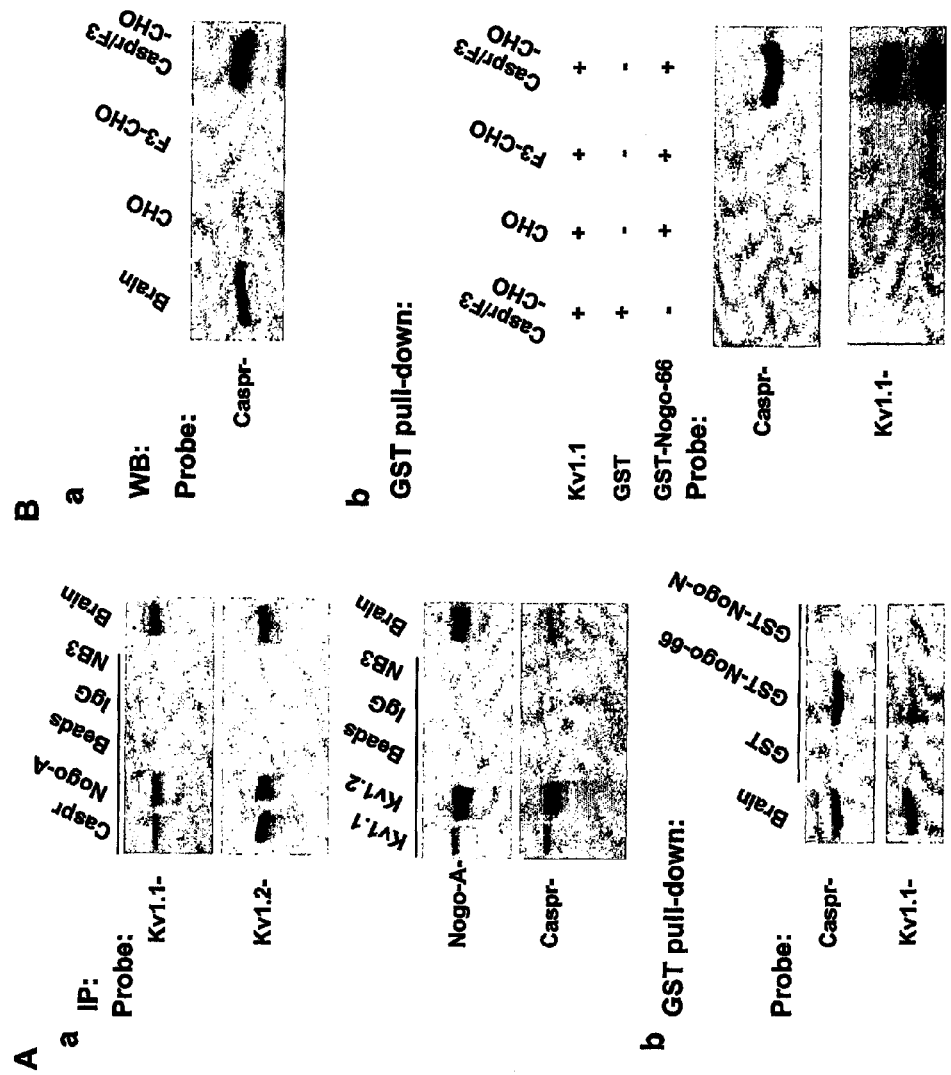

FIG. 5. The Nogo-A/Caspr complex interacts with K$^+$ channels.
A. (a) P7 mouse brain membrane extracts were immunoprecipitated with Caspr, Nogo-A, Kv1.1, Kv1.2 and NB3 antibodies as well as non-immune IgG. The indicated immunoprecipitates and brain extracts (Brain) were subjected to Western blot analysis using antibodies against Kv1.1, Kv1.2, Nogo-A and Caspr. (b) GST pull-down assay was performed using recombinant GST-Nogo-66, GST-Nogo-N and GST from adult mouse brain extracts. The indicated precipitates and brain extracts (brain) were probed with Caspr and Kv1.1 antibodies, following SDS-PAGE separation.
B. (a) Membrane fraction of CHO, F3-CHO, Caspr/F3 CHO cells, as well as brain extracts were immunoblotted using Caspr antibodies, following SDS-PAGE separation. (b) After transient transfection with the Kv1.1 expression construct RBG4/Kv1.1, membrane extracts of CHO, F3-CHO, Caspr/F3 CHO cells were incubated with GST-Nogo-66 or GST, respectively. The eluted proteins were separated by SDS-PAGE and probed with Caspr and Kv1.1 antibodies. IP: immunoprecipitation; WB: Western blot.

Figure 6:
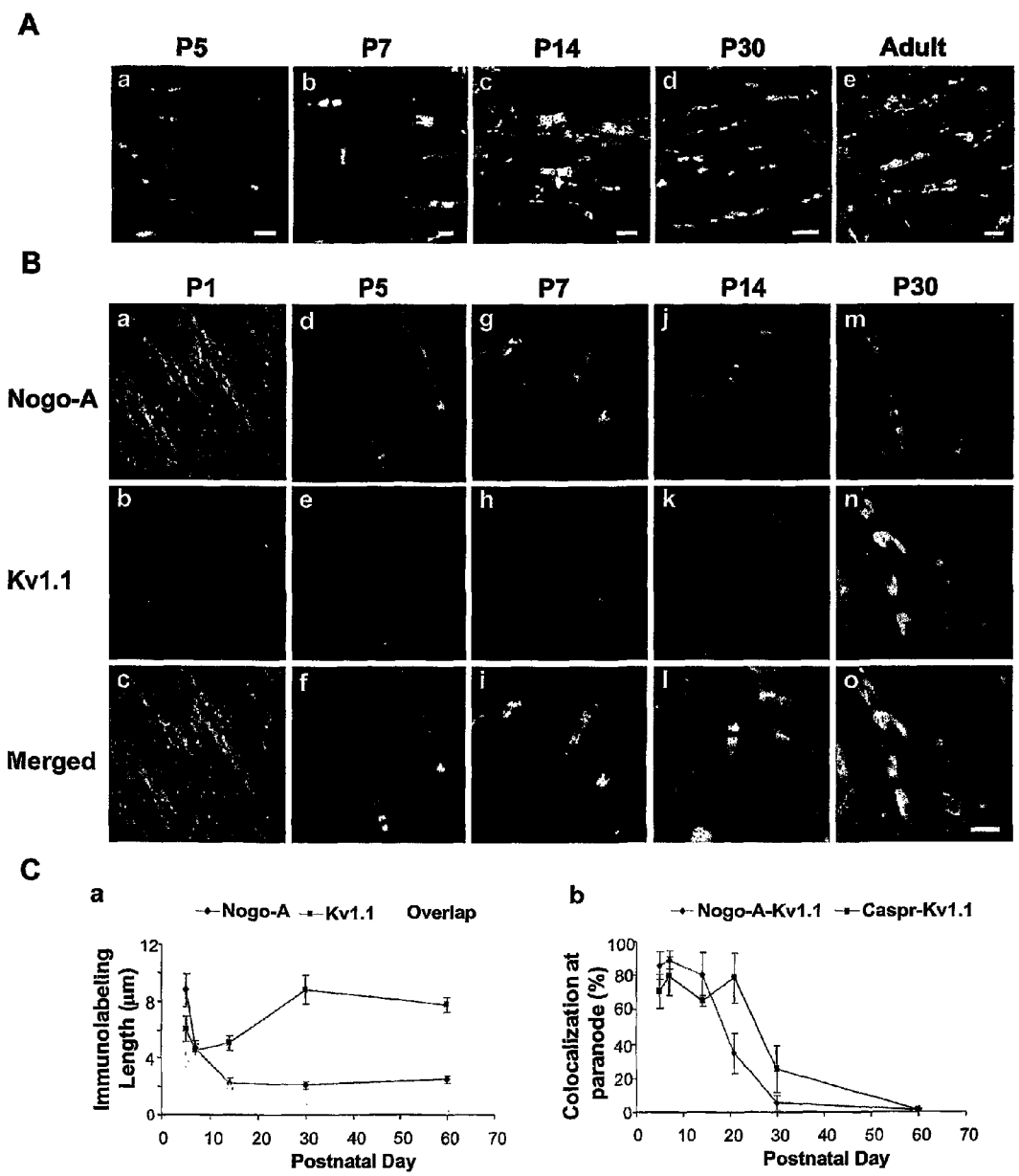

FIG. 6. Immunohistochemical labeling of Nogo-A, Caspr and Kv1.1 at different postnatal days in rat brainstem.
A. Brainstem sections of P5 to adult rats were double labeled for Caspr (green) and Kv1.1 (red). Scale bar: 5 µm. B. Sections from Pd to P30 rats were double labeled for Nogo-A (green) and Kv1.1 (red). Scale bar (in o): 5 µm. C. (a) The lengths of Nogo-A, Kv1.1 immunostaining and their overlap were measured from micrographs (µm, mean±SEM). (b) The number of overlapping Nogo-A/Kv1.1 or Caspr/Kv1.1 clusters at paranodes was counted.

Figure 7:
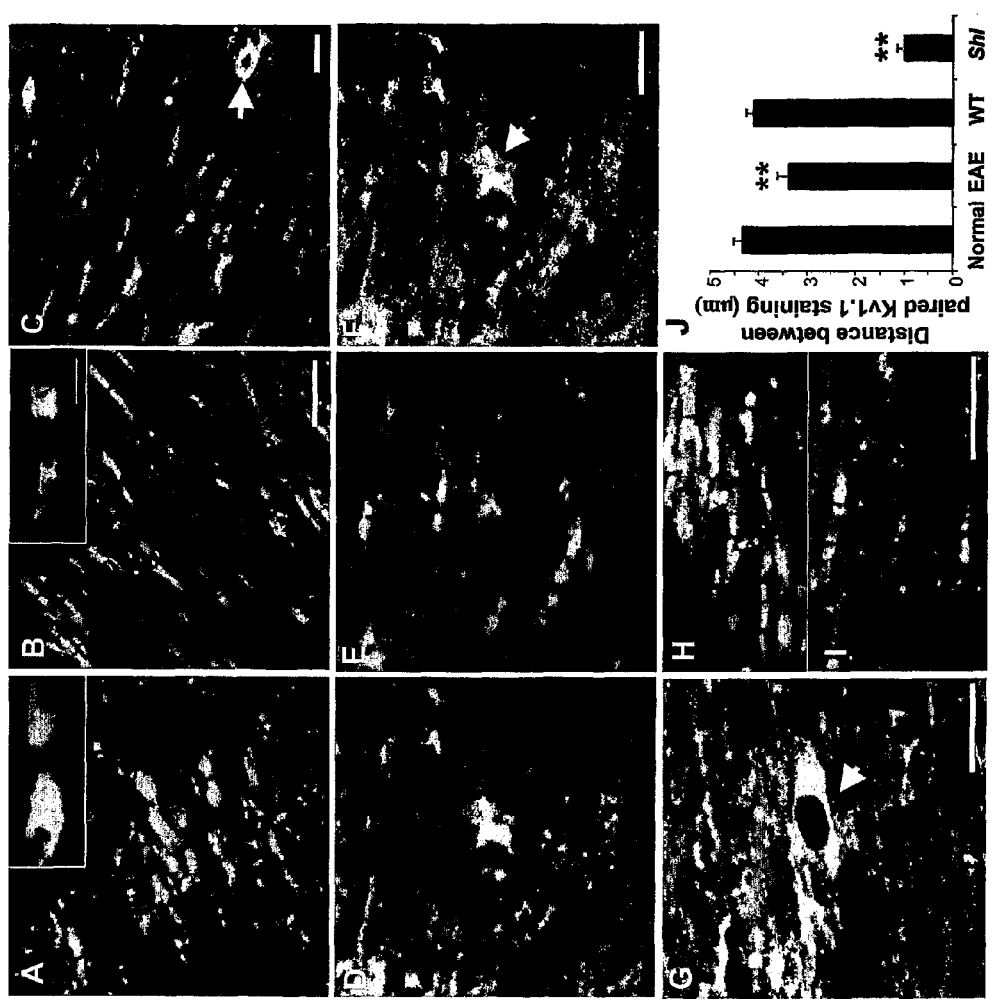

FIG. 7. Distribution of Nogo-A, Caspr and Kv1.1 in EAE rats and Shiverer mice.
A and B. Double immunofluorescence labeling for Caspr (green) and Kv1.1 (red) in brainstem sections of EAE (A) and control (B) rats. The insets represent magnified views of the Kv1.1 labeling. Scale bars: 10 µm for A-B and 5 µm for insets of A-B. C to G. Double labeling for Nogo-A (green) and Kv1.1 (red) in spinal cord sections of wild type (C) and Shiverer (D-G) mice. F is a merged picture of D and E. Arrows in C, F and G indicate Nogo-A positive cell bodies. Bars: 10 µm. H and I. Double immunofluorescence staining of Caspr (green) and Kv1.1 (red) in brainstem sections of wild-type (H) and Shiverer (I) mice. Bar: 10 μm. J. The distances between paired Kv1.1 staining in EAE with control rats and Shiverer (Shi) with wild-type (WT) mice were measured from micrographs (μm, mean±SEM), respectively. The values in EAE rats or Shiverer mice were significantly reduced when compared to their controls, respectively (asterisks ** indicates a significance level of P<0.01).

Figure 8:
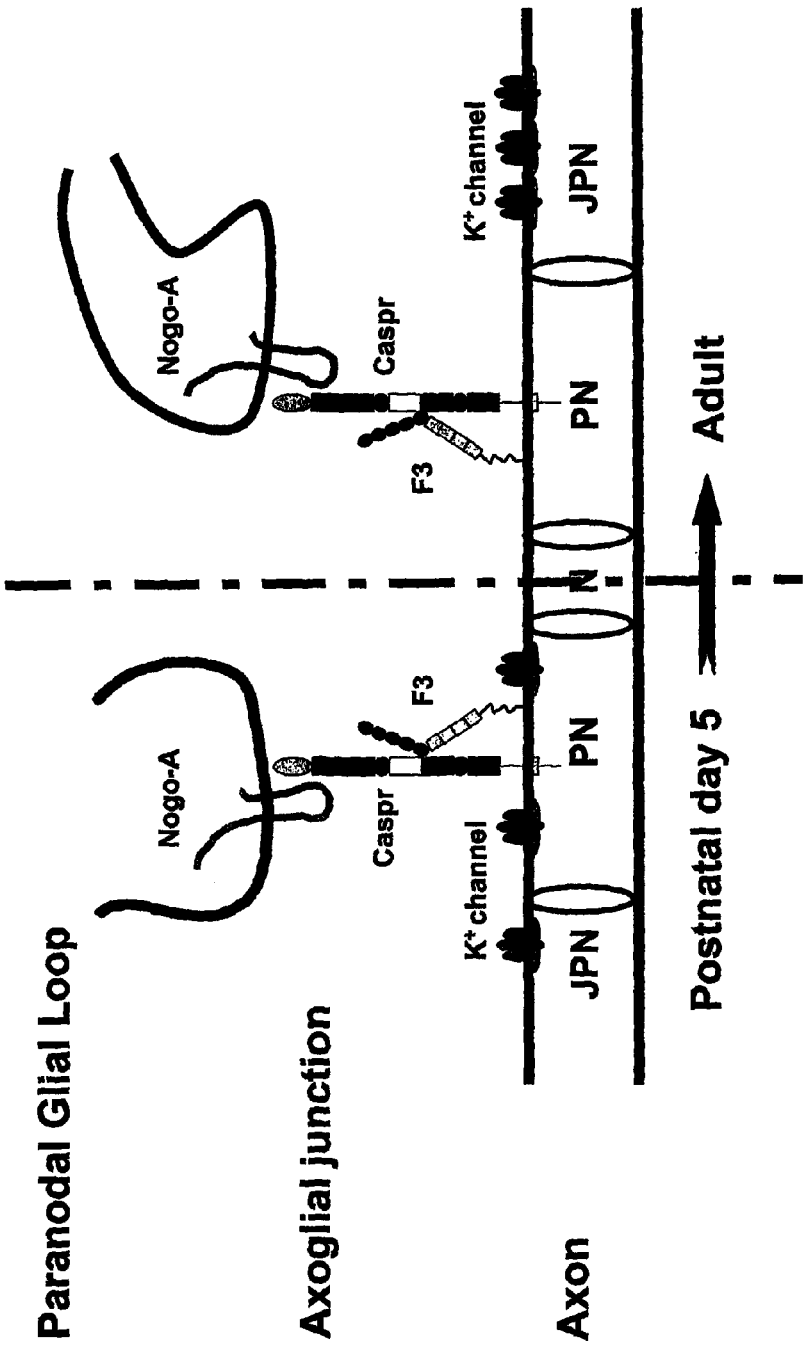

FIG. 8. The interaction between Nogo-A and Caspr at the paranodes may play a role during myelination.

In addition to NF155, the inventors' findings suggest that paranodal Nogo-A is a glial ligand for neuronally expressed Caspr. Paranodal Nogo-A trans-interacts with axonal Caspr, and may play a role in $K^+$ channel localization during the early stages of myelination (from P5). With the firm establishment of axoglial junctions in the adults, $K^+$ channels were excluded from paranodes where Nogo-A/Caspr interaction is maintained, however, the detail mechanism for this separation remains to be explored. N: Node of Ranvier, PN: paranode, JPN: juxtaparanode.

Figure 9:
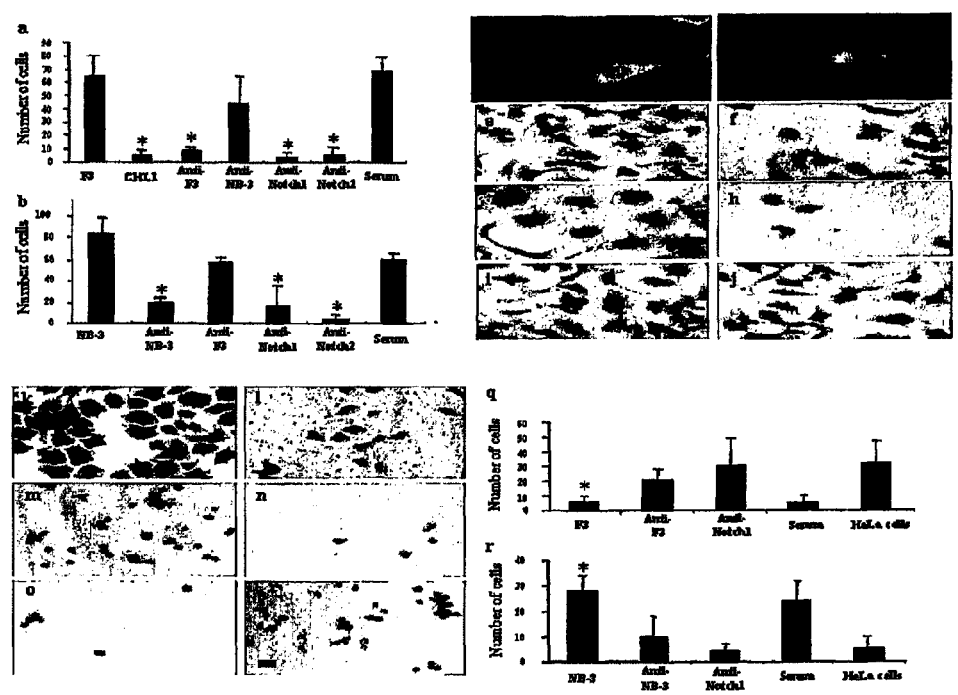

FIG. 9 Adhesion of OLN-93 cells or mouse Notch 1 transfected Hela cells with or without antibosy blocking treatment to spots of proteins, such as F3-Fc (a, k-l, and q), CHL-Fc (a) and NB-3-His (b, e-j, m-p, and r), applied to nitrocellulose was determined. Bars (a-b and q-r) represent the number of adherent cells (mean±SD) from at least three independent experiments. Bar marked * is highly significantly (P<0.05) different from the control.

Adhesion of OLN-93 cells on coated F3-Fc and NB-3-His substrates.

a. Effect of antibody blockade on OLN-93 cell adhesion to F3-Fc substrate. F3:F3 protein substrate only (as a control); CHL1:CHL1 protein substrate only; Anti-F3 or Anti-NB-3: addition of these two antibodies, respectively, to block the F3-Fc coated substrates before plating OLN-93 cells; Anti-Notchi, Anti-Notch2 or Serum: pre-treated OLN-93 cells with these two specific blocking antibodies or pre-immune serum respectively before plating upon a F3-Fc coated substrate.

b. Effect of antibody blockade on OLN-93 cell adhesion to NB-3 substrate. NB-3:NB3.His protein substrate only (as control); Anti-NB-3 or Anti-F3: addition of these two antibodies, respectively, to block the NB-3-His coated substrates before plating OLN-93 cells; Anti-Notch1, Anti-Notch2 or Serum: pre-treated OLN-93 cells with these two specific blocking antibodies or pre-immune serum respectively before plating upon a NB-3-His coated substrate.

c-d: Immunofluorescence micrographs of OLN-93 cells stained using anti-Notch1 antibody (c) and anti-Notch2 antibody (d). Cell surface staining is present in both instances.

e-j: Bright-field micrographs of OLN-93 cells upon contact with coated NB-3-His substrate after 0.5 hour in culture (e) and in the presence of blocking antibodies against Notch1 (f), NB-3 (g), Notch2 (h), F3 (i), and pre-immune serum (j). Scale bar in (j): 8 μm for (c-j).

Adhesion of mouse Notch1 transfected Hela cells on coated F3-Fc and NB-3-His substrates.

k-p: Bright-field micrographs of mock-transfected Hela cells (k) and mouse Notch1 transfected Hela cells (1-p) upon contact with F3-Fc (k-1) or NB-3-His (m-p) and in the presence of blocking antibodies against NB-3 (n), Notch1 (o), and pre-immune serum (p). Scale bar in (p): 8 μm for (k-p).

q. Effect of antibody blockade on mouse Notchi transfected Hela cells interaction with F3-Fc substrate. F3: F3-Fc coated substrate only; Anti-F3: addition of these antibodies to block the F3-Fc coated substrates before plating mouse Notch1 transfected Hela cells; Anti-Notch1 or Serum: pre-treated mouse Notch1 transfected Hela cells with these specific blocking antibodies or pre-immune serum respectively before plating upon a F3-Fc coated substrate; Hela cells: plating mock-transfected Hela cells upon a F3-Fc coated substrate (as a control).

r. Effect of antibody blockade on mouse Notchl transfected Hela cells adhesion to NB-3-His coated substrate. NB-3: NB-3.His coated substrate only; Anti-NB-3: addition of these antibodies to block the NB-3.His coated substrates before plating mouse Notch1transfected Hela cells; Anti-Notch1or Serum: pre-treated mouse Notch1 transfected Hela cells with these specific blocking antibodies or pre-immune serum respectively before plating upon a NB-3.His coated substrate; Hela cells: plating mock-transfected Hela cells upon a NB-3.His coated substrate (as a control).

Figure 10:
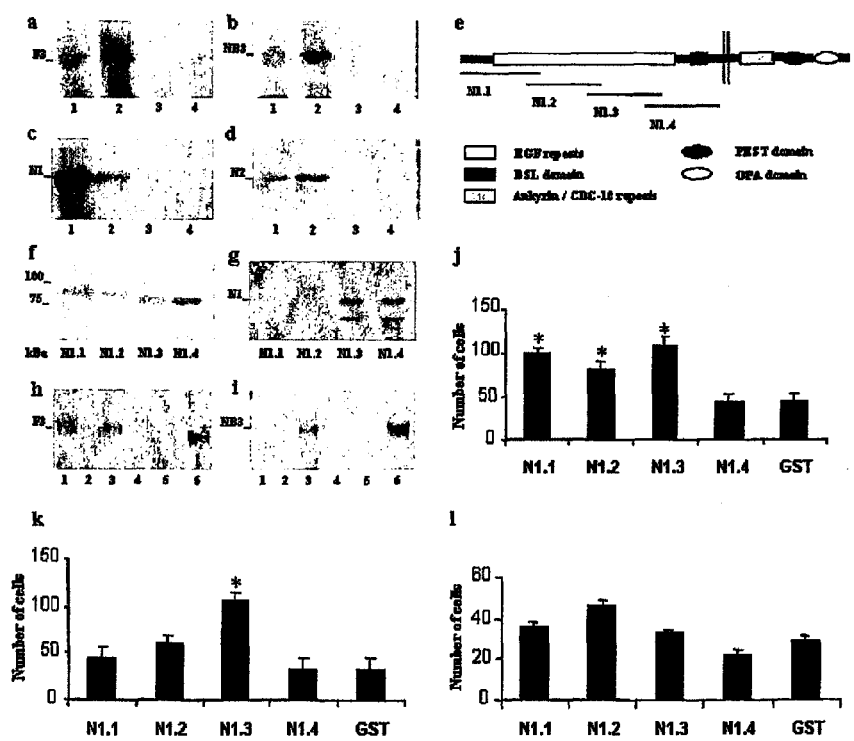

FIG. 10. Biochemical and cellular analysis of the interaction between Notch and F3/NB-3.

a-d: Reciprocal association of both F3 and NB-3 with Notch1 and Notch2. Lysates of rat brain were analyzed by co-immunoprecipitation with these four antibodies and beads and non-immune IgG (as controls). In each case, lanes correspond to antibodies as marked (Anti-N1: Anti-Notchi antibody, Anti-N2: Anti-Notch2 antibody). Western blots were probed with antibodies against F3 (a), NB-3 (b), Notchi (a) and Notch2 (d).

e: Schematic diagram of the Notchi molecule showing the terminology assigned to each subcloned fragment.

f-g: Coomassie Brilliant blue staining (f) and immunoblot analysis (g) of the four fragments are shown. The anti-Notchi antibody specifically recognizes N1.3 and N1.4.

h-i: Analysis of the interaction between Notch 1 fragments with F3/NB-3 by using a pull down assay. Rat brain lysates were incubated with GST or GST-fusion proteins (N1.1, N1.2, N1.3, N1.4) bound to Sepharose 4B beads. Bound proteins were eluted with SDS sample buffer and analysed by SDS-PAGE and Western blotting with antibodies against F3 or NB-3.

j-l: Adhesion of F3-transfected CHO cells (j), NB-3-transfected CHO cells (k), and mock-transfected CHO cells (l) to four different Notch1fragments and GST. The protein fragments N1.1, N1.2, N1.3 and N1.4, together with GST as control were coated onto surfaces of petri dishes and F3-transfected CHO cells (j), NB-3-transfected CHO cells (k) and mock-transfected CHO cells (1) were plated and maintained in chemically defined medium for 2 hours. Bars represent the number of adherent cells (mean±SD) from at least three independent experiments, Bar marked * is highly significantly (P<O.05) different from the control (GST).

Figure 11:
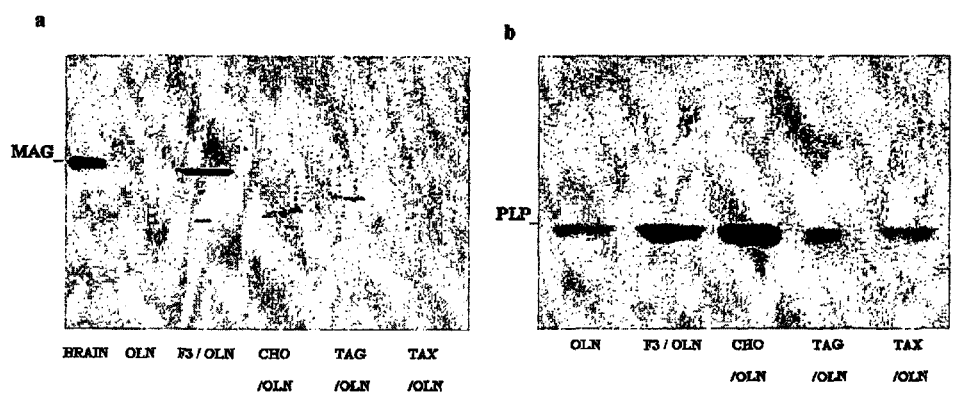

FIG. 11 Western blot analysis of expression of MAG and PLP in co-culture of F3-transfected CHO cells and OLN-93 cells.

a: Immunoblot analysis of MAG in rat brain homogenates (BRAIN) and cell co-culture extracts. b: Inimunoblot analysis of PLP in cell co-culture extracts. OLN: OLN-93 cell culture only; F3/OLN: co-culture of OLN-93 cells and F3-transfected CHO cells; CHO/OLN: co-culture of OLN-93 cells and mock-transfected CHO cells; TAG/OLN: co-culture of OLN-93 cells and TAG-1-transfected CHO cells; TAX/OLN: co-culture of OLN-93 cells and TAX-transfected CHO cells.

Figure 12:
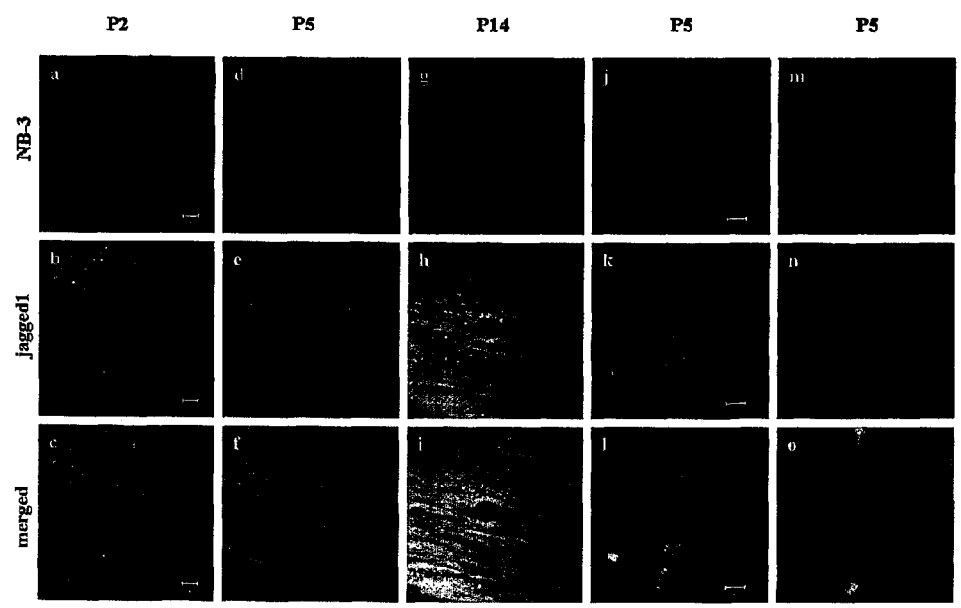

FIG. 12. Immunofluorescence localization of Jagged1 and NB-3.

a-c: At P2, hardly any NB-3 staining was detectable. Jagged1 staining was present as linear streaks consistent with an axonal localization. Scale bar in a-c: 20 μm for a-i.

d-f: At PS, NB-3 can be observed to cluster at paranodal locations. Significantly, there is a distinct boundary between Jagged1 and NB-3 immunofluorescence, best seen in the enlarged images j-o. Scale bar in j-l: 2 μm for j-o.

g-i: At P14, the distribution of NB-3 and Jagged1 remains unchanged from the P5 pattern, apart from the fact that axon density and hence numbers of paranodes have increased.

Figure 13:
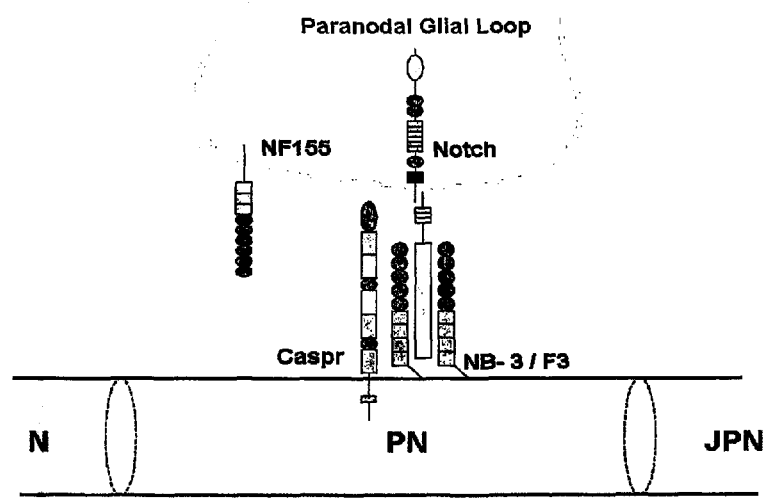

FIG. 13. The schematic diagram of the molecular constituents of the paranode in the central nervous system.

At this location, multiple oligodendroglial cytoplasmic loops (here pictured only as a single loop) intimately contact the axolemma. The present study has revealed that in addition to axonal F3/contactin and Caspr and glial neurofascin 155 (NF-155), other members of the axoglial junction include axonal NB-3 and glial Notch. It has also been demonstrated that a functional signalling interaction exists between F3/NB-3 and Notch. (N: Node of Ranvier, PN: Paranode, JPN: Juxtaparanode).

Table I

Primary rat oligodendrocytes were plated on coated F3-Fc, NB-3-His or BSA (control) substrates, respectively. After 2 hours in culture, total RNA was extracted and subjected to real time RT-PCR analysis of MAO and PLP mRNA expression levels. Relative expression levels were derived using the comparative CT method. (CT:cycle threshold).

Figure 14:
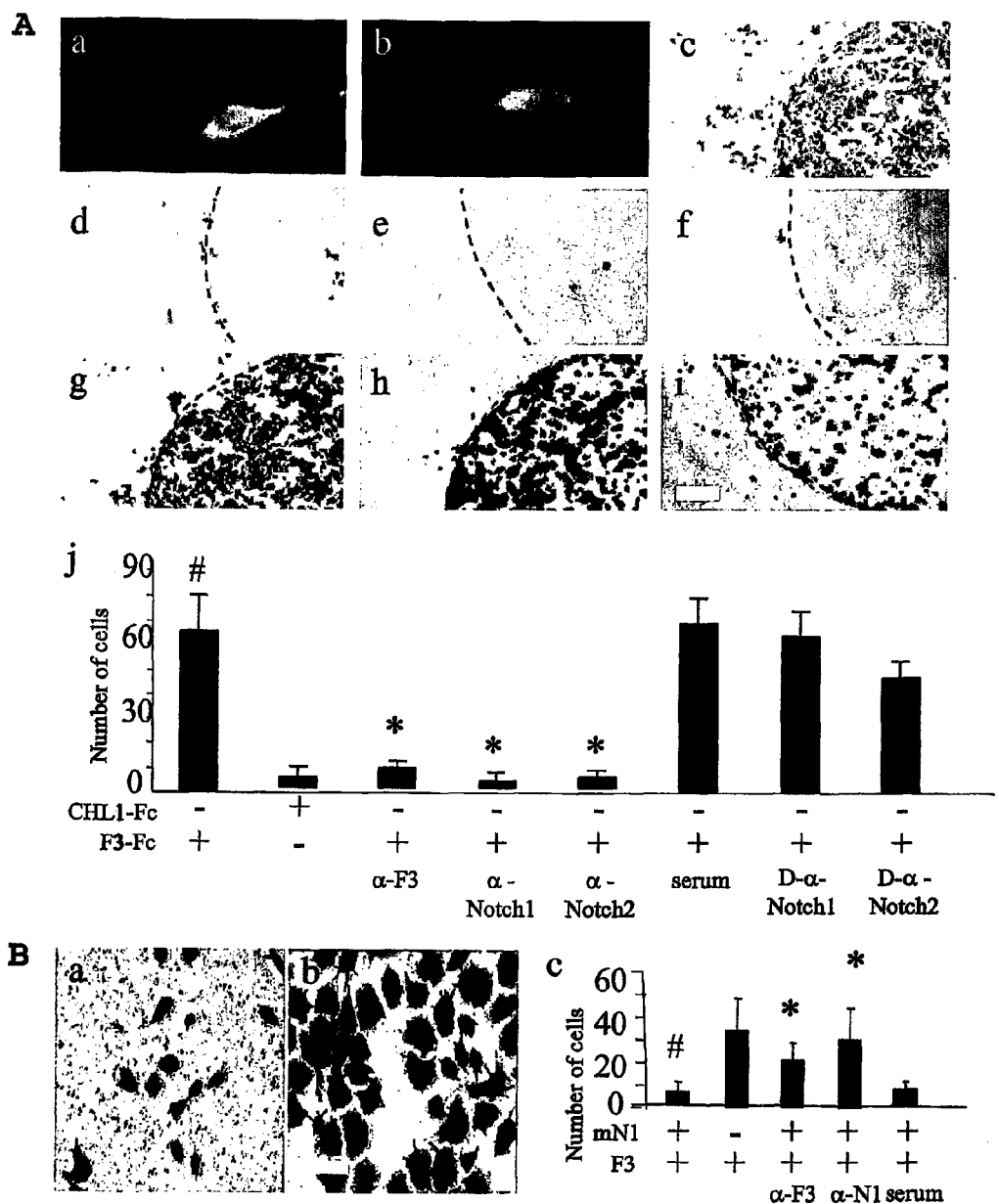

FIG. 14. Notch and F3 are binding partners.

(A) Cell adhesion assay. OLN cells were labeled with α-Notch1 (a) or α-Notch2 (b). OLN cells were plated on dishes spotted with F3 (c, e-i) or CHL1 (d). Cells were untreated or pre-treated prior to plating with α-Notch1 (e) or α-Notch2 (f), pre-immune serum (serum) (g), or with antigen-depleted α-Notch1 (D-α-Notch1) (h) or α-Notch2 (D-α-Notch2) (i). Dotted lines depict the edges of the protein-Fc spots. Adherent cells were visualized by staining with Coomassie Blue. j: Quantification of OLN cell adherence to F3 substrate and the effects of blocking antibodies. #$p<0.05$ compared with CHL1, *$p<0.05$ compared with pre-immune serum. Scale bar in (i): 20 μm for a, b; 120 μm for c-i.

(B) Cell repulsion assay. mN1-transfected HeLa cells (a) or mock-transfected HeLa cells (b) were plated on F3 coated dishes. Adherent cells were stained with Coomassie Blue. c: Quantification of HeLa cell adherence to F3 and the effects of blocking antibodies. In some experiments, mN1-transfected HeLa cells were pretreated with α-F3 or α-Notch1, or with pre-immune serum (serum). #$p<0.05$ compared with mock-transfected HeLa cells, *$p<0.05$ compared with pre-immune serum. Scale bar in (b): 15 μm for a, b. Bar graphs (Aj, Bc) represent the number of adherent cells (mean±SD).

Figure 15:
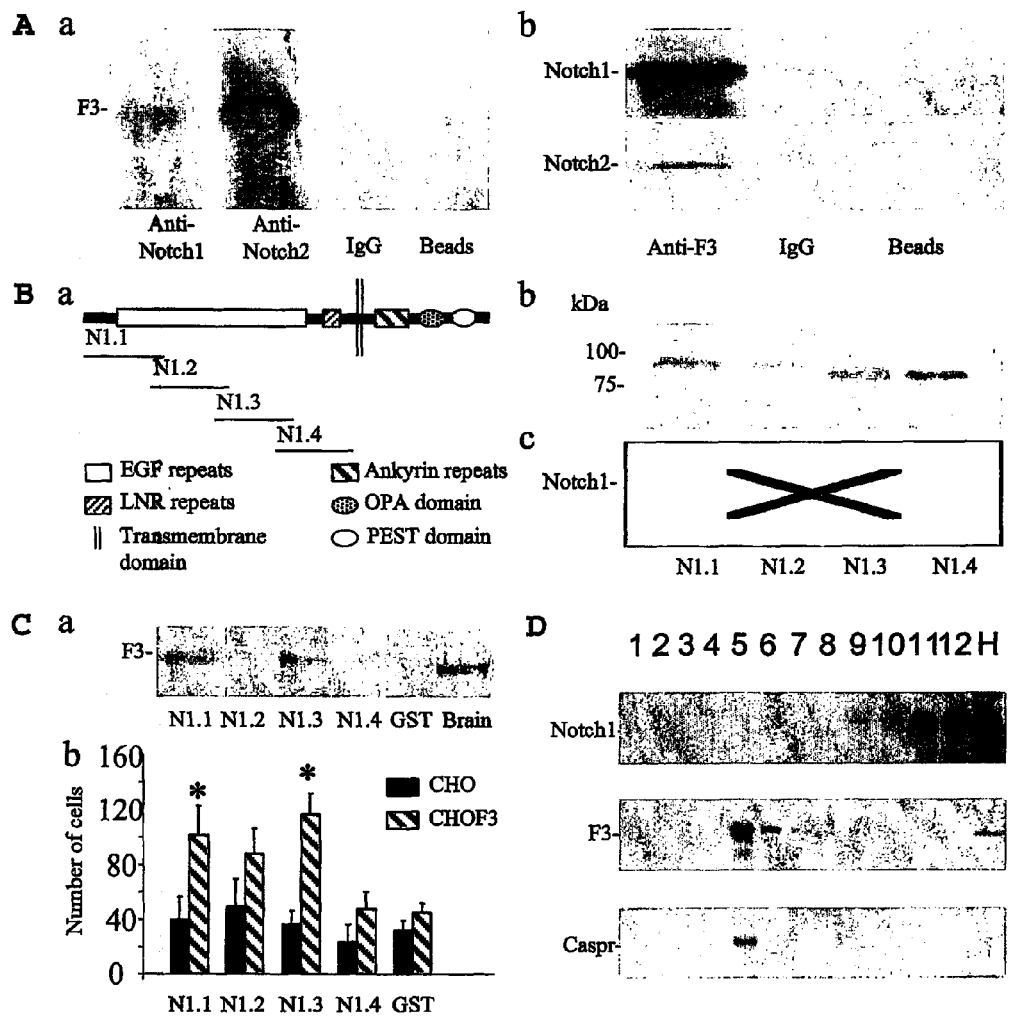

FIG. 15. Notch and F3 associate as a protein complex.

(A) F3 co-immunoprecipitates with Notch1 or Notch2. a: Immunoprecipitates from rat brain lysate were prepared using α-Notch1, α-Notch2, non-immune IgG or unconjugated beads, and were probed with α-F3. b: Reciprocal assays used α-F3 to capture the protein complex, followed by immunoblotting with α.-Notch1 or α-Notch2 to detect the binding partner.

(B) Subcloning of the Notch1 extracellular domain, a: Schematic diagram of Notch1 and its subcloned fragments. b, c: Coomassie Blue staining and α-Notch1 immunoblot of the four fragments, respectively.

(C) F3 binds to specific domains of Notch1. a: The GST-Notch1 extracellular fragments (N1.1, N1.2, N1.3 and N1.4) or GST alone were used in a GST pull-down assay with rat brain lysate. The precipitates and rat brain lysate (right lane) were probed for F3. b: Quantification of mock- and F3-transfected CHO cells adhering to culture dishes coated with the four GST fusion fragments or GST alone. Bars represent the number of adherent cells (mean±SD). *$p<0.05$ compared with GST.

(D) Lipid raft analysis. F3 was mainly localized to the fifth fraction while Notch1 was enriched in fractions 9-12. Caspr was used as a positive control to mark lipid raft fractions. H: Total homogenate.

FIG. 16. NICD translocation.

(A) F3-induced NICD nuclear translocation. mNotch1-myc transfected OLN cells were treated with 11.2 nM F3 (a), Jagged1 (b), BSA (c) or pre-incubated with α-Notch1 EGF (11-12) prior to F3 treatment (d) and then stained with ct-NICD. e: Quantification of cells with nuclear staining of NICD after treatment with increasing concentrations of F3 and Jagged1. Data are mean±SEM. f: OLN cells were cultured with Jagged1-, F3- or mock-transfected CHO cells, and lysates were immunoprobed with α-Notch1, α-Notch2 and α-tubulin.

(B) Upregulation of Notch1 and Notch2. Total (cytoplasmic plus nuclear) NICD staining intensity was quantified in F3-treated and BSA-treated mNotch1-myc transfected OLN cells (a). OLN cells cultured alone or with F3-, mock, TAG-1-, or TAX-transfected CHO cells were lysed and probed with α-Notch1, α-Notch2 and α-Notch3 (b). c: Real-time PCR assay of Notch mRNA levels in OLN cells treated with 11.2 nM F3, Jagged (or PBS. Notch mRNA levels were normalized to β-actin. Bars are mean±SEM. *$p<0.05$ compared with PBS.

Figure 17A:
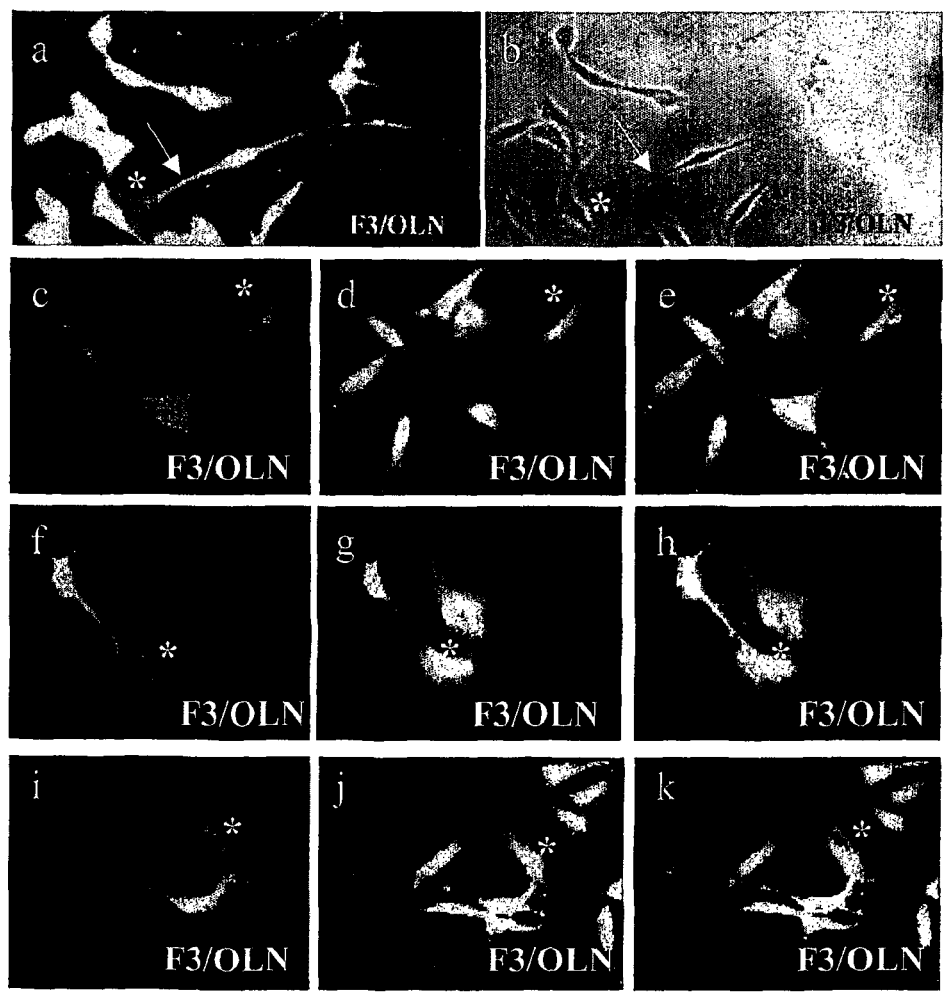
Figure 17B:
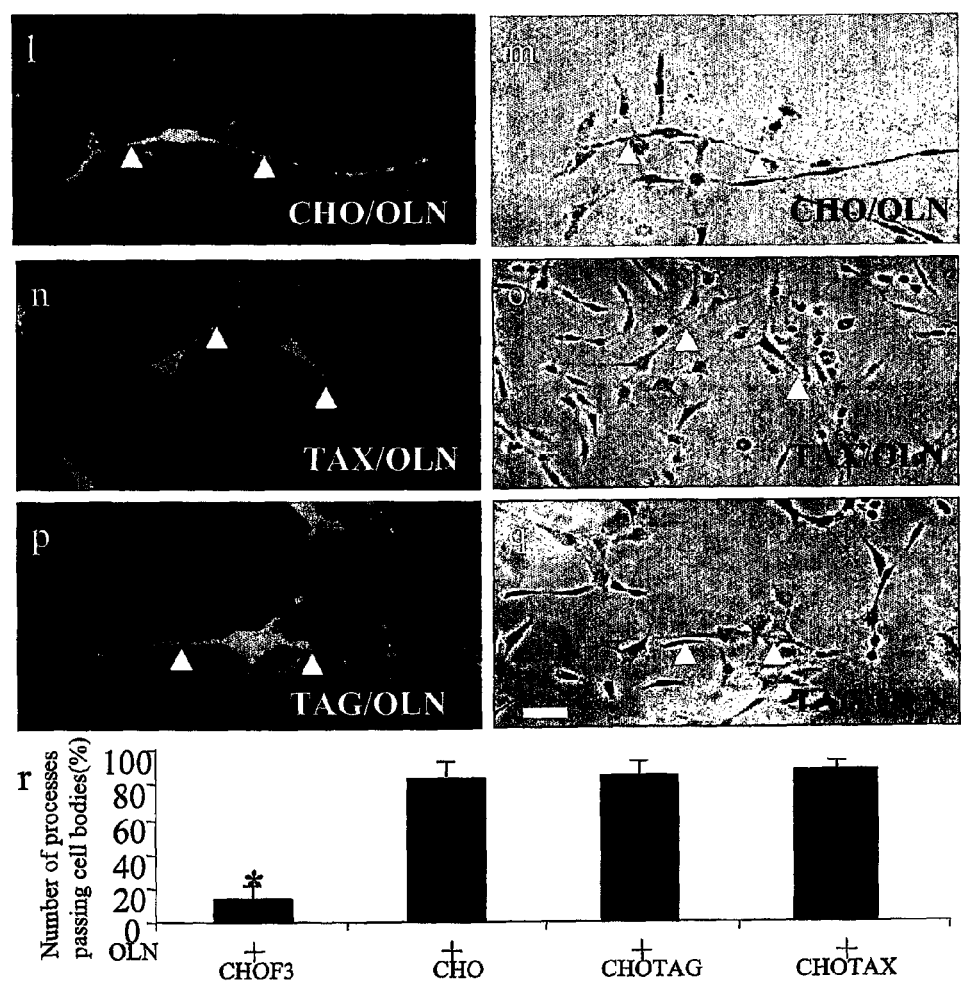
Figure 18A:
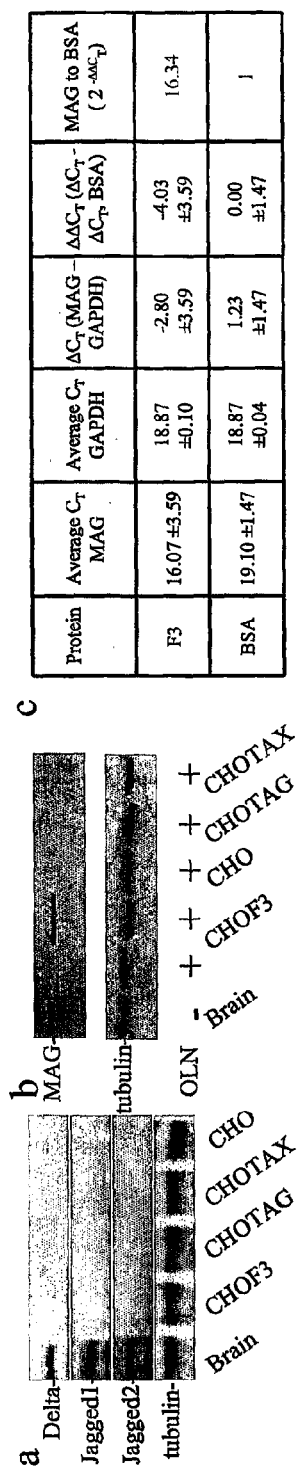
Figure 18B:
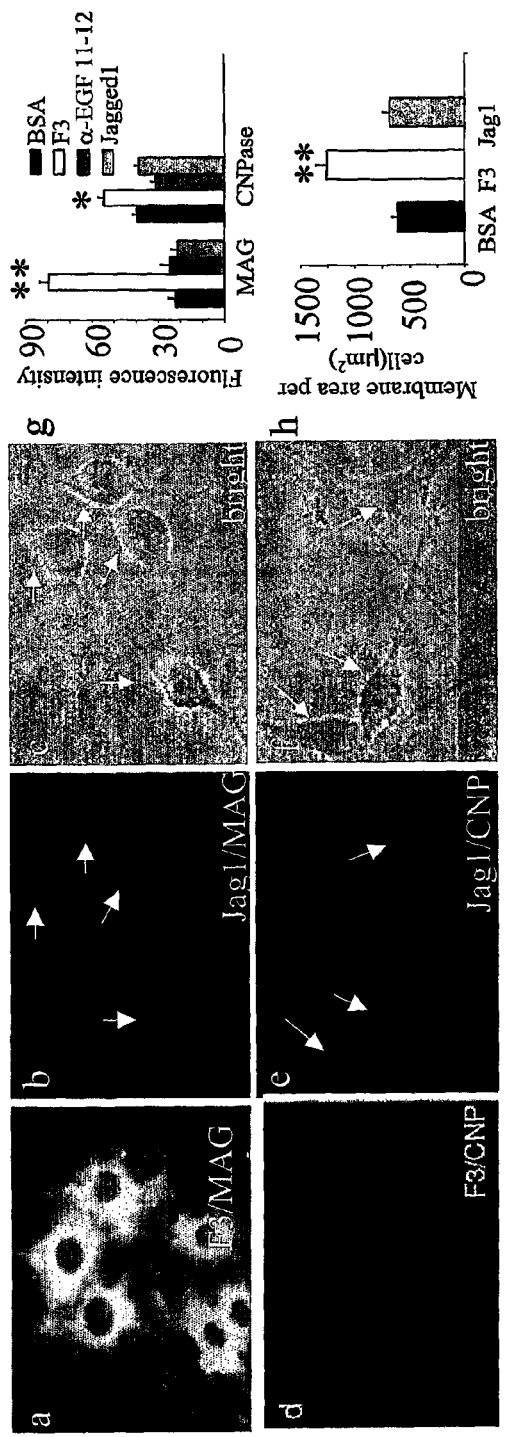
Figure 18C:
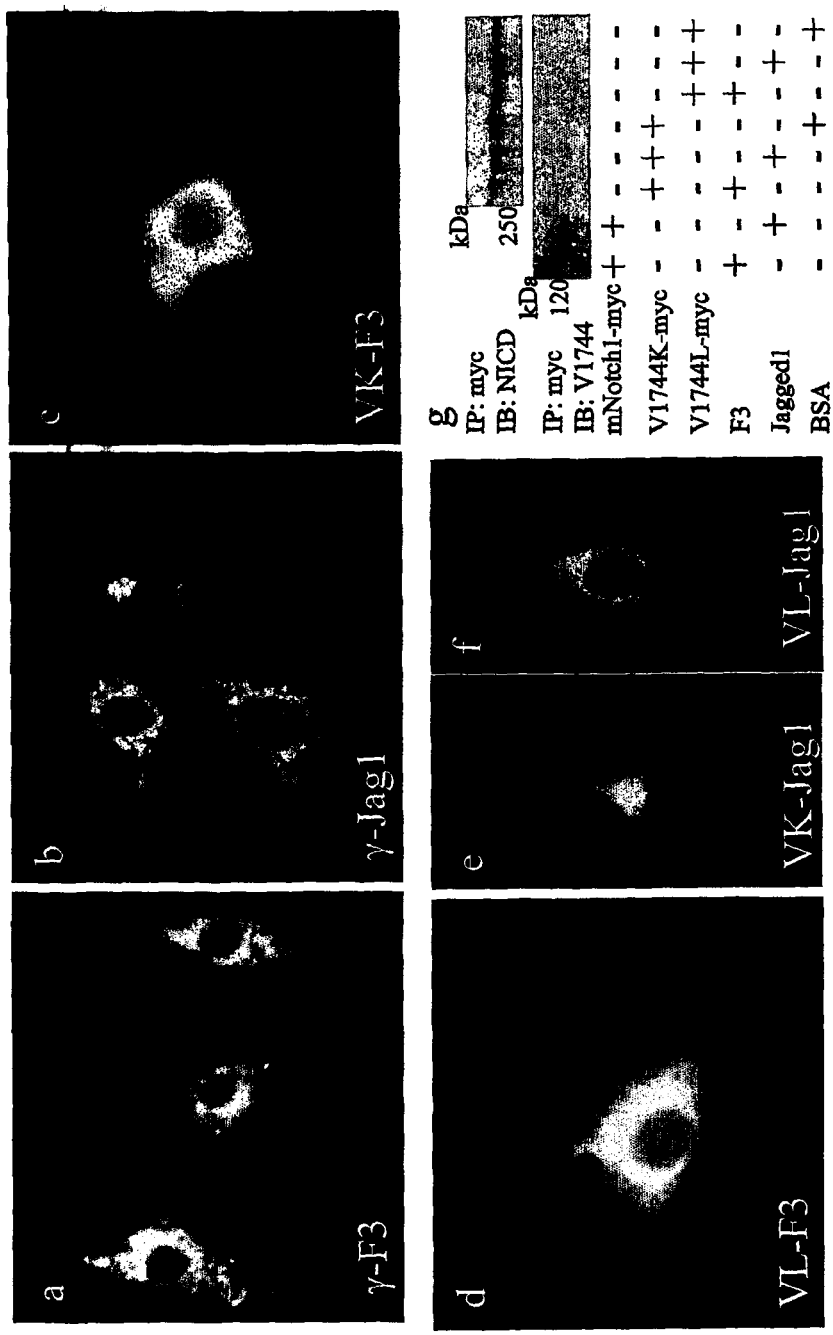
Figure 18D:
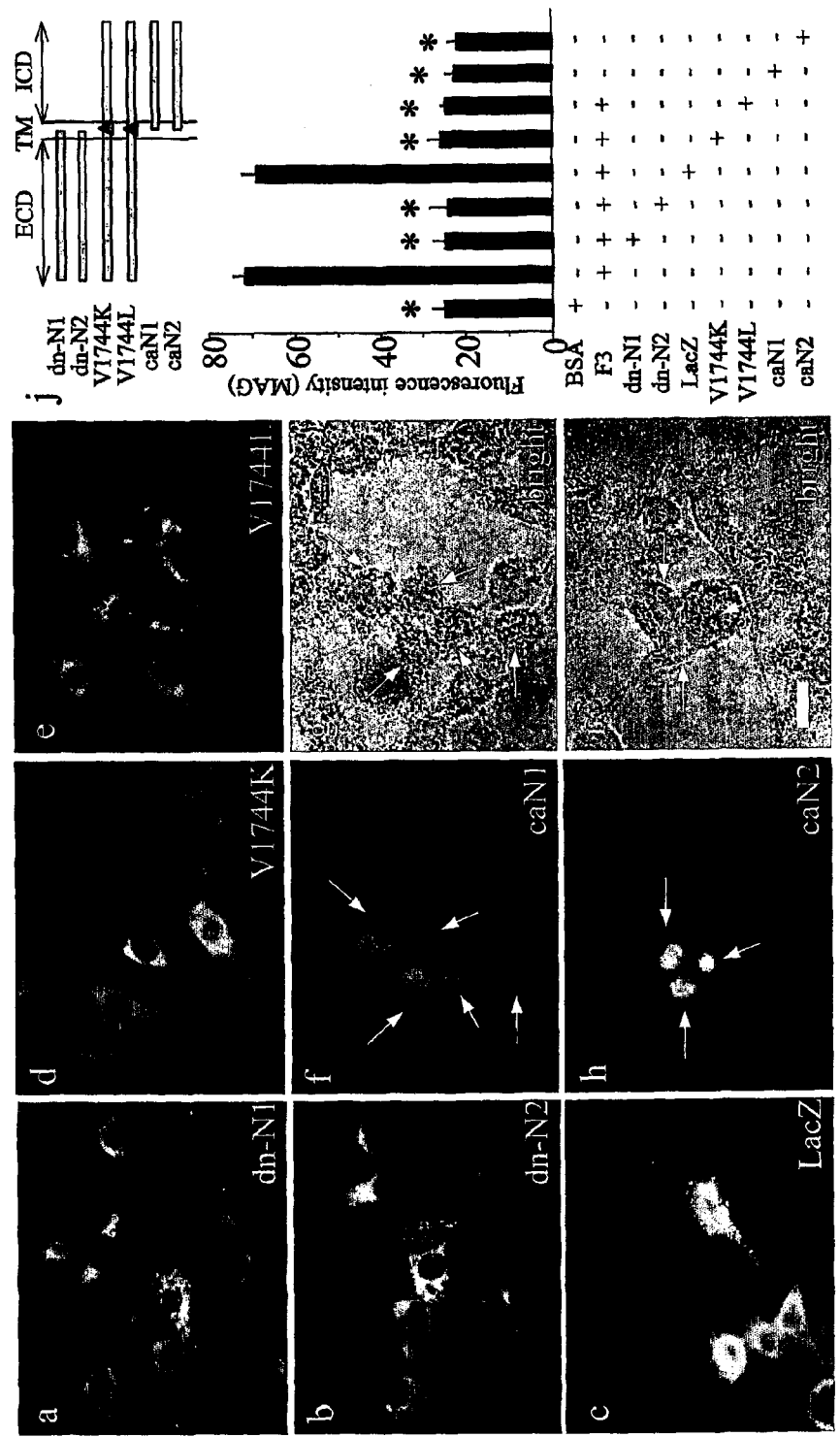

FIGS. 17A & 17B. OLN cellular processes halt and alter their morphology upon contact with F3-transfected CHO cells.

Cellular processes (arrows in a and b) of OLN cells extend towards F3-transfected CHO cell somata and upon contact with them, terminate and elaborate a flattened cytoplasmic sheet that envelops the cell body. This phenomenon is indicated by asterisks (*). a: Both OLM and F3-transfected CHO cells were pre-stained with PKH26 red fluorescent dye. b: The bright-field micrograph cofresponding to (a). a, f, i: OLN cells were pre-stained with PKH26 red fluorescent dye. d, g, j: Both OLN cells and F3-transfected CHO cells were stained for c-myc (green). e, h, k: Merged images of (c, d), (f, g), (i, j), respectively. l-q: In the control systems, cellular processes (arrowheads) of OLN cells extend past transfected CHO cell bodies. (l, m), (m, o) and (p, q) are corresponding PKH26 red fluorescent and bright-field micrographs of co-cultures of OLN cells with mock-(l, m), TAX-(n, o) and TAG-i-(p, q) transfected CHO cells. r: Quantification of OLN cellular processes extending past transfected CHO cell bodies in the co-cultures. Data are mean.+−.SD. *$p<0.01$ compared with controls. Scale bar in (q): 25 μm for (a,b,l-q) and 15 μm for (c-k).

FIG. 18. MAG is upregulated by F3/Notch interaction.

(A) MAG is upregulated by F3. CHO cells and transfected derivatives do not express classic ligands of Notch, Delta, Jagged1 and Jagged2 (a). Lysates of rat brain, OLN alone, and the indicated co-cultured cells were probed with α-MAG (upper panel) or α-γ-tubulin (bottom panel) (b). (C) Measured by real-time PCR, MAG mRNA in primary OLs is elevated significantly by F3, versus BSA treatment. The raw data were normalized to GAPDH using comparative $C_T$ method.

(B) F3, but not Jagged1, upregulates MAG. mNotch1-myc transfected OLN cells were treated with 11.2 nM F3-Fc (a, d) or Jagged1 (b, c, e, f) and labeled using .alpha.-MAG (a, b) or α-CNPase (d, e). The arrows in (b, e) indicate the cell bodies, which can be better viewed in bright-field pictures (c, f). g: Fluorescence intensities of MAG and CNPase staining in cells treated with F3, Jagged1, BSA, or pretreated with α-Notch1 EGF (11-12) followed by F3. Data are mean±SEM.

h: Quantification of the surface area (mean±SEM) occupied by cells treated with F3, Jagged1 or BSA. *p<0.05; **p<0.01 compared with BSA.

(C) MAG upregulation is F3/Notch interaction-dependent.

a-j: OLN cells transfected with Notch ICD-deleted mutants, dn-N1 (a), dn-N2 (b); LacZ (a); S3 cleavage mutants, V1744K (d) and V1744L (e); Notch ECD-deleted mutants, caN1 (f, g) and caN2 (h, i), were treated (a-e) or untreated (f-i) with 11.2 nM F3 and double labeled for MAG (red) and VS (a-c, f, h) (green) or c-myc (d, e) (green). The transfected cells in f, h can be better viewed as indicated by arrows in brightfield pictures g, i, respectively. j: MAG fluorescence intensities in cells transfected with various indicated constructs followed by different protein treatments. Data are mean±SEM. ECD: extracellular domain; TM: transmembrane domain: ICD: intracellular domain. The S3 site mutations in V1744K and V1744L constructs were indicated by triangles in the transmembrane region. *p<0.01 compared with F3-treated OLN cells. Scale bar in (Ci): 20 μm for (Ba-f); 40 μm for (Ca-i).

FIG. 19. MAG expression is independent of Hes1 and dependent on DTX1.

(A) MAG upregulation is independent of Hesi expression. (a) OLN cells were treated with the indicated ligands or compounds. At the times shown, Hes1 transcripts were quantified using real-time PCR and normalized to that at the start of the time course. (b, d, e) OLN cells were untreated or pre-treated with Hes1 sense (Hes1-S) or antisense (Hes1-AS) oligonucleotides followed by 11.2 nM F3. Cell lysates were probed with a-Hes1 (upper panel) or α-nuclear matrix protein (N-matrix) (bottom panel) (b) or cells were labeled for MAG (d, e). Also, OLN cells transfected with pGVB/Hes1 reporter alone or together with constructs expressing caN, RBP-J, or myc-tagged dn-RBP-J were subjected to luciferase assay (c). Data are mean i SD. f: OLN cells transfected with dn-RBP-J-myc were treated with 11.2 nM F3 and double stained for MAG (red) and c-myc (green). g: MAG staining intensity in OLN cells with various treatments indicated above. Data are mean±SEM. *p<0.01 compared with cells treated with F3 alone.

(B) MAG upregulation involves DTX1. a: DTX1 constructs used in luciferase reporter assays and immunostaining study. N terminal: N terminal domain; Pro: Proline-rich motif; Ring finger: Ring-H2 finger motif. OLN cells were transfected with pGVB/Hes1 reporter alone or together with indicated expression constructs. b: Luciferase reporter activity in these cells. Data are mean±SD.

DTX1 (c-e)-, DTX1-D1-HA (f-h)-, or DTX1-D2-Flag (i-k)-transfected OLN cells were treated with 11.2 nM F3 and double labeled for MAG (red) and related tags (green). 1: MAG fluorescence intensity in OLN cells transfected with indicated constructs followed by different protein treatments. Data are mean±SEM. *p<0.01 compared with F3-treated OLN cells. Scale bar in (Bk): 30 μm for Ac-f, Bc-k.

Figure 20:
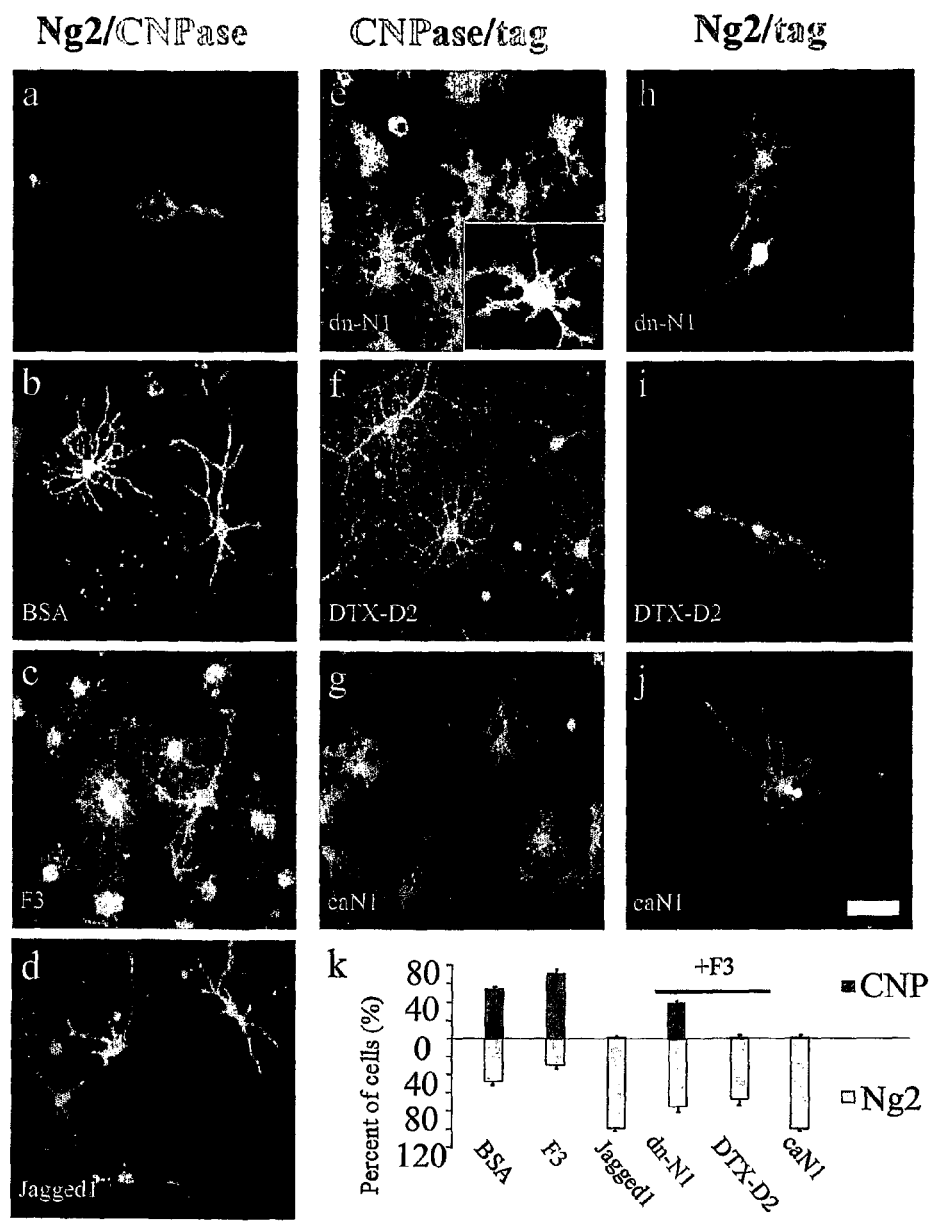

FIG. 20. F3/Notch signaling via DTX1 promotes OPC differentiation.

Purified Ng2+/CNPase-OPCs (a), were treated with BSA (b), F3 (c) or Jagged1 (d) for 2 days, double labeled for Ng2 (red) and CNPase (green) and counted (k). OPCs were also transfected with tagged dn-N1 (e, h) and DTX1-D2 (f, i), followed by F3 treatment or with caN1 and left untreated (g, j). Cells were double stained for the appropriate tag (green) and CNPase (red; e-g) or Ng2 (red; h-j), and counted (k). Scale bar in (j): 25 μm for (a, e-inset), 100 μm for (b-j).

Figure 21:
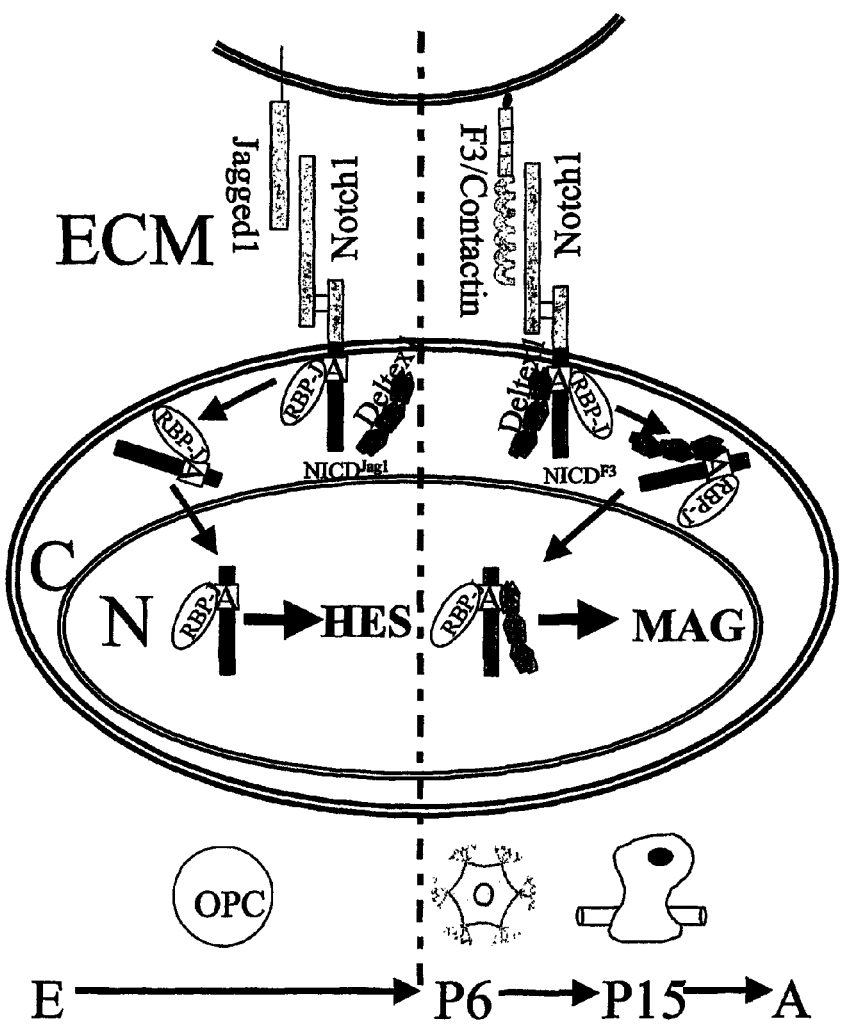

FIG. 21. Proposed model of distinct ligand-dependent Notch signaling pathways during development.

F3 interacts with the Notch receptor on the opposing cell surface to stimulate Notch/RBP-J signaling pathway to recruit DTX1 before or after releasing NICD into the cytoplasm. The NICD/RBP-J/DTX1 complex may undergo specific but unidentified modification prior to translocation into the nucleus where it activates target genes such as MAG. This signaling may contribute to OL maturation after P6 when decreased Jagged1 expression favors the initiation of F3/Notch signaling. In contrast, before P6, Jagged1/Notch signaling activates the NICD/RBP-J-dependent transcription of target genes such as Hes1 and predominantly inhibits OPC differentiation. ECM: Extracellular matrix; C: Cytoplasm; N: Nucleus; $NICD^{Jag1}$, $NICD^{F3}$:NICD released upon Jagged1 and F3 activation, respectively; E: embryo; P6, P15: postnatal day 6 and 15, respectively; A: adult; OPC: oligodendrocyte precursor cell; O: oligodendrocyte; right bottom cartoon: myelinating oligodendrocyte ensheathing the axon.

FIG. 22. NB-3 is a paranodal neuronal molecule.

A. NB-3 is expressed by neurons. Purified neurons, OLs and astrocytes of E17 rats were double stained for NB-3 and corresponding surface marker: NF200 (a), Gal-C (b) and GFAP (c), respectively. Scale bar in (c): 30 μm for (a-c).

(d) NB-3 is expressed from E17. Brain stem from rats with indicated ages were homogenized and subjected to immunoblot for NB-3, P3, MAO.

(B) NB-3 is localized at the paranode. Brain stem sections from 90 day old rats were double labeled for NB-3 and Caspr (a-c) or NB-3 and sodium channels (d-f). Scale bar in (f): 15μm for (a-f).

(C) Lipid raft assay. NB3 was enriched in fraction 5, the same fraction as F3 and Caspr. H: Total homogenate.

Figure 23A:
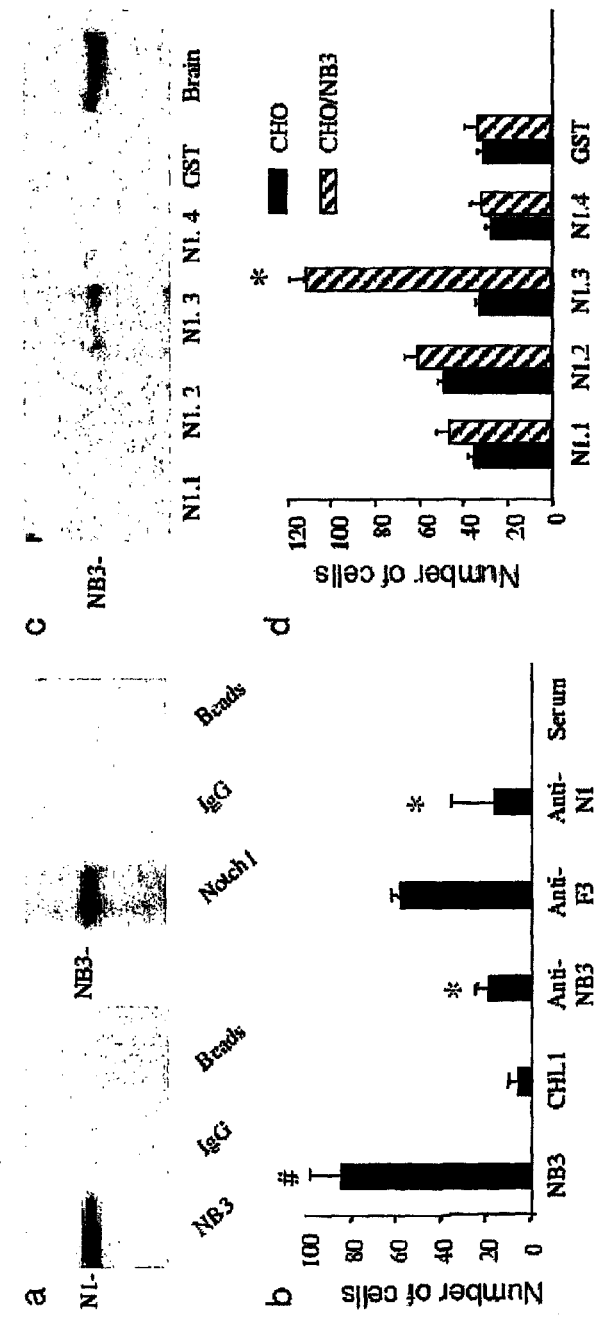
Figure 23B:
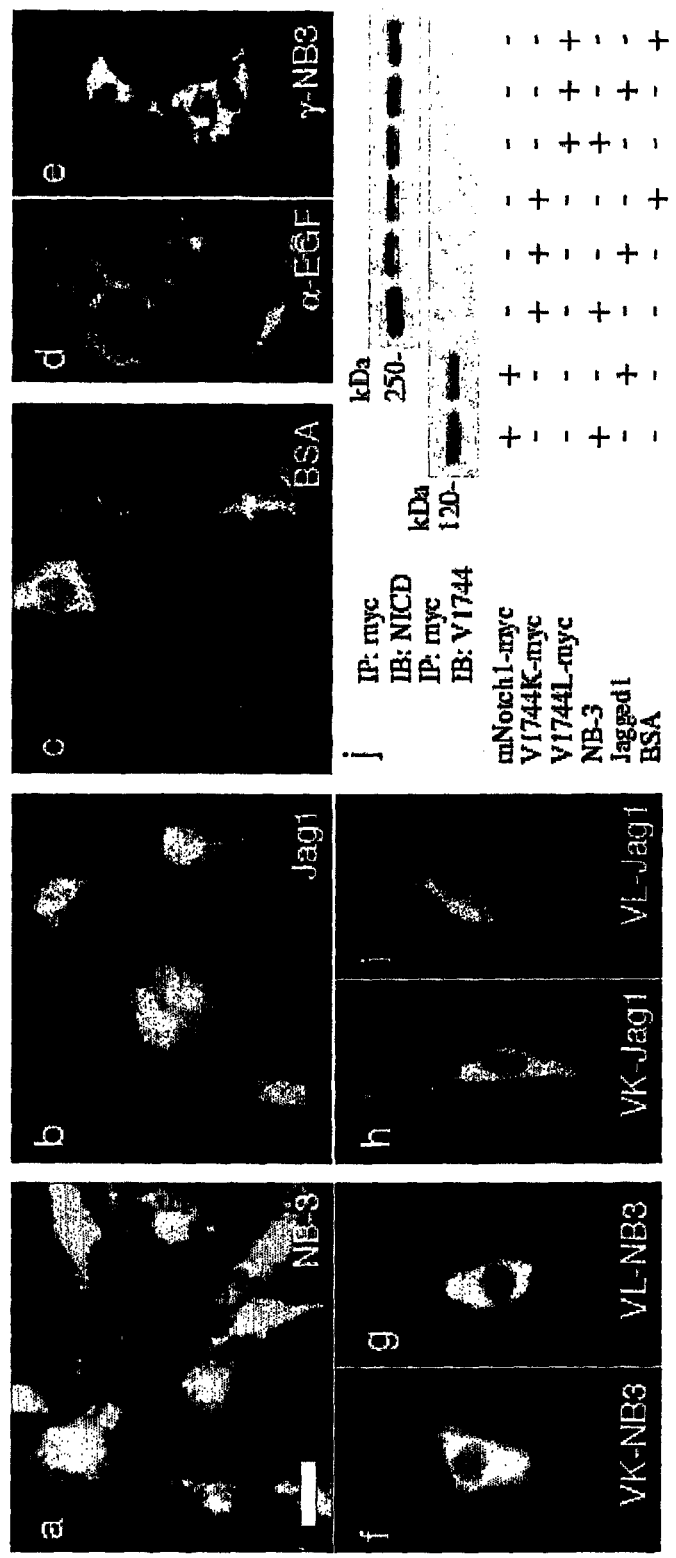
Figure 23C:
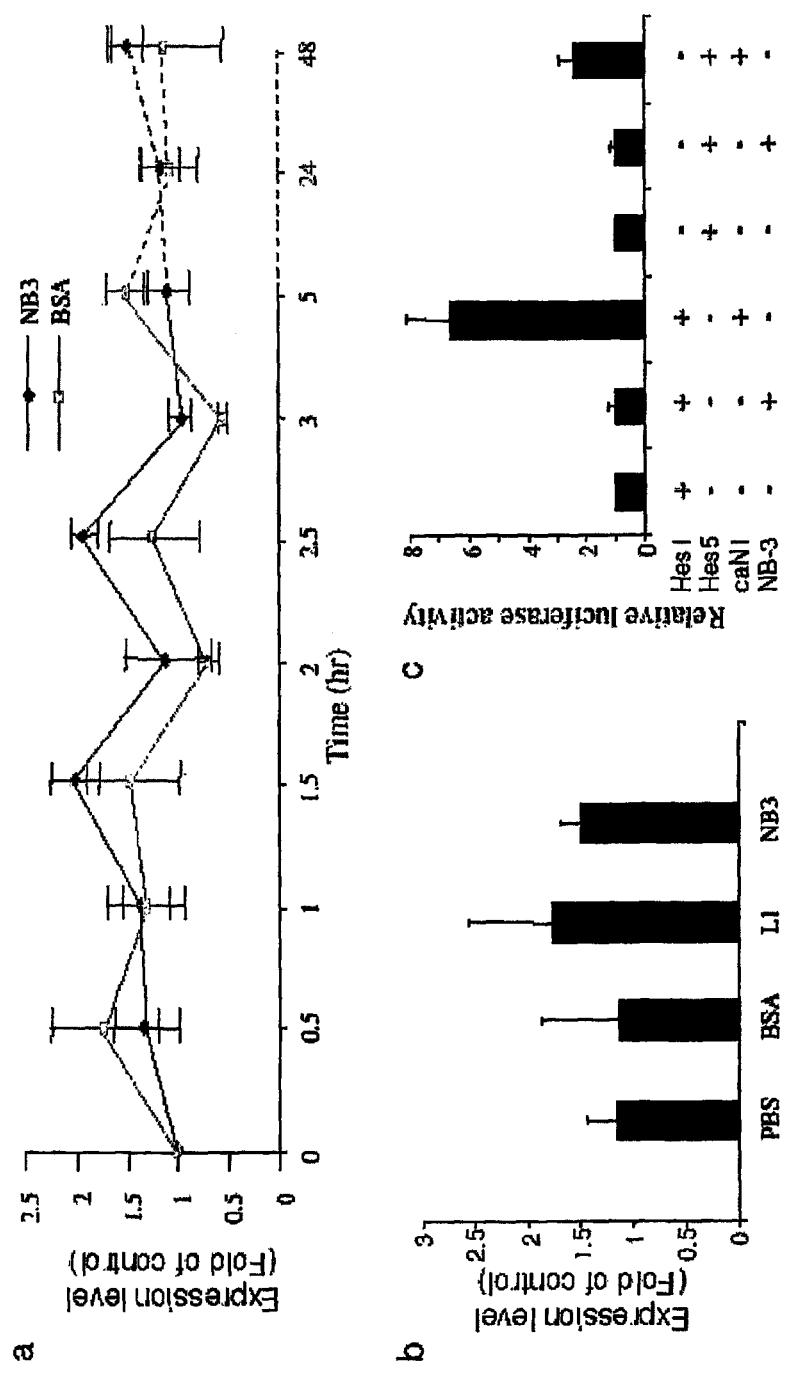

FIG. 23. NB-3 is a functional ligand of Notch1.

(A) NB-3 binds to Notch1. (a) NB-3 co-immunoprecipitated with Notch1. Immunoprecipitates from rat brain lysates using ct-Notch1 and α-NB-3 were probed with α-NB-3 or α-Notch1, respectively. (b) Cell adhesion assay. OLN cells were seeded on NB-3 substrate and adhere to it. Adhesion was specifically blocked by α-Notch1 or α-NB-3. #p<0.05 compared with CHL1; *p<0.05 compared with pre-immune serum. (c) NB-3 binds to specific region on Notch1. The Notch1 GST fusion proteins or GST alone were used in a GST pull-down assay from rat brain lysates. The precipitates and brain lysates were probed for NB-3. (d) Quantification of adherent NB-3- and mock-transfected CHO cells to the four Notch1 GST fusion fragments. *p<0.05 compared with GST. Bar graphs (b, d) represent the number of adherent cells (mean±SD).

(B) NB-3/Notch interaction induces NICD nuclear translocation in OLN cells. mNotch1-myc transfected OLN cells treated with NB-3 (a), Jagged1 (b) and BSA (a) were immunostained for NICD. Some cells were treated with EGP antibody (d) or γ-secretase inhibitor (e) before NB-3 stimulation. OLN cells were also transfected with V1744K-myc (f, h) or V1744L-myc (g, i), treated with NB-3 (f, g) or Jagged1 (h, i), and immunostained with c-myc antibody to locate NICD. Scale bar in (a): 20 μm for (a-i) (j) After NB-3 or Jagged1 treatment, α-c-myc precipitates from mNotch1-myc, V1744K-myc or V1744L-myc transfected OLN cells were immunoblotted by α-NICD (upper panel) or α-V1744 (lower panel)

(c) Hes1 and Hes5 are not activated by NB-3. OLN cells treated with NB-3 for different durations as indicated were lysed and the extracted mRNA subjected to real-time PCR (a). The data were normalized to the mRNA level at the starting point. Other cells were treated with PBS, BSA, L1 or NB-3 for 48 hours and analysed by real-time PCR (b). (c) OLN cells were transfected with Hes1 or Hes5 luciferase reporter alone followed by NB-3 treatment or with caN1 construct. 24 hours post-transfection, cells were subjected to luciferase assay. Data are mean±SD.

FIG. 24. NB-3/Notch Interaction Upregulates MAG via DTX1.
(A) MAG was upregulated in the co-culture of OLN-93 cells and NB-3-transfected CHO cells (a). N-matrix: nuclear matrix protein. CHO/OLN, NB3/OLN: co-culture of OLN-93 cells and mock- or NB-3-transfected CHO cells, respectively. (b) MAG mRNA in primary OLs increased about 24 fold after NB-3 stimulation as monitored by real-time PCR. GAPDH was used as an internal control. OLN cells were treated with NB-3 (c), Jagged1 (d, e) and BSA (not shown) and immunostained for MAG. The fluorescence intensity of MAG was counted (f). Data are mean±SEM.
(B) NB-3-induced MAG upregulation involves DTX1. OLN cells were transfected with dn-N-1-V5 (a), V1744K-myc (b), V1744L-myc (c), caN1 (d, e), dn-RBP-J-myc (h), DTX1-myc (i), DTX1-D1-HA (j), and DTX1-D2-Flag (k), and treated with NB-3. The cells were then immunostained for MAG and corresponding tag. The fluorescence intensity of MAG was counted in transfected and non-transfected cells (1). Data are mean±SD. (f) Schematic structure of DTX1 and its two deletion mutants. Number 1, 2, 3 correspond to N-terminal, proline-rich region and Ring-H2 finger motif, respectively. (g) Hes1 luciferase reporter assays to confirm the validity of indicated constructs. Data are mean±SD. The scale bar in (k): 30 μm for (Ac-e, Ba-k).

Figure 25:
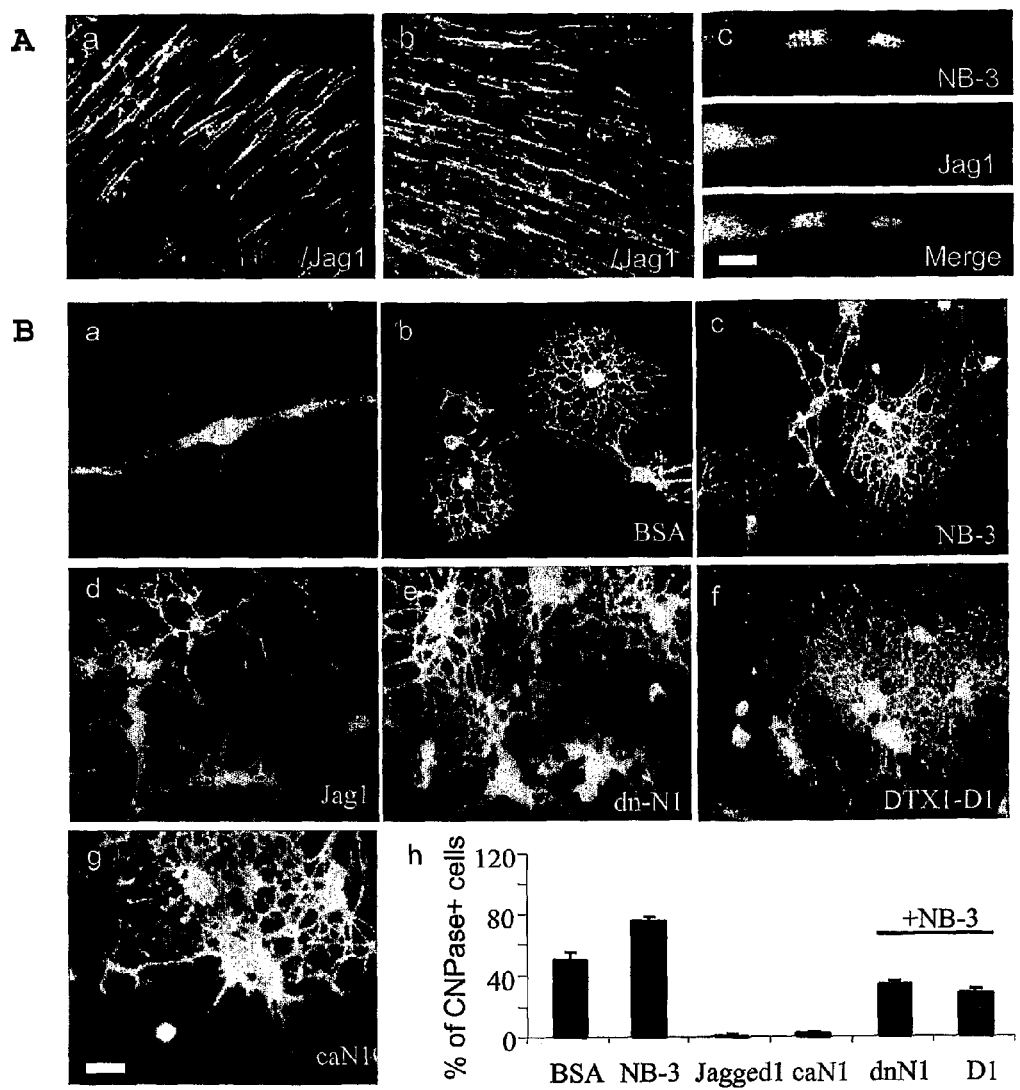

FIG. 25. NB-3 developmentally clustering at paranodes promotes OPC differentiation via Notch1/DTX1 signaling pathway.
(A) NB-3 and Jagged1 are distinctly distributed during development. Brain stems from P2 (a), P5 (b, e) rats were double stained for Jagged1 (green) and NB-3 (red). The scale bar in (e): 30 μm for (a, b), 5 μm for (a).
(B) NB-3/Notch accelerates OPC differentiation via DTX1. Purified Ng2+ OPCs from P7 rat optic nerve (a) were treated with BSA (b), NB-3 (a) or Jagged1 (d) for 2 days and double labelled for Ng2 (red) and CNPase (green). Other cells were transfected with dn-N1 (e), DTX1-D1 (f) followed by NB-3 stimulation or caN1 (g) alone. Cells were then immunostained for tags (green) and CNPase (red). The percentage of CNPase+cells were counted (h). Data are mean±SEM. The scale bar in (g): 40 μm for (a-g).

Figure 26:
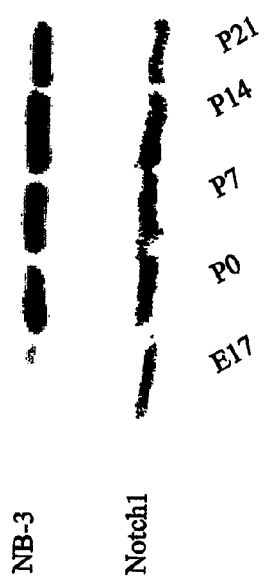
Figure 27A:
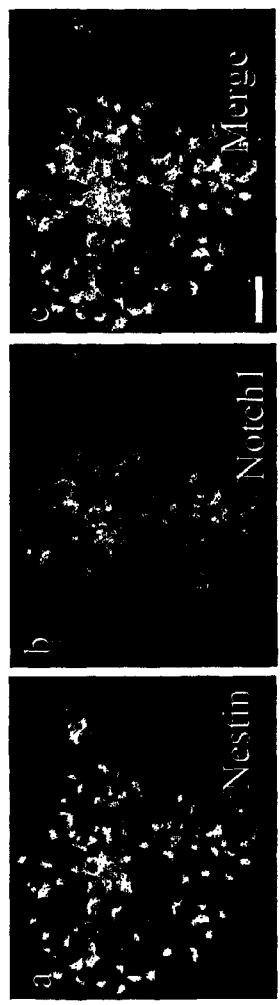
Figure 27B:
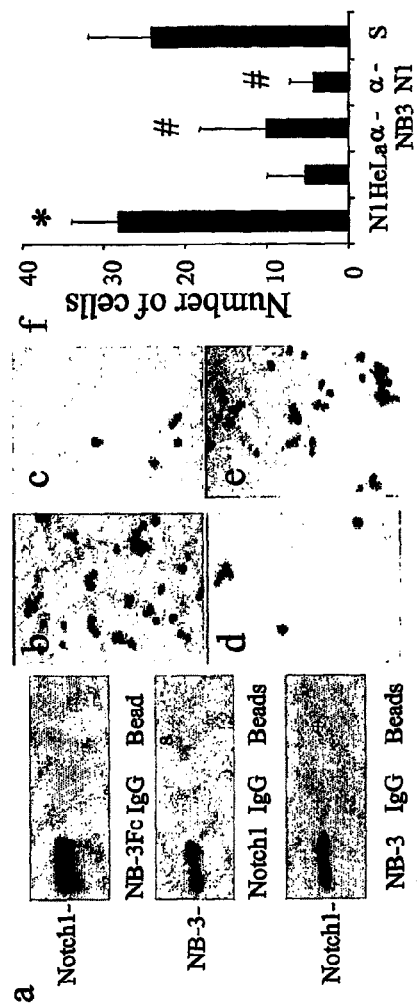
Figure 27C:
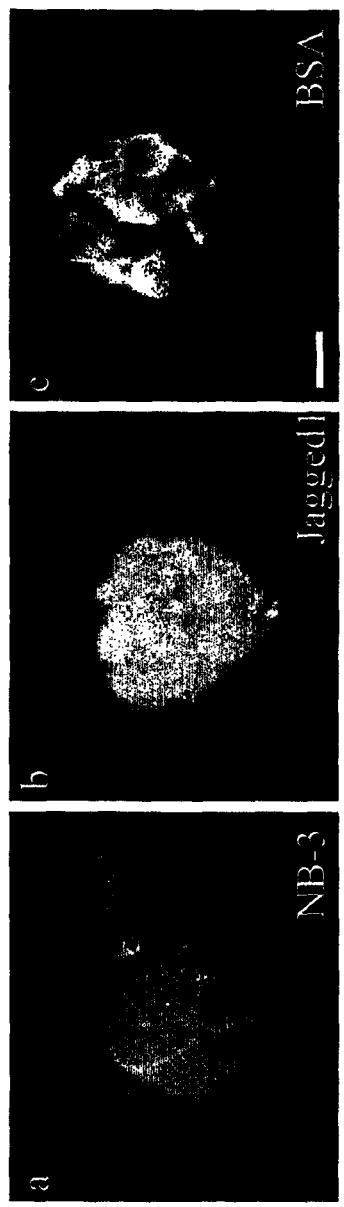
Figure 27D:
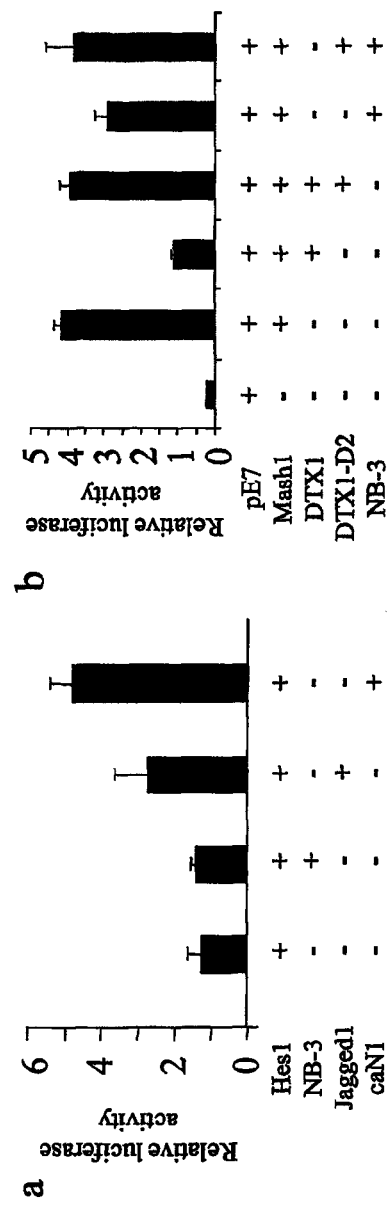

FIG. 26. NSC: Rat brain stems of indicated ages were subjected to Western blot for NB-3 and Notch1 expression patterns.

FIG. 27. NSC: NB-3 is a functional ligand of Notch1.
(A) NSCs express Notch1. NSCs were double stained for precursor marker nestin (a) and Notch1 (b). (a) is the merged picture. Scale bar in (e): 60 μm for (a-e).
(B) NB-3 binds to Notch1. P0 rat brain samples were precipitated by Protein A beads coupled with NB-3-Fc fusion protein, α-Notch1 or α-NB-3 and the precipitates were blotted as indicated (a). N1-transfected Hela cells (N1) were seeded onto coated NB-3 substrate in the absence (b) or presence of blocking antibodies: α-NB-3 (c), α-Notch1 (d) or pre-immune serum (s) (e). The adherent cells were counted (f). Data are mean±SD. *p<0.05 compared with mock-transfected Hela cells; #p<0.05 compared with pre-immune serum.
(C) NB-3 induces NICD nuclear translocation. NSCs were individually treated with NB-3(12.5 nM) (a), Jagged1(50 nM) (b) or BSA (c) for 24 hours then fixed and triple stained for nestin (green), NICD (red) and Hoechst 33258 (blue) to locate NICD. Scale bar in (c): 20 μm for (a-c).
(D) NB-3 does not activate Hes1. NSCs were transfected with Hes1luciferase reporter construct followed by NB-3 or Jagged1 treatment or cotransfected with caN1. 24 hours post-transfection, the cells were lysed and subjected to luciferase assays (a). Other NSCs were transfected with pE7 luciferase reporter together with indicated constructs with or without NB-3 treatment and subjected to luciferase assays (b). Data are mean±SD.

Figure 28:
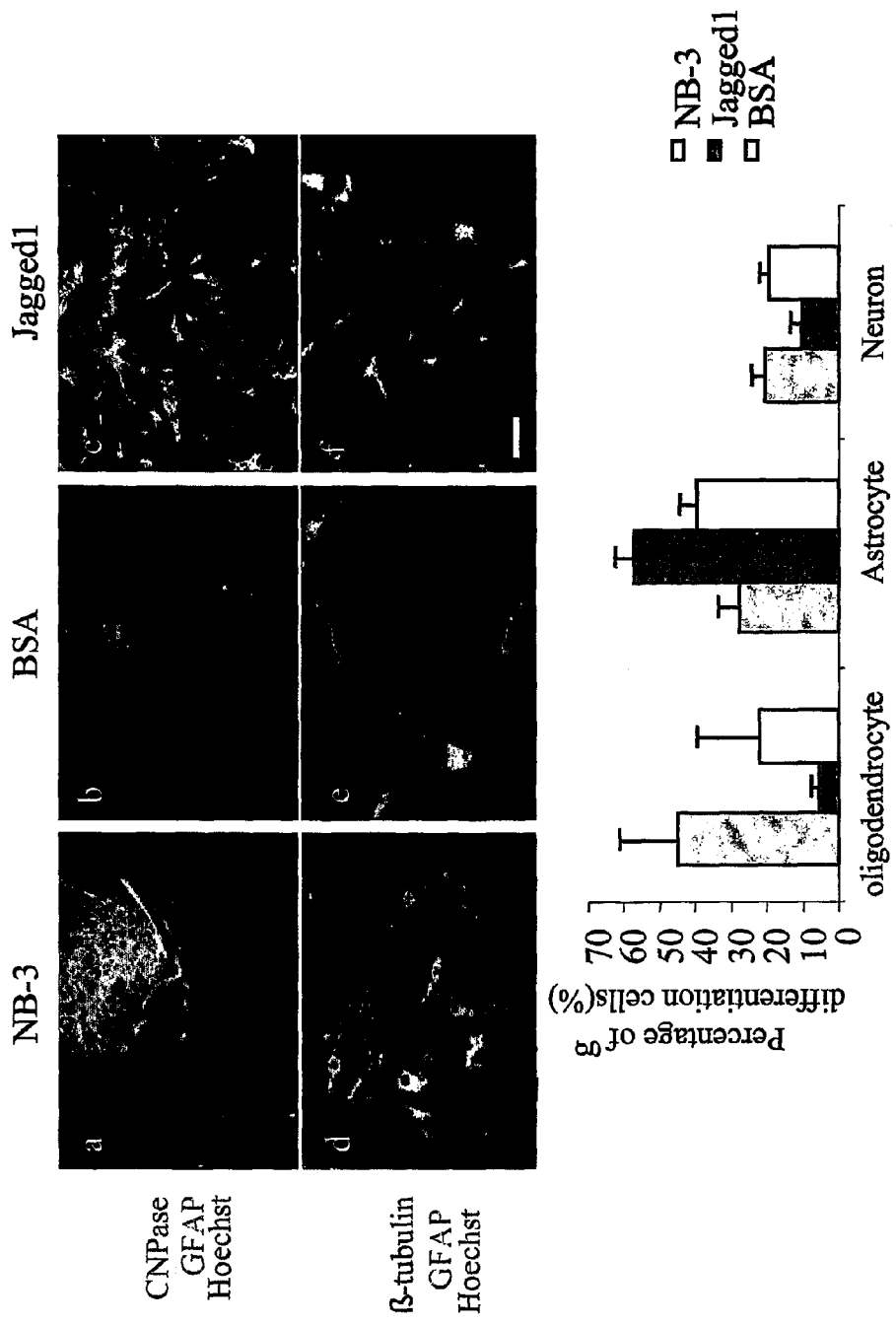

FIG. 28. NSCs: NB-3 promotes OL generation.
NSCs were passaged into mitogen-withdrawn culture medium that was supplemented with NB-3 (a, d), BSA (b, e) or Jagged1 (c, f). After 7 DIV differentiation, the cells were triple stained for CNPase (a-c, red) or β-tubulin (d-f, red), GFAP (a-f, green) and Hoechst 33258 (a-f, blue). Other NSCs were individually immunolabelled with marker antibody and subjected to flow cytometry. The percent of each type of cells: OLs, neurons and astrocytes were counted (g). Data are mean±SEM. Scale bar in (f): 40 μm for (a-f).

Figure 29A:
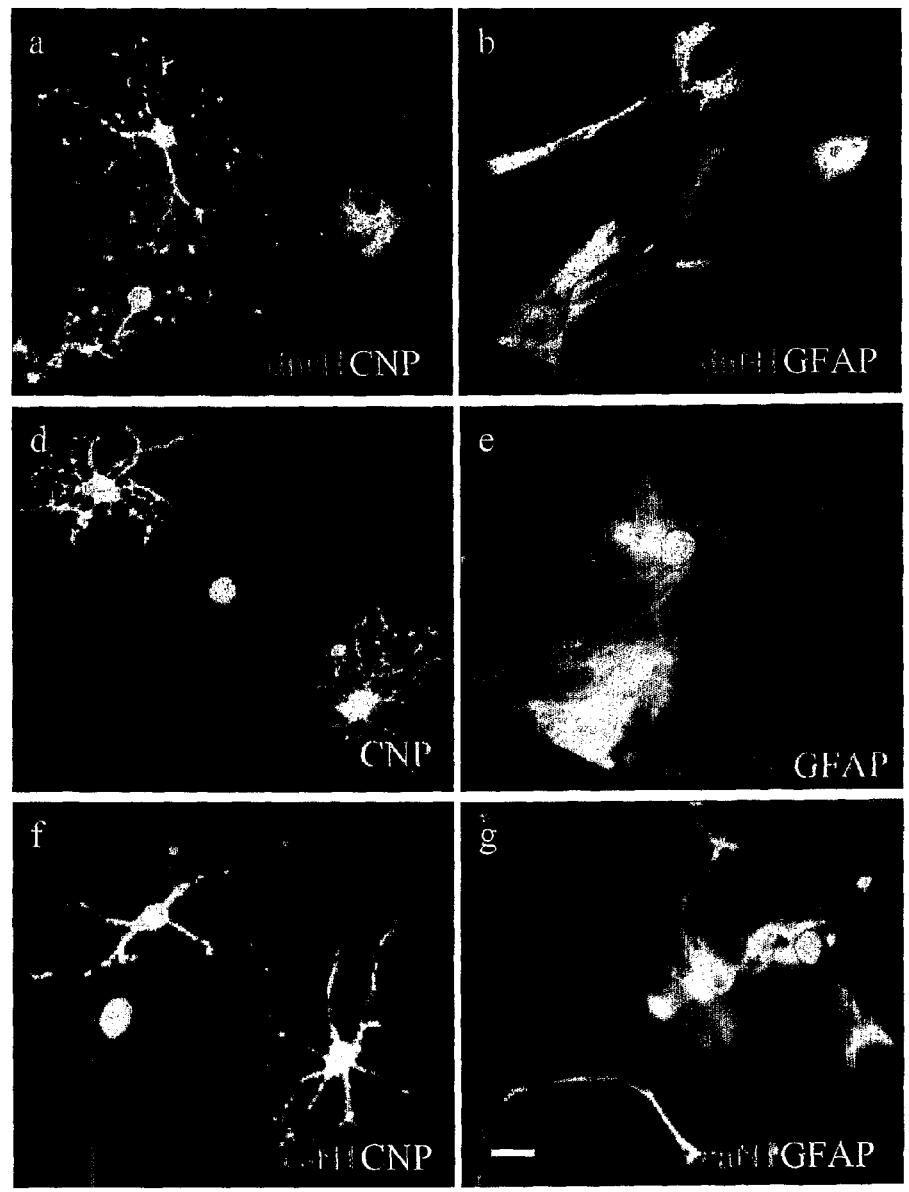
Figure 29B:
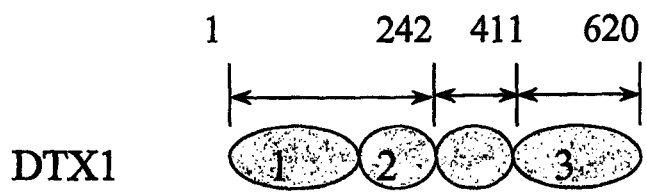
Figure 29B:
Figure 29B:
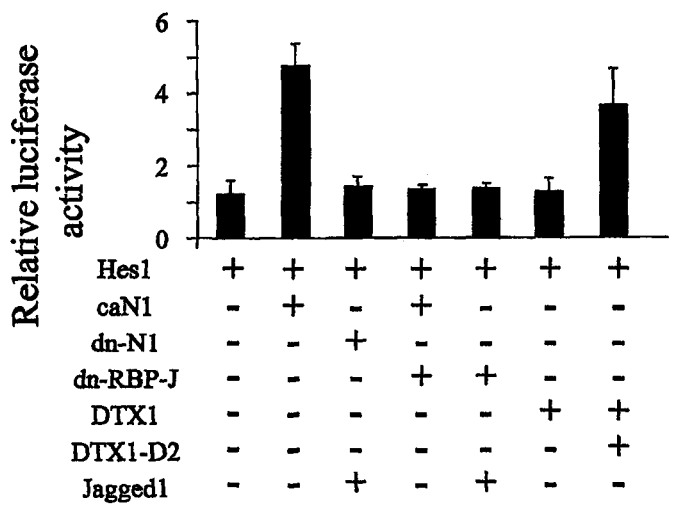
Figure 29B:
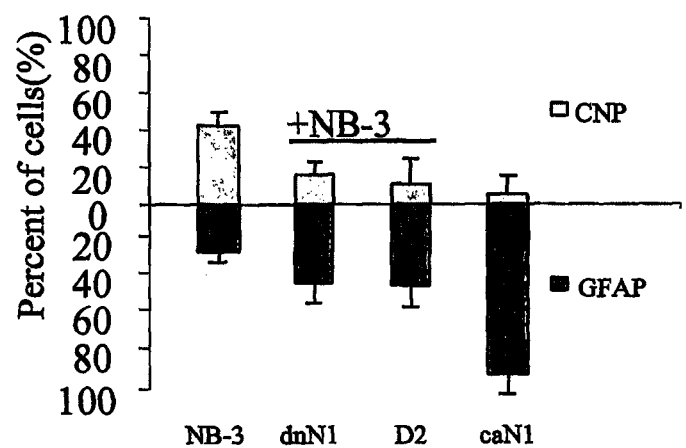

FIGS. 29A and 29B. NB-3/Notch signalling pathway via DTX1 instructs oligodendrogliogenesis.
NSCs were transfected with dn-N1 (a, b), DTX1-D2 (d, e) followed by NB-3 treatment or caN1 (f, g) and double stained for appropriate tags and CNPase (a, d, f) or GFAP (b, e, g). (c) Schematic structure of DTX1 and DTX1-D2 constructs. The validity of the constructs utilized here was confirmed in Hes1 luciferase reporter assays (h). The percents of transfected cells that were positive for CNPase or GFAP were counted (i). Data are mean±SD. Scale bar in (g): 20 μm for (a, b, d-g)

Figure 30:
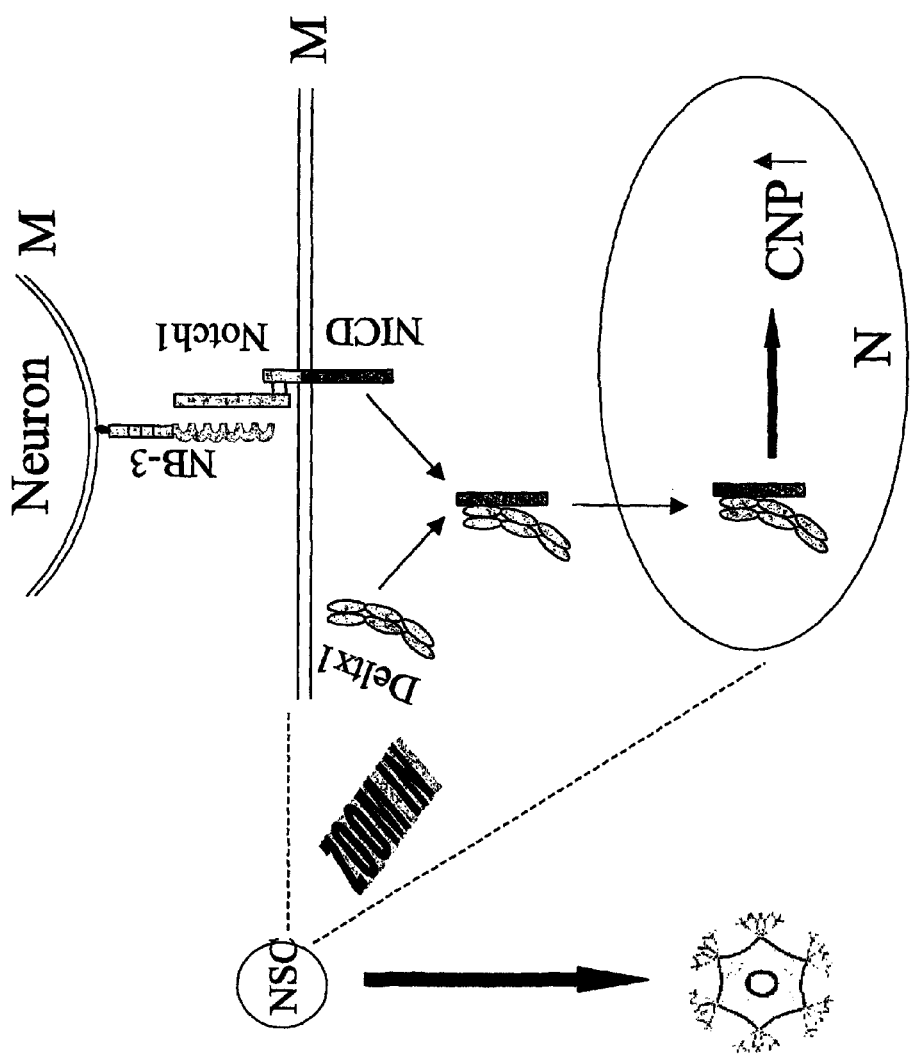

FIG. 30. The putative model.
The extracellular NB-3/Notch interaction releases from the membrane NICD, which recruits DTX1 and translocates into the nucleus where the complex mediates directly or indirectly CNPase expression, thus promoting oligodendrogliogenesis. NSC: neural stem cell; 0: OLs; M: membrane; N: nucleus; CNP: CNPase.

DETAILED DESCRIPTION OF THE INVENTION

Results

Nogo-A is Localized to the Paranodes of Myelinated Axons

Figure 1:
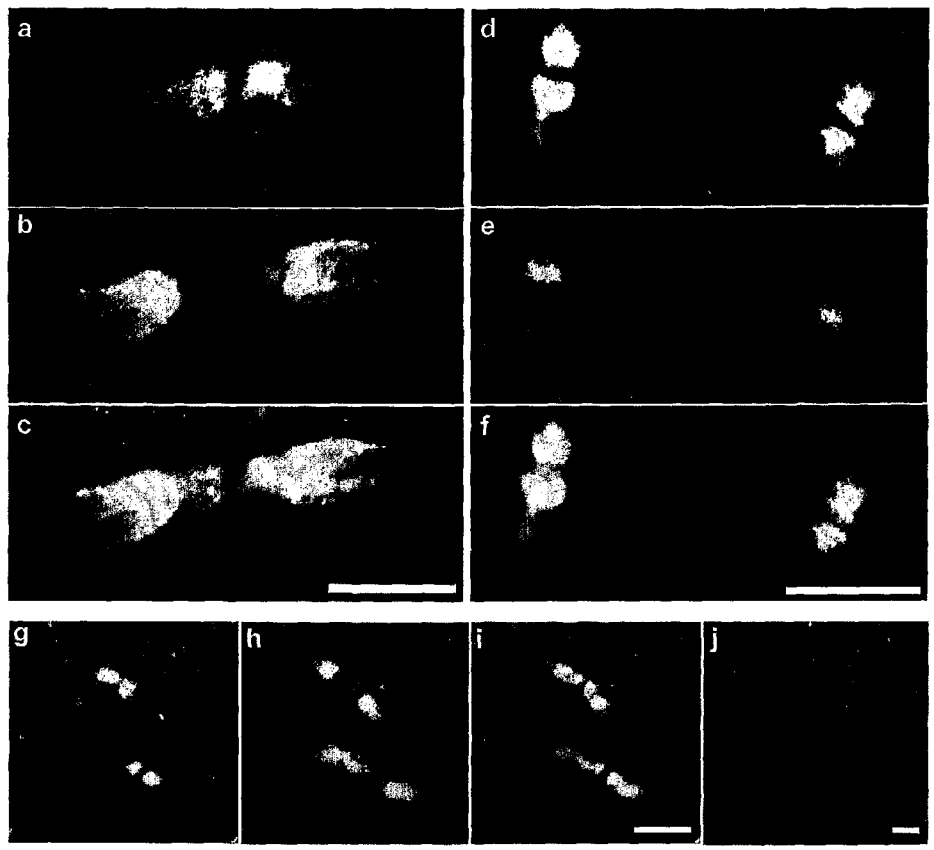
FIG. 1. Glia-derived Nogo-A clusters at the paranodes in CNS.
A. Adult rat brain stem sections were double immunolabeled for Nogo-A (green; a, c, d, f, g, and i) and the Kv1.1 K$^+$ channel α-subunit (red; b, c, h, and i) or PAN Na$^+$ channel (red; e and f). For negative control, Nogo-A antiserum (1:200) was premixed with antigen before staining of an adult brain stem section (j). Two Nogo-A antibodies, one developed in the inventor's lab (a-f) and another was developed in Dr. Stritmatter's lab (g-i), were used in this study. c, f and i are merged images of a-b, d-e and g-h, respectively.
B. Ultrastructural localization of Nogo-A at the paranodes in rat spinal cord. (a) Immunogold labeling of cross sections of myelinated axons revealed that the gold particles were detected at the inner and outer myelin sheaths. (b and c) Immunogold particles of Nogo-A are found within glial loops and the compacted myelin. (d and e) In longitudinal sections of paranodes, immunogold particles of Nogo-A located at the tips of glial loops in the axoglial junction and some within the axon in d. A higher magnification of the boxed areas of d and e were shown in d' and e'. ax: axon; OL: oligodendrocyte.
Figure 1:
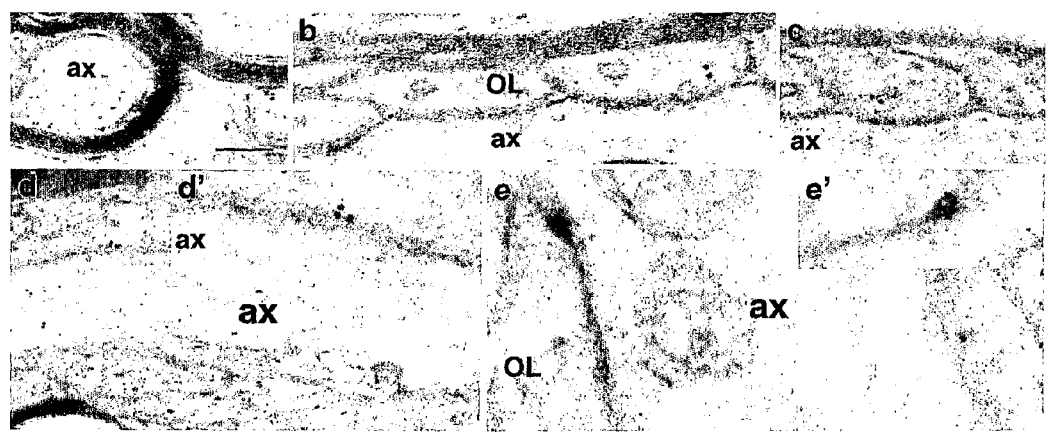

The distribution of Nogo-A was examined along the white matter tracts of adult rat brainstem. In longitudinal sections, similar localization patterns of Nogo-A were observed with two different Nogo-A antibodies: one was developed in the inventor's lab (FIG. 1A, a-f; Liu et al, 2002) and another was a kind gift from Dr. Stephen Stritmatter (Yale University) (FIG. 1A, g-i; Wang et al, 2002). Nogo-A immunoreactivity (green) was confined specifically to paranodal segments along myelinated axons (FIG. 1A), as evidenced by double immunofluorescence labeling with Kv1.1 (red: FIG. 1A, a-c, g-i) or the Na+ channel (red; FIG. 1A, d-f). The specific labeling of Nogo-A in axonal domains was undetectable after the Nogo-A antisera (1:200) were premixed with 100 fold molar excess of antigen (FIG. 1Aj). The Nogo-A staining (green) flanks nodal Na+ channel labeling (red), and is flanked by juxtaparanodal Kv1.1 labeling (red), thus reflecting its paranodal location. Similar observations were made in other nerve fiber-rich CNS sites such as the corpus callosum and the spinal cord (not shown). In the sections examined, Nogo-A was also detected in both neurons and oligodendrocytes (not shown), consistent with other published studies (Huber et al, 2002; Wang et al, 2002; Liu et al, 2002). These observations suggest that Nogo-A may be enriched at the paranode and is a component of the paranodal protein complex.

The specific paranodal location of Nogo-A was further investigated using immuno-electromicroscopy (IEM). Consistent with previous observations (Huber et al, 2002), Nogo-A immuno-reactivity was high in the inner and outer loops of the myelin sheath (FIG. 1B*a*), and low in the compact myelin of rat spinal cord (FIG. 1B*b*). Notably, in longitudinal sections, Nogo-A immunoreactivity was high in the expanded terminal glial loops (FIG. 1B*b* and *c*) and the axoglial junction between the loops and the axolemma (FIG. 1B*d* and *e*) at paranodes, and is present only occasionally in the paranodal axon (FIG. 1B*d*). These observations indicate that Nogo-A is a component of the CNS paranodes.

Nogo-A is a Paranodal Element Mainly Derived from Oligodendroglia

Nogo-A is predominantly expressed in oligodendroglial cell bodies and white matter of the adult CNS (Huber et al., 2002). To characterize the cellular origin of the paranodal Nogo-A, we examined Nogo-A's distribution in two animal models: experimental autoimmune encephalomyelitis (EAE), a condition involving progressive CNS demyelination (Swanborg 2001), and CGT−/− mice known to display a presence of reversed lateral loops but an absence of transverse bands, and abnormal localization of $K^+$ channels along their axons (Dupree et al, 1999). At the peak of demyelination in adult EAE rats, their longitudinal spinal cord sections were prepared for double immunofluorescence staining for Nogo-A or Caspr, and Kv1.1. The density of Nogo-A positive paranodal congregates was significantly decreased (by around 90%) in sections from EAE rats (FIGS. 2A and C) compared to those from control animals. Only occasional foci of Nogo-A positive paranodal clusters (arrowhead; FIG. 2A) and oligodendroglial immunoreactivity remained (star; FIG. 2A). In correlation with the loss of paranodal staining, Nogo-A expression in the spinal cord was downregulated in EAE rats (FIG. 2D). However, Caspr expression was affected to a much lesser extent by this disorder in the spinal cord (FIG. 2B-D).

In P16 wild-type mice, Nogo-A (green) clusters beside the congregated $Na^+$ channels (red) at paranodes (FIG. 2E). In P16 $CGT^{-/-}$ mice, however, congregation of both Nogo-A (green) and $Na^+$ channels (red) was hardly detected along the axons (FIG. 2F). Immunofluorescence analysis on spinal cord sections from P21 wild type and $CGT^{-/-}$ mice was performed using another axonal marker, the 200 kDa neurofilament, in combination with Nogo-A antibodies. Loose spiral-like labeling of Nogo-A was detected along the neurofilament labeled axon in $CGT^{-/-}$ mice (FIG. 2H). This rather deranged labeling pattern is clearly different from the compact clustering pattern of Nogo-A labeling in wild type animals (FIGS. 2E and G), revealing that the congregation of the glial Nogo-A along the axon was severely disrupted in the mutants. IEM observations showed that Nogo-A immunoreactivity was clearly present in the reversed lateral loops at paranodes in these mutant mice (FIGS. 2I and J). Given widespread demyelination and oligodendroglial damage in EAE rats and abnormal nodal and paranodal structures in $CGT^{-/-}$ mice, lost of Nogo-A congregation at the paranodes suggests that paranodal Nogo-A is predominantly associated with OLs.

NgR is Uniformly Distributed Along Myelinated Axons

The inventor next investigated the expression and distribution of the Nogo-66 receptor (NgR), to find out if it also exhibits domain specific congregation patterns in myelinated axons.

Figure 3A:
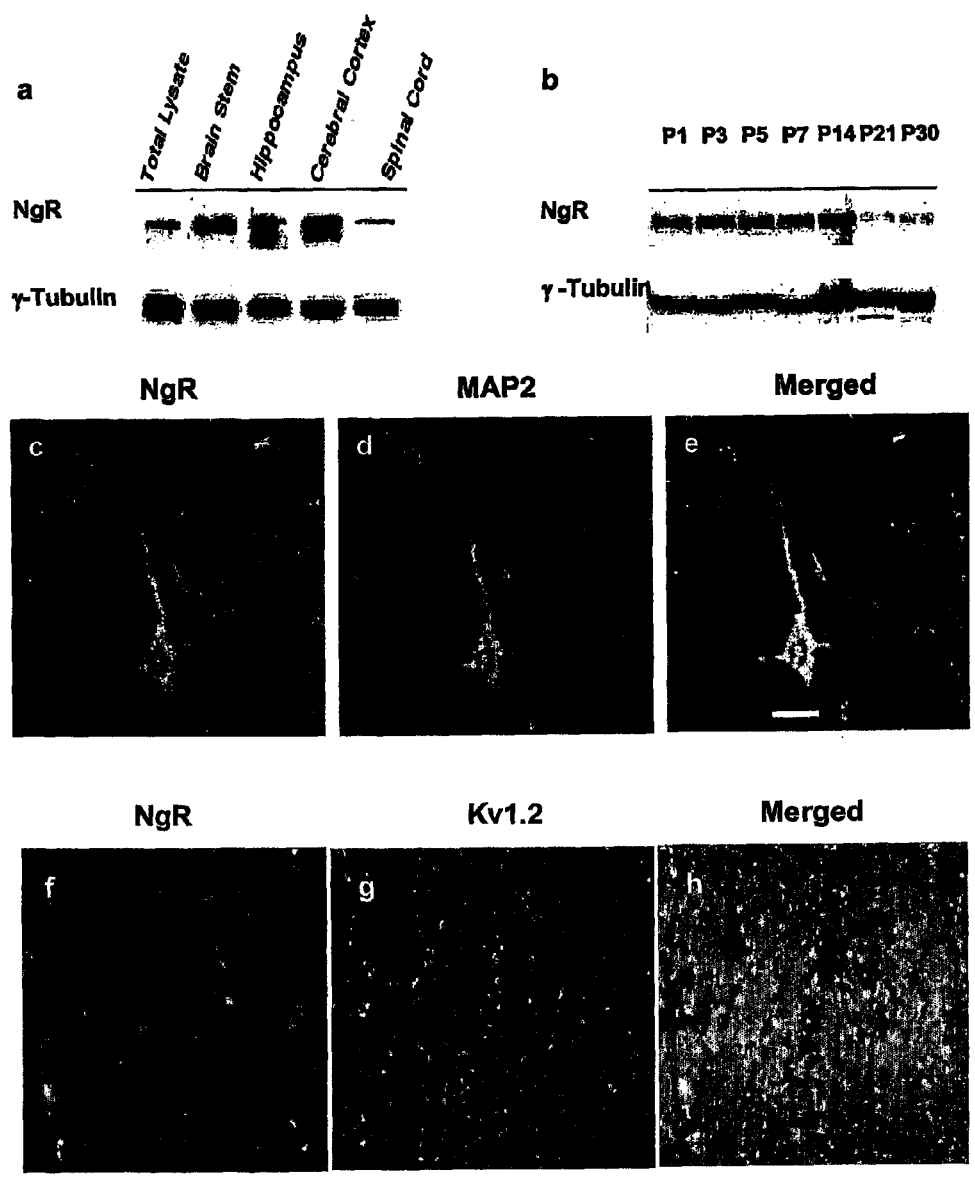

Immunoblot analyses using NgR antibodies demonstrated that NgR expression is higher in adult brainstem, hippocampus, and cerebral cortex, but is much lower in spinal cord (FIG. 3A*a*). NgR is detectable as early as postnatal day 1, with its expression level maintained till postnatal day 14, and subsequently showing a gradual decrease from 3 weeks of age (FIG. 3A*b*). To confirm that the NgR antibodies used could label NgR on neurons, the inventor stained rat hippocampal sections and showed that NgR co-localized with the neuron-specific microtubule-associated protein 2 (MAP2) in cell bodies and processes (FIG. 3A, c-e). Double labeling for NgR and Nogo-A is difficult due to the rabbit polyclonal origin of both antibodies. The inventor instead performer double labeling of NgR and Kv1.1. In longitudinal brainstem sections, NgR is uniformly distributed along axons, contrasting with the congregated $K^+$ channel labeling (FIG. 3A, f-h). Similar NgR labeling was observed in P1, P5, P14, and P30 age groups (not shown). The observation that the NgR localization pattern is distinctly different from the congregated Nogo-A at the paranode raises the possibility that Nogo-A may interact with an axonal receptor other than NgR in these specific axon-glial domains.

Nogo-A Interacts with Paranodal Caspr/F3 Complex

Figure 3B:
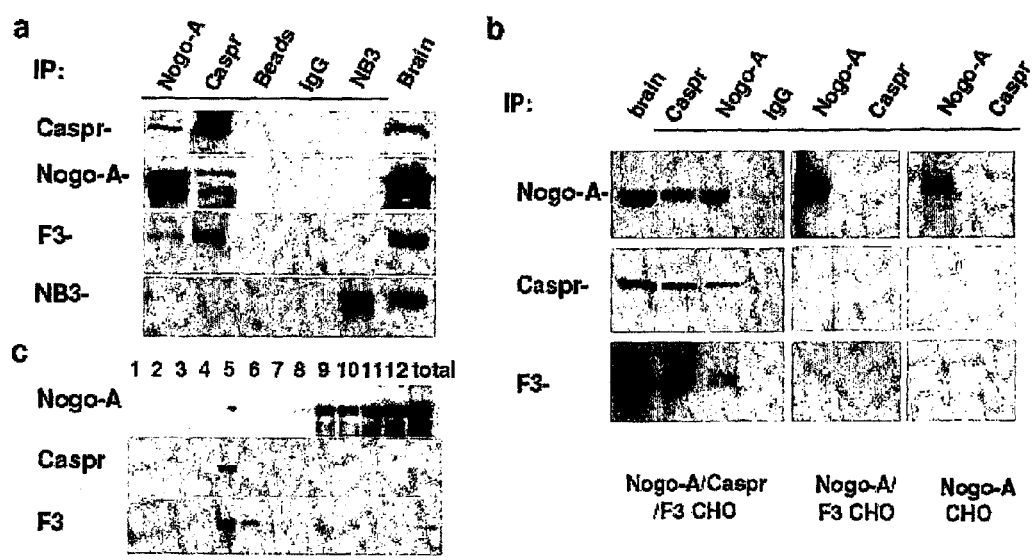

Given the paranodal location of Nogo-A, the inventor investigated whether paranodal axonal components, such as Caspr, F3, and NB3 (an F3-related molecule) (Lee et al, 2000), are Nogo-A binding partners. Nogo-A, Caspr, F3, and NB3 were immunoprecipitated from membrane extracts of adult rat brain. Western blot analysis of the immunoprecipitates resolved on SDS-PAGE revealed that Nogo-A, Caspr, and F3, but not NB3, were present in the immunocomplexes pulled down by either Nogo-A or Caspr antibodies (FIG. 3B*a*). Immunoprecipitation (IP) studies were also performed on Caspr/F3-, F3-, and wild type CHO cells transiently transfected with a Nogo-A expression construct. Transfection was performed using Caspr/F3 expressing cells because F3 is required for proper cell surface expression of transfected Caspr (Faivre-Sarrailh et al, 2000). Western blotting demonstrated that Nogo-A and Caspr indeed associate with each other in Caspr/F3-, but not F3- and wild type CHO cells (FIG. 3B*b*). These observations suggest that Nogo-A interacts specifically with Caspr rather than F3.

The Majority of Nogo-A and Caspr/F3 Complex are not Co-Localized in Lipid Rafts

F3 and Caspr are associated with lipid rafts in neurons, transfected CHO cells, and OLs (Buttiglione et al, 1998; Kramer et al, 1999; Faivre-Sarrailh et al, 2000). To investigate the relationship between Nogo-A and the Caspr/F3 associated microdomains during development, rat cerebral cortexes were lysed and fractionated in a sucrose density gradient according to an established procedure (Kramer et al, 1999). The majority of the known raft-associated protein F3 was detected in fraction 5, and all Caspr in the lysate was virtually found in this fraction, suggesting that both molecules are located in neuronal rafts. On the other hand, the majority of Nogo-A was found in fractions 8-12 that are enriched in cytoskeleton-associated proteins, although a minor portion was present in fractions 5-7 (FIG. 3B*c*). Similar results were obtained using cerebral cortex lysates of both P15 and adult (not shown). These observations demonstrate that the majority of Nogo-A is not present in the neuronal rafts in vivo, and provides indirect support for the notion that paranodal Nogo-A is derived from the oligodendroglial membrane.

Nogo-A Interacts Directly in Trans with Caspr Via the Extracellular Nogo-66 Loop The extracellular domain of Nogo-A consists of a 66 amino acid loop between its two transmembrane domains, known as the Nogo-66 domain (Fournier et al, 2001). Any interaction in trans between Nogo-A and Caspr should involve the Nogo-66 domain. The inventor next investigated whether the Nogo-A and Caspr associate directly in a trans-manner that is independent of F3 using a cell adhesion assay. Different CHO cell lines (expressing Caspr or otherwise) were plated onto substrates coated with the Nogo-66 peptide or recombinant GST fusion proteins containing Nogo-66 (GST-Nogo-66) or the cytoplasmic N-terminal domain of Nogo-A (GST-Nogo-N) as well as GST. Only Caspr/F3-expressing, but neither F3-expressing nor wild type CHO cells, adhered readily to Nogo-66 (FIG. 4A-C) or GST-Nogo-66 (FIG. 4E-G). None of these CHO cell types adhered well to GST (FIG. 4I-K) or GST-Nogo-N (not shown). Quantification of adhering cells indicated that the number of Caspr/F3-CHO cells binding to both Nogo-66 and GST-Nogo-66 was much higher than in other experimental groups (FIG. 4M).

To investigate if Nogo-66 interacts with Caspr only or a binding pocket generated by the cell surface Caspr/F3 complex, the inventor removed the GPI-linked F3 using phosphatidylinositol-specific phospholipase C (PI-PLC). After a PI-PLC treatment, Caspr/F3-CHO cells still adhered to both Nogo-66 and GST-Nogo-66, but not to GST coated substrates (FIGS. 4D, H, L and M). To ensure that F3 was completely removed from the cell surface after PI-PLC treatment, increasing concentrations of PI-PLC (0.02, 0.04 and 0.06 units/ml) were used. Cell binding was constant in all three different concentrations of PI-PLC (FIG. 4N). In agreement with previous work (Faivre-Sarrailh et al, 2000), Western blot (FIG. 4O) and immunostaining (not shown) using F3 antibodies demonstrated that a significant amount of F3 was indeed removed from Caspr/F3-CHO cells after treatment with PI-PLC. This lack of effect of PI-PLC on the cell adherence to Nogo-66 substrates suggests that F3 is not directly involved in the trans-interaction between Nogo-66 and Caspr.

The Nogo-A/Caspr Complex Interacts with $K^+$ Channels

During myelination, the proper segregation of $K^+$ channels to juxtaparanodes requires an intact paranodal axoglial junction (Vabnick and Shrager, 1998). This structure is formed and maintained by axonal molecules such as Caspr and F3, as well as by glial specific molecules during myelination and remyelination (Girault and Peles, 2002). The inventor hypothesized that the interaction of Nogo-A with Caspr forms an axo-glial signaling connection that could influence $K^+$ channel's final location at juxtaparanodes during the early stages of myelination. Immunoprecipitation analyses were performed to investigate whether $K^+$ channels could physically interact with Nogo-A/Caspr complex in the CNS. Both Nogo-A and Caspr antibodies reciprocally precipitated Kv1.1 and Kv1.2, but not Kv2.1 (not shown), from P7 and adult (not shown) mouse brain extracts, while NB3 antibody and non-immune IgG did not (FIG. 5Aa). Kv2.1 is generally found in neuronal cell bodies and proximal dendrites, but is excluded from axons (Trimer et al, 1991). In GST pull-down assays using membrane extracts of adult mouse brain, both Caspr and Kv1.1 could be pulled down by GST-Nogo-66, but not by GST-Nogo-N or GST itself (FIG. 5Ab). These results support the notion that Nogo-66 is a trans-interacting partner of Caspr, and that $K^+$ channels may interact with the complex.

Nogo-66 Via Caspr Interacts Indirectly with $K^+$ Channels

The inventor next investigated whether Nogo-66 could directly interact with $K^+$ channels. Kv1.1 cDNA was transiently transfected into Caspr/F3-, F3- and wild type CHO cells and the membrane extracts were subjected to a GST pull-down assay using GST and GST-Nogo-66 fusion proteins, respectively. Wild type and F3-expressing CHO cells did not express Caspr (FIG. 5Ba). Western blot analysis showed that both Kv1.1 and Caspr could only be precipitated by GST-Nogo-66, but not GST, from the Caspr/F3-expressing, but not F3-expressing and wild type CHO cells (FIG. 5Bb). These results demonstrate that Nogo-66 could interact indirectly, at least in vitro, with $K^+$ channels via Caspr.

Nogo-A and Caspr Share a Similar Spatial and Temporal Relationship to Kv1.1 Along Myelinated Axons In view of the potential interaction between the paranodal Nogo-A/Caspr and Kv1.1 established above, the inventor explored the dynamic relationship between Nogo-A/Caspr and Kv1.1 distribution along myelinated axons during development. Double immunofluorescence labelings of Caspr and Kv1.1, and of Nogo-A and Kv1.1, were performed on brainstem sections of rats at various postnatal days. Congregations of both Caspr and Kv1.1 labeling were apparent from approximately P5 onwards (FIG. 6Aa). From P5-P14 (FIG. 6A, a-c), Caspr staining at paranodes overlapped that of Kv1.1, suggesting co-localization of both molecules at this critical early period of myelination. At P30 (FIG. 6Ad), Kv1.1 labeling became more distinctly juxtaparanodal, with only minimal bands of overlap with Caspr at paranodal-juxtaparanodal borders. In the adults (FIG. 6Ae), Caspr and Kv1.1 were segregated into their different microdomains along the myelinated axons. Double immunofluorescence staining for Nogo-A and Kv1.1 at P1 (FIG. 6B, a-c) revealed that Nogo-A was diffusely labeled along the nerve fibers. At P5 (FIG. 6B, d-f), clustering and aggregation of Nogo-A staining became more evident. However, the staining pattern still did not have well-defined domains or borders. Nodal gaps were apparent and hemi-nodes were seen as well. From P7 (FIG. 6B, g-i), Nogo-A distribution demonstrated an obvious clustering towards the paranodes. From P5-P14 (FIG. 6B, j-l), there were varying degree of overlap between congregates of Nogo-A and Kv1.1 immunostaining at both paranodal and juxtaparanodal regions. At P30 (FIG. 6B, m-o), the Kv1.1 congregates were exclusively localized to juxtaparanodes, akin to the situation in adult animals.

Co-localization of the Nogo-A/Kv1.1 and Caspr/Kv1.1 was quantified by measuring the lengths of Nogo-A and Kv1.1 labeled regions on captured images (FIG. 6Ca). The average length of a Nogo-A labeled region was about 9 μm at P5, 5 μm at P7, but this shortened to about 2 μm from P14 to adult, suggesting that Nogo-A is progressively congregated into narrower bands during the early stages of myelination. The average length of a Kv1.1 labeled region did not demonstrate such a marked change with time: 6 μm at P5 to 8 μm in the adult. Of note was the change in terms of the length of overlap between Nogo-A and Kv1.1 labeling: it decreased from 4 μm at P5, 2 μm at P14, and 1 μm at P30 to approximately 0 μm in the adult. This change demonstrates a transient co-localization of Nogo-A and Kv1.1 in paranodal regions before compact myelin is fully laid down. The degree of co-localization between Nogo-A/Kv1.1 and Caspr/Kv1.1 was also compared (FIG. 6Cb). From P5-P14, >60% of paranodes in every field of view were double labeled for Nogo-A/Kv1.1 and Caspr/Kv1.1, respectively. In adults, Nogo-A and Caspr separated from Kv1.1 and a complete segregation was observed. Given that $K^+$ channels bind to the Nogo-A/Caspr complex, these observations imply that the Nogo-A/Caspr complex may transiently interact with $K^+$ channels, and as such may cooperatively regulate the paranodal localization of Kv1.1 during the early stages of myelination.

Nogo-A and $K^+$ Channel in Demyelinating Animal Models

Shiverer is a hypomyelinating mutant mouse that lacks myelin basic protein (MBP) and has axons with normal oligodendroglial ensheathment, but displays aberrant axoglial junctions and abnormal localization of $K^+$ channels along its axons (Rasband and Trimmer, 2001a). To investigate the roles of glia-related molecules in the regulation of $K^+$ channel localization in myelinated axons, the distribution of Nogo-A, Caspr, and Kv1.1 was examined in both EAE rats and Shiverer mice. Double immunofluorescence staining demonstrated that both disorganized Caspr (green) and Kv1.1 (red) labelings were still detectable in the paranodal region of EAE rat (FIG. 7A), compared to normal rat (FIG. 7B) brainstem. In contrast to the location of paranodal Nogo-A (green) and juxtaparanodal Kv1.1 (red) in the spinal cord sections of normal mice (FIG. 7C), Nogo-A staining was diffused along the axons and its congregates were hardly detectable in the paranodal region of Shiverer mice (FIG. 7D-G). Nogo-A immunoreactivity in OLs, however, remained intact and distinct (arrows; FIGS. 7C, F and G). In accordance with previous observations (Poliak et al, 2001), disorganized Caspr and Kv1.1 labeling co-localized at paranodes in Shiverer mice (FIG. 7I) but not normal mice (FIG. 7H). Quantitative analysis of the distance between paired Kv1.1 immuno-stainings demonstrated that the distances between the pairs were significantly reduced in both EAE and Shiverer mice versus normal animals (P<0.01; FIG. 7J). These observations suggest that, in both pathological conditions of EAE rats and Shiverer mice displaying paranodal junction defects, $K^+$ channels are actually relocated to the paranodes. Concomitantly, the congregation of Nogo-A at the paranode was markedly reduced. Thus, in addition to axonal molecules, certain glia-derived molecules involved in formation of axoglial junctions may also be essential for proper $K^+$ channel localization at juxtaparanodes in normal adult animals. At the moment, the molecular structural basis for these changes is unknown to the inventor, but may well be related to the interaction between $K^+$ channels and the Nogo-A/Caspr complex.

Discussion Relating to the First Aspect of the Invention

Nogo-A, but Not the Nogo-66 Receptor, is a Hallmark of the Paranode

The location of Nogo-A in oligodendroglia and CNS myelin has already been described (Huber et al, 2002; Liu et al, 2002; Wang et al, 2002). Specifically, Nogo-A has been localized to oligodendrocyte cell bodies and processes and to the innermost loop and outer loop of the myelin sheath (Huber et al, 2002). In the developing cerebellum, the time course of appearance of Nogo-A mRNA and protein parallel the time frame for myelination, occurring in a period just prior to the expression of myelin basic protein. These observations suggest a role for Nogo-A during myelination.

Increasing evidence points to the importance of axon-glial communication in the regulation of oligodendrocyte differentiation (Barres et al, 1999; Marcus et al, 2000) and ion channel clustering on neurites (Dupree et al, 1999; Ishibashi et al, 2002). The inventor has investigated whether Nogo-A was localized to distinct sites involved in such intercellular signaling and has shown that Nogo-A is mainly localized at the gaps between $Na^+$ and $K^+$ channels along axons and its immunoreactivity is clearly located at sites where glial loops make contact with the axonal membrane surface in adult CNS. This suggests that Nogo-A is a paranodal component, which is further confirmed by the observations in several pathological animal models. In accordance with Nogo-A downregulation, its congregates are significantly reduced at paranodes in EAE animals. Nogo-A immunoactivity presents in the reversed paranodal loops in $CGT^{-/-}$ mice, however, congregated Nogo-A is also hardly detectable at paranodes in both $CGT^{-/-}$ and Shiverer mice. Altogether, these observations support the notion that Nogo-A is a paranodal glial component (FIG. 8).

The staining pattern and oligodendroglial origin of paranodal Nogo-A raised the question as to whether it interacts with components on the axonal surface. So far, the only known high affinity neuronal receptor for Nogo-A is the Nogo-66 receptor (NgR). Previous work has shown that NgR expression in neurons and along myelinated axons is predominantly found in adult animals and that its expression during myelination is minimal (Fournier et al, 2001; Hunt et al, 2002; Wang et al, 2002). The inventor's results are consistent with these findings, in that they show that NgR is located in the brainstem on neuronal cell bodies and uniformly distributed along myelinated axons from the early stages of development until adulthood. It is intriguing that there is significant Nogo-A clustering at paranodes, while the NgR distribution pattern remained diffuse along axons. As the congregation of Nogo-A coincides with the developmental period of myelination, paranodal Nogo-A may therefore participate in this process and may interact with a molecule other than NgR, for a function distinct from inhibition of axonal sprouting.

Paranodal Nogo-A is a Glial Ligand of Caspr

At the paranodes, the GPI-anchored axonal F3/contactin exists as a complex with the membrane protein Caspr. The Caspr/F3 complex interacts with NF155, a glial-derived molecule, in trans, and is an example of axoglial molecular connection at the paranode (Girault and Peles, 2002). The inventor has shown that Nogo-A associates specifically with the Caspr/F3 complex, but not NB3, another paranodal molecule, in co-IP assays, implicating an interaction between Nogo-A and the complex in vivo. The observation that the majority of CNS Nogo-A is not co-localized with the complex in neuronal lipid rafts implies that this interaction probably occurs in a trans-manner, with Nogo-A from the OL membrane interacting with Caspr/F3 from the axonal membrane. Although it remains a possibility that axonal Nogo-A is a cis-binding partner of Caspr/F3 complex, and is dependent upon myelination for congregation, this seems unlikely since the paranodal Nogo-A is predominantly expressed by OLs in the CNS (Huber et al, 2002: Liu et al, 2002; Wang et al, 2002). To support the notion, the inventor has further shown that Caspr/F3-expressing CHO cells bind to both substrates coated with Nogo-66 peptides and GST-Nogo-66, where the binding must occur in a trans manner. That binding occurs even after removal of F3 from the cells via PI-PLC treatment further implies that Nogo-A interacts directly with Caspr (FIG. 8).

Nogo-A May Complement Caspr in Regulating Kv1.1 Location

There is strong evidence suggesting that $K^+$ channel accumulation at the juxtaparanode is influenced by myelinating OLs (Vabnick and Shrager, 1998). Shaker-type $K^+$ channels are multi-protein complexes composed of Kv1.1, Kv1.2 and Kvβ2 subunits (Rasband and Trimmer, 2001b). In the myelinated axons of the CNS, $K^+$ channel labeling becomes more prominent during the progression of postnatal development, initially localizing to juxtaparanodes and also to paranodal bands that alternate with Caspr immunoreactivity (Rasband et al, 1999). At later stages of postnatal development, $K^+$ channels are excluded from the paranodes and become exclusively juxtaparanodal. The inventor has shown that Nogo-A, via Caspr, associates indirectly with Kv1.1. However, the developmental changes in the distribution pattern of Nogo-A and Kv1.1, as well as in those of Caspr and Kv1.1, are similar, implying that the interaction between Kv1.1 and Nogo-A/Caspr complex occurs, at least transiently, when Nogo-A/Caspr colocalizes with Kv1.1 at paranodes during the early stages of myelination. Nogo-A may therefore play a complementary or regulatory role to Caspr in the organization of mature axonal domains and in so doing aid in the coordinated localization of $K^+$ channels to juxtaparanodes (FIG. 8).

Investigation of Nogo-A (or Nogo-A/Caspr) conditional transgenic or knockout animals in viva, possibly using OL specific promoters, may help to further reveal the role of Nogo-A during myelination. According to the inventor's quantitative analyses, the distances of the gap within paired K+ channel clusters were significantly reduced. This occurs in conjunction with a significant reduction in Nogo-A clusters in both EAE rats and Shiverer demyelinated axons compare d to normal myelinated axons. These observations imply that K+ channels co-localize with Caspr again in the pathological conditions, although it would be interesting to explore whether this transient interaction also occurs during remyelination.

A point that also warrants further investigation is the structural and functional nature of the interaction between Nogo-A, Caspr, and the K+ channels. It should be noted that the localization of Caspr family members demarcate distinct domains in myelinated axons. Caspr2, which is about 45% identical to Caspr, is localized to the juxtaparanodes of adult myelinated axons. It associates with K+ channels indirectly via its C-terminus, which contains a putative PDZ binding site (Poliak et al, 1999), a feature shared by two other recently described members of the mammalian Caspr family, Caspr3 and Caspr4 (Spiegel et al, 2002). The C-terminus of Caspr is rather unique compared to other members of the family in terms of its length, and the antibody the inventor has raised is unlikely to cross react with the other Caspr isoforms. The C-terminus of Caspr does not have a putative PDZ binding motif, but shares a band 4.1 binding domain with Caspr2 (Scherer and Arroyo, 2002) It would be interesting to determine if this domain of Caspr mediates its interaction with Kv1.1 and Kv1.2.

Nogo-A Interactions in the CNS

The only known interacting partners of Nogo-A other than NgR are the Nogo-interacting mitochondrial protein (NIMP) (Hu et al, 2002), α-tubulin, and MBP (Taketomi et al, 2002). All these interactions are likely to involve the intracellular domains of Nogo-A, and not the Nogo-66 extracellular loop, which is the Nogo-A domain most likely to function as an intercellular signaling ligand. The inventor's results indicate that the oligodendrocyte surface Nogo-66 loop binds directly to axonal surface Caspr, thus implying a previously unsuspected function of Nogo-A at the axoglial junction. This interaction does not appear to involve NgR. In fact, it is unclear if any permanently recurring interaction between adult oligodendroglial Nogo-A and axonal NgR is required under normal physiological conditions. The inventors believe that the Nogo-A/Caspr interaction may in some manner shape and maintain the architecture of the axoglial junctions during and after myelination (FIG. 8). More specifically, this interaction may have a role in organizing the location of other molecules at specific junction domains.

In summary, the inventor has shown that oligodendrocyte Nogo-A is clustered at specific axoglial junctions, where it interacts directly via its extracellular Nogo-66 loop with axonal Caspr, and indirectly with K+ channel proteins. This represents the first NgR-independent Nogo-66 interaction described to date, and has significant implications for the role of Nogo-A in formation and maintenance of axoglial junction architecture.

Materials and Methods Relating to the First Aspect of the Invention

Antibodies

The polyclonal antibody against Nogo-A was previously described (Liu et al, 2002). Two polyclonal antibodies against NgR were used in the inventor's experiments. One raised in rabbit with a glutathione S-transferase (GST) fusion protein to amino acids 277-430 of human NgR and another a gift from Dr. Stephen Strittmatter (Yale University School of Medicine, New Haven; Wang et al, 2002). Antibodies against F3 and NB-3 were described previously (Ang et al, 2001).

To raise polyclonal antibodies against Caspr, a 230 bp fragment encoding the cytoplasmic region (amino acids 1308-1377) of human Caspr (Einheber et al, 1997) was amplified from human brain cDNA using primers 5'-AGTCGGATCCACAAAATC ATCGA/CTAT/CA/CAGGG-3' (forward) and 5'-ACTCGAATTCAGACCTG-GACT CCTCCTCCAA/GGATCTGG-3' (reverse) with an added BamH1 or EcoR1 site, respectively. The amplified fragment was digested with BamH1 and EcoR1 and subcloned in-frame into pGEX-3C, and the sequence of the final construct was verified by DNA sequencing. The plasmid was transformed into *E. coli* BL21, and upon induction a Caspr-GST fusion protein of the expected size was recovered from bacterial lysates using glutathione-agarose beads. Caspr-GST was eluted from the beads using reduced glutathione, concentrated by lyophilization, and used to immunize rabbits. The immune serum obtained from the rabbits was confirmed for its ability to recognize chick and mouse Caspr through immunoblotting and immunoprecipitation experiments.

Mouse monoclonal antibodies against Kv1.1 α-subunit (K20/78) and Na+ channel (K58/35) were purchased from Upstate Biotechnology and Sigma, respectively. Polyclonal antibodies against Kv1.1, Kv1.2 and Kv2.1 were purchased from Chemicon. The monoclonal anti-MAP2 was purchased from Sigma. The Cy2-conjugated goat anti-rabbit and Cy3-conjugated goat anti-mouse secondary antibodies were purchased from Amersham Pharmacia Biotech, and the ABC kit was purchased from Vector Laboratories.

EAE Model

The Experimental Autoimmune Encephalomyelitis (EAE) model in rats was developed according to a previous report (Ahn et al, 2001). In brief, Lewis rats (2 months old, female) received an injection of 0.5 ml/rat of fresh rat spinal cord homogenate (SCH) in complete Freund's Adjuvant (CFA, containing 1 mg/ml *Mycobacteria Tuberculosis*; Sigma) (1:1) in the hind footpads bilaterally. Animals were closely observed for symptoms associated with EAE to determine disease progression. At 13 days post-injection (dpi)-14 dpi, animals at the peak stage of EAE were sacrificed for further experiments.

Immunohistochemistry and Immunoelectron Microscopy

Wistar rats at different postnatal ages (P1, P5, P7, P14, P30, P60 and adults), CGT$^{-/-}$ (P16 and P21; Coetzee et al, 1996) and Shiverer (adults; Jackson Laboratories) mice were perfused with 4% paraformaldehyde. The spinal cords and brainstems were removed and post-fixed in 4% paraformaldehyde for 2 hr, and sequentially incubated in 15% and 30% sucrose. Cryostat sections (10 μm) were double-labeled with polyclonal antibodies to Nogo-A (1:200) or Caspr (1:200) in conjunction with a monoclonal Kv1.1 α-subunit (1:200) or Na+ channel (1:100) antibodies respectively, or with polyclonal NgR antibodies in conjunction with a monoclonal MAP2 (1:100) or Kv1.1 α-subunit antibodies. Immunostainings were visualized and photographed using a Carl Zeiss LSM5 confocal microscope. The lengths for Nogo-A and Kv1.1 immuno-labeling and their overlaps at different postnatal days were measured. Co-localization for Nogo-A and Kv1.1, or Caspr/Kv1.1 at paranodes at different postnatal days was counted. In brainstem sections of normal and EAE rats, wild-type and shiverer mice, distances between paired Kv1.1 immuno-labelings were measured and the Nogo-A clusters were counted. Values were presented as mean±SEM. Statistical analyses were carried out using the paired group T-test.

For electron microscopy, samples from adult Wistar rats and CGT-/- (P16) were prepared according to published protocols (Huber et al, 2002). Ultrathin sections of 90 nm thickness on nikel grids were blocked for 40 min at room temperature with 1% BSA, 0.1% Tween 20, 1% normal goat serum and 0.025% NaN$_3$ in 0.1 M sodium phosphate buffer (pH8.3), followed by overnight incubation at 4° C. with Nogo-A polyclonal antibodies in the same buffer, respectively. After washing thoroughly with the above buffer, grids were incubated for 1 h with goat anti-rabbit IgG conjugated to 10 nm gold (1:20, Aurion) and fixed with 2.5% aqueous glutaraldehyde for 15 min. After double staining with uranyl acetate and lead citrate, the grids were examined under a Philips 208 electron microscope.

Western Blot and Co-Immunoprecipitation Assays

From adult, postnatal day 1 (P1) to 30 (P30) Wistar rats, various regions of the CNS (total brain, brainstem, hippocampus, cerebral cortex and spinal cord), spinal cords from EAE and control rats, were harvested and extracted in phosphate-buffered saline containing 1% Triton X-100 and a cocktail of protease inhibitors. Lysates were electrophoresed on SDS-PAGE gel and blotted onto nitrocellulose membranes (Hybond C-extra, Amersham). Identical blots were probed with antibodies against Nogo-A, Caspr, Nogo-66 Receptor (NgR) and γ-tubulin (for loading normalization), and visualized with the Pierce chemiluminescent detection reagents.

For co-immunoprecipitation (IP) experiments, brain membrane fractions were prepared as described previously (Lei et al, 2002). Briefly, brain tissue was homogenized in ice-cold homogenizing buffer (320 mM sucrose, 10 mM Tris-HCl pH7.4, 1 mM NaHCO$_3$ pH7.4, 1 mM MgCl$_2$) supplemented with 1% protease inhibitor cocktail (Amersham), and subsequently centrifuged at 5,000 g for 15 min. The supernatant was collected and spun at 60,000 g (Beckman ultracentrifuge) for 60 min at 4° C. Pellets were then dissolved in a lysis buffer (10 mM Tris-HCl pH9, 150 mM NaCl, 0.5% Triton X-100, 1% sodium deoxycholate (DOC), 0.5% SDS, 2 mM EDTA, and 1% protease inhibitor cocktail) for subsequent experiments. Immunoprecipitated proteins, using of non-immune IgG, Caspr, Nogo-A and NB3 antibodies, respectively, were eluted from the beads with Laemmli sample buffer and separated on 8% SDS-PAGE gels, prior to being transferred to nitrocellulose membrane and probed for Caspr, Nogo-A, Kv1.1, Kv1.2, F3, or NB3. In separate experiments, a Nogo-A expression construct in the mammalian expression vector pCIneo (Promega) was transiently transfected into Caspr/F3-expressing CHO (Faivre-Sarraih et al, 2000), F3-expressing CHO (Gennarini et al, 1991) or wild type CHO cells for co-IP studies.

Cell Adhesion Assay and PI-PLC Treatment

The Nogo-66 peptide (KLSDVLDDVLFLRRLEKITCN-VHGLASNSYKQVLEES IAVESELYARFPHGEDSKQIA-QIVGKYIR) was purchased from Loke Diagnostics ApS (Denmark). To generate recombinant proteins of Nogo-66-GST and Nogo-N-terminal-GST (Nogo-N-GST), the encoding sequences for Nogo-66 and Nogo-N-terminus were amplified from human brain cDNA clone HK07722 (Nogo-A) using the primer sets below: 5'-CTGAATTCTTAG-GATATACAAGGGTGT-3' (forward) 5'-GCTAAGCTTTCACTTCAGAGAATCAACTA-3' (reverse) for Nogo-66-GST 5'-AGGAATTCTAGATGAGAC-CCTTTTTGC-3' (forward) 5'-CCCAAGCTTTCAAT-TAAAACTGTCTTTTGCTTT-3' (reverse) for Nogo-N-GST. The PCR products were digested with EcoRI and HindIII and ligated into EcoRI/Hind III-digested pGEX-KG (Guan and Dixon, 1991). Then, these recombinant plasmids were transformed into E. coli Top 10 cells. GST fusion proteins were recovered from the bacterial lysates and purified using glutathione-agarose beads. The cell adhesion assay was carried out as previously described (Xiao et al, 1996). Protein spots (1.5 µl of 5 µM GST, Nogo-66-GST or 100 µM Nogo-66) were applied onto nitrocellulose-coated surfaces of the Petri dishes (Becton Dickinson) and incubated for 2 hours at 37° C. in a humidified atmosphere. The dishes were then incubated overnight with PBS containing 2% heat-inactivated fatty acid-free BSA (Sigma) to block residual non-specific protein binding sites. Mock-transfected CHO, F3-transfected or Caspr/F3 co-transfected CHO cells were then plated in 2 ml of chemically defined medium at a density of $2.5 \times 10^5$ cells/ml and incubated at 37° C. in a humidified atmosphere. After 12 hours, cells were fixed by flooding with PBS containing 2.5% glutaraldehyde. Cells adhering to the various spots were photographed and counted. All experiments were performed at least three times. Statistical analysis was carried out by Student-t test. The level of significance was chosen at $p<0.05$.

Where indicated, Caspr/F3-transfected CHO cells were treated with PI-PLC (0.02, 0.04 or 0.06 U/ml) (Sigma), incubated for 2 hours and then plated into the dishes following the same procedures as described above. PI-PLC treated cells were subjected to Western blot analysis and immunochemistry for F3/Contactin as described above.

GST Pull-Down Assay

The bead-bound GST, GST-Nogo-66 and GST-Nogo-N (20 µg) were mixed respectively with 1.5 ml of membrane extracts of adult brain or of wild type, F3-expressing and Caspr/F3-expressing CHO cells that had been transiently transfected with Kv1.1 (a gift from Dr. Trimmer, Nakahira K et al, 1996) in 0.1 M sodium phosphate buffer (pH7.4) and incubated overnight at 4° C. The bound proteins were eluted with 2× Laemmli sample buffer, separated by SDS-PAGE and probed with Caspr and Kv1.1 antibodies.

Lipid Rafts Analysis

Preparation of detergent extracts from rat cerebral cortex (15 days and adult) was carried out primarily according to the procedures described by Kramer et al, 1999. In brief, dissected rat cerebral cortex (2 g wet weight total) was homogenized in 12.5 ml TBS (pH 7.4) containing 2% Triton-X 100, 2 mM pervanadate, protease inhibitor tablet (Roche) and stirred for 30 min at 4° C. The detergent extracts were adjusted to 40% sucrose by adding equal volumes of 80% sucrose in TBS and placed in the ultracentrifuge tube for the SW28 rotor. A linear gradient from 5% to 30% sucrose in TBS were layered onto the lysate sample. Gradients were centrifuged for 18 hrs at 25,000 rpm. Two ml fractions were collected from top to bottom. Proteins in each fraction were analyzed by SDS-PAGE followed by Western blot. Detergent insoluble floating materials were mostly recovered in fraction 5.

SECOND ASPECT OF THE INVENTION

Background Information to the Second Aspect of the Invention

Myelination is a complex multistep process where the underlying molecular mechanism remains far from being completely defined. However, it is believed that the interaction between axons and myelin competent cells at the paranode play an important role in the insulation of axonal segments in spiral wraps of myelin. This axo-glial contact has been likened to invertebrate septate junctions and has been proposed to serve as an anchor point between axons and myelin loops, to act as a partial diffusion barrier into the periaxonal space and to segregate the axon into domains by preventing the lateral diffusion of membrane components (Rosenbluth, 1995). In recent years, specific molecules have been found to be located at the paranodal region.

F3/contactin is a glycosyl-phosphatidylinositol (GPI) linked molecule of the immunoglobulin superfamily of neural cell adhesion molecules (Gennarini et al, 1989; Faivre-Sarrailh et al, 2000). The molecule is composed of a string of modular immunoglobulin domains and fibronectin type III repeats. The inventor previously (Xiao et al, 1998 incorporated herein by reference) demonstrated that F3 is a neuronal receptor for the extracellular matrix glycoprotein tenascin-R, a glia-derived molecule specifically located at nodes of Ranvier (Wintergerst et al, 1993). The binding site on tenascin-R, in its interaction with F3, was localized to the EGF (epidermal growth factor) like repeats (Xiao et al, 1996, 1997, incorporated herein by reference). Tenascin-R is a functional modulator of sodium channel subunits. F3 interacts in trans with RPTPζ/β (receptor protein tyrosine phosphatase) to promote neurite outgrowth (Sakurai et al, 1997) and in cis with RPTPα (Zeng et al, 1999) to transduce extracellular signals to myelination-related Fyn kinase (Umemori et al, 1994). Additionally, F3 co-localizes and interacts in cis with Caspr/Paranodin and in trans with glial neurofascin 155 at the paranode (Girault and Peles, 2002), a key site of axoglial contact for myelination. F3 null mice exhibit partially disrupted paranodal structure and die by P18 (Berglund et al, 1999), suggesting that F3 may be critical for development.

F3-associated protein (Caspr), also known as paranodin, is an additional axonal component of the paranode (Einheber et al, 1997; Menegoz et al, 1997). Rios et al (2000) further showed that F3 and Caspr co-localize and interact in a cis fashion at the paranode during myelination. In adult sciatic and optic nerves, F3 staining localized to the paranodes, although staining also extended to the nodes in the optic nerve.

NB-3 is a neural cell adhesion molecule in the same subfamily as F3 (Lee et al, 2000). In the cerebrum, NB-3 mRNA analysis revealed a low level of expression during embryogenesis with an abrupt increase in the postnatal period, reaching a maximum level in the postnatal seventh day which corresponds to the time frame for myelination. Subsequently, levels decreased to one-fifth of the peak and remained so in adulthood.

Myelination in the vertebrate central nervous system (CNS) is essential for rapid impulse conduction. In the CNS, oligodendrocyte (OL) differentiation is mediated by neuron derived signals (Barres and Raff, 1999). Jagged1/Notch1, an axoglial interaction, promotes oligodendrocytes precursor cell (OPC) migration and inhibits OPC differentiation (Wang et al, 1998). Notch/Jagged1 signaling pathway plays a critical role in promoting gliogenesis, such as radial glial cells in the fetal forebrain, Schwann cells in dorsal root ganglia, and Müller glial cells in the retina (Furukawa et al, 2000; Hojo et al, 2000; Gaiano et al, 2000; Morrison et al, 2000; Wakamatsu et al, 2000; Tanigaki et al, 2001). Conditional ablation of Notch1 in OPCs results in the appearance of ectopic premature OLs and subsequent apoptosis (Genoud et al, 2002) and the failure of efficient remyelination is partly attributed to the activation of OPC Notch receptor by astrocyte-expressed Jagged1 in multiple sclerosis (John et al, 2002) indicating that OPC differentiation could be disordered when Notch1 is absent or inadequately activated by Jagged1. Thus, other pathways via Notch1, besides the inhibitory Jagged1/Notch1 signalling pathway, may instructively mediate OPC differentiation into OLs. However, the molecular mechanisms controlling the timing of OPC differentiation to OLs and the subsequent OL maturation remain poorly defined. Given that Jagged1 is downregulated significantly before the maturation of oligodendrocytes, it is conceivable that other molecules may interact with Notch, which continually plays a role in myelination. Molecules congregated at distinct segments of the axon are potential Notch1 ligands.

Notch is a type I transmembrane protein mediating cell fate selection via lateral inhibition. Its core signaling mechanism involves Regulated Intramembrane Proteolysis (RIP) (Ebinu and Yankner, 2002). Upon binding the classic ligands, Delta, Serrate/Jagged and Lag-2 (collectively called DSL), Notch undergoes two proteolytic cleavages that release its intracellular domain (NICD). NICD translocates to the nucleus and interacts with RBP-J transcription factor to activate, for instance, Hes genes (Martinez Arias et al, 2002). In addition, Deltex1 (DTX1) has been identified as a cytoplasmic downstream element of the Notch signaling pathway. DTX homologs share three common domains, namely, the N-terminal region, proline-rich and RING-H2 finger motifs (Kishi et al, 2001). Particularly, the N-terminal region interacts with NICD. Notch signaling via DTX1 represses JNK signaling, a pathway regulating OL differentiation, and cooperates with Wingless signaling (Brennan and Gardner, 2002; Martinez Arias et al, 2002). Although several studies imply the existence of an extracellular ligand that activates Notch/DTX1 signaling, the putative ligand has not yet been identified.

Notch has been shown to regulate glial differentiation (Wang et al, 1998; Gaiano et al, 2000; Morrison et al, 2000). Of significance to the inventor was that the Notch extracellular portion contains, as does tenascin-R, multiple EGF-like repeats which are sites of potential ligand-receptor interactions (Rebay et al, 1991). It thus becomes conceivable to the inventor that glia-derived Notch could be a binding partner of axonal F3 and NB-3. In the rat optic nerve, Wang et al (1998) demonstrate Jagged1 expression on retinal ganglion cell axons. Jagged1 signals to Notch on oligodendrocyte precursors to inhibit their differentiation. Of interest is the expression pattern of Jagged1 which becomes developmentally downregulated with a time course that parallels myelination (Dugas et al, 2001). This led to the conclusion that Jagged1 signals to oligodendrocytes thus as part of a localized timing mechanism to regulate oligodendrocyte differentiation and thus myelination. But how is the segmental nature of the myelin sheath preserved? What is the stop signal that prevents myelinating oligodendrocytes from encroaching upon putative nodes of Ranvier? The inventor hypothesized that such axonal stop signals should logically exist on either side of the nodes, namely at the paranodes. As detailed below, the inventor has indeed demonstrated that F3 is able to act as a stop signal for oligodendrocyte processes and that NB-3 may participate in the triggering of oligodendrocyte differentiation.

Summary of the Second Aspect of the Invention

The present inventor has for the first time shown that both F3 and NB-3 are physiological ligands of the oligodendroglial Notch receptor—establishing the presence of a signalling pathway via Deltex1 to co-ordinate events during myelination.

Thus, the inventor has identified a new paranodal molecule—NB-3 and showed that stop signals are located at paranodes which involve F3/NB-3 signalling to Notch on the surface of oligodendroglia. In a co-culture system between OLN-93 cells and F3-transfected CHO cells, oligodendroglial cellular processes terminate and spread over the F3-transfected cell bodies but bypass control CHO cells. Cell adhesion, co-immunoprecipitation and GST pull-down assays confirm that F3/NB-3 and Notch associate as a complex. MAG becomes upregulated when OLN-93 cells and F3-transfected CHO cells are co-cultured and when OLN-93 cells and primary oligodendrocytes contact F3 and NB-3 protein substrates. These results describe a novel and functionally significant signalling interaction between F3/NB-3 and Notch that is involved in the regulation of myelination. The present inventor also shows in cell adhesion tests and biochemical assays that F3 is able to bind to Notch1 and Notch2. Furthermore the interaction induces radical morphological change in oligodendrocyte cell line OLN-93 which develops the ensheathing feature and significantly upregulates myelin-related proteins, such as MAG (myelin-associated glycoprotein), CNPase (2',3'-cyclic nucleotide 3'-phosphodiesterase), and PLP. These results suggest that F3 is a physiological ligand of Notch receptor and the signaling plays an important role in oligodendrocyte maturation.

This determination shows that F3 and NB-3 interaction with Notch plays an important role in oligodendrocyte maturation.

The inventor has further determined that F3 induces Notch intramembrane cleavage at the S3 site and that F3/Notch-induced MAG upregulation is independent of HES1 and involves Deltex 1 (DTX1). DTX1 is a known cytoplasmic downstream element of the Notch signaling pathway. It has previously been shown that Notch signaling via DTX1 represses JNK signalling, a pathway that regulates oligodendrocyte differentiation. However, the previous studies have not identified the extracellular ligand that activates Notch/DTX1 signaling.

Here the inventor reports that NB-3 is a neuron-derived cell recognition molecule developmentally clustering at the CNS paranodes and identify NB-3 as a functional ligand of Notch1. The NB-3/Notch signalling pathway promotes OPC differentiation and OL maturation via Deltex1. Moreover, Jagged1 is localized to juxtaparanodes and internodes. Thus a spatial signal switch mechanism from Jagged1/Notch1 to NB-3/Notch1 may exist along the axon, which coordinates oligodendroglial maturation.

Neurons and glia in the vertebrate CNS arise in temporally distinct, albeit overlapping phases. Neurons are generated first, followed by astrocytes and then oligodendrocytes (OLs) from common progenitor cells (Sauvageot and Stile, 2002). Increasing evidence indicates that axon-derived signals are temporally and spatially required for modulating OL maturation as well as myelin formation (Barres and Raff, 1999; Hu et al, 2003). However, little is known about how neuronal molecules participate in OL generation from neural stem cells (NSCS). The inventor's investigation on how to favorably direct embryonic neural stem cells to differentiate into OLs showed that NB-3, a neuronal cell recognition molecule, bound to Notch1 and triggered nuclear translocation of the Notch1 intracellular domain in the stem cells. This NB-3/Notch1 interaction promotes oligodendrogliogenesis from embryonic neural stem cells, which can be blocked by dominant-negative Notch1 and deletion mutants of Deltex1 that lacks the Ring-H2 motif. However, constitutively active Notch1 alone fails to promote OL generation, suggesting that NB-3-induced NICD is required in this event. Taken together, the observations here demonstrate that the NB-3/Notch1 signalling pathway via Deltex1 instructs oligodendrogliogenesis.

Thus the present invention provides a method of stimulating differentiation of an oligodendrocyte or precursor thereof, comprising contacting said oligodendrocyte or precursor with F3, NB-3, or a mimetic of either.

The present invention further provides a method of stimulating myelination of a neuron, specifically a neural axon, comprising contacting an oligodendrocyte, a precursor thereof, or a neuron, with F3, NB-3, or a mimetic of either.

In either of the methods described above, the oligodendrocyte, precursor, or neuron as appropriate, is preferably contacted with both F3 and NB-3, or mimetics thereof. F3 and NB-3 may be present as a complex.

Expression of myelin proteins, such as MAG, will typically be upregulated in said oligodendrocyte or precursor in response to the contacting step.

Without wishing to be bound by any particular theory, it is believed that upregulation of MAG is induced through binding of F3, NB-3 or mimetics thereof to Notch, particularly to Notch 1 or 2, on the surface of the oligodendrocyte or precursor thereof. Such binding is believed to induce Notch signalling, via Deltex-1.

The oligodendrocyte precursor may be an oligodendroglial precursor cell (OPC) or a neural stem cell (NSC). OPCs typically display CNpase, Gal C and MAG on their surface; NSCs display Nestin marker. OPCs and NSCs are described by Wang et al, 1998 (Notch receptor activation inhibits oligodendrocyte differentiation. Neuron 21, 63-75); Morrison S. J., 2001 (Neuronal potential and lineage determination by neural stem cells. Curr. Opin. Cell Biol. 13, 666-672); Sauvageot, C. M. and Stiles, C. D., 2002 (Molecular mechanism controlling cortical gliogenesis. Curr. Opin. Neurobiol. 12, 244-249); Xiao et al, 2003 (F3/Contactin is a notch ligand. Cell, Vol 115, 163-175).

The methods may be performed in vitro or ex vivo. The methods are particularly applicable to the generation of differentiated oligodendrocytes which may be used for therapeutic purposes. Thus, after said contacting step, the OPC or NSC may be introduced or implanted into a subject having disease of, or injury to, the central nervous system; for example, any condition characterised by demyelination of neurons, such as multiple sclerosis (MS), epilepsy, stroke and spinal cord injury (SCI). Following introduction or implantation, these treated cells may continue to differentiate and provide myelination for de-myelinated neurons.

It may be desirable to obtain the oligodendrocyte precursor cells from the subject to whom they are to be administered after treatment.

The invention further provides a composition comprising F3 and NB-3, or mimetics thereof, in combination with a carrier. The composition may comprise a complex between F3 and NB-3, or a mimetic thereof.

In certain embodiments, the composition is a pharmaceutical composition, and so comprises a pharmaceutically acceptable carrier. Preferably pharmaceutical compositions are formulated for injection in vivo, and still more preferably for direct injection into the CNS.

Also provided are compositions as described above for use in a method of medical treatment. In particular the compositions are provided for use in the treatment of injury to, or disease of, the CNS. They may be used for treatment of any condition characterised by demyelination of neurons, such as SCI, MS, epilepsy or stroke.

Also provided is the use of F3 and/or NB-3 in the preparation of a medicament for the treatment of injury or disease to the CNS. They may be formulated individually or separately. Separately formulated NB-3 and F3 may nevertheless be administered together.

Thus there is also provided the use of F3 in the preparation of a medicament for the treatment of injury or disease to the CNS, wherein the medicament is for administration in combination with NB-3 or a mimetic thereof.

Likewise, there is provided the use of NB-3 in the preparation of a medicament for the treatment of injury or disease to the CNS, wherein the medicament is for administration in combination with F3 or a mimetic thereof.

The invention further provides a method of stimulating myelination of a neuron, specifically a neural axon, comprising contacting a neuron or an oligodendroglial cell with a composition as described herein.

The invention further provides a method of treating a subject having disease of, or injury to, the central nervous system, comprising administering to the subject a pharmaceutical composition as described herein.

As will be clear from the foregoing, the subject will typically have a condition characterised by demyelination, such as SCI, MS, epilepsy or stroke.

The invention further provides a method of screening for a substance capable of modulating (preferably promoting) interaction between Notch and F3 and/or NB-3, the method comprising contacting F3 and/or NB-3, Notch and a candidate substance, and determining the interaction between Notch and F3 and/or NB-3.

The method may further comprise contacting Notch and F3 and/or NB-3 in the absence of the candidate substance under otherwise analogous conditions, and determining the interaction between Notch and F3 and/or NB-3.

Preferably the method comprises contacting a complex between Notch and F3 and/or NB-3 with the candidate substance. The complex is preferably formed before it is contacted with the candidate substance.

The method may be performed by any appropriate method. The skilled person will be well aware of many suitable assay formats, and will be capable of designing further examples.

Any or all of NB-3, F3 and Notch may be present in, or on, a cell. The gene from which the protein is expressed may be endogenous to the cell in question, or it may be present on a vector introduced into the cell. The protein is preferably expressed on the surface of the cell.

Additionally or alternatively, any or all of NB-3, F3 and Notch may be immobilised on a solid support. One or both may comprise a detectable label as described in more detail below.

In particular embodiments, Notch is present on a cell surface, and the method comprises determining Notch signalling, particularly via Deltex 1. If the cell in question is an oligodendrocyte or precursor thereof, the method may comprise determination of upregulation of MAG expression.

The invention further provides a method of manufacturing a pharmaceutical formulation comprising, having identified a substance capable of modulating interaction between Notch and F3 and/or NB-3 by a screening method described herein, the further step of formulating said substance with a pharmaceutically acceptable carrier. The method may comprise the further step of optimising said identified substance for administration in vivo prior to formulation.

In specific embodiments, the present invention firstly provides a method for enhancing myelination in an individual comprising administering to said patient an activating agent of Notch receptor, said activating agent comprising F3, NB-3, or a mimetic thereof.

The method is preferably used in the treatment of SCI, MS, epilepsy or stroke.

The invention also provides a pharmaceutical composition comprising an activating agent of a Notch receptor, said activating agent comprising F3, NB-3, or a mimetic thereof.

Also provided is a method of screening for substances capable of modulating the interaction between a ligand and a Notch receptor, the ligand being F3, NB-3, or a mimetic thereof, comprising contacting a substance with the ligand and the receptor; determining the interaction between the ligand and the receptor and comparing this with the interaction between the receptor and ligand under comparable conditions but in the absence of said substance.

The method may further comprise producing a pharmaceutical composition containing said substance.

Cells

The term oligodendrocyte is used herein to refer to oligodendroglial cells capable of laying down a myelin sheath around a neuronal axon in the central nervous system (CNS).

The term oligodendrocyte precursor cell is used to refer to cells capable of differentiating into oligodendrocytes on administration of suitable stimuli, such as F3 and NB-3. Such cells include oligodendroglial precursor cells (OPC) and neural stem cells (NSC).

Protein Sequences

The term "Notch" is used to encompass all isoforms of the Notch protein, including Notch 1, 2 and 3, as well as portions and isolated domains thereof, such as the extracellular domain, as well as mutants and variants thereof having greater than 80%, 85%, 90%, 95%, 96%, 97% 98% or 99% identity to the sequence given below. Preferred proteins are Notch 1 and 2. Orthologous proteins from other mammalian species are also included. Preferably the Notch protein has the ability to bind to a NB-3 and/or a F3 protein. It may also have the ability to induce upregulation of MAG protein expression via Deltex 1 signalling in an oligodendrocyte or precursor thereof.

The term "F3" is used to encompass isoforms of the F3 protein, and isolated domains of such proteins, as well as mutants and variants thereof having greater than 80%, 85%, 90%, 95%, 96%, 97% 98% or 99% identity to the sequence given below. Orthologous proteins from other mammalian species are also included. The F3 protein preferably has the ability to bind to the extracellular domain of a Notch protein, particularly of Notch 1 and 2.

The term "NB-3" is used to encompass isoforms of the NB-3 protein, and isolated domains of such proteins, as well as mutants and variants thereof having greater than 80%, 85%, 90%, 95%, 96%, 97% 98% or 99% identity to the sequence given below. Orthologous proteins from other mammalian species are also included. The NB-3 protein preferably has the ability to bind to the extracellular domain of a Notch protein, particularly of Notch 1 and 2.

The amino acid sequences of Notch, F3 and NB-3 proteins are shown below, along with their GenBank accession numbers;

```
F3/Contac-                         gi: 414791 (CAA79696)
tin
  1       mkmwllvshl viisittcla eftwyr-
          rygh gvseedkgfg pifeeqpint iypeeslegk
 61       vslncraras pfpvykwrmn ngdvdlts-
          dr ysmvggnlvi nnpdkqkdag iyyclasnny
121       gmvrsteatl sfgyldpfpp eerpe-
          vrvke gkgmvllcdp pyhfpddlsy rwllnefpvf
181       itmdkrrfvs qtngnlyian veasd-
          kgnys cfvsspsitk svfskfipli piperttkpy
```

```
    241   padivvqfkd vyalmgqnvt lecfalgn-
          pv pdirwrkvle pmpstaeist sgavlkifni
    301   qledegiyec eaenirgkd-
          k hqariyvqaf pewvehindt evdigsdlyw pcvatgkpip
    361   tirwlkngya yhkgelrlyd vtfenag-
          myq ciaentygai yanaelkila laptfemnpm
    421   kkkilaakgg rviieckpka apkpkfaw-
          sk gtewlvnssr iliwedgsle innitrndgg
    481   iytcfaennr gkanstgtlv itdptri-
          ila pinaditvge natmqcaasf dpaldltfvw
    541   sfngyvidfn kenihyqrnf mldsngel-
          li rnaqlkhagr ytctaqtivd nssasadlvv
    601   rgppgppggl riediratsv altwsrgs-
          dn hspiskytiq tktiladdwk daktdppiie
    661   gnmeaaravd lipwmeyefr vvat-
          ntlgrg epsipsnrik tdgaapnvap sdvggggggrn
    721   reltitwapl sreyhygnnf gyivafk-
          pfd geewkkvtvt npdtgryvhk detmspstaf
    781   qvkvkafnnk gdgpysllav in-
          saqdapse aptevgvkvl ssseisvhwe hvlekivesy
    841   qirywaahdk eeaanrvqvt sqeyaar-
          len llpdtqyfie vgacnsagcg ppsdmieaft
    901   kkappsqppr iissvrsgsr yiitwdhv-
          va lsnestvtgy kvlyrpdgqh dgklysthkh
    961   sievpiprdg eyvvevrahs dggdgvvsqv kisgaptlsp sllglllpaf gilvylef NB3                              gi: 5631291 (BAA82612)
      1   mrllwklvil lplinssagd g-
          llsrpiftq ephdvifpld lsksevilnc aangypsphy
     61   rwkqngtdid ftmsyhyrld ggslain-
          sph tdqdigmyqc latnllgtil srkaklqfay
    121   iedfetktrs tvsvreqqgv vllcgpp-
          phf gdlsyawtfn dnplyvqedn rrfvsqetgn
    181   lyiakvepsd vgnytcfitn keaqrs-
          vqgp ptplvqrtdg vmgeyepkie vrfpetiqaa
    241   kdssvklecf algnpvpdis wrrldg-
          splp gkvkysksqa ileipnfqqe degfyecias
    301   nlrgrnlakg qli-
          fyappew eqkiqnthls iydnllweck asgkpnpwyt wlkngerlnp
    361   eeriqiengt liitmlnvsd sgvyq-
          caaen kyqiiyanae lrvlasapdf skspvkkksf
    421   vqvggdivig ckpnaf-
          praa iswkrgtetl rqskriflle dgslkiynit rsdagsytci
    481   atnqfgtakn tgalivkert vitvppsk-
          md vtvgesivlp cqvshdpsie vvfvwffngd
    541   vidlkkgvah ferigges-
          vg dlmirniglh hsgkylctvq ttleslsava diivrgppgp
    601   pedvqvedis sttsqlswra gpdnnspi-
          qi ftiqtrtpfs vgwqavatvp eilngktyna
    661   tvvglspwve yefrvvagns igigeps-
          eps ellrtkasvp vvapvnihgg ggsrselvit
    721   wesipeelqn gegfgyiimf rpvgst-
          twsk ekvssvessr fvyrnesiip lspfevkvgv
    781   ynnegegsls tvtivysged epqla-
          prgts lqsfsaseme vswnaiawnr ntgrvlgyev
    841   lywtddskes migkirvsgn vttknit-
          glk antiyfasvr ayntagtgps sppvnvttkk
    901   sppsqppani awkltnsklc lnwehvkt-
          me nesevlgyki lyrqnrqskt hiletnntsa
    961   ellvpfeedy lieirtvsdg gdgsss-
          seeir ipkmsslssr giqflepsth flsivivifh
   1021   cfaiqpli Notch1                           gi: 11275980 (AAG33848)
      1   mppllapllc lallpalaar gprc-
          sqpget clnggkceaa ngteacvcgg afvgprcqdp
     61   npclstpckn agtchvvdrr gvadyacs-
          ca lgfsgplclt pldnacltnp crnggtcdll
    121   tlteykcrcp pgwsgkscqq adpcasnp-
          ca nggqclpfea syichcppsf hgptcrqdvn
    181   ecgqkprlcr hggtchnevg syrcv-
          crath tgpncerpyv pcspspcqng gtcrptgdvt
    241   hecaclpgft gqnceenidd cpgnnck-
          ngg acvdgvntyn cpcppewtgq yctedvdecq
    301   lmpnacqngg tchnthggyn cvcvngwt-
          ge dcseniddca saacfhgatc hdrvasfyce
    361   cphgrtgllc hlndacisnp cneg-
          sncdtn pvngkaictc psgytgpacs qdvdecslga
    421   npcehagkci ntlgsfecqc lqgytgpr-
          ce idvnecvsnp cqndatcldq igefqcmcmp
    481   gyegvhcevn tdecasspcl hngrcldk-
          in efqcecptgf tghlcqydvd ecastpckng
    541   akcldgpnty tcvctegytg thcevdid-
          ec dpdpchygsc kdgvatftcl crpgytghhc
    601   etninecssq pcrlrgtcqd pdnaylcf-
          cl kgttgpncei nlddcasspc dsgtcldkid
```

```
 661   gyecacepgy tgsmcnsnid ecagnpch-
       ng gtcedgingf tcrcpegyhd ptclsevnec
 721   nsnpcvhgac rdslngykcd cdpgwsgt-
       nc dinnnecesn pcvnggtckd mtsgivctcr
 781   egfsgpncqt ninecasnpc lnkgtcid-
       dv agykcncllp ytgatcevvl apcapspcrn
 841   ggecrqsedy esfscvcpta gakgqt-
       cevd inecvlspcr hgascqnthg xyrchcqagy
 901   sgrncetdid dcrpnpchng gsctdgin-
       ta fcdclpgfrg tfceedinec asdpcrngan
 961   ctdcvdsytc tcpagfsgih cenntp-
       dcte sscfnggtcv dginsftclc ppgftgsycq
1021   hvvnecdsrp cllggtcqdg rgl-
       hrctcpq gytgpncqnl vhwcdsspck nggkcwqtht
1081   qyrcecpsgw tglycdvps-
       v scevaaqrqg vdvarlcqhg glcvdagnth hcrcqagytg
1141   sycedlvdec spspcqngat ctdylggy-
       ac kcvagyhgvn cseeidecls hpcqnggtcl
1201   dlpntykcsc prgtqgvhce invddcnp-
       pv dpvsrspkcf nngtcvdqvg gysctcppgf
1261   vgercegdvn eclsnpc-
       dar gtqncvqrvn dfhcecragh tgrrcesvin gckgkpckng
1321   gtcavasnta rgfickcpag fegatcen-
       da rtcgalrcln ggtcisgprs ptclclgpft
1381   gpecqfpass pclggnpcyn qgtcept-
       ses pfyrclcpak fngllchild ysfgggagrd
1441   ippplieeac elpecqedag nkv-
       calqcnn hacgwdggdc slnfndpwkn ctqslqcwky
1501   fsdghcdsqc nsagclfdgf dcqrae-
       gqcn plydqyckdh fsdghcdqgc nsaecewdgl
1561   dcaehvperl aagtlvvvvl mppeql-
       rnss fhflrelsrv lhtnvvfkrd ahgqqmifpy
1621   ygreeelrkh pikraaegwa ap-
       dallgqvk asllpggseg grrrreldpm dvrgsivyle
1681   idnrqcvqas sqcfqsatdv aaflga-
       lasl gslnipykie avqsetvepp ppaqlhfmyv
1741   aaaafvllff vgcgvllsrk rrrqhgql-
       wf pegfkvseas kkkrreplge dsvglkplkn
1801   asdgalmddn qnewgdedle tkkfr-
       feepv vlpdlddqtd hrqwtqqhld aadlrmsama
1861   ptppqgevda dcmdvnvrgp dgftplmi-
       as csgggletgn seeeedapav isdfiyqgas
1921   lhnqtdrtge talhlaarys rsdaakrl-
       le asadaniqdn mgrtplhaav sadaqgvfqi
1981   lirnratdld armhdgttpl ilaar-
       laveg mledlinsha dvnavddlgk salhwaaavn
2041   nvdaavvllk ngankdmqnn reet-
       plflaa regsyetakv lldhfanrdi tdhmdrlprd
2101   iaqermhhdi vrlldeynlv rapqlhga-
       pl ggtptlsppl cspngylgsl kpgvqgkkvr
2161   kpsskglacg skeakdlkar-
        rkksqdgkgc lldssgmlsp vdslesphgy lsdvasppll
2221   pspfqqspsv plnhlpgmpd thlgighl-
       nv aakpemaalg gggrlafetg pprlshlpva
2281   sgtstvlgss sggaln-
       ftvg gstslngqce wlsrlqsgmv pnqynplrgs vapgplstqa
2341   pslqhgmvgp lhsslaasal sqlm-
       myqglp strlatqphl vqtqqvqpqn lqmqqqnlqp
2401   aniqqqqslq ppppppqphl gvssaas-
       ghl grsflsgeps qadvqplgps slavhtilpq
2461   espalptslp sslvppvtaa qflt-
       ppsqhs ysspvdntps hqlqvpehpf ltpspespdq
2521   wssssphsnv sdwsegvssp ptsmqsqiar ipeafk Notch2                           gi: 11275978 (AAA36377)
   1   mpalrpallw allalwlcca apa-
       halqcrd gyepcvnegm cvtyhngtgy ckcpegflge
  61   ycqhrdpcek nrcqnggtcv aqam-
       lgkatc rcasgftged cqystshpcf vsrpclnggt
 121   chmlsrdtye ctcqvgftgk ecqwtda-
       cls hpcangstct tvanqfsckc ltgftgqkce
 181   tdvnecdipg hcqhggtcln lpgsyqc-
       qcp qgftgqycds lyvpcapspc vnggtcrqtg
 241   dftfecnclp gfegstcern iddcpn-
       hrcq nggvcvdgvn tyncrcppqw tgqfctedvd
 301   ecllqpnacq nggtcanrng-
        gygcvcvngw sgddcsenid dcafasctpg stcidrvasf
 361   scmcpegkag llchlddaci snpchk-
       galc dtnplngqyi ctcpqgykga dctedvdeca
 421   mansnpceha gkcvntdgaf hceclkgy-
       ag prcemdinec hsdpcqndat cldkiggftc
 481   lcmpgfkgvh celeinecqa npcvn-
       ngqcv dkvnrfqclc ppgftgpvcq ididdcsstp
 541   clngakcidh pngyecqcat gftgvl-
       ceen idncdpdpch hgqcqdgids yticnpgym
 601   gaicsdqide cysspclndg r-
       cidlvngyq cncqpgtsgv nceinfddca snpcihgicm
```

```
                    -continued
 661    dginryscvc spgftgqrcn ididecas-
        np crkgatcing vngfrcicpe gphhpscysq
 721    vneclsnpci hgnctgglsg ykclcdag-
        wv gincevdkne clsnpcqngg tcdnlvngyr
 781    ctckkgfkgy ncqvnideca snpcln-
        qgtc fddisgytch cvlpytgknc qtvlapcspn
 841    pcenaavcke spnfesytcl capg-
        wqgqrc tididecisk pcmnhglchn tqgsymcecp
 901    pgfsgmdcee diddclanpc qnggsc-
        mdgv ntfsclclpg ftgdkcqtdm neclsepckn
 961    ggtcsdyvna ytckcqagfd gvhcenni-
        ne ctesscfngg tcvdginsfs clcpvgftgs
1021    fclheinecs shpclnegtc vdglg-
        tyrcs cplgytgknc qtlvnlcsrs pcknkgtcvq
1081    kkaesqclcp sgwagaycdv pnvscdi-
        aas rrgvlvehlc qhsgvcinag nthycqcplg
1141    ytgsyceeql decasnpcqh gatcsd-
        figg yrcecvpgyq gvnceyevde cqnqpcqngg
1201    tcidlvnhfk cscppgtrgl lceenid-
        dca rgphclnggq cmdriggysc rclpgfager
1261    cegdinecls npcssegsld ciqlt-
        ndylc vcrsaftgrh cetfvdvcpq mpclnggtca
1321    vasnmpdgfi crcppgfsga rcqss-
        cgqvk crkgeqcvht asgprcfcps prdcesgcas
1381    spcqhggsch pqrqppyysc qcappfsg-
        sr celytappst ppatclsqyc adkardgvcd
1441    eacnshacqw dggdcsltme npwancss-
        pl pcwdyinnqc delcntvecl fdnfecqgns
1501    ktckydkyca dhfkdnhcnq gcnseecg-
        wd gldcaadqpe nlaegtlviv vlmppeqllq
1561    darsflralg tllhtnlrik rdsqgelm-
        vy pyygeksaam kkqrmtrrsl pgeqeqevag
1621    skvfleidnr qcvqdsdhcf knt-
        daaaall ashaiqgtls yplvsvvses ltpertqlly
1681    llavavviil fiillgvi-
        ma krkrkhgslw lpegftlrrd asnhkrrepv gqdavglknl
1741    svqvseanli gtgtsehwvd degpqp-
        kkvk aedeallsee ddpidrrpwt qqhleaadir
1801    rtpslaltpp qaeqevdvld vnvrgp-
        dgct plmlaslrgg ssdlsdeded aedssaniit
1861    dlvyqgaslq aqtdrtgema lhlaarys-
        ra daakrlldag adanaqdnmg rcplhaavaa
1921    daqgvfqili rnrvtdldar mndgttp-
        lil aarlavegmv aelincqadv navddhgksa
1981    lhwaaavnnv eatlllllkng anrdmqdn-
        ke etplflaare gsyeaakill dhfanrditd
2041    hmdrlprdva rdrmhhdivr lldeyn-
        vtps ppgtvltsal spvicgpnrs flslkhtpmg
2101    kksrrpsaks tmptslpnla keakdakg-
        sr rkkslsekvq lsessvtlsp vdsleaphty
2161    vsdttsspmi tspgilqasp npm-
        lataapp apvhaqhals fsnlhemqpl ahgastvlps
2221    vsqllshhhi vspgsgsags lsrlh-
        pvpvp adwmnrmevn etqynemfgm vlapaegthp
2281    giapqsrppe gkhittprep lppivt-
        fqli pkgsiaqpag apqpqstcpp avagplptmy
2341    qipemarlps vafptammpq qdgqva-
        qtil payhpfpasv gkyptppsqh syassnaaer
2401    tpshsghlqg ehpyltpspe sp-
        dqwssssp hsasdwsdvt tsptpggagg gqrgpgthms
2461    epphnnmqvy a
```

Assay Methods

As described above, the skilled person is well aware of numerous assay formats which may be appropriate for determining interaction between Notch and NB-3 and/or F3, and identifying substances which modulate, preferably promote, such interaction.

For example, interaction between the proteins may be studied in vitro by labelling one or more with a detectable label and bringing it into contact with another which has been immobilised on a solid support. Suitable detectable labels, especially for petidyl substances include $^{35}$S-methionine which may be incorporated into recombinantly produced peptides and polypeptides. Alternatively the complex formed on the solid support may be detected by labelling with an antibody directed against an epitope present on a protein which is not immobilised on the solid support. If no suitable antibody is available, a recombinantly-produced peptide or polypeptide may be expressed as a fusion protein containing an epitope against which a suitable antibody is available.

The protein which is immobilized on a solid support may be immobilized using an antibody against that protein bound to a solid support or via other technologies which are known per se.

A preferred in vitro interaction may utilise a fusion protein including glutathione-S-transferase (GST). This may be immobilised on glutathione agarose beads. In an in vitro assay format of the type described above a test compound can be assayed by determining its ability to affect the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

An assay according to the present invention may also take the form of a cell-based assay in which at least one of the proteins is expressed by, preferably on the surface of, a suitable cell. The assay may utilise a cell line, such as a yeast strain or mammalian cell line, in which the relevant polypeptides or peptides are expressed from one or more vectors introduced into the cell.

Modulators of Notch/NB-3/F3 interaction identified by the methods described may be further modified to increase their suitability for in vivo administration.

Formulations

The compositions of the invention may be prepared as pharmaceutical formulations comprising at least one active compound, as defined above, together with one or more other pharmaceutically acceptable ingredients well known to those skilled in the art, including, but not limited to, pharmaceutically acceptable carriers, adjuvants, excipients, buffers, preservatives and stabilisers. The formulation may further comprise other active agents.

Thus, the present invention further provides a method of making a pharmaceutical composition as previously defined, the method comprising admixing at least one active agent as described herein together with one or more pharmaceutically acceptable ingredients well known to those skilled in the art, e.g., carriers, adjuvants, excipients, etc.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example Remington's Pharmaceutical Sciences, 20th Edition, 2000, pub. Lippincott, Williams & Wilkins; and Handbook of Pharmaceutical Excipients, 2nd edition, 1994.

Formulations may suitably be injectable formulations, e.g. in the form of aqueous, isotonic, pyrogen-free, sterile solutions, in which the active compound is dissolved. Such liquids may additional contain other pharmaceutically acceptable ingredients, such as anti-oxidants, buffers, preservatives, stabilisers, bacteriostats, suspending agents, thickening agents, and solutes which render the formulation isotonic with the blood or cerebrospinal fluid. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Administration

Administration of the compositions of the invention will generally be by injection, preferably directly into the CNS. Injection may be directly into the site of damage. Alternatively, injection may be into the cerebro-spinal fluid, typically near the site of injury or illness.

Sequence Identity

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Percent (%) amino acid similarity is defined in the same way as identity, with the exception that residues scoring a positive value in the BLOSUM62 matrix are counted. Thus, residues which are non-identical but which have similar properties (e.g. as a result of conservative substitutions) are also counted.

In a similar manner, percent (%) nucleic acid sequence identity with respect to a reference nucleic acid is defined as the percentage of nucleotide residues in a candidate sequence that are identical with the nucleotide residues in the reference nucleic acid sequence. The identity values used herein may be generated by the BLASTN module of WU-BLAST-2 set to the default parameters, with overlap span and overlap fraction set to 1 and 0.125, respectively.

The Subject

The subject to which the compositions and/or treatments of the invention will be administered will be a mammal, preferably an experimental animal such as a rodent (e.g. a rabbit, rat or mouse), dog, cat, monkey or ape, or a farm animal such as a cow, horse, sheep, pig or goat. More preferably, the subject is human.

Generally, the subject will have CNS damage, usually resulting from a disease or disorder characterised by inadequate myelination. Such conditions include MS. In experimental animals, the damage or disorder may be experimental. The CNS damage may also result from physical injury e.g. spinal cord injury (SCI) other diseases or disorders, e.g. stroke, epilepsy or a neurodegenerative condition, learning memory-related condition and/or dementia such as Alzheimer's disease or Parkinson's disease.

The treatments of the invention may be used in conjunction with other therapies, such as surgery and/or rehabilitation.

Mimetics

Non-peptide "small molecules" are often preferred to peptides or polypeptides for in vivo pharmaceutical use. Accordingly, mimetics of F3 and/or NB-3 and complexes thereof may be designed, especially for pharmaceutical use. Typically a mimetic of one or both of F3 and NB-3 will be capable of binding to a Notch molecule, preferably the extracellular domain of Notch 1 or 2, to mimic the effects of that protein or proteins binding to the same molecule.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. Alanine scans of peptide are commonly used to refine such peptide motifs. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

In the present case, peptide mapping studies may be used to identify the minimal portion of either F3 or NB-3 required to interact with Notch. This peptide may then be used as a lead compound for mimetic design, as described above.

Antibodies

As antibodies can be modified in a number of ways, the term "antibody" should be construed as covering any specific binding substance having an binding domain with the required specificity. Thus, this term covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444-6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al, Embo Journal, 10, 3655-3659, (1991).

It may be desirable to "humanisel" non-human (e.g. murine) antibodies to provide antibodies having the antigen binding properties of the non-human antibody, while minimising the immunogenic response of the antibodies, e.g. when they are used in human therapy. Thus, humanised antibodies comprise framework regions derived from human immunoglobulins (acceptor antibody) in which residues from one or more complementary determining regions (CDR's) are replaced by residues from CDR's of a non-human species (donor antibody) such as mouse, rat or rabbit antibody having the desired properties, e.g. specificity, affinity or capacity. Some of the framework residues of the human antibody may also be replaced by corresponding non-human residues, or by residues not present in either donor or acceptor antibodies. These modifications are made to the further refine and optimise the properties of the antibody.

Aspects and embodiments of the second aspect of the present invention will now be illustrated, by way of example, with reference to the accompanying figures. Further aspects and embodiments will be apparent to those skilled in the art. All documents mentioned in this text are incorporated herein by reference.

FIG. 9. Adhesion of OLN-93 cells or mouse Notch1 transfected Hela cells with or without antibody blocking treatment to spots of proteins, such as F3-Fc (a, k-l, and q), CHL1-Fc (a) and NB-3-His (b, e-j, m-p, and r), applied to nitrocellulose was determined. Bars (a-b and q-r) represent the number of adherent cells (mean.+−.SD) from at least three independent experiments. Bar marked * is highly significantly ($P<0.05$) different from the control.

Adhesion of OLN-93 cells on coated F3-Fc and NB-3-His substrates.

a. Effect of antibody blockade on OLN-93 cell adhesion to F3-Fc substrate. F3: F3 protein substrate only (as a control); CHL1: CHL1 protein substrate only; Anti-F3 or Anti-NB-3: addition of these two antibodies, respectively, to block the F3-Fc coated substrates before plating OLN-93 cells; Anti-Notch1, Anti-Notch2 or Serum: pre-treated OLN-93 cells with these two specific blocking antibodies or pre-immune serum respectively before plating upon a F3-Fc coated substrate.

b. Effect of antibody blockade on OLN-93 cell adhesion to NB-3 substrate. NB-3: NB-3.His protein substrate only (as control); Anti-NB-3 or Anti-F3: addition of these two antibodies, respectively, to block the NB-3-His coated substrates before plating OLN-93 cells; Anti-Notch1, Anti-Notch2 or Serum: pre-treated OLN-93 cells with these two specific blocking antibodies or pre-immune serum respectively before plating upon a NB-3-His coated substrate.

c-d: Immunofluorescence micrographs of OLN-93 cells stained using anti-Notch1 antibody (c) and anti-Notch2 antibody (d). Cell surface staining is present in both instances.

e-j: Bright-field micrographs of OLN-93 cells upon contact with coated NB-3-His substrate after 0.5 hour in culture (e) and in the presence of blocking antibodies against Notch1 (f), NB-3 (g), Notch2 (h), F3 (i), and pre-immune serum (j). Scale bar in (j): 8 µm for (c-j).

Adhesion of mouse Notch1 transfected Hela cells on coated F3-Fc and NB-3-His substrates.

k-p: Bright-field micrographs of mock-transfected Hela cells (k) and mouse Notch1 transfected Hela cells (l-p) upon contact with F3-Fc (k-l) or NB-3-His (m-p) and in the presence of blocking antibodies against NB-3 (n), Notch1 (o), and pre-immune serum (p). Scale bar in (p): 8 µm for (k-p).

q. Effect of antibody blockade on mouse Notch1 transfected Hela cells interaction with F3-Fc substrate. F3: F3-Fc coated substrate only; Anti-F3: addition of these antibodies to block the F3-Fc coated substrates before plating mouse Notch1 transfected Hela cells; Anti-Notch1 or Serum: pre-treated mouse Notch1 transfected Hela cells with these specific blocking antibodies or pre-immune serum respectively before plating upon a F3-Fc coated substrate; Hela cells: plating mock-transfected Hela cells upon a F3-Fc coated substrate (as a control).

r. Effect of antibody blockade on mouse Notch1 transfected Hela cells adhesion to NB-3-His coated substrate. NB-3: NB-3.His coated substrate only; Anti-NB-3: addition of these antibodies to block the NB-3.His coated substrates before plating mouse Notch1 transfected Hela cells; Anti-Notch1 or Serum: pre-treated mouse Notch1 transfected Hela cells with these specific blocking antibodies or pre-immune serum respectively before plating upon a NB-3.His coated substrate; Hela cells: plating mock-transfected Hela cells upon a NB-3.His coated substrate (as a control).

FIG. 10. Biochemical and cellular analysis of the interaction between Notch and F3/NB-3.

a-d: Reciprocal association of both F3 and NB-3 with Notch1 and Notch2. Lysates of rat brain were analyzed by co-immunoprecipitation with these four antibodies and beads and non-immune IgG (as controls). In each case, lanes correspond to antibodies as marked (Anti-N1: Anti-Notch1 antibody, Anti-N2: Anti-Notch2 antibody). Western blots were probed with antibodies against F3 (a), NB-3 (b), Notch1 (a) and Notch2 (d).

e: Schematic diagram of the Notch1 molecule showing the terminology assigned to each subcloned fragment.

f-g: Coomassie Brilliant blue staining (f) and immunoblot analysis (g) of the four fragments are shown. The anti-Notch1 antibody specifically recognizes N1.3 and N1.4.

h-i: Analysis of the interaction between Notch1 fragments with F3/NB-3 by using a pull down assay. Rat brain lysates were incubated with GST or GST-fusion proteins (N1.1, N1.2, N1.3, N1.4) bound to Sepharose 4B beads. Bound proteins were eluted with SDS sample buffer and analysed by SDS-PAGE and Western blotting with antibodies against F3 or NB-3.

j-l: Adhesion of F3-transfected CHO cells (j), NB-3-transfected CHO cells (k), and mock-transfected CHO cells (l) to four different Notch1 fragments and GST. The protein fragments N1.1, N1.2, N1.3 and N1.4, together with GST as control were coated onto surfaces of petri dishes and F3-transfected CHO cells (j), NB-3-transfected CHO cells (k) and mock-transfected CHO cells (l) were plated and maintained in chemically defined medium for 2 hours. Bars represent the number of adherent cells (mean±SD) from at least three independent experiments, Bar marked * is highly significantly ($P<0.05$) different from the control (GST).

FIG. 11. Western blot analysis of expression of MAG and PLP in co-culture of F3-transfected CHO cells and OLN-93 cells.

a: Immunoblot analysis of MAG in rat brain homogenates (BRAIN) and cell co-culture extracts. b: Immunoblot analysis of PLP in cell co-culture extracts. OLN: OLN-93 cell culture only; F3/OLN: co-culture of OLN-93 cells and F3-transfected CHO cells; CHO/OLN: co-culture of OLN-93 cells and mock-transfected CHO cells; TAG/OLN: co-culture of OLN-93 cells and TAG-1-transfected CHO cells; TAX/OLN: co-culture of OLN-93 cells and TAX-transfected CHO cells.

FIG. 12. Immunofluorescence localization of Jagged1 and NB-3.

a-c: At P2, hardly any NB-3 staining was detectable. Jagged1 staining was present as linear streaks consistent with an axonal localization. Scale bar in a-c: 20 µm for a-i.

d-f: At P5, NB-3 can be observed to cluster at paranodal locations. Significantly, there is a distinct boundary between Jagged1 and NB-3 immunofluorescence, best seen in the enlarged images j-o. Scale bar in j-l: 2 µm for j-o.

g-i: At P14, the distribution of NB-3 and Jagged1 remains unchanged from the P5 pattern, apart from the fact that axon density and hence numbers of paranodes have increased.

FIG. 13. The schematic diagram of the molecular constituents of the paranode in the central nervous system.

At this location, multiple oligodendroglial cytoplasmic loops (here pictured only as a single loop) intimately contact the axolemma. The present study has revealed that in addition to axonal F3/contactin and Caspr and glial neurofascin 155 (NF-155), other members of the axoglial junction include axonal NB-3 and glial Notch. It has also been demonstrated that a functional signalling interaction exists between F3/NB-3 and Notch. (N: Node of Ranvier, PN: Paranode, JPN: Juxtaparanode).

Table I

Primary rat oligodendrocytes were plated on coated F3-Fc, NB-3-His or BSA (control) substrates, respectively. After 2 hours in culture, total RNA was extracted and subjected to real time RT-PCR analysis of MAG and PLP mRNA expression levels. Relative expression levels were derived using the comparative $C_T$ method. ($C_T$: cycle threshold).

FIG. 14. Notch and F3 are binding partners.

(A) Cell adhesion assay. OLN cells were labeled with α-Notch1 (a) or α-Notch2 (b). OLN cells were plated on dishes spotted with F3 (c, e-i) or CHL1 (d). Cells were untreated or pre-treated prior to plating with α-Notch1 (e) or α-Notch2 (f), pre-immune serum (serum) (g), or with antigen-depleted α-Notch1 (D-α-Notch1) (h) or α-Notch2 (D-α-Notch2) (i). Dotted lines depict the edges of the protein-Fc spots. Adherent cells were visualized by staining with Coomassie Blue. j: Quantification of OLN cell adherence to F3 substrate and the effects of blocking antibodies. # $p<0.05$ compared with CHL1, *p<0.05 compared with pre-immune serum. Scale bar in (i): 20 µm for a, b; 120 µm for c-i.
(B) Cell repulsion assay. mN1-transfected HeLa cells (a) or mock-transfected HeLa cells (b) were plated on F3 coated dishes. Adherent cells were stained with Coomassie Blue. c: Quantification of HeLa cell adherence to F3 and the effects of blocking antibodies. In some experiments, mN1-transfected HeLa cells were pretreated with α-F3 or α-Notch1, or with pre-immune serum (serum). # p<0.05 compared with mock-transfected HeLa cells, *p<0.05 compared with pre-immune serum. Scale bar in (b): 15 µm for a, b. Bar graphs (Aj, Bc) represent the number of adherent cells (mean±SD).

FIG. 15. Notch and F3 associate as a protein complex.
(A) F3 co-immunoprecipitates with Notch1 or Notch2. a: Immunoprecipitates from rat brain lysate were prepared using α-Notch1, α-Notch2, non-immune IgG or unconjugated beads, and were probed with α-F3. b: Reciprocal assays used α-F3 to capture the protein complex, followed by immunoblotting with α-Notch1 or α-Notch2 to detect the binding partner.
(B) Subcloning of the Notch1 extracellular domain. a: Schematic diagram of Notch1 and its subcloned fragments. b, c: Coomassie Blue staining and α-Notch1 immunoblot of the four fragments, respectively.
(C) F3 binds to specific domains of Notch1. a: The GST-Notch1 extracellular fragments (N1.1, N1.2, N1.3 and N1.4) or GST alone were used in a GST pull-down assay with rat brain lysate. The precipitates and rat brain lysate (right lane) were probed for F3. b: Quantification of mock- and F3-transfected CHO cells adhering to culture dishes coated with the four GST fusion fragments or GST alone. Bars represent the number of adherent cells (mean±SD). *p<0.05 compared with GST.
(D) Lipid raft analysis. F3 was mainly localized to the fifth fraction while Notch1 was enriched in fractions 9-12. Caspr was used as a positive control to mark lipid raft fractions. H: Total homogenate.

Figure 16A:
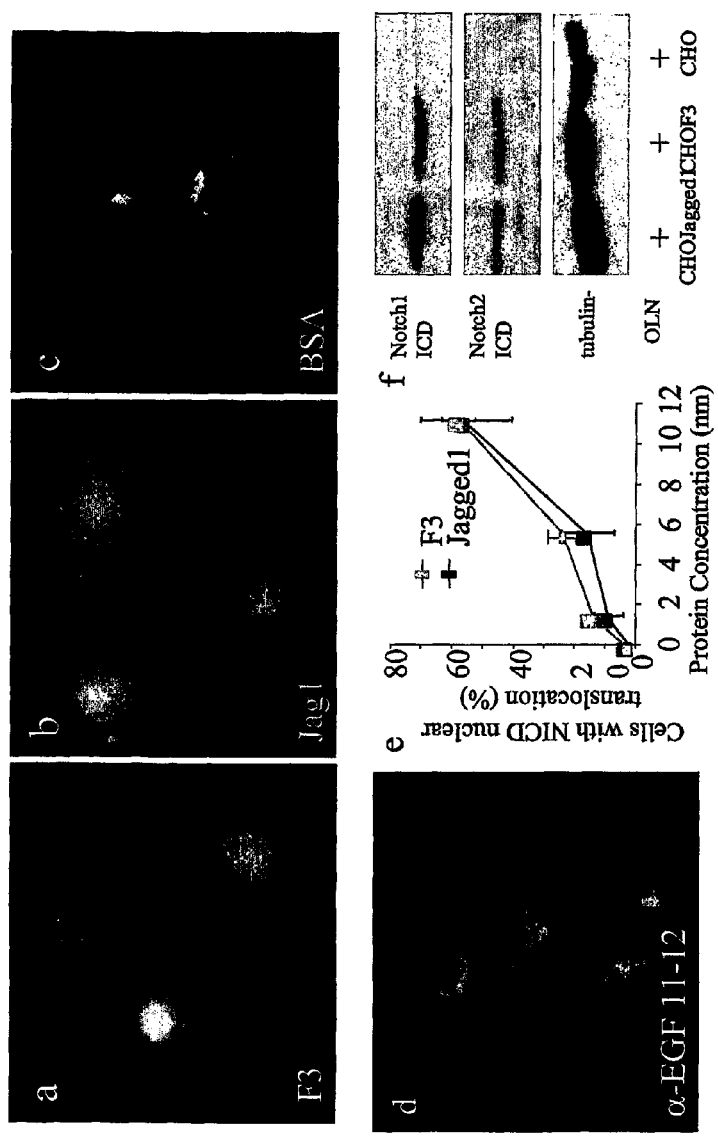
Figure 16B:
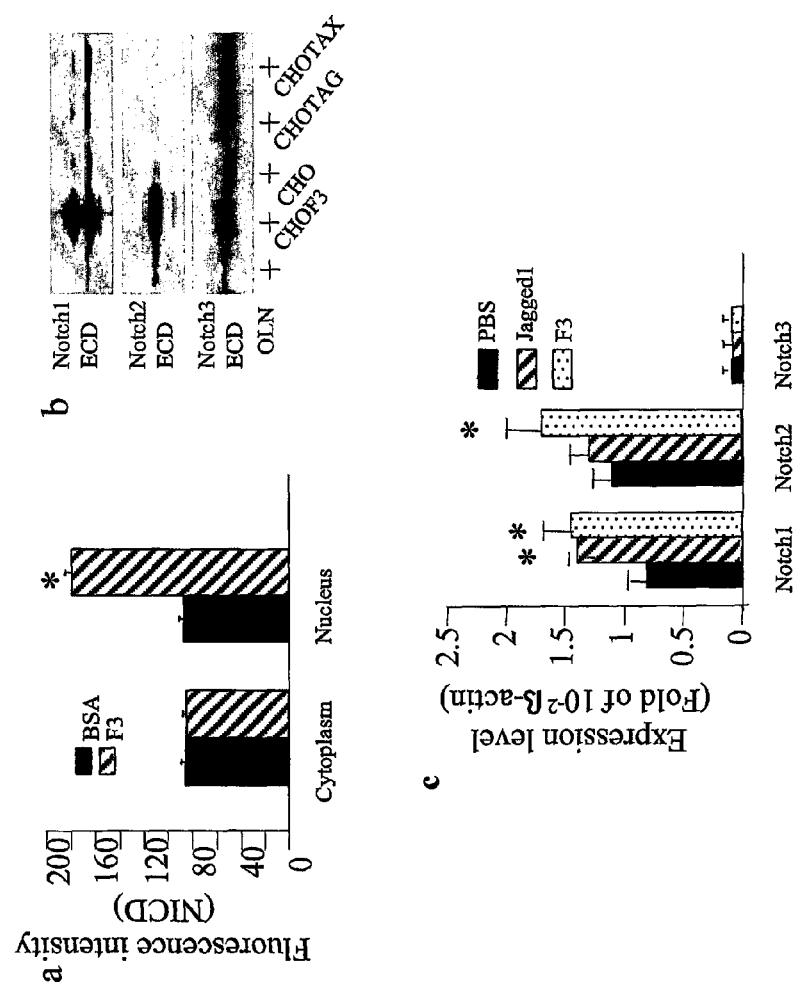

FIGS. 16A & 16B. NICD translocation.
(A) F3-induced NICD nuclear translocation. mNotch1-myc transfected OLN cells were treated with 11.2 nM F3 (a), Jagged1 (b), BSA (c) or pre-incubated with α-Notch1 EGF (11-12) prior to F3 treatment (d) and then stained with α-NICD. e: Quantification of cells with nuclear staining of NICD after treatment with increasing concentrations of F3 and Jagged1. Data are mean±SEM. f: OLN cells were cultured with Jagged1-, F3- or mock-transfected CHO cells, and lysates were immunoprobed with α-Notch1, α-Notch2 and α-tubulin.
(B) Upregulation of Notch1 and Notch2. Total (cytoplasmic plus nuclear) NICD staining intensity was quantified in F3-treated and BSA-treated mNotch1-myc transfected OLN cells (a). OLN cells cultured alone or with F3-, mock, TAG-1-, or TAX-transfected CHO cells were lysed and probed with .alpha.-Notch1, o-Notch2 and .alpha.-Notch3 (b). c: Real-time PCR assay of Notch mRNA levels in OLN cells treated with 11.2 nM F3, Jagged1 or PBS. Notch mRNA levels were normalized to .beta.-actin. Bars are mean.+-.SEM. *p<0.05 compared with PBS.

FIGS. 17A & 17B. OLN cellular processes halt and alter their morphology upon contact with F3-transfected CHO cells.
Cellular processes (arrows in a and b) of OLN cells extend towards F3-transfected CHO cell somata and upon contact with them, terminate and elaborate a flattened cytoplasmic sheet that envelops the cell body. This phenomenon is indicated by asterisks (*). a: Both OLN and F3-transfected CHO cells w ere pre-stained with PKH26 red fluorescent dye. b:

The bright-field micrograph corresponding to (a). a, f, i: OLN cells were pre-stained with PKH26 red fluorescent dye. d, g, j: Both OLN cells and F3-transfected CHO cells were strained for c-myc (green), e, h, k: Merged images of (c, d), (f, g), (i, j), respectively. l-q: In the control system, cellular processes (arrowheads) of OLN cells extend past transfected CHO cell bodies. (l, m), (n, o), and (p, q) are corresponding PKH26 red fluorescent and bright-field micrographs of co-cultures of OLN cells with mock-(l, m), TAX-(n, o) and TAG-1-(p, q) transfected CHO cells. r: Quantification of OLN cellular processes extending past transfected CHO cell bodies in the co-cultures. Data are mean±SD -p<0.01 compared with controls. Scale bar in (q): 25 µm for (a, b, l-q) and 15 µm for (c-k).

FIGS. 18A-D. MAG is upregulated by F3/Notch interaction.
(A) MAG is upregulated by F3. CHO cells and transfected derivatives do not express classic ligands of Notch, Delta, Jagged1 and Jagged2 (a). Lysates of rat brain, OLN alone, and the indicated co-cultured cells were probed with α-MAG (upper panel) or α-γ-tubulin (bottom panel) (b). (G) Measured by real-time PCR, MAG mRNA in primary OLs is elevated significantly by F3, versus BSA treatment. The raw data were normalized to GAPDH using comparative $C_T$ method.
(B) F3, but not Jagged1, upregulates MAG. mNotch1-myc transfected OLN cells were treated with 11.2 nM F3-Fc (a, d) or Jagged1 (b, c, e, f) and labeled using α-MAG (a, b) or α-CNPase (d, e). The arrows in (b, e) indicate the cell bodies, which can be better viewed in bright-field pictures (c, f). g: Fluorescence intensities of MAG and CNPase staining in cells treated with F3, Jagged1, BSA, or pretreated with α-Notch1 EGF (11-12) followed by F3. Data are mean±SEM. h: Quantification of the surface area (mean±SEM) occupied by cells treated with F3, Jagged1 or BSA. *p<0.05; **p<0.01 compared with BSA.
(C) MAG upregulation is F3/Notch interaction-dependent.
a-j: OLN cells transfected with Notch ICD-deleted mutants, dn-N1 (a), dn-N2 (b); LacZ (a); S3 cleavage mutants, V1744K (d) and V1744L (e); Notch ECD-deleted mutants, caN1 (f, g) and caN2 (h, i), were treated (a-e) or untreated (f-i) with 11.2 nM F3 and double labeled for MAG (red) and V5 (a-c, f, h) (green) or c-myc (d, e) (green). The transfected cells in f, h can be better viewed as indicated by arrows in bright-field pictures g, i, respectively. j: MAG fluorescence intensities in cells transfected with various indicated constructs followed by different protein treatments. Data are mean±SEM. ECD: extracellular domain; TM: transmembrane domain: ICD: intracellular domain. The S3 site mutations in V1744K and V1744L constructs were indicated by triangles in the transmembrane region. *p<0.01 compared with F3-treated OLN cells. Scale bar in (Ci): 20 µm for (Ba-f); 40 µm for (Ca-i).

Figure 19A:
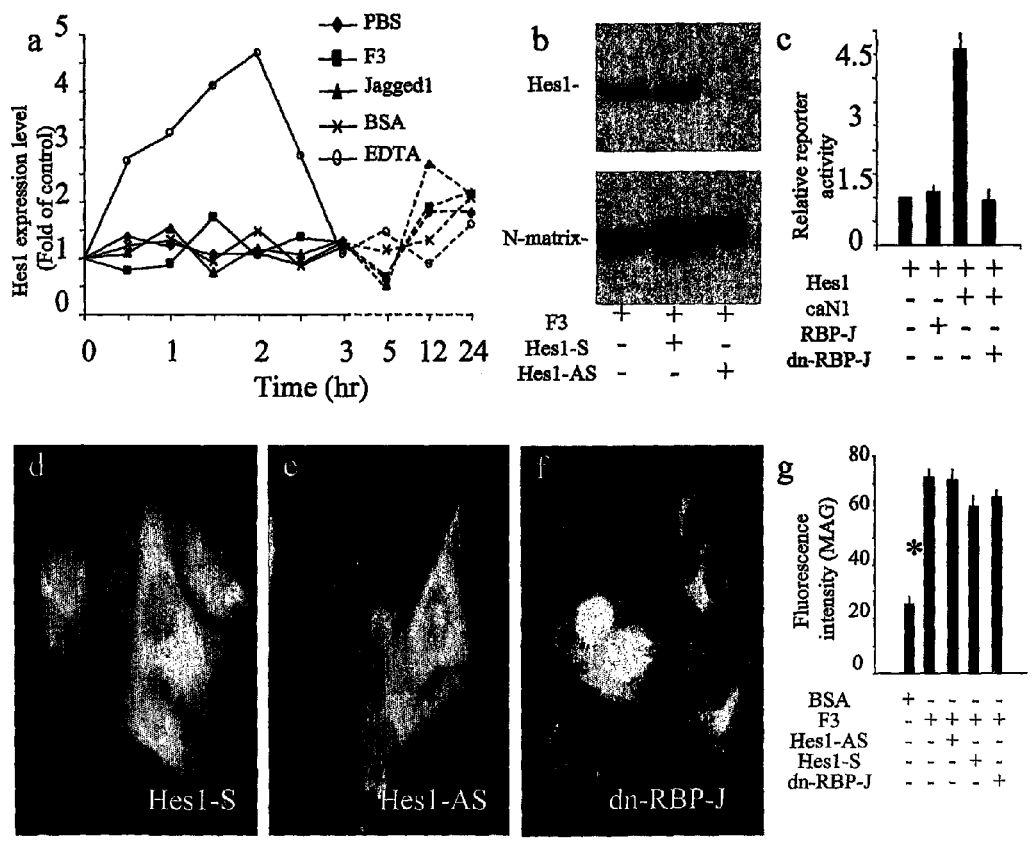
Figure 19B:
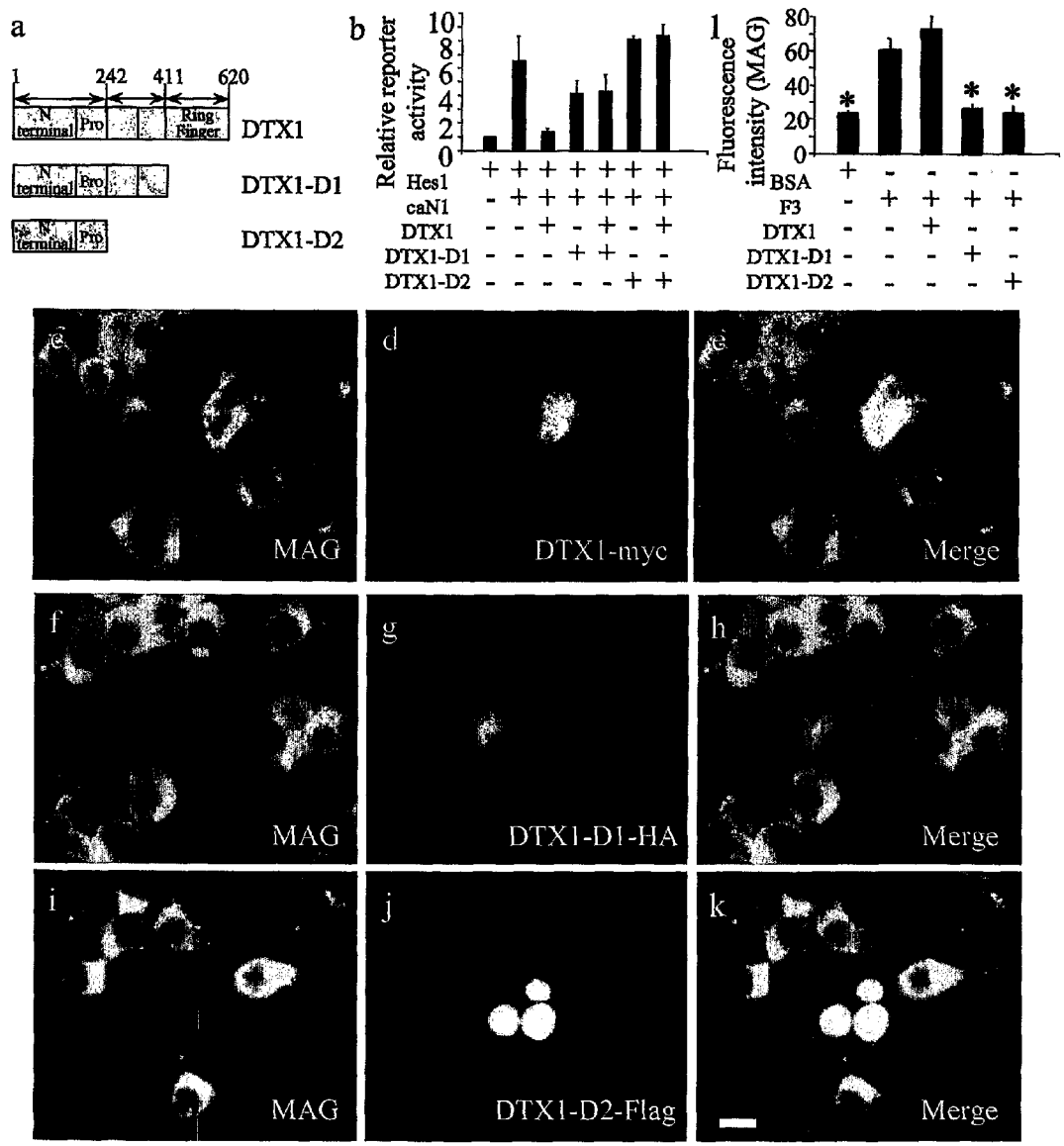

FIGS. 19A & 19B. MAG expression is independent of Hes1 and dependent on DTX1.
(A) MAG upregulation is independent of Hes1 expression. (a) OLN cells were treated with the indicated ligands or compounds. At the times shown, Hes1 transcripts were quantified using real-time PCR and normalized to that at the start of the time course. (b, d, e) OLN cells were untreated or pre-treated with Hes1 sense (Hes1-S) or antisense (Hes1-AS) oligonucleotides followed by 11.2 nM F3. Cell lysates were probed with ax-Hes1 (upper panel) or α-nuclear matrix protein (N-matrix) (bottom panel) (b) or cells were labeled for MAG (d, e). Also, OLN cells transfected with pGVB/Hes1 reporter alone or together with constructs expressing caN[1], RBP-J, or myc-tagged dn-RBP-J were subjected to luciferase assay (c).

Data are mean i SD. f: OLN cells transfected with dn-RBP-J-myc were treated with 11.2 nM F3 and double stained for MAG (red) and c-myc (green). g: MAG staining intensity in OLN cells with various treatments indicated above. Data are mean±SEM. *$p<0.01$ compared with cells treated with F3 alone.

(B) MAG upregulation involves DTX1. a: DTX1 constructs used in luciferase reporter assays and immunostaining study. N terminal: N terminal domain; Pro: Proline-rich motif; Ring finger: Ring-H2 finger motif. OLN cells were transfected with pGVB/Hes1 reporter alone or together with indicated expression constructs. b: Luciferase reporter activity in these cells. Data are mean±SD. DTX1 (c-e)-, DTX1-D1-HA (f-h)-, or DTX1-D2-Flag (i-k)-transfected OLN cells were treated with 11.2 nM F3 and double labeled for MAG (red) and related tags (green). 1: MAG fluorescence intensity in OLN cells transfected with indicated constructs followed by different protein treatments. Data are mean±SEM. *$p<0.01$ compared with F3-treated OLN cells. Scale bar in (Bk): 30 μm for Ac-f, Bc-k.

FIG. 20. F3/Notch signaling via DTX1 promotes OPC differentiation.

Purified Ng2+/CNPase-OPCs (a), were treated with BSA (b), F3 (c) or Jagged1 (d) for 2 days, double labeled for Ng2 (red) and CNPase (green) and counted (k). OPCs were also transfected with tagged dn-N1 (e, h) and DTX1-D2 (f, i), followed by F3 treatment or with caN1 and left untreated (g, j). Cells were double stained for the appropriate tag (green) and CNPase (red; e-g) or Ng2 (red; h-j), and counted (k). Scale bar in (j): 25 μm for (a, e-inset), 100 μm for (b-j).

FIG. 21. Proposed model of distinct ligand-dependent Notch signaling pathways during development.

F3 interacts with the Notch receptor on the opposing cell surface to stimulate Notch/RBP-J signaling pathway to recruit DTX1 before or after releasing NICD into the cytoplasm. The NICD/RBP-J/DTX1 complex may undergo specific but unidentified modification prior to translocation into the nucleus where it activates target genes such as MAG. This signaling may contribute to OL maturation after P6 when decreased Jagged1 expression favors the initiation of F3/Notch signaling. In contrast, before P6, Jagged1/Notch signaling activates the NICD/RBP-J-dependent transcription of target genes such as Hes1 and predominantly inhibits OPC differentiation. ECM: Extracellular matrix; C: Cytoplasm; N: Nucleus; NICD$^{Jag1}$, NICD$^{F3}$: NICD released upon Jagged1 and F3 activation, respectively; E: embryo; P6, P15: postnatal day 6 and 15, respectively; A: adult; OPC: oligodendrocyte precursor cell; O: oligodendrocyte; right bottom cartoon: myelinating oligodendrocyte ensheathing the axon.

Figure 22A:
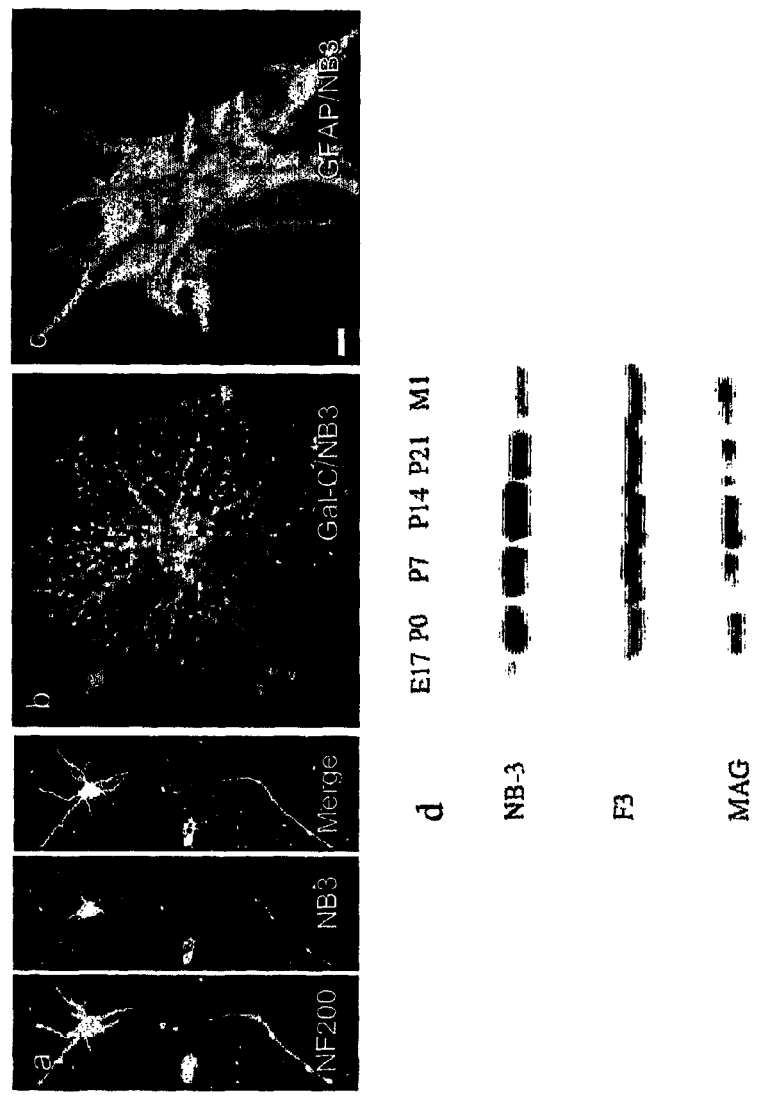

FIGS. 22A-C. NB-3 is a paranodal neuronal molecule.
A. NB-3 is expressed by neurons. Purified neurons, OLs and astrocytes of E17 rats were double stained for NB-3 and corresponding surface marker: NF200 (a), Gal-C (b) and GFAP (c), respectively. Scale bar in (c): 30 μm for (a-c).
(d) NB-3 is expressed from E17. Brain stem from rats with indicated ages were homogenized and subjected to immunoblot for NB-3, F3, MAG.
(B) NB-3 is localized at the paranode. Brain stem sections from 90 day old rats were double labeled for NB-3 and Caspr (a-c) or NB-3 and sodium channels (d-f). Scale bar in (f): 15 μm for (a-f).
(C) Lipid raft assay. NB3 was enriched in fraction 5, the same fraction as F3 and Caspr. H: Total homogenate.

23. NB-3 is a functional ligand of Notch1.
(A) NB-3 binds to Notch1. (a) NB-3 co-immunoprecipitated with Notch1. Immunoprecipitates from rat brain lysates using α-Notch1 and α-NB-3 were probed with α-NB-3 or α-Notch1, respectively. (b) Cell adhesion assay. OLN cells were seeded on NB-3 substrate and adhere to it. Adhesion was specifically blocked by α-Notch1 or α-NB-3. # $p<0.05$ compared with CHL1; *$p<0.05$ compared with pre-immune serum. (c) NB-3 binds to specific region on Notch1. The Notch1 GST fusion proteins or GST alone were used in a GST pull-down assay from rat brain lysates. The precipitates and brain lysates were probed for NB-3. (d) Quantification of adherent NB-3- and mock-transfected CHO cells to the four Notch1 GST fusion fragments. *$p<0.05$ compared with GST. Bar graphs (b, d) represent the number of adherent cells (mean±SD).
(B) NB-3/Notch interaction induces NICD nuclear translocation in OLN cells. mNotch1-myc transfected OLN cells treated with NB-3 (a), Jagged1 (b) and BSA (a) were immunostained for NICD. Some cells were treated with EGF antibody (d) or γ-secretase inhibitor (e) before NB-3 stimulation. OLN cells were also transfected with V1744K-myc (f, h) or V1744L-myc (g, i), treated with NB-3 (f, g) or Jagged1 (h, i), and immunostained with c-myc antibody to locate NICD. Scale bar in (a): 20 μm for (a-i) (j) After NB-3 or Jagged1 treatment, α-c-myc precipitates from mNotch1-myc, V1744K-myc or V1744L-myc transfected OLN cells were immunoblotted by α-NICD (upper panel) or α-V1744 (lower panel)
(C) Hes1 and Hes5 are not activated by NB-3. OLN cells treated with NB-3 for different durations as indicated were lysed and the extracted mRNA subjected to real-time PCR (a). The data were normalized to the mRNA level at the starting point. Other cells were treated with PBS, BSA, L1 or NB-3 for 48 hours and analysed by real-time PCR (b). (c) OLN cells were transfected with Hes1 or Hes5 luciferase reporter alone followed by NB-3 treatment or with caN1 construct. 24 hours post-transfection, cells were subjected to luciferase assay. Data are mean±SD.

Figure 24A:
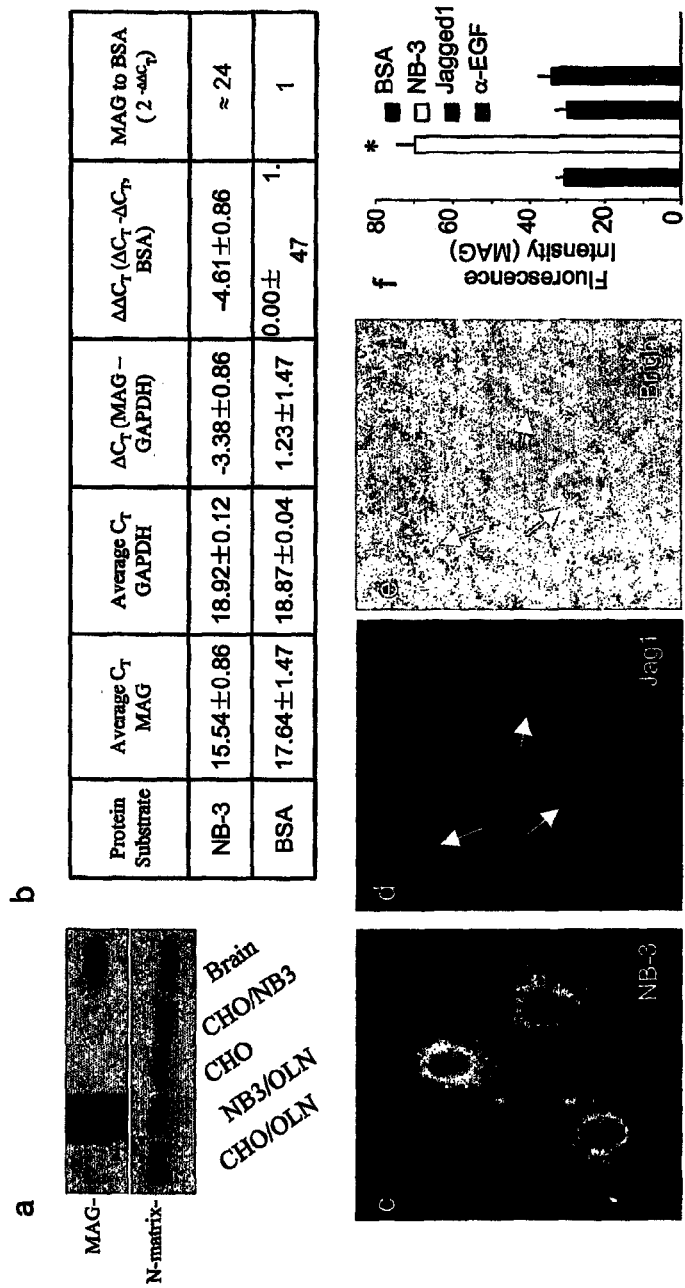
Figure 24B:
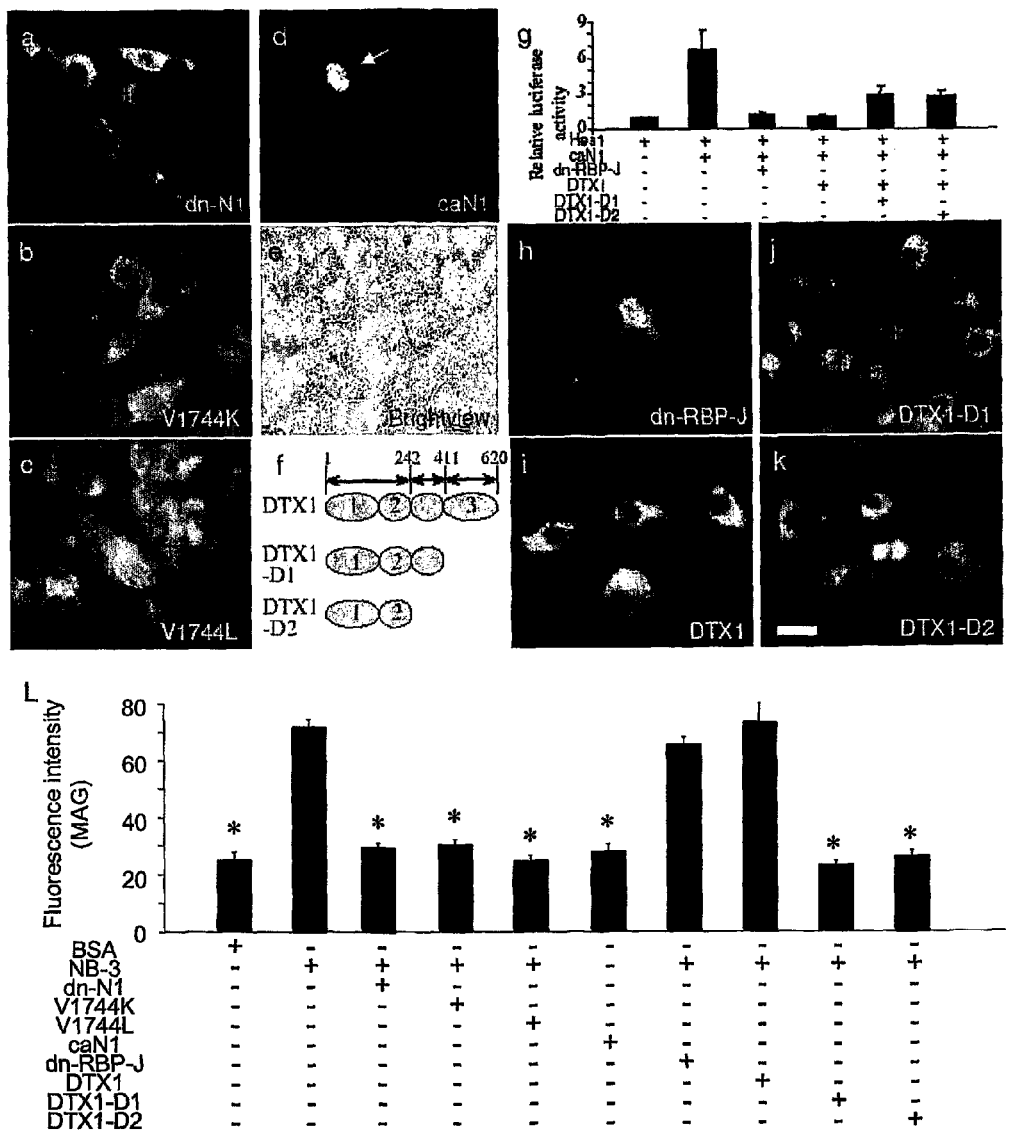

FIGS. 24A & 24B. NB-3/Notch interaction upregulates MAG via DTX1.
(A) MAG was upregulated in the co-culture of OLN-93 cells and NB-3-transfected CHO cells (a). N-matrix: nuclear matrix protein. CHO/OLN, NB3/OLN: co-culture of OLN-93 cells and mock- or NB-3-transfected CHO cells, respectively. (b) MAG mRNA in primary OLs increased about 24 fold after NB-3 stimulation as monitored by real-time PCR. GAPDH was used as an internal control. OLN cells were treated with NB-3 (c), Jagged1 (d, e) and BSA (not shown) and immunostained for MAG. The fluorescence intensity of MAG was counted (f). Data are mean±SEM.
(B) NB-3-induced MAG upregulation involves DTX1. OLN cells were transfected with dn-N-1-V5 (a), V1744K-myc (b), V1744L-myc (c), caN1 (d, e), dn-RBP-J-myc (h), DTX1-myc (i), DTX1-D1-HA (j), and DTX1-D2-Flag (k), and treated with NB-3. The cells were then immunostained for MAG and corresponding tag. The fluorescence intensity of MAG was counted in transfected and non-transfected cells (l). Data are mean±SD. (f) Schematic structure of DTX1 and its two deletion mutants. Number 1, 2, 3 correspond to N-terminal, proline-rich region and Ring-H2 finger motif, respectively. (g) Hes1 luciferase reporter assays to confirm the validity of indicated constructs. Data are mean±SD. The scale bar in (k): 30 μm for (AC-e, Ba-k).

FIG. 25. NB-3 developmentally clustering at paranodes promotes OPC differentiation via Notch1/DTX1 signaling pathway.
(A) NB-3 and Jagged1 are distinctly distributed during development. Brain stems from P2 (a), P5 (b, e) rats were double stained for Jagged1 (green) and NB-3 (red). The scale bar in (e): 30 μm for (a, b), 5 μm for (a).

(B) NB-3/Notch accelerates OPC differentiation via DTX1. Purified Ng2+ OPcs from P7 rat optic nerve (a) were treated with BSA (b), NB-3 (a) or Jagged1 (d) for 2 days and double labelled for Ng2 (red) and CNPase (green). Other cells were transfected with dn-N1 (e), DTX1-D1 (f) followed by NB-3 stimulation or caN1 (g) alone. Cells were then immunostained for tags (green) and CNPase (red). The percentage of CNPase+ cells were counted (h). Data are mean±SEM. The scale bar in (g): 40 μm for (a-g).

FIG. 26. NSC: Rat brain stems of indicated ages were subjected to Western blot for NB-3 and Notch1 expression patterns.

FIGS. 27A-D. NSC: NB-3 is a functional ligand of Notch1.
(A) NSCs express Notch1. NSCs were double stained for precursor marker nestin (a) and Notch1 (b). (a) is the merged picture. Scale bar in (e): 60 μm for (a-e).
(B) NB-3 binds to Notch1. P0 rat brain samples were precipitated by Protein A beads coupled with NB-3-Fc fusion protein, α-Notch1 or α-NB-3 and the precipitates were blotted as indicated (a). N1-transfected Hela cells (N1) were seeded onto coated NB-3 substrate in the absence (b) or presence of blocking antibodies: α-NB-3 (c), α-Notch1 (d) or pre-immune serum (s) (e). The adherent cells were counted (f). Data are mean i SD. *p<0.05 compared with mock-transfected Hela cells; # p<0.05 compared with pre-immune serum.
(C) NB-3 induces NICD nuclear translocation. NSCs were individually treated with NB-3 (12.5 nM) (a), Jagged1 (50 nM) (b) or BSA (c) for 24 hours then fixed and triple stained for nestin (green), NICD (red) and Hoechst 33258 (blue) to locate NICD. Scale bar in (c): 20 μm for (a-c).
(D) NB-3 does not activate Hes1. NSCs were transfected with Hes1 luciferase reporter construct followed by NB-3 or Jagged1 treatment or cotransfected with caN1. 24 hours post-transfection, the cells were lysed and subjected to luciferase assays (a). Other NSCs were transfected with pE7 luciferase reporter together with indicated constructs with or without NB-3 treatment and subjected to luciferase assays (b). Data are mean±SD.

FIG. 28 NSCs: NB-3 promotes OL generation.
NSCs were passaged into mitogen-withdrawn culture medium that was supplemented with NB-3 (a, d), BSA (b, e) or Jagged1 (c, f). After 7 DIV differentiation, the cells were triple stained for CNPase (a-c, red) or β-tubulin (d-f, red), GFAP (a-f, green) and Hoechst 33258 (a-f, blue). Other NSCs were individually immunolabelled with marker antibody and subjected to flow cytometry. The percent of each type of cells: OLs, neurons and astrocytes were counted (g). Data are mean±SEM. Scale bar in (f): 40 μm for (a-f).

FIGS. 29A & 29B. NB-3/Notch signalling pathway via DTX1 instructs oligodendrogliogenesis.
NSCs were transfected with dn-N1 (a, b), DTX1-D2 (d, e) followed by NB-3 treatment or caN1 (f, g) and double stained for appropriate tags and CNPase (a, d, f) or GFAP (b, e, g). (c) Schematic structure of DTX1 and DTX1-D2 constructs. The validity of the constructs utilized here was confirmed in Hes1 luciferase reporter assays (h). The percents of transfected cells that were positive for CNPase or GFAP were counted (i). Data are mean±SD. Scale bar in (g): 20 μm for (a, b, d-g)

FIG. 30. The putative model.
The extracellular NB-3/Notch interaction releases from the membrane NICD, which recruits DTX1 and translocates into the nucleus where the complex mediates directly or indirectly CNPase expression, thus promoting oligodendrogliogenesis. NSC: neural stem cell; O: OLs; M: membrane; N: nucleus; CNP: CNPase.

Results

Notch is the Oligodendroglial Surface Receptor for F3 and NB-3

The inventor set out to identify the glial receptor for F3 and NB-3. Both molecules have a basic structure composed of immunoglobulin and fibronectin type III repeats. Previous work investigated the effect of F3/tenascin-R (TN-R) interaction in various in-vitro models (Xiao et al, 1996, 1997, and 1998 all incorporated herein by reference). Of relevance to the present study, the inventor had demonstrated that the epidermal growth factor-like repeats of TN-R constituted the binding site for its neuronal receptor F3. The extracellular domain of Notch is composed primarily of epidermal growth factor-like repeats, hence making it a plausible candidate as the glial receptor of F3 and NB-3. In addition to this structural factor, the temporal and spatial location of Notch on the maturing oligodendrocyte in contact with the axon additionally attests to its suitability as a receptor for paranodal F3 and NB-3. As the experiments utilized the oligodendrocyte cell line OLN-93, it was confirmed using immunocytochemistry that these cells indeed express both Notch1 and Notch2 on their surface (FIG. 1c-d).

The inventor first carried out substrate adhesion assays to determine if F3 and NB-3 could be binding partners of Notch. To do this, the OLN-93 cells were cultured on F3 and NB-3 protein substrates in the presence or absence of respective blocking antibodies against F3, NB-3 and Notch. The results show that OLN-93 cells adhered readily to F3 and that the adhesive effects were blocked by antibodies against the F3 substrate and both Notch1 and Notch2 (FIG. 1a-j). Cell adhesion to the F3 substrate was also reduced when NB-3 antibodies were added. The OLN-93 cells also adhered to NB-3 and incubation with antibodies against NB-3, Notch1 and Notch2 reduced cellular adhesion. In addition, when OLN-93 cells were plated upon NB-3, they rapidly underwent a marked morphological change. They enlarged and transformed into oval-shaped to circular flattened cells characterized most strikingly by an expansive cytoplasmic sheet (FIG. 1c-j). This alteration in morphology also occurred when OLN-93 cells were plated upon the F3 substrate, but only after a longer duration (not shown). As controls, the inventor used bovine serum albumin and CHL1 (Holm et al, 1996), another neural cell adhesion molecule of the immunoglobulin superfamily, but neither substrate promoted OLN-93 cell adhesion. This suggests that the F3/NB-3 signal may constitute a mechanism that triggers oligodendroctye differentiation.

Additional evidence for the interaction between F3/NB-3 and Notch was provided using the same assay system and blocking antibodies, but using mouse Notch1-transfected HeLa cells instead of OLN-93 cells (FIG. 1k-r). In this instance, the inventor noted interestingly that Notch1-transfected HeLa cells were repelled from F3-Fc and this repulsive effect was reversed when antibodies against F3 and Notch1 were added. In the case of NB-3-His, there was adhesion of the Notch1-transfected HeLa cells, which was inhibited when antibodies against NB-3 and Notch1 were added. These cellular studies strongly suggest that Notch is a receptor for F3 and NB-3.

F3 and NB-3 Bind to Distinct Sites on Notch

To analyse further the presence of an association between F3 and Notch and between NB-3 and Notch, the inventor carried out several biochemical and molecular approaches (FIG. 2). Rat brain membrane preparations were solubilized in 2% Triton X-100 and were immunoprecipitated with antibodies to Notch1 and Notch2. Western Blot analysis using anti-F3 and anti-NB-3 showed that the anti-Notch1 and 2 antibodies precipitates contained both F3 and NB-3 (FIG. 2a-b). Control immunoprecipitates with non-immune IgG were negative for both F3 and NB-3. In the reverse co-immunoprecipitation experiment, anti-F3 and anti-NB-3 was used to immunoprecipitate similar brain preparations and the blot probed with antibodies to Notch1 and Notch2 (FIG. 2c-d). These co-immunoprecipitation results provide evidence that both F3/Notch and NB-3/Notch interactions may underlie the formation of protein complexes in the brain.

To allow the inventor to further characterize this interaction, the extracellular domain of Notch1 was arbitrarily divided into four equal sized overlapping 1.5 kb fragments (FIG. 2e) and subcloned each of them in frame into pGEX-KG (Guan and Dixon, 1991) for GST fusion protein production. The four protein fragments were expressed by induction of transformed E. coli. The inventor's nomenclature for the four Notch1 protein GST fusion protein fragments is N1.1, N1.2, N1.3 and N1.4, proceeding in a N- to C-terminal direction. Coomassie Blue staining and immunoblots of the four fragments are shown (FIG. 2f-g). The antibody to Notch1 specifically recognized N1.3 and N1.4 (FIG. 2g). Given the inventor's finding that the adhesion of OLN93 cells to F3 and NB-3 were blocked by same Notch1 antibodies, F3 and NB-3 may at least have a common binding site on either N1.3 or N1.4.

The inventor then carried out a GST pull-down assay to provide further biochemical evidence that an association exists between Notch and both F3 and NB-3. The four Notch1 GST fusion proteins were used to bind both F3 and NB-3 in a rat brain lysate. Upon analysis by Western blotting, they discovered that F3 associated with two fragments—N1.1 and N1.3 (FIG. 2h) whilst NB-3 associated with N1.3 only (FIG. 2i). These results serve to refine the inventor's earlier data that F3 and NB-3 are binding partners of Notch and that they have a common binding site on N1.3.

As an added confirmation of this biochemical interaction, the inventor used the four Notch1 protein fragments to carry out cell adhesion assays in which F3-transfected CHO cells and NB-3-transfected CHO cells were plated upon each individual fragment. The results support the findings from the GST pull-down assay, in that the F3-transfected cells bound predominantly to N1.1 and N1.3 (FIG. 2j) and the NB-3-transfected cells bound predominantly to N1.3 (FIG. 2k). Altogether, these results provide biochemical evidence to support the notion that Notch acts as a receptor for F3 and NB-3.

The Expression of MAG is Upregulated by the Interaction Between Notch and F3/NB-3

The above results substantiated the inventor's hypothesis that a molecular interaction occurs between paranodal F3 and NB-3 and oligodendroglial Notch as he has provided evidence of their physical association and also their respective axonal (F3, NB-3) and glial (surface expression of Notch1 on oligodendrocytes) locations. Next, he explored how this signalling event could be related to myelination. As the myelinating oligodendrocyte contacts and wraps the axons in a multi-layered spiral sheath, the protein components of the myelin sheath logically become upregulated as the event progresses. Thus using co-cultured OLN-93 cells and F3- or NB-3-transfected CHO cells, the inventor investigated the expression of myelin-specific proteins in these cellular models of F3/NB-3-Notch interactions. Pure OLN-93 cultures and co-cultures between OLN-93 cells and mock-, TAG- or TAX-transfected cells were used as controls. These cellular cultures were homogenized to prepare membrane extracts and analyzed them by immunoblotting to ascertain the levels of MAG (myelin-associated glycoprotein) and PLP (proteolipid protein), components of the myelin sheath in the CNS. It was shown that when OLN-93 cells were co-cultured with F3-transfected CHO cells or with NB-3-transfected CHO cells (not shown), MAG became specifically upregulated (FIG. 3). PLP levels, however, were the same in all the culture systems investigated. This suggested that the F3/Notch or NB-3/Notch interaction was active in the setting of myelination. To provide further evidence to support this finding, the inventor proceeded to analyze if a similar alteration in myelin-specific proteins occurred when primary oligodendrocytes were employed instead of the OLN-93 cell line. Therefore, primary cultures of rat (postnatal day 1 or 2) oligodendrocytes were prepared and plated them upon F3-Fc and NB-3-His fusion protein substrates. BSA (bovine serum albumin) was used as a control substrate. Again, this direct cell-protein contact strived to simulate the contact between axonal ligands and glia. Two hours after the cells were plated onto the proteins, total RNA was isolated from each of these interacting systems and performed real-time RT-PCR assays to measure the mRNA expression levels of MAG and PLP. It was noticed that in both the systems where primary oligodendrocytes were plated upon F3 and NB-3, MAG expression levels were approximately 8-fold higher than in the control system where BSA was used as a substrate (Table I). Message levels of PLP however were not found to be elevated when compared with the control. These findings are in agreement with the western blot results and further confirm the presence of myelin-specific gene up-regulation arising as a result of F3/Notch and NB-3/Notch signalling.

NB-3 and Jagged1 Localize to Distinct Axonal Domains

It has been explained how Jagged1 influences oligodendrocyte differentiation via Notch (Wang et al, 1998). When the oligodendrocyte cellular processes encounter F3 and NB-3 at the paranodes, a separate instruction could be conveyed to the myelinating cell, nevertheless via the same receptor—Notch. Having established that F3 and NB-3 are confined to paranodal regions, it became apparent that if Jagged1 were confined to the axonal segment enclosed by paranodes, namely the internode, a signal switch mechanism at work during axonal ensheathment could exist. The inventor therefore analyzed the distribution of NB-3 and Jagged1 in rat brain stem sagittal cryosections using immunofluorescence (FIG. 4). Three separate age groups were analyzed—postnatal days 2, 5 and 14, thus allowing the axonal pattern of NB-3 distribution to be investigated as the animal matured. The inventors could not observe any staining for NB-3 at P2 (FIG. 4a-c), whereas by P5 (FIG. 4d-f), NB-3 could be seen clustered at paranodes. From this result, the inventors inferred that NB-3 is likely diffusely distributed over the axonal surface initially and then translocates to the paranodes during development to form distinct clusters. Importantly, Jagged1 immunoreactivity was confined to internodes and was separate from paranodes (FIG. 4f). These findings suggest that the Notch receptors on myelinating oligodendrocytes may switch axonal binding partners from Jagged1 to F3/NB-3 when they migrate along the axon from the internodes to adjacent paranodes, thus becoming sequentially exposed to different signals.

Notch is the Oligodendroglial Surface Binding Partner of F3.

Axonal F3 congregates at the paranode, a potential site for F3 to interact with myelinating glia (Girault and Peles, 2002). Notch is a plausible binding partner since its extracellular portion possesses many EGF-like repeats (Martinez Arias et al, 2002) and is abundantly expressed on maturing OLs (Lardelli et al, 1994; Wang et al, 1998). To investigate this potential interaction an OL cell line OLN-93 (OLN) was utilized. OLN cells were derived from spontaneously transformed cells in rat brain glial cultures and resemble maturing OLs (Richter-Landsberg and Heinrich, 1996). OLN cells no longer express the progenitor cell surface marker A2B5, and are positive for only one isoform of myelin basic protein (MBP) (~14 kDa), characteristic of immature OLs. Immunocytochemistry confirmed that OLN cells express Notch1 and Notch2 on their surface (FIG. 6A*a, b*).

To investigate if F3 could bind to Notch, cell adhesion assays were performed as described (Xiao et al, 1996). OLN cells were plated on F3-Fc (F3) substrate in the absence or presence of blocking antibodies. OLN cells adhered readily to F3 (FIG. 6A*c*), but not to CHL1-Fc (CHL1), another neural cell adhesion molecule (Holm et al, 1996) (FIG. 6A*d*). Adhesion was blocked by pre-incubation with F3 (FIG. 6A*j*), Notch1 or Notch2 antibodies (FIG. 6A*e, f, j*), but not by pre-immune serum or antigen-depleted antibodies to Notch1 or Notch2 (FIG. 6A*g, h, i*). Murine Notch1 (mN1)-transfected HeLa cells (Logeat et al, 1998) were also used in cell repulsion assays, another approach to investigate ligand-receptor relationships (FIG. 6B). mN1-transfected HeLa cells were repelled from F3 (FIG. 6B*a*) compared with mock-transfected HeLa cells (FIG. 6B*b*). Repulsion was reversed by pre-treating the cells with F3 or Notch1 antibodies, but not with pre-immune serum (FIG. 6B*c*). These studies suggest that Notch1 interacts with F3.

F3 Binds to Specific Sites on Notch1

To confirm F3/Notch interaction, rat brain membrane samples were immunoprecipitated with Notch1 or Notch2 antibodies.

Immunoblotting of the precipitates using F3 antibody showed that they contained F3 (FIG. 7A*a*). In a reciprocal assay, an F3 antibody-precipitate was probed with Notch1 or Notch2 antibodies (FIG. 7A*b*). These results indicate that Notch and F3 can form complexes.

To identify the specific site(s) on Notch1 for F3 binding the mouse Notch1 extracellular domain was divided into four equal-sized fragments termed N1.1, N1.2, N1.3 and N1.4 (FIG. 7B*a*) and produced them as recombinant GST fusion proteins as identified (FIG. 7B*b, c*). The Notch1 antibody used in the aforementioned cellular studies recognized N1.3 and N1.4, but not N1.1 or N1.2. GST pull-down assays with rat brain lysates revealed that F3 associated with N1.1 and N1.3 (FIG. 7C*a*). To confirm this, F3-transfected CHO cells (Gennarini et al, 1991) were seeded onto culture dishes coated with the four GST fusion proteins. Cells bound predominantly to N1.1 and N1.3. Mock-transfected CHO cells did not bind (FIG. 7C*b*).

F3 and Notch1 are not Co-Localized in Lipid Rafts

F3 is a surface molecule localized in lipid rafts of OLs (Kramer et al, 1999). To ascertain whether F3/Notch interaction could occur in cis in these microdomains, they were isolated from P15 rat cerebral cortex. Both F3 and Caspr were detected in fraction 5 of the sucrose density gradient (FIG. 7D) as reported (Faivre-Sarrailh et al, 2000). Notch1 was found only in fractions 9-12 that are enriched in cytoskeleton-associated proteins (FIG. 7D). The same results were obtained using adult rat cerebral cortex (not shown). Thus, F3 and Notch1 are unlikely to complex laterally within lipid rafts. Altogether, these observations suggest that F3 is a trans-binding partner of Notch.

NICD Translocates to the Nucleus after Notch Interacts with F3

The immediate consequence of Notch activation is the release and transport of NICD to the nucleus (Schroeter et al, 1998). To determine if F3 acts as a functional ligand to initiate these events, myc-tagged full-length mouse Notch1 (mNotch1-myc) was transfected into OLN cells. Cells were treated with different proteins and immunolabeled for NICD using NICD antibody (Logeat et al, 1998). In F3-treated cells concentrated NICD staining was observed mainly in the nuclei (FIG. 8A*a*), similar to Jagged1-induced NICD translocation (FIG. 8A*b*). BSA failed to trigger this event (FIG. 8A*c*). Pre-incubation with antibody to Notch1 EGF repeats 11-12 (EGF 11-12 antibody, which crossreacts with Notch2, not shown) abolished F3-induced NICD translocation (FIG. 8A*d*). Brefeldin A and monensin (not shown), compounds that inhibit the membrane insertion of Notch1 (Schroeter et al, 1998), also prevented NICD translocation. Cell treatment with increasing concentrations of F3 or Jagged1 led to a similar increase in nuclear clustering of NICD, indicating that translocation occurs in an F3 or Jagged1 concentration-dependent manner (FIG. 8A*e*). OLN co-cultured with either F3- or Jagged1-transfected CHO cells, but not with mock-transfected CHO cells, also resulted in production of Notch2 intracellular domain (ICD) (FIG. 8A*f*). Notch2 ICD antibody was not crossreactive with Notch1 ICD (not shown). These results demonstrate that F3, like Jagged1, can activate Notch1 and Notch2, leading to subsequent nuclear translocation of NICD.

F3 induces Notch Intramembrane Cleavage at the S3 Site.

As a prerequisite for activation, Notch undergoes RIP at the S3 site (V1744) by the presenilin-dependent γ-secretase (Schroeter et al, 1998; Huppert et al, 2000). To clarify the nature of F3-induced cleavage, mNotch1-myc transfected OLN cells were pre-incubated with γ-secretase inhibitor and then treated with F3 or Jagged1. In both cases, no NICD staining was observed in the nuclei (FIG. 8B*a, b*). Moreover, two S3 cleavage mutants: V1744K-myc and V1744L-myc, which showed reduced proteolysis and parallel reduction in activity (Schroeter et al., 1998), were transfected into OLN cells that were then treated with F3 or Jagged1. Cells showed c-myc immunostaining mainly in the cytoplasm and on the cell surface, but not in the nuclei (FIG. 8B*c-f*). In immunoprecipitation assays, c-myc antibody-precipitates from F3- or Jagged1-treated V1744K-myc and V1744L-myc transfected OLN cells could only be labeled with NICD antibody that also recognizes full-length Notch1 (300 kDa) (FIG. 8B*g*, upper panel), indicating that these mutant Notch1 molecules remained intact. Only the precipitates from F3- or Jagged1-treated mNotch1-myc transfected OLN cells showed a reactive band upon probing with V1744 antibody that solely recognizes NICD released from S3 (120 kDa) (FIG. 8B*g*, lower panel). Altogether, these observations suggest that F3 induces RIP at the Notch1 S3 site.

F3/Notch Interaction Upregulates Notch1 and Notch2 Expression

F3, but not BSA, induced a two-fold increase in nuclear NICD (FIG. 8C*a*), while there was no noticeable change in cytoplasmic NICD, suggesting that F3 upregulates Notch expression. To investigate this, OLN cells were cultured with mock-, F3-, TAG-1- or TAX-transfected CHO cells. TAG-1 and TAX are members of F3 subfamily (Tsiotra et al, 1993). Expression of Notch1 and Notch2, but not Notch3, increased when OLN cells were cultured with F3-transfected CHO cells (FIG. 8C*b*). Real-time PCR confirmed that soluble F3 increased Notch1 and Notch2, but not Notch3 transcripts (FIG. 8C*c*), while Jagged1 only upregulated Notch1, but not Notch2. Thus, F3/Notch interaction may provide a feedback loop to specifically upregulate Notch1 and Notch2.

Oligodendroglial Processes Alter their Morphology Upon Contact with F3

To model the scenario of axoglial contact during myelination, the morphology of OLN processes was studied when they contact cell surface-expressed F3. Since OLN cells extend longer processes than primary OLs they are ideally suited for observing subtle morphological changes that occur during contact. F3-transfected CHO cells mimicked the paranodal axonal component. Mock-, TAG-1- and TAX-transfected CHO cells were used as controls. Remarkably, most OLN processes terminated upon contact with F3-transfected CHO cells and flattened to form a cytoplasmic sheet spreading over the surface of CHO cells, as if in an attempt to envelop the cell (FIG. 9a-k). But this was not observed with mock- (FIG. 9l, m), TAG-1- (FIG. 9n, o) or TAX-transfected (FIG. 9p, q) CHO cells. While approximately 80% of extending processes halted upon reaching F3-transfected CHO cells, with other CHO cells the proportion was only 20% (FIG. 9r). These results show that a signal inducing the morphological change is presented to the oligodendroglial processes when F3 is encountered.

F3, but not Jagged1, Upregulates MAG

To explore how the morphological change described above could relate to F3/Notch signaling, the expression of myelin-associated glycoprotein (MAG) in the aforementioned co-cultures was investigated. Parental and transfected CHO cells did not express Delta, Jagged1 and Jagged2 (FIG. 10Aa). Membrane extracts of co-cultured cells were immunoblotted for MAG. The constitutive level of MAG in OLN cells was very low, if not, undetectable. However, when OLN cells were cultured with F3-transfected CHO cells, MAG was upregulated (FIG. 10Ab). F3-transfected CHO cells do not express MAG (not shown). On the other hand, in real-time PCR, purified primary OLs plated upon F3 substrate showed approximately sixteen-fold increase in MAG transcripts, versus cells seeded on BSA (FIG. 10Ac). OLN cells showed a similar efficiency of MAG upregulation (not shown).

In immunostaining assays, mNotch1-myc transfected OLN cells were immunolabeled for MAG and 2',3'-cyclic nucleotide 3'-phosphodiesterase (CNPase), an OLs specific antigen. Treatment with soluble F3 resulted in a remarkable increase in MAG staining (FIG. 10Ba) and enhanced CNPase staining (FIG. 10Bd), compared with Jagged1 (FIG. 10Bb, c, e, f) or BSA (not shown) treatment. Quantification of MAG and CNPase fluorescence intensities revealed an approximately 300% increase in MAG and 40% increase in CNPase labeling in F3-versus Jagged1- or BSA-treated cells (FIG. 10Bg). Cell pre-treatment with Notch 1 EGF 11-12 antibody prevented F3-induced increase in MAG and CNPase (FIG. 10Bg), suggesting that Notch is required for this event. In addition, F3 induced the cells to flatten and form a sheet-like structure (FIG. 10Ba). Quantification of the substratum area covered by cells revealed a two-fold increase in that covered by F3-versus Jagged1- or BSA-treated cells (FIG. 10Bh). These findings confirm F3-induced MAG upregulation.

MAG is Upregulated by F3/Notch Interaction

To better understand the involvement of NICD in this event, OLN cells were transiently transfected with V5-tagged dominant-negative Notch1 (dn-N1) or Notch2 (dn-N2) (Small et al, 2001), which lack the intracellular regions but can bind to extracellular ligands. Cells were then treated with F3 and double stained with V5 and MAG antibodies. Notably, both dn-N-1-V5- (FIG. 10Ca) and dn-N2-V5- (FIG. 10Cb) positive cells were poorly labeled for MAG. pcDNA4/V5/LacZ (LacZ) was used as a vector control (FIG. 10Cc). Moreover, OLN cells transfected with two S3 mutants, myc-tagged V1744K (FIG. 10Cd) and V1744L (FIG. 10Ce) were treated with F3 and double stained for c-myc and MAG. In either case, F3 failed to upregulate MAG in c-myc-positive cells. Quantification of MAG fluorescence intensity confirmed that Notch1 or Notch2 dysfunction, in other words, the absence of NICD, abolished F3-induced MAG upregulation (FIG. 10Cj), suggesting that NICD is required for MAG expression.

The inductive role of F3 in this event was further investigated by introducing into OLN cells V5-tagged constitutive-active Notch1 (caN1) (FIG. 10Cf, g) and Notch2 (caN2) (FIG. 10Ch, i), which lack the extracellular domains and are ligand-independently active (Small et al, 2001). That is, even in the absence of F3 stimulation, NICD is generated and translocates to the nucleus. And in OLN cells, caN1 (FIG. 10Ac) and caN2 (not shown) did lead to the transactivation of Hes1 in luciferase reporter assays. After transfection, cells were double stained for V5 and MAG. Immunolabeling showed that V5-positive cells were faintly stained for MAG (FIG. 10Cj). Given that Jagged1 also induces NICD release, but does not increase MAG expression, these results demonstrate that MAG upregulation requires F3 induced NICD.

F3/Notch-Induced MAG Upregulation is Independent of Hes1

A prominent feature of Notch signaling is the activation of Hes genes in an oscillatory manner (Hirata et al, 2002). Hes1 mRNA expression in OLN cells was thus investigated. In real-time PCR, non-physiological treatment of cells with 2 mM EDTA (Rand et al, 2000) triggered a sharp increase in Heal mRNA during the first two hours and a return to basal level by three hours (FIG. 11Aa), reflecting the exquisite intrinsic regulation of endogenous Hes1 expression (Dale et al, 2003). However, F3, Jagged1 or BSA treatment did not significantly alter the baseline oscillating levels of endogenous Hes1 transcription at short (the first three hours) or long (12 and 24 hours) times after treatment (FIG. 11Aa).

To investigate whether F3-induced MAG upregulation is related to constitutive levels of Hes1 protein, Hes1 antisense oligonucleotides (Kabos et al, 2002) were used to block basal Hes1 protein expression in OLN cells (FIG. 11Ab). MAG upregulation was not influenced by this treatment or control sense oligonucleotides (FIG. 11Ad, e, g).

RBP-J is a Notch-regulated transcription factor that can activate Hes genes (Martinez Arias et al, 2002). OLN cells were transfected with dominant-negative RBP-J-myc (dn-RBP-J-myc), bearing a mutation of lysine 218 to histidine, which abolishes effective high affinity binding to Hes1 promoter region (Kato et al, 1997). Hes1 luciferase reporter assay showed that the mutant prevented Hes1 activation by caN1 (FIG. 11Ac). After transfection, cells were treated with F3 and double labeled for c-myc and MAG. c-myc positive cells showed the same level of MAG as neighboring nontransfected cells (FIG. 11Af, g). These results indicate that MAG upregulation triggered by F3/Notch signaling is independent of endogenous Hes1 expression.

F3/Notch-Induced MAG Upregulation Involves DTX1

Increasing evidence indicates that DTX1 is another downstream element of the Notch signaling pathway (Martinez Arias et al, 2002). Given that F3-induced MAG upregulation is not related to Hes1 expression, the role of DTX1 in this event was investigated using myc-tagged wild-type DTX1 (Yamamoto et al, 2001) and its two deletion mutants as depicted (FIG. 11Ba), namely, HA-tagged DTX1 mutant (DTX1-D1) containing amino acids 1-411 (Yamamoto et al, 2001) and Flag-tagged DTX1 mutant (DTX1-D2) containing amino acids 1-242 (Izon et al, 2002). The two mutants lack the Ring-H2 finger motif, which contributes to DTX1 oligomerization, an essential step for DTX1 functioning (Matsuno et al, 2002). As previously observed (Yamamoto et al, 2001), Hes1 luciferase reporter assay showed overexpressed DTX1 inhibited the transactivation of Hes1 by caN1 (FIG. 11Bb). On the other hand, both DTX1-D1 and DTX1-D2 restored Hes1 response to caN1 (FIG. 11Bb). After transfection, OLN cells were treated with F3 and double labeled for MAG and corresponding tags. Overexpression of DTX1 had no effect on F3-induced MAG upregulation (FIG. 11B*c-e, l*). Interestingly, MAG upregulation was abolished in the HA-positive or Flag-positive cells (FIG. 11B*f-l*). These observations strongly suggest that F3/Notch-induced MAG upregulation involves DTX1.

F3/Notch Signaling Pathway Via DTX1 Promotes OPC Differentiation into OLs

The Jagged1/Notch signaling pathway inhibits differentiation of OPCs into OLs (Wang et al., 1998). To explore whether F3/Notch signaling via DTX1 instructs OPC differentiation, purified OPCs positive for the progenitor marker Ng2 (Dawson et al., 2000) (FIG. 12*a*), were treated with BSA, F3 or Jagged1 for 2 days and then double stained for Ng2 and the OL-specific CNPase (FIG. 12*b-d*). After F3 treatment, over 70% of OPCs differentiated into CNPase+ OLs compared to ~50% after BSA stimulation, while Jagged1 treatment resulted in nearly all OPCs remaining undifferentiated (FIG. 12*k*). F3-stimulated cells were more bifurcated and inclined to form a web-like structure (FIG. 12*c*) than BSA-treated cells (FIG. 12*b*). Notch and DTX1 involvement was examined by transfecting OPCs with dn-N1-V5 (FIG. 12*e, h*) and DTX1-D2-Flag (FIG. 12*f, i*), respectively, followed by F3 treatment for 2 days. Other OPCs were transfected with caN1-V5 and left untreated (FIG. 12*g, j*). Notably, immunolabeling for tags and CNPase (FIG. 12*e-g*) or Ng2 (FIG. 12*h-j*) showed that most dn-N1 (~75%) or DTX1-D2 (~67%) transfected OPCs remained Ng2+ (FIG. 12*k*), despite the presence of F3. In particular, ~40% of dn-N1-transfected cells were CNPase+, but these cells were less bifurcated (FIG. 12*e*, inset), compared to surrounding non-transfected cells, indicating a relatively immature stage. However, CNPase+DTX-D2-transfected cells were hardly detectable. Consistent with a previous report (Wang et al., 1998), caN1-transfected cells remained Ng2+ and almost none became CNPase+OLs (FIG. 12*k*), indicating that F3-induced NICD is specifically required for accelerated OPC differentiation. These results demonstrate that F3/Notch signaling via DTX1 promotes OPC development.

NB-3 is Located at the Paranode

Central to the inventor's aims is the characterization of an interaction between an axonal ligand and an oligodendroglial receptor at the paranode, acting as a stop signal to prevent extending oligodendrocyte cellular processes from impinging upon axonal domains destined to become nodes of Ranvier. The first step was to demonstrate the identity of the axonal ligands. Among the potential candidates, there is F3 which exists as a complex with Caspr at the paranode (Rios et al, 2000). Previous results (Kazarinova-Noyes et al, 2001) are in agreement, showing that in rat optic nerve fibres, double-labelling with Caspr revealed the presence of F3 in both paranodal and nodal locations.

Recently, NB-3, a GPI-linked cell adhesion molecule, has been identified as a member of F3/Contactin family (Lee et al, 2000). To determine the cell type(s) that express NB-3, purified primary neurons, OLs and astrocytes from E17 rat cerebella were separately cultured and double stained for NB-3 and specific markers: neurofilament 200 (NF200) for neurons (FIG. 14A*a*), galactocerebroside (Gal-C) for OLs (FIG. 14A*b*) and glial fibrillary acidic protein (GFAP) for astrocytes (FIG. 14A*c*). The results confirmed that only neurons expressed NB-3. NB-3 expression in rat brain stem development was next investigated by Western blot. Compared with F3, NB-3 expression started from E17, reached a plateau between P0 to P21, and declined afterwards (FIG. 14A*d*), which parallels the time frame of OL development, as marked by increased expression of MAG. These observations indicate that NB-3 is a neuron-derived molecule. These results suggest that NB-3/Notch signalling may play certain roles in multiple phases of OL development. However, NB-3's exact localization and physiological role has not been fully clarified.

F3/contactin and TAG-1, two members of the F3/contactin family, locate specifically at nodal, paranodal, and juxtaparanodal regions (Girault and Peles, 2002). In particular, the paranode flanks the node of Ranvier and forms the adhesive site for axoglial junctions, which is crucial for initiating myelination and stabilization of myelin loops (Girault and Peles, 2002). To explore the role of NB-3 in axoglial interaction, NB-3 distribution was analysed along myelinated axons. Double immunofluorescence staining was performed by using monoclonal NB-3 antibody, which does not cross-react with F3 (not shown), and polyclonal antibodies against Caspr or sodium channels on adult rat brain stem sagittal cryosections. Note that NB-3 overlapped exactly with Caspr (FIG. 14B*a-c*) and flanked nodal sodium channels (FIG. 14B*d-f*). To confirm this spatial specificity, NB-3 distribution in lipid rafts from P15 and adult (not shown) rat cerebral cortex was studied. F3 and Caspr are colocalized in lipid rafts. In agreement with the previous finding (Faivre-Sarrailh et al, 2000), these two paranodal molecules were colocalized in fraction 5 of a sucrose density gradient. Interestingly, NB-3 was also mainly located in this fraction (FIG. 14C). Taken together, these results indicate that NB-3 as a paranodal component may co-localize with the F3/Caspr complex on myelinated axons.

NB-3 is a Functional Ligand of Notch1

Given its expression profile and specific location during OL maturation, the inventor was interested in finding whether NB-3 could interact with OL-derived Notch1. Immunoprecipitation assay showed that Notch1 extracellular domain (~190 kDa) was detected in a NB-3 antibody-precipitate from adult rat brain membrane extracts while a Notch1 antibody-precipitate contained NB-3 (FIG. 15A*a*), implying the existence of NB-3/Notch complex. OLN-93 (OLN) cells, a permanent cell line resembling maturing Ols (Richter-Landsberg and Heinrich, 1996) were used in cell adhesion assays. Immunocytochemistry showed that OLN cells expressed Notch1 on the surface (not shown). Cells adhered to the coated NB-3 substrate, but not to CHL1, another neural cell adhesion molecule (Holm et al, 1996). Adhesion was blocked by pre-incubation with NB-3 or Notch1 antibodies, but not with F3 antibody or pre-immune serum (FIG. 15A*b*). The same results were obtained by using Notch1-transfected Hela cells (not shown). To map the binding site(s) on Notch1, four subcloned sequential equal-sized portions of the mouse Notch1 extracellular domain, labelled as N1.1, N1.2, N1.3, and N1.4 were used in a GST pull-down assay from rat brain lysates. Immunoblotting showed that NB-3 associated only with N1.3, a region containing EGF repeats 22-34 (FIG. 15A*c*). The specificity was confirmed by the observations that NB-3-transfected CHO cells plated upon the individual recombinant fragments bound predominantly to N1.3 (FIG. 15A*d*) while mock-transfected CHO cells did not bind. Together, these results support the concept that NB-3 is a ligand of Notch1.

NB-3/Notch Interaction Induces NICD Nuclear Translocation in OLN Cells

Upon binding its ligands, the core signalling mechanism of Notch involves Regulated Intramembrane Proteolysis (RIP) at the S3 site, which releases NICD into the nucleus (Schroeter et al, 1998). To explore whether NB-3 is a functional ligand of Notch1, OLN cells transfected with myc-tagged full-length mouse Notch1 (mNotch1-myc) were treated with NB-3 (FIG. 15B*a*), Jagged1 (FIG. 15B*b*), or BSA (FIG. 15B*c*) and immunostained with NICD antibody (Logeat et al, 1998). Both NB-3 and Jagged1, but not BSA, induced NICD to concentrate in the nucleus. Notch1 EGF antibody targeting EGF-like repeats on Notch1 prevented NB-3-induced NICD nuclear clustering (FIG. 15B*d*). To study the properties of NB-3-induced NICD release, OLN cells were pre-incubated with γ-secretase inhibitor before exposure to NB-3 (FIG. 15B*e*) or Jagged1 (not shown). In both cases, nuclear NICD clustering was abolished, indicating that NB-3-induced NICD release involves γ-secretase. Moreover, OLN cells transfected with two S3 mutants: myc-tagged V1744K and V1744L which abolished S3 cleavage (Schroeter et al, 1998), successfully prevented NB-3- (FIG. 15B*f, g*) as well as Jagged1- (FIG. 15B*h, i*) induced NICD nuclear translocation. In Western blot (FIG. 15B*j*), c-myc antibody precipitates from either NB-3 or Jagged1-treated V1744K-myc or V1744L-myc-transfected OLN cells could only be blotted by NICD antibody, which also recognizes intact Notch1 (~250 kDa) (upper panel), but not by V1744 antibody, which only recognizes released NICD from the S3 site. In contrast, mNotch-myc transfected OLN cells generated NICD (~120 kDa) that was blotted by V1744 antibody after NB-3 or Jagged1 treatment (lower panel). Together, these results demonstrated that NB-3 induced γ-secretase-dependent Notch1 RIP at the S3 site.

Hes1 and Hes5 are not Activated by NB-3

In the nucleus NICD interacts with transcription factors, such as RBP-J and/or Deltex1 (DTX1), thus activating target genes, such as HES genes (Martinez Arias et al, 2002). Thus the correlation between Notch1 activation by NB-3 and endogenous Hes1 mRNA level in OLN cells was investigated. Real-time PCR showed that compared to BSA, NB-3 induction resulted in the similar level of Hes1 mRNA and oscillatory expression pattern (Ref) (FIG. 15C*a*). 48 hours after various treatments, including another cell adhesion molecule L1, Hes1 mRNA still remained at basal level (FIG. 15C*b*). To further clarify whether NB-3 activates Hes1, Hes luciferase reporter assay (FIG. 15C*c*) was used. Neither Hes1 nor Hes5 was activated by NB-3 treatment, while constitutive-active Notch1 (caN1) (Small et al, 2001) activated both luciferase reporters, indicating that NB-3 did not activate Hes1 and Hes5.

NB-3/Notch Interaction Upregulates MAG Via DTX1

The effect of NB-3/Notch1 signalling in myelination was further explored. The membrane extracts from co-cultured OLN cells with NB-3- or mock-transfected CHO cells were immunoblotted for MAG, a hallmark of OL maturation. MAG was upregulated only in OLN cells cultured with NB-3-transfected CHO cells (FIG. 16A*a*). Real-time PCR showed that NB-3 increased MAG transcripts about 24 folds in primary OLs from P5-P7 rat cerebral cortex (FIG. 16A*b*). Immunostaining showed that in response to NB-3, mNotch1-myc transfected OLN cells produced a 2.5-fold increase in MAG staining (FIG. 16A*c, f*), compared with Jagged1 (FIG. 16A*d-f*) or BSA (FIG. 16A*f*). MAG upregulation was blocked by pre-treating the cells with Notch1 EGF antibody (FIG. 16A*f*). To study the role of NB-3/Notch1 in MAG upregulation, OLN cells were transfected with dominant-negative Notch1 (dn-N1) (Small et al, 2001) that lacks the intracellular portion but still can bind to extracellular ligands. After treatment with NB-3, MAG upregulation was not observed in transfected cells (FIG. 16B*a*, green). Moreover, V1744K or V1744L-transfected OLN cells (green) also abolished MAG elevation (FIG. 16B*b, c*). Since caN1 alone failed to increase MAG expression in transfected cells (FIG. 16B*d, e*, green), these observations indicate that NB-3-generated NICD is essential for MAG upregulation.

NB-3-Induced MAG Upregulation Involves DTX1

To identify the transcription factor involved in this event, OLN cells were transfected with dominant-negative RBP-J (dn-RBP-J) (Kato et al, 1997), which lack effective high affinity binding to DNA (FIG. 16B*h*) or DTX1 (Yamamoto et al, 2001) (FIG. 16B*i*) or two DTX1 deletion mutants that lack the Ring-H2 motif required for oligomerization of DTX1 (FIG. 16B*f, j, k*): DTX1-D1 (Yamamoto et al, 2001) and DTX1-D2 (Izon et al, 2002). Hes1 luciferase reporter assay confirmed the validity of these constructs in OLN cells in that dn-RBP-J inhibited Hes1 transactivation by caN1 and the competitive binding of DTX1 to caN1 also affected this, which was restored by DTX1-D1 or DTX1-D2 (FIG. 16B*g*). After NB-3 treatment, cells were immunostained for MAG and fluorescence intensity counted (FIG. 16B*l*). It was found that the ablation of Hes1 basal expression in OLN cells (green) by dn-RBP-J (FIG. 16B*h*) did not affect NB-3-induced MAG upregulation. Similarly, DTX1-transfected cells (FIG. 16B*i*, green) responded to NB-3 stimulation. However, the dysfunction of endogenous DTX1 by DTX1-D1 and DTX1-D2 (FIG. 16B*j, k*, green) abolished this event, indicating that DTX1 is involved in NB-3-mediated MAG expression. Thus NB-3 may activate the Notch1 receptor and release NICD, which recruits DTX1 during myelination.

NB-3 Developmentally Clustering at Paranodes Promotes OPC Differentiation via Notch1/DTX1 Signaling Pathway Since NB-3 is expressed from E17, it is conceivable that the two pairs of interaction: Jagged1/Notch1 and NB-3/Notch1 may coexist along the axon at early developmental stage. To explore whether NB-3 and Jagged1 coordinate myelination in a step-wise fashion, the spatial correlation between these two molecules along axons during development was first studied. Sections of P2, P5, and P14 (not shown) rat brain stems were double labelled for Jagged1 (green) and NB-3 (red). At P2, Jagged1 was evenly distributed along the axon and congregated NB-3 was hardly detectable (FIG. 17A*a*), which was in agreement with the previous observation that Jagged1/Notch1 signalling may predominate to promote migration of young OL loops along axons at this stage (Wang et al, 1998). At P5, NB-3 clustered at the paranode (FIG. 17A*b, c*) and Jagged1 occupied the juxtaparanode and internode, separated from paranodal NB-3 (FIG. 17A). Given the decrease of Jagged1 expression (Wang et al, 1998) after P6, the inventor's observations suggest that the balance between these two pairs of interactions may be disrupted during the later stage of OL maturation, in other words, NB-3/Notch1 interaction predominates to induce OL maturation at the CNS paranode. To attest this notion, purified OPCs from P7 Wistar rat optic nerve (FIG. 17B*a*) were treated with BSA, NB-3 or Jagged1 for 2 days and then immunostained for Ng2 (red), a progenitor marker and CNPase (green), a young OL marker (FIG. 17B*b-d*). Statistical counting showed that NB-3 promoted OPC differentiation into CNPase-positive OLs (~75%), compared to BSA (~50%) or Jagged1 (~0%) treatment (FIG. 17B*h*). To further confirm the involvement of Notch1 and DTX1 in NB-3-promoted OPC differentiation, OPCs were transfected with dn-N1 (FIG. 17B*e*) or DTX1-D1 (FIG. 17B*f*) and treated simultaneously with NB-3. Double labelling for tags (green) and CNPase (red) showed that introduction of either construct significantly blocked NB-3-promoted OPC differentiation into OLs (FIG. 17B*h*). And consistent with the previous study (Wang et al, 1998), caN1-transfected OPCs remained undifferentiated (FIG. 17B*g, h*).

NB-3/Notch Signalling via Deltex1 Directs Differentiation of Embryonic Neural Stem Cells into Oligodendrocytes To explore whether NB-3/Notch1 interaction is also involved in oligodendrogliogenesis from Neural Stem Cells (NSCs), the developmental expression patterns of NB-3 and Notch1 was investigated. Western blot of rat brain samples showed that both NB-3 and Notch1 were expressed at embryonic day 17 (E17) and an abrupt increase after birth reached a maximum level between postnatal day 0 (P0) and 21 (P21), which corresponds to the time frame of oligodendrogliogenesis from NSCs (FIG. 18).

NSCs: NB-3 is a Functional Ligand of Notch1

The expression of Notch1 on NSCs by immunofluorescence was studied next. The NSCs used in this study were isolated from embryonic day 14 BALB/c mouse embryo striatum (Arsenijevic et al, 2001). These cells expressed intermediate filament protein nestin (FIG. 19A*a*), a progenitor marker, and Notch1 (FIG. 19A*b, a*). To confirm the NB-3/Notch interaction previously observed, NB-3-Fc fusion protein coupled to Protein A beads was used to precipitate binding partner of NB-3 from NSC membrane extracts. The precipitate was positively blotted with Notch1 antibody (FIG. 19B*a*). Further, P0 rat brain membrane extracts were immunoprecipitated using NB-3 antibody and blotted with Notch1 antibody and vice versa (FIG. 19B*a*). Western blot showed that NB-3 and Notch1 co-immunoprecipitated. Moreover, cell adhesion assay was performed by plating murine Notch1-(N1) and mock-transfected HeLa cells onto NB-3 substrate coated proteins. N1-transfected HeLa cells adhered to NB-3 (FIG. 19B*b*), but mock-transfected HeLa cells did not bind (FIG. 19B*f*). Adhesion was prevented by pre-incubation of cells with NB-3 or Notch1 antibodies (FIG. 19B*c, d*), but not with pre-immune serum (FIG. 19B*e*). These studies corroborate that NB-3 is a binding partner of Notch.

NSCs: NB-3 Induces NICD Nuclear Translocation but does not Activate Hes1

Notch activation by ligand binding is featured by NICD nuclear translocation (Schroeter et al, 1998). The inventor studied whether NICD nuclear translocation in NSCs could occur in response to NB-3 stimulation. It has been observed above that NB-3 induces γ-secretase dependent NICD nuclear translocation in OLN cells. In agreement with that study, merged triple staining showed that NB-3 treatment of nestin (green) positive NSCs resulted in NICD clustering (red) in the nucleus visualized by Hoechst 33258 staining (blue) (FIG. 19C*a*), which was similar to Jagged1 stimulation (FIG. 19C*b*). However, BSA failed to trigger this event (FIG. 19C*c*), suggesting that NB-3 specifically interacts with Notch1 to effect typical NICD nuclear translocation. Another prominent feature of classic Notch signalling pathway is that nuclear NICD transactivates target genes, such as Hes genes (MartinezArias et al, 2002). Thus the Hes1 luciferase reporter assay was utilized to investigate whether NB-3-generated NICD could activate Hes1. The results showed that NB-3 did not upregulate Hes1, while either Jagged1 or constitutive-active Notch1 (caN1) (Small et al, 2001) activated Hes1 as expected (FIG. 19D*a*). As increasing evidence showed that Deltex1 (DTX1) is another Notch downstream element (Yamamoto et al, 2001), the impact of NB-3 on DTX1-mediated Mash1 transcriptional activity in pE7 luciferase reporter assays was studied (FIG. 19D*b*). Consistent with the previous report (Yamamoto et al, 2001), DTX1 inhibited Mash1 transactivation of pE7 reporter. However, NB-3 treatment mimicked this inhibition partly, which was abolished by one DTX1 deletion mutant, Flagged-tagged DTX1-D2 (Izon et al, 2002) that lacks the domain 3, Ring-H2 motif which is required for functional DTX1 homodimer formation (Matsuno et al, 2002) (FIG. 21*c*). These results suggest that NB-3-generated NICD may mediate DTX1-related transcription events.

NSCs: NB-3 Promotes OL Generation

Given that the expression of both NB-3 and Notch1 parallel the time frame of OL development, the inventor explored whether NB-3/Notch interaction was involved in oligodendrogliogenesis from NSCs. To do this, NSCs were allowed to differentiate for 7 days in the absence of mitogen and in the presence of serum and NB-3 (FIG. 20*a, d*), BSA (FIG. 20*b, e*), or Jagged1 (FIG. 20*c, f*). The cells, identified by Hoechst 33258 (FIG. 20*a-f*, blue), were immunostained for OL marker: CNPase (FIG. 20*a-c*, red); neuronal marker: β-tubulin (FIG. 20*d-f*, red); and astrocyte marker: GFAP (FIG. 20*a-f*, green). The results showed that distinct from BSA and Jagged1, NB-3 promoted OL generation. On the other hand, compared to BSA, NB-3 had little impact on neurogenesis, while Jagged1 inhibited this as reported (Morrison et al, 2000). Flow cytometry confirmed these observations in that NB-3 induced a 2-fold increase in OL generated, compared to BSA treatment, while Jagged1 inhibited OL development (FIG. 20*g*).

NSCs: NB-3/Notch Signalling Pathway Via DTX1 Instructs Oligodendrogliogenesis

To confirm the involvement of Notch1 in this event, NSCs were transfected with V5-tagged dominant-negative Notch1 (dn-N1) (Small et al, 2001). dn-N1 lacks the intracellular domain but can still bind to the extracellular ligand. The Hes1 luciferase reporter assay showed that dn-N1 failed to respond to Jagged1 treatment to activate Hes1 (FIG. 21*h*). Mitogens were then withdrawn and NB-3 added to the culture medium. Double labeling for V5 and CNPase or GFAP showed that dysfunction of Notch1 by dn-N1 abolished NB-3-promoted oligodendrogliogenesis, while favouring astrocyte formation (FIG. 21*a, b, i*). To further investigate whether DTX1 participates in NB-3-induced OL formation, NSCs were transfected with Flag-tagged DTX1-D2 (FIG. 21*c*). Hes1 luciferase reporter assay confirmed that DTX1 inhibited Hes1 activation by caN1 while DTX1-D2 restored Hes1 elevation by caN1 (FIG. 21*h*). After differentiation in the presence of NB-3, NSCs were immunostained for Flag and CNPase or GFAP. The results showed that DTX1-D2 transfected cells failed to differentiate into OL after NB-3 stimulation but were directed to astrocytes (FIG. 21*d, e, i*). And consistent with previous studies (Tanigaki et al, 2001) introduction of caN1 into NSCs resulted in astrogliogenesis while inhibiting OL generation (FIG. 21*f, g, i*). These observations indicate that NB-3 promoted oligodendrogliogenesis via Notch/DTX1 signalling pathway (FIG. 22).

Discussion Relating to the Second Aspect of the Invention

Using molecular, cellular, and morphological approaches, the inventor has identified a functional molecular interaction between Notch and F3/NB-3 at the paranode, a vital site for axoglial signalling in myelination. A new axonal adhesion molecule—NB-3, has been localized to the paranode. This interaction may regulate the differentiation of the myelinating oligodendrocyte during axonal ensheathment and act to prevent putative nodes of Ranvier from becoming invested in myelin. In addition to established Notch/Jagged1 signaling pathway, the inventor provides evidence for novel Notch ligands—F3 and NB-3 in the context of the myelinating process, suggesting that signaling via Jagged1 and F3/NB-3 may contribute in a co-ordinated fashion to myelination.

The data designates the adhesion molecule F3 as a new functional ligand of Notch. F3/Notch interaction induces the generation and nuclear translocation of NICD and elevates Notch1 and Notch2 expression. It promotes OPC differentiation and upregulates MAG in OLN cells and primary OLs, thus revealing a potential regulatory role for F3 in OL maturation. Thus, ligand-specific Notch signaling via Jagged1 as an inhibitory factor and F3 as a positive instructor may regulate myelination in a coordinated fashion (FIG. 13).

The data also designates NB-3 as another new functional ligand of Notch. The extracellular NB-3/Notch interaction releases from the membrane NICD, which recruits DTX1 and translocates into the nucleus where the complex mediates directly or indirectly CNPase expression, thus promoting oligodendrogliogenesis (FIG. 22).

Notch is an Oligodendroglial Surface Receptor of F3/NB-3

Intuitively, both axons and oligodendrocytes must actively participate and achieve two-way communication if myelination is to be properly co-ordinated. The emerging concept is that of an active signaling axoglial channel sited at paranodes, where cytoplasm-filled glial loops spiral and indent the adjacent axolemmal membrane. Although paranodal axonal and glial molecular members have been described, their functional interactions in regulating myelination remain ill-defined. In support of the notion that glial Notch could act as the receptor for axonal F3 and NB-3, the inventor shows through co-immunoprecipitation experiments and GST pull-down assays that these molecules physically interact. Furthermore, he has identified two regions of F3 interaction (N1.1 and N1.3) in the extracellular domain of Notch1, one of which (N1.3) is shared with or overlaps with that involved in NB-3 binding.

Notch is a Functional Receptor for F3/NB-3

This study proposes the presence of a molecular stop signal to prevent mature myelinating oligodendrocytes from encroaching upon and myelinating putative nodes of Ranvier. The inventor has direct evidence of oligodendroglial processes emanating from OLN-93 cells terminating and spreading over the surface of F3 transfected CHO cells. The molecular basis for this signal is an interaction between F3 and Notch. In support of this, adhesion assays using OLN-93 and Notch1-transfected HeLa cells cultured upon a F3 substrate demonstrate that cellular interactions are disrupted by specific antibodies against the proposed ligand-receptor pair. Together with previous morphological data that confirm the presence of F3 at the paranodes and the inventor's data that reveal surface expression of Notch receptors on oligodendrocytes, the inventor suggests that an F3 signalling interaction indeed exists at the paranode and acts to prevent further extension of oligodendroglial processes. This interesting outcome is unique in postulating a mechanism that regulates the lateral limits of the myelinated internodes. In a similar manner to F3, the inventor has also provided evidence that NB-3 is a ligand for Notch1. Plating the Notch1-expressing HeLa cells on F3 or NB-3 led to different interactive outcomes; adherence to the NB-3 substrate, but repulsion from the F3 substrate. This could be due to distinct signals originating from the dual site F3-Notch interaction (resulting in cell repulsion) and the single site NB-3-Notch interaction (mediating adhesion). OLN-93 cells plated on NB-3 undergo a rapid differentiation and morphological alteration which ultimately leads to a flattened sheet-like appearance of the cell body, possibly representing a differentiation step in the multiphase process of myelination as the oligodendrocytes prepare to ensheath contacting axons. However, the common theme underlying the F3/Notch and NB-3/Notch interactions is that both are linked to myelination as evidenced by the upregulation of MAG at both protein and mRNA levels.

Different Ligands Signal to Glial-Derived Notch to Co-Ordinate Myelination

The complex nature of myelination demands a co-ordinated, dynamic series of axon-glial interactions which are likely regulated by the temporal and spatial distribution of trans interacting components. One such regulated interaction involves the interaction of axonal Jagged1 and oligodendrocyte-derived Notch1 in rat optic nerve (Wang et al, 1998). Notch receptor activation by Jagged1 inhibits differentiation and promotes migration of oligodendrocyte cellular processes along the axon. In an optic nerve model, Jagged1 is downregulated with a time course that parallels myelination. In accord with the finding that myelination begins only after target innervation (Schwab and Schnell, 1989), further studies showed that Jagged1 downregulation occurred only after axons reached their targets (Dugas et al, 2001). The Jagged1/Notch-signal that keeps oligodendrocytes in an immature state thus abates and differentiation of oligodendrocytes into mature myelin-forming cells progressively occurs. This key signal may then allow contact and extension of oligodendroglial cellular processes along the axon. The inventor's results support the idea that the Notch receptors may switch to other ligands, such as clustered F3/NB-3 as positive signals at paranodes, triggering the onset of the ensheathing process. This ligand switch mechanism may also underlie a phase transition from differentiating oligodendrocytes held in check by an axonal inhibitory signal to subsequent maturation into myelinating cells.

Spatial regulation of myelination may be achieved by the clustering of molecules along the axon. Clustering of sodium channels has been described (Salzer, 1997). In the maturing nerve, Caspr molecules are progressively herded towards the node to form tight bands, the "Caspr spiral", on either side of it (Pedraza et al, 2001).

Oligodendrocytes themselves appear crucial in promoting paranode formation through directing molecular localization. FIAU-induced ablation of oligodendrocytes in MBP-TK led to mis-localization of Caspr (Mathis et al, 2001). Significantly, the few myelinating oligodendrocytes in the MBP-TK brains were associated with focal clusters of Caspr close to MBP-positive domains. In jimpy mice, spontaneous degeneration of oligodendrocytes and mis-localization of Caspr occurs (Mathis et al, 2001). The inventor's previous work has also shown in re-myelinating peripheral nerves how F3, initially diffusely distributed along the demyelinated nerve fibre, becomes clustered at the paranodes by the effect of re-myelinating Schwann cells. Specifically, F3 clustering is seen at the extending edge of the Schwann cell (Kazarinova-Noyes et al, 2001). The results provided herein suggest that NB-3 also undergoes a similar clustering process, as it is barely detectable along P2 axons but forms distinct pairs of bands corresponding to paranodal staining at P5 and P14 (FIG. 4). This result also supports the notion that oligodendrocytes may be required for clustering of axonal molecules, such as Caspr, F3, and NB-3.

The oligodendroglial-dependent clustering may not only result in a redistribution of axonal proteins into domains but also lead to a "dose effect", in that molecules that were once sparsely distributed become packed together in highly dense bands. Only the concentrated axonal ligand may productively signal to glial receptors to achieve the "stop" effect, explaining why stop signals are not prematurely activated at the initial phase of axoglial contact when the axonal molecules are diffusely distributed. In this way, clustering could promote the switch of axonal cues, for example for Notch receptor switching from internodal Jagged1 to paranodal F3 and NB-3. This switch in cues would represent an essential regulatory mechanism during axonal ensheathment. In essence, the myelinating oligodendrocyte can be likened, albeit simplistically, to a machine with excavators at its lateral tips, its motor engine started (oligodendrocyte differentiation triggered by downregulation of Jagged1/Notch inhibitory signal), heaping up larger and larger mounds of earth as it progresses forwards (clustering of nodal and paranodal molecules) and then braking to a halt via an in-built feedback mechanism (clustered "high dose" F3 signalling to oligodendroglial Notch).

A number of studies have addressed signalling mechanisms that may play a part during myelination, such as the roles of neurofascin (Martin-Collinson et al, 1998) and N-cadherin (Schnadelbach et al, 2001). The inventor favours the concept proposed by Pedraza et al (2001) that membrane proteins of the axoglial junction at paranodes, as a conduit for bi-directional signal transduction, may act as selective molecular sieves and diffusion barriers whose purpose is to contribute to the organization of axonal domain architecture. Membrane proteins of the apposing axolemma and glial membrane loop interact via adhesion molecules to form mobile constructs of molecular sieves and barriers that "travel" along the axolemmal surface, pushing sodium channels and packing them at the nodes and allowing potassium channels to pass through to reach the juxtaparanode. Intracellular proteins linked to the cytoplasmic domains of the axolemmal and glial molecules may also contribute in a significant fashion to this barrier/sieving effect. Given that both F3 and NB-3 are GPI-linked molecules on the axonal surface, it will be interesting to investigate their cis interactions with transmembrane proteins and the nature of associated intracellular signal transduction pathways. Caspr, which associates with F3, interacts with members of the protein 4.1 family (Baumgartner et al, 1996; Ward et al, 1998) via its intracellular segment. This connects Caspr to spectrin and the axonal cytoskeleton (Hoover and Bryant, 2000). The presence of intact nodes of Ranvier containing clustered sodium channels but abnormally distributed F3, Caspr and potassium channels in the CGT-deficient mouse testifies to the fact that other important signalling mechanisms may exist (Coetzee et al, 1996; Bosio et al, 1998). As this enzyme (UDP-galactose-ceramide galactosyltransferase) is required for galactolipid synthesis, lipid molecules may also be crucial regulators of myelination. Further work to define the configuration and components of the axoglial junction will no doubt help create a knowledge base from which it is hoped that meaningful strategies to promote re-myelination of the damaged CNS will arise.

This study also reveals a new facet of Notch signalling— the existence of F3 and NB-3 as signalling ligands. These neural cell adhesion molecules are relatively widely distributed in the nervous system and may regulate Notch mediated processes. At present, Notch receptors are mostly investigated in the context of DSL (Delta, Serrate, Lag-2) ligands, CSL (CBF1, Suppressor of hairless, Lag-1) transcriptional cofactors and gene targets which are categorized as the HES (Hairy/Enhancer of Split) family of basic helix-loop-helix transcriptional regulators. The Notch receptor classically plays a critical role in cell fate selection during development (Artavanis-Tsakanos et al, 1999; Baker, 2000; Mumm and Kopan, 2000). Apart from neurogenesis during development, Notch also participates in gliogenesis (Morrison et al, 2000) and has been implicated in T-lymphocyte development (Robey et al, 1996), haematological malignancies (Ellisen et al, 1991) and familial stroke syndromes (Joutel et al, 1997). Notch is also unique as one of a few proteins that undergo regulated intramembrane proteolysis (Weinmaster, 2000). The modulation of these processes by cell adhesion molecules thus becomes another avenue for research.

Notch is an Oligodendroglial Surface Receptor of F3

Adhesive contacts at axoglial junctions are partly contributed by the F3-Caspr-neurofascin 155 heterotrimer (Girault and Peles, 2002), but the exact role of this complex remains to be further characterized. Herein the inventor defines a novel ligand-receptor interaction between F3 and Notch. Cell adhesion/repulsion assays and biochemical approaches demonstrate that Notch and F3 are binding partners. Further two extracellular sites on Notch1 for F3 binding have been identified, namely, N1.1 and N1.3. The former contains the EGF repeats 11-12 involved in DSL binding (Rebay et al, 1991). F3 is also expressed on OLs (Koch et al, 1997) and transduces signals to glial intracellular Fyn which then interacts with Tau protein to mediate myelination (Klein et al, 2002). Since soluble F3 is sufficient to trigger F3/Notch signaling and the lipid raft assay demonstrated that Notch1 is not localized to the F3-enriched fraction, F3 may not interact with Notch1 in cis. Given that Notch and F3 co-localize in various regions of the brain (Lardelli et al, 1994; Revest et al, 1999), particularly at axoglial junctions, the results suggest a role for F3 as a trans-acting ligand of Notch.

F3/Notch Signaling Induces Proteolytic Release of NICD and Upregulates Notch Homologs RIP, the generation of nuclear signaling proteins derived from non-nuclear precursors such as Notch and APP, is a new paradigm of signal transduction that potentially adds unforeseen diversity to the signaling repertoire of a cell (Ebinu and Yankner, 2002). As with DSL, the inventor has shown that F3 binding triggers Notch intramembrane proteolysis at the S3 site and nuclear translocation of the resultant NICD in OLN cells. The ability of Notch1 EGF (EGF 11-12) antibody, or brefeldin A and monensin, to block this event suggests that the extracellular F3/Notch interaction is essential for the intramembrane cleavage-derived generation and transport of NICD. Thus, it is another example of RIP. In addition, the F3/Notch signaling pathway may activate a feedback loop that specifically increases Notch1 and Notch2 (but not Notch3) expression or protects Notch1 and Notch2 from rapid degradation. Either way, this may serve to replenish consumed receptors on the cell surface and thus sustain signal continuity.

A Possible Model for F3/Notch Signaling Via DTX1

Given that F3 and Jagged1 share a common binding domain on Notch1, Jagged1 downregulation that occurs prior to myelination may act to permit the alternate interaction of Notch with F3. In OLN cells, both Jagged1 and F3 trigger γ-secretase-mediated and S3-directed release of NICD followed by its nuclear translocation. Moreover, caN1 transactivates Hes1, which is blocked by co-expression of dn-RBP-J-myc or DTX1. Thus it is conceivable that F3-induced Notch intracellular signaling is associated with RBP-J. However, only F3-induced NICD, but not Jagged1-induced NICD or caN1 and caN2, increases MAG expression, suggesting that this event may require specific extracellular ligand-receptor interaction. Moreover, experiments utilizing either dn-RBP-J-myc or Hes1 antisense oligonucleotides indicate that the blockage of endogenous Hes1 expression is not involved in F3/Notch-induced MAG upregulation. On the other hand, two truncated mutants of DTX1, which lack the Ring-H2 finger motif that is indispensable for the formation of functional homodimeric DTX1 (Matsuno et al, 2002), prevent both F3-promoted OPC differentiation and MAG upregulation. Thus it is proposed that a switch in ligands may alter Notch intracellular signaling effectors (FIG. 13). The binding of different ligands may induce the formation of distinct Notch conformations. Such conformational alterations could result from different, albeit overlapping, regions of Notch recognized by Jagged1 and F3. Notch receptors with distinct conformations may interact, before or after cleavage, with different cytoplasmic factors, such as DTX1. The form of NICD subsequently arriving at the nucleus then specifies further potential interactions and determines its transcriptional target. It will be of significance to investigate this hypothesis and identify DTX1-related transcription cofactors that are required for F3/Notch signaling.

Potential Role of F3/Notch Signaling Via DTX1 in OL Maturation

Jagged1/Notch signaling contributes to maintaining OPCs in an undifferentiated stage (Wang et al, 1998). The failure of efficient remyelination in multiple sclerosis (MS) has been partly attributed to the activation of OPC Notch by astrocyte-expressed Jagged1 (John et al, 2002). However, Jagged1 expression sharply decreases from around P6 (Wang et al, 1998), a time point concurrent with the onset of myelination and the clustering of axonal F3 at the paranode (Kazarinova-Noyes et al, 2001), an ideal position to interact with Notch receptors on the surface of newly formed OLs. Mutant animals, in which Notch1 is selectively ablated in OPCs (Genoud et al, 2002), are characterized by ectopic immature OLs, most of which undergo apoptosis, indicating that autonomous differentiation in the absence of the Notch receptor may be disruptive and that other regulatory signaling cascades besides Jagged1/Notch may be needed to ensure correct differentiation and survival of OLs. It was observed here that F3 promotes OPC differentiation, which can be blocked by both dominant-negative Notch and DTX1 deletion mutants, and oligodendroglial processes emanating from OLN cells terminate and spread over the surface of F3-transfected CHO cells, an event related to the upregulation of myelin-specific proteins, such as MAG and CNPase. Upon Notch interaction with either immobilized or soluble F3, MAG, a specific marker of mature OLs, is significantly upregulated at both the protein and mRNA levels. MAG upregulation can be blocked by dominant-negative construct of Notch1, Notch2, or deletion mutants of DTX1. These observations indicate that OL maturation involves F3/Notch signaling via DTX1 (FIG. 13).

In summary, the study reveals a new facet of the Notch signaling pathway. Upon activation by F3, Notch signaling via DTX1 continues to participate in OL maturation through upregulating certain myelin-related proteins instead of solely functioning to inhibit OPC differentiation into OLs. Hence, this finding may prove to be an efficient molecular handle for promoting remyelination in degenerative diseases, such as MS, by creating an environment in which Notch predominantly interacts with endogenous or exogenous F3 to initiate the F3/Notch/DTX1 signaling pathway.

NB-3 is a New Constituent of the Paranodal Architecture

The construction of a myelinated axon during nervous system development is a well-orchestrated phenomenon, yet the molecular details of this process remain unclear. Apart from the segmental nature of myelin ensheathment, a redistribution of axonal molecules occurs to create distinct axonal domains in the mature nerve fibre. The molecular architecture of the various axonal domains has been extensively reviewed (Morell and Quarles, 1999; Arroyo et al, 2000; Peles and Salzer, 2000; Denisenko-Nehrbass et al, 2002). Constituents of the paranode include axonal F3 in association with the neurexin superfamily molecule, Caspr, and oligodendroglial neurofascin-155 (NF-155) (Rios et al, 2000; Tait et al, 2000). Studies of F3-null mice highlight F3 as a key player in the synthesis of the axoglial apparatus in the peripheral nervous system (PNS). Prior to their death by postnatal day 18, the mutant mice have an ataxic phenotype with hindlimb weakness, attributed to defective connections involving cerebellar interneurons and to reduced nerve conduction velocity and excitability (Berglund et al, 1999; Boyle et al, 2001). The latter problem with nerve impulse conduction reflects abnormalities in axoglial junction formation in myelinated peripheral nerve. Consistent with a paranodal function of F3, these abnormalities include disruption of the axoglial junction and defective transport of Caspr, a cis binding partner of F3, to the axon membrane (Boyle et al, 2001). The fact that adhesive axoglial interactions still form in the F3 mutant mice points to the involvement of other paranodal molecules, with NB-3 being one such candidate. Although the distribution/localization of NB-3 in the PNS is unknown, in the CNS NB-3 is expressed in the olfactory bulb, layers I, III and V of the cerebral cortex, piriform cortex, anterior thalamic nuclei, locus coeruleus, mesencephalic trigeminal nucleus and the Purkinje cells of the cerebellum (Lee et al, 2000). The inventor shows that NB-3 clusters and co-localizes with Caspr at paranodes from P5 to adulthood, certainly suggesting the likehood of it being similarly localized in the PNS.

NB-3 Clustering at the CNS Paranode Promotes Maturation of Oligodendrocyte Precursor Cells Via Notch/Deltex1 Signalling Pathway In summary, the above study has shown that NB-3, a neuron-derived molecule, is a functional ligand of Notch1. Acting as a spatial switch signal by developmentally clustering at the CNS paranode, it releases NICD at the S3 site via RIP and triggers Notch/DTX1 signalling pathway, which promotes OPC differentiation and OL maturation to coordinate myelination.

NB-3/Notch Signalling Via Deltex1 Directs Differentiation of Embryonic Neural Stem Cells into Oligodendrocytes Multiple sclerosis (MS) is a chronic demyelinating disease in the CNS. Neural stem cell transplantation is a promising treatment for such diseases (Pluchino et al, 2003). It will be of significance to establish a reliable method for selectively predifferentiating appropriate donor stem cells to OPCs or OLs. In the present study, pre-clinical validation has been provided of a novel signalling pathway allowing for the first time using NB-3, a neuronal cell recognition molecule, to direct neuronal stem cells to OPC and/or OLs lineages in vitro. Moreover, recent studies have shown that the failure of efficient remyelination in MS is partly attributed to the activation of OPC Notch receptor by astrocyte-expressed Jagged1 (John et al, 2002). The ectopic immature OLs and subsequent apoptosis appear in mutant mice in which Notch1 signalling is selectively inhibited in OPCs (Genoud et al, 2002). These observations implicate that, in addition to Jagged1/Notch1 interaction, there may exist other axon-derived Notch1 ligands that mediate OL differentiation by properly activating the Notch1 signalling pathway (Hu et al, 2003). In support of this notion, the inventor's present observations in NSCs incriminate that NB-3/Notch signalling via Deltex1 may modulate OL differentiation from NSCs and thus represent a potential target for therapeutic intervention in demyelinating diseases.

Materials and Methods Relating to the Second Aspect of the Invention

Antibodies

Monoclonal Notch1 EGF repeats 11-12 (Neomarker), CNPase, Flag, beta-tubulin and MAP2 (2a+2b) (Sigma), c-myc (9E10) and HA (Santa Cruz Biotechnology), nuclear matrix protein, Gal-C and nestin (Chemicon), GFAP (DAKO) and V5 epitope (Invitrogen) antibodies; polyclonal V1744-cleaved NICD (Cell Signaling), N21CD, Jagged1, Jagged2, Delta (Santa Cruz Biotechnology), γ-tubulin (Sigma), Ng2a sodium channels (NaCh), NF200 (Chemicon), Hes1 (Kaneta et al, 2000), NICD (Logeat et al, 1998), Notch1, Notch2, Notch3 (kind gifts from Dr. Lendahl) and F3 (Shimazaki et al, 1998).

Polyclonal Caspr antibody was obtained by immunization of rabbits with a GST fusion protein of amino acids 277-430 of human Caspr and polyclonal MAG antibody (7610) by immunization of rabbits with the following peptide: N'-CISCGAPDKYESREVST-C' (Eurogentec).

Secondary antibodies conjugated to Cy2, Cy3 and FITC were obtained from Amersham Pharmacia Biotech. Inc.

Anti-NB-3 serum and monoclonal antibodies were generated against recombinant protein expressed in E. coli transformed with the pET15b vector (Novagen) containing rat NB-3 cDNA encoding Ig domains I-II (amino acids 30-227). To construct this expression vector, two oligonucleotide primers were used in PCR reactions to amplify cDNA encoding the corresponding region from a cDNA library synthesized from rat brain total RNA. The two oligonucleotide primers are:

5'-TCCGGATCCCATGGAGCCACAGGATGTCATTTT-3' (forward)

5'-TCCGGATCCGTCGACTGGCACATATTCCCCCATGA-3', (reverse)

The PCR was carried out for 30 cycles at 94° C. for 30s, 60° C. for 30s and 72° C. for 45s after denaturation at 94° C. for 3 min. The amplified cDNA fragments were digested with BamHI and inserted into a BamHI-cut pET15b vector after DNA sequencing. The protein was expressed in E. coli BL21 (DE3) pLysS by induction with IPTG. It was partially purified as inclusion bodies, and these were solubilized and applied to SDS-PAGE and the recombinant protein eluted electrophoretically from the gel. The protein was used to immunize rabbits for antiserum and BALB/c mice for monoclonal antibodies (Harlow, 1998).

Cell Co-Culture

F3 transfected CHO cells (Gennarini et al, 1991), TAX, TAG-1 and mock transfected CHO cells (Furley et al, 1990; Tsiotra et al, 1993) were co-cultured with the oligodendrocyte cell line OLN-93 (Richter-Landsberg and Heinrich, 1996) in a 2:1 ratio in Dulbecco's modied Eagle's medium (DMEM, Gibco), 10% fetal calf serum (Gibco) and penicillin/streptomycin (Gibco) for 2 days at 37° C. in a humidified atmosphere. Cells were pre-stained with the PKH26 red fluorescent cell linker kit (Sigma). The cells were also stained with primary monoclonal antibodies to c-myc (Santa Cruz Biotechnology) and Cy-2 labelled goat anti-mouse secondary antibodies (Sigma). To determine the number of the stopped processes in the co-cultures, OLN-93 cells (more than 100 cells) from three randomly selected areas in each of three cover slips were counted per experiment. Raw data from at least three independent experiments were analyzed by analysis of variance and then Newman-Keuls test with $p<0.05$ and $p<0.01$ being considered significant or highly significant, respectively.

NB-3- or mock-transfected CHO cells were cultured with OLN in a 2:1 ratio for 2 days. The membrane portions of the co-cultures were extracted as described (Xiao et al, 1996).

Transfection and Characterization of NB-3-Transfected CHO Cells

CHO cells were transfected with 10 μg of pcDNA3-NB-3 using lipofectin (GIBCO BRL) according to the manufacturer's instructions. Following drug selection with G418 (Life Technologies, Inc), surviving cell clones were expanded and analyzed by Western blot and immunohistochemical staining for surface NB-3 expression.

Transfection of Cells

OLN cells were transiently (V1744K-myc, V1744L-myc, dn-N1-V5, dn-N2-V5, pcDNA4/V5/LacZ (Invitrogen), dn-RBP-J-myc, DTX1-myc, DTX1-D1-HA, DTX1-D2-Flag, caN1, caN2) or stably (mNotch1-myc) transfected using Lipofectamine (Invitrogen). CHO cells were stably transfected with full-length Jagged1 (Small et al, 2001) using Lipofectamine. The stable transfectants were screened with 400 μg/ml G418 (Sigma) or 250 μg/ml Zeocin (Invitrogen) and identified by immunostaining and Western blot.

Immunocytochemistry

Cells were cultured on 13 mm coverslips (Nalge Nunc International). After various treatments, including γ-secretase inhibitor (Sigma), cells were fixed with 4% paraformaldehyde and blocked with 1% BSA. Cells were then incubated with primary antibodies in 0.2% BSA for 1 hour, followed by Cy3-labeled or Cy2-labeled secondary antibody (Sigma). After mounting in fluorescent mounting medium (DAKO), cells were visualized with a Leica DM RXA2 fluorescent microscope. The photos were taken using the same optical parameters to ensure the comparable luminosity. At least ten different viewing fields from three independent experiments were used to calculate the percentage of cells showing NICD translocation or differentiation. Two hundred cells from at least three independent experiments were quantified for fluorescence intensities by Adobe Photoshop™ (Jack et al, 2001) and measured for cytoplasmic area by Leica QFluoro software. The raw data were analyzed by Student's t test with $p<0.05$ and $p<0.01$ being considered a significant or highly significant difference, respectively.

For detection of primary NF200, GFAP and Gal-C antibodies, Alexa Fluor 488-conjugated anti-mouse IgG or Alexa Fluor 546-conjugated anti-rabbit IgG (1:1500; Molecular Probes) were used. For transfected NSCs, cells were first transfected with plasmid caN1, DTX-D2, dnN1 using Lipofectamine 2000 (Invitrogen) and treated with or without NB-3 in serum free culture medium without growth factor for 24 hours, and then cells were allowed to differentiate on 13 mm coverslips in 1% FCS medium.

Cell Adhesion and Repulsion Assay

This was carried out as previously described (Xiao et al, 1996). Briefly, 35 mm tissue culture petri dishes (Becton Dickinson) were coated with methanol solubilized nitrocellulose (Lagenaur and Lemon, 1987) and air-dried under a sterile hood. Proteins (2.5 μl of 12 μM F3-Fc, CHL1-Fc, or different subcloned Notch1 extracellular fragments) were then applied to these dishes and incubated for 2 hours at 37° C. in a humidified atmosphere. Subsequently, the dishes were washed three times with calcium- and magnesium-free Hank's balanced salt solution (CMF-HBSS) and blocked overnight with 2% heat-inactivated fatty acid-free BSA (Sigma) in CMF-HBSS (this blocking step is skipped in the repulsion test). The dishes were then rinsed again and the respective cells, such as OLN-93, murine Notch1 transfected HeLa cells (Logeat et. al., 1998), F3-transfected CHO cells, and NB-3-transfected CHO cells, were plated in 2 ml of chemically defined medium at a density of $1.5 \times 10^6$ cells/ml. After 0.5 hour (in the adhesion test) or 12 hours (in the repulsion test), the dishes were gently washed three times with CMF-HBSS and the cells were fixed with 2.5% glutaldehyde in CMF-HBSS. Blockage of adhesion was carried out using anti-F3 (Gennarini et al, 1991; 1:100), polyclonal anti-Notch1 (Mitsiadis et al, 1995; 1:200) and anti-Notch2 (Mitsiadis et al, 1995; 1:200) antibodies. Cells adhering to the various spots were photographed and counted. The results were analyzed by Student's t test with p<0.05 and p<0.01 being considered significant or highly significant difference, respectively.

Western Blot Analysis

Co-cultures of F3, TAX, TAG-1 and mock transfected CHO cells with OLN-93 cells were harvested and lysed by sonication in PBS containing the protease inhibitor cocktail tablet. After centrifuging at 100,000 g for 1 hour at 4° C., the pellets were further solubilized in 2% Triton X-100. Subsequently, the membrane portion of the cells, about 201 g protein per cell line, was analyzed by SDS-PAGE (8% gels; Laemmli, 1970) and Western blotting (Towbin et al, 1979) with antibodies against Notch1, Notch2, Notch3, myelin-associated glycoprotein, MAG (Yang et al, 1999) and proteolipid protein (PLP) (Jung et al, 1996).

Western Blot Analysis of Developmental Expression Patterns

The brain stem was dissected from embryos at E17 or neonates at between P0 and P21 of Wistar rats. The specimens were homogenized in 9 volumes of reducing sample buffer and boiled for 5 min. Each 10-µl aliquot of the homogenates was subjected to Western blot. Detection was carried out with ECL western Blotting System (Amersham Biosciences).

Fusion Proteins

Production of recombinant F3-Fc, Jagged1-Fc and CHL1-Fc fusion proteins. Recombinant cDNA encoding mouse F3 with the GPI-anchor substituted with human IgG Fc was inserted at the Hind III-Not I sites of pDX with an amplification-promoting sequence (APS) (Hemann et al, 1994) and introduced into Ltk−/− cells. Fc fusion proteins were purified as described (Shimizu et al, 1999).

Production of recombinant NB-3-His fusion protein. A soluble form of NB-3 recombinant protein, NB-3-His, was produced in HEK293 cells. The region of rat NB-3 cDNA encoding the signal sequence of the GPI-anchor was substituted with 6×His followed by a termination codon. The NB-3 cDNA thus manipulated was inserted into pREP4 between Hind III and BamHI sites, and the resulting vector was transfected into HEK293 cells. When the cells expressing NB-3-His reached confluence they were cultured in serum-free medium for a week. The culture medium was collected, concentrated and dialyzed against 50 mM $NaH_2PO_4$, 300 mM NaCl, pH 8.0. Ni-NTA resin (Qiagen) was added to the dialysate and incubated for at least 30 min. NB-3 recombinant protein was eluted from the Ni-NTA resin using 50 mM $NaH_2PO_4$, 300 mM NaCl, 250 mM imidazole.

Production of Notch1 GST fusion proteins. Production of Notch1 GST fusion proteins has been described (Hu et al, 2003). Recombinant proteins comprising different regions of the extracellular domain of mouse Notch1 (mN1) were produced as follows. Primers with added Hind III and BspE1 sites (underlined below) were used to amplify regions of mN1 cDNA (gift from Dr. Jeffrey Nye) in polymerase chain reactions.

```
N1.1 forward: 5'-GGTGGAATTCTAATGCCACGGCTCCTG-3'
     reverse: 5'-TTGAAGTTCCTCATCCGTGTTGATTT-3'

N1.2 forward: 5'-TGTGGAATTCTATGTGATCTGGGTGCC-3'
     reverse: 5'-CGTCAAGTTCGTCATCGATGTCACTCT-3'

N1.3 forward: 5'-CTTGGAATTCTATGTGCTACCAGCCCC-3'
     reverse: 5'-TTGAAGCTTGCCATTGATGACTGACT-3'

N1.4 forward: 5'-ACTGGAATTCTATGCCATCCCCCCCTT-3'
     reverse: 5'-AAGGAAGCTTCTGCGAGGGCAGCGGAG-3'
```

The regions amplified were N1.1 (nucleotides 79-1557; 1478 bp fragment encoding amino acids 27-519; EGF repeats 1-13), N1.2 (nucleotides 1324-2808; 1484 bp fragment encoding amino acids 442-936; EGF repeats 11-24), N1.3 (nucleotides 2575-4008; 1433 bp fragment encoding amino acids 859-1336; EGF repeats 22-34), and N1.4 (nucleotides 3751-5247; 1496 bp fragment encoding amino acids 1251-1749; EGF repeats 32-36, LNR repeats). Recombinant GST fusion proteins were produced using pGEX-KG vector and purified as described (Xiao et al, 1996).

The PCR was performed on plasmid DNA in the presence of 1 mM $MgCl_2$. The cycles were: first five cycles at 93° C. for 1 min, 45° C. for 30 s and 72° C. for 1 min; the subsequent 30 cycles were carried out at 93° C. for 1 min, 50° C. for 30s and 72° C. for 1 min; and a final extension at 72° C. for 5 min. These amplified fragments were respectively used to create vectors pN1.1, pN1.2, pN1.3, and pN1.4 by restriction at their extended HindIII and BspEI sites and ligation into similarly digested PGEX-KG vector. Transformed E. coli JM 109 cells were induced with IPTG, and the expressed GST-N1.1, -N1.2, -N1.3, and -N1.4 fusion proteins were purified using glutathione-agarose beads.

Production of recombinant NB-3-Fc proteins. The signal sequence of the GPI-anchor was substituted with human IgG Fc followed by a termination codon. The cDNA thus manipulated was inserted into pREP4 between Hind III and BamHI sites, and transfected into 293T cells. NB-3-Fc was purified from the conditioned medium using Protein A-Agarose beads (Roche).

Immunohistochemistry

Following deep anaesthesia, adult Wistar rats were transcardially perfused with Ringer's saline followed by 4% paraformaldehyde in 0.1 M phosphate buffer (PB; pH 7.4). Brain stem segments were harvested and post-fixed for 2 hours before being transferred into 0.1M PB containing 15% sucrose overnight. The tissue was frozen in O.C.T. compound (Tissue-Tek) and sagittal cryosections (10 µm) were collected on gelatin-coated slides. For immunostaining, the slides were dried at 37° C. for 30 min, then immersed in cold acetone (−20° C.) for 15 minutes for permeabilization. Blockade of non-specific binding sites was carried out using 10% goat serum solution in 0.1M PB for 30 minutes at room temperature. Between steps involving antibodies, preparations were washed three times for 5 minutes each with 0.3% Triton X-100 in 0.1M PBS. All antibodies were diluted in 0.1M PB. Sections were double labeled. Tissue sections were typically first incubated overnight with the polyclonal primary antibody, followed by a secondary goat anti-rabbit antibody. Sections were then exposed to the monoclonal primary antibody and labeled with an anti-mouse secondary antibody. For examination, coverslips were applied and the slides viewed on a Zeiss laser scanning confocal microscope.

Co-Immunoprecipitation and GST Pull-Down Assay

Rat brain membrane samples were prepared as described (Xiao et al, 1996) and incubated overnight at 4° C. with antibody-coupled Protein A agarose beads (Roche) or glutathione-agarose beads (Sigma) bound to GST-N1.1, N1.2, N1.3 or N1.4. Captured proteins were eluted from beads with SDS-PAGE sample buffer, subjected to Western blot and detection using ECL reagent (Amersham).

NSCs and Rat brain membrane portions were prepared as described (Xiao et al, 1996) and incubated overnight at 4° C. with NB-3-Fc and antibody-coupled Protein A-Agarose beads. Captured proteins were eluted from beads with SDS-PAGE sample buffer, subjected to Western blot and detection using ECL reagent.

Immunoprecipitation of Caspr. Chick or mouse brain lysate (800 μg), prepared as described (Zeng et al, 1999), was incubated with rabbit pre-immune serum (PI) or anti-Caspr serum followed by Protein A+G-Sepharose (Sigma). The immunoprecipitates were washed, resolved by SDS-PAGE and probed with anti-Caspr serum. For immunoblotting, pre-immune and immune sera were used at a 1:1000 dilution.

Co-immunoprecipitation. Brain membranes were prepared as described previously (Isom et al, 1995). Membranes were solubilized in 2% Triton X-100 and the soluble fraction was incubated overnight at 4° C. with Notch antibodies (anti-Notch1 and anti-Notch2). Protein A Sepharose beads (50 μl of a 1:1 suspension) were then added and the incubation continued for a further 2 hours or overnight at 4° C. The beads were washed with 50 mM Tris HCL, pH 7.5, containing 0.1% Triton X-100 and protease inhibitors. Immunoprecipitated proteins were eluted from the beads with SDS-PAGE sample buffer and separated on 7.5% acrylamide SDS-PAGE gels. Proteins were transferred to nitrocellulose and probed with antibodies against F3 and NB-3. Chemiluminescent detection of immunoreactive bands was accomplished with ECL reagent. The reciprocal experiment was carried out using anti-Notch1 and anti-Notch2 antibodies to probe immuno-precipitates obtained using anti-F3 and anti-NB-3.

GST Pull Down Assay. Purified GST fusion proteins (mNotch 1.1, 1.2, 1.3 and 1.4) were coupled to Sepharose 4B beads (Amersham Pharmacia Biotech Inc) according to the manufacturer's instructions. Fresh cerebral hemispheres of adult rats were harvested and were solubilized in 2% Triton X-100. The homogenate was centrifuged at 13,000 g for 60 minutes. The cleared lysate was then incubated for 45 min at room temperature with GST fusion protein bound to the beads. The beads were washed 3 times with lysis buffer and proteins were eluted with SDS-PAGE gel sample buffer, resolved on 7.5% SDS-PAGE, transferred to nitrocellulose and analyzed by Western blotting using anti-F3 and anti-NB-3 antibodies.

Culture of Primary OLS and OPCs

The inventor employed a glial cell separation technique in which oligodendrocytes are separated by Percoll gradient centrifugation as previously described (Colello and Sato-Bigbee, 1998). Briefly, an hour before plating cells, culture dishes (Falcon) were coated with poly-L-lysine. Postnatal day 1-2 rats were sacrificed by decapitation and their cerebral hemispheres rapidly dissected out. Meninges and blood vessels were carefully teased away using microdissecting forceps. Hemispheres were transferred to ice-cold HEPES/HBSS in a petri dish and finely minced using a scalpel blade. The tissue was transferred to a 50 ml conical tube and centrifuged for 5 minutes at 200×g after which the supernatant was discarded and the cell pellet resuspended in 10 g/ml DNAase I in HEPES/HBSS before subjecting it to centrifugation again. A single cell suspension was prepared by forcing the tissue through a 70 μm nylon mesh Falcon cell strainer, applied to a Percoll gradient, and the oligodendrocyte-containing fraction recovered after centrifugation. The cell suspension was diluted with HEPES/HBSS and oligodendrocytes were separated by differential adhesion. Oligodendrocytes obtained in this manner were suspended in chemically defined DMEM/F12 medium.

Culture of primary neurons, Ols, and astrocytes. Neurons, OLs, and astrocytes of E17 Wistar rats were isolated and cultured as described (Itoh, 2002). OLs of P5-7 Wistar rat cerebella were obtained by Percoll gradient centrifugation (Colello and Sato-Bigbee, 1998) and OPCs were purified from P5-7 Wistar rat optic nerve (Bogler, 1997).

Culture of NSCs. Murine striatal neural stem cells were isolated from 14-d-old BALB/c mouse embryos (IFFA Credo, L'Arbresle, France) and cultured in DMEM/F12 with N2 supplement and EGF (20 ng/ml) (Invitrogen) (Arsenijevic et al, 2001). To induce differentiation, the spheres were mechanically dissociated into single cells and treated with NB-3 or Jagged1 in culture medium without growth factor for 24 hrs, and then added into culture medium with 1% fetal calf medium.

Real-Time RT-PCR Analysis

Primary oligodendrocytes were plated onto protein spots of F3-Fc, NB-3-His and BSA in a similar fashion to the cell adhesion assay previously described. After 2 hours in culture, total RNA was extracted according to the manufacturer's instructions using a QIAGEN RNAeasy kit. Total RNA (0.5 μg) was reverse transcribed using the TaqMan RT Kit (Applied Biosystems). To measure the level of mRNA expression, we performed real-time quantitative PCR using the Taq-Man system on an ABI PRISM 7700 Sequence Detection System. All primers and probes were designed using Primer Express Software (ABI). Primer and probe sequences are as follows.

```
Myelin Associated Glycoprotein (MAG)
Forward Primer:    5'-ATCCTGGCCACGGTCATC-3'
Reverse Promer:    5'-CACACCAGTACTCCCCATCGT-3'
Taqman Probe:      5'-CAGCTGGAACTCCCTGCAGTGACG-3'

Proteolipid Protein (PLP)
Forward Primer:    5'-AGGCCAACATCAAGCTCATTCT-3'
Reverse Primer:    5'-CGGGATGTCCTAGCCATTTTC-3'
Taqman Probe:      5'-CCAAACAATGACACACCCGCTCCA-3'
```

Independent amplifications of each target and the GAPDH RNA were performed according to the manufacturer's instructions. Relative expression levels of each transcript were determined by employing the comparative $C_T$ method as outlined in the ABI User's manual.

Total RNA from OLs or OLN cells was extracted using the QIAGEN RNeasy kit and treated with RNase-free DNaseI (Invitrogen) to eliminate genomic DNA. Samples were used for reverse transcription with random hexamer primers using SuperScript First-Strand Synthesis System (Invitrogen) (Notch homologs, Hes1) or TaqMan RT Kit (Applied Biosystems) (MAG). β-actin and GAPDH were used as internal controls. Real-time PCR was performed using the SYBR Green PCR Master Mix (Notch homologs, Hes1) or TaqMan system (MAG) on an ABI PRISM 7700 Sequence Detection System. The primers and TaqMan probes were designed using Primer Express Software (ABI) and sequences are available upon request. The raw data from at least four independent experiments were used to determine the relative expression levels of each transcript by employing the comparative $C_T$ method (ABI User's manual)

Lipid Raft Assay

This was performed as described (Kramer et al, 1999).

Hes1 Luciferase Reporter Assay

OLN cells ($1.5 \times 10^5$/well) in 12-well dishes were used for Hes1 luciferase reporter assays. Cells were transiently transfected using Lipofectamine and Lipofectamine Plus reagents (Invitrogen). Each well received 0.2 μg pGVB/Hes1 luciferase reporter plasmid together with various expression plasmids (0.1 or 0.2 μg caN1; 0.3 or 0.6 μg RBP-J, dn-RBP-J-myc, DTX1, DTX1-D1-HA, DTX1-D2-Flag). The β-galactosidase expression plasmid pCMV/β-Gal was included as internal control to monitor the transfection efficiency. Cells were lysed 24 hours post-transfection and assayed using the Steady-Glo Luciferase Assay Kit (Promega). The raw data from at least four independent experiments were used to determine the relative reporter activity.

The NSC experiments was performed as described (Hu et al, 2003). In brief, NSCs in 24-well dishes were transiently transfected with indicated constructs using Lipofectamine 2000 (Invitrogen). pCMV/β-Gal expressing β-galactosidase was cotransfected to monitor the transfection efficiency. Cells were subjected to luciferase assay 24 hours post-transfection using the Steady-Glo Luciferase Assay Kit (Promega). The raw data from at least four independent experiments were used to determine the relative reporter activity.

Flow Cytometric Analysis

The cells were trypsinized, washed with PBS and treated with FACSPerm (Becton Dickinson). Cells were stained with antibody to MAP2 (2a+2b), GFAP, CNPase and FITC-conjugated anti-mouse IgG1 and anti rabbit IgG, then analyzed by flow cytometer (FACScalibur, Becton Dickinson) with CELLQuest software Version (Becton Dickinson).

REFERENCES FOR THE FIRST ASPECT OF THE INVENTION

Ahn, M., D. S. Min, J. Kang, K. Jung, and T. Shin. 2001. Increased expression of phospholipase D1 in the spinal cords of rats with experimental autoimmune encephalomyelitis. *Neurosci. Lett.* 316:95-98.

Ang, B. T., M. Karsak, S. Lee, Y. Takeda, U. Lendahl, G. Rougon, A. Israel, M. Schachner, K. Watanabe, and Z. C. Xiao. 2001. Notch is a receptor for F3/contactin and NB-3: a paranodal axon-glial signaling mechanism during myelination. *Soc. Neurosci. Abst.* 900.5

Barres, B. A., and M. C. Raff. 1999. Axonal control of oligodendrocyte development. *J. Cell Biol.* 147:1123-1128.

Bhat, M. A., J. C. Rios, Y. Lu, G. P. Garcia-Fresco, W. Ching, M. St Martin, J. Li, S. Einheber, M. Chesler, J. Rosenbluth, J. L. Salzer, and H. J. Bellen. 2001. Axon-glia interactions and the domain organization of myelinated axons requires neurexin IV/Caspr/Paranodin. *Neuron.* 30:369-383.

Boyle, M. E., E. O. Berglund, K. K. Murai, L. Weber, E. Peles, and B. Ranscht. 2001. Contactin orchestrates assembly of the septate-like junctions at the paranode in myelinated peripheral nerve. *Neuron.* 30:385-97.

Brittis, P. A., and J. G. Flanagan. 2001. Nogo domains and a Nogo receptor: implication for axon regeneration. *Neuron.* 30:11-14.

Buttiglione, M, J. M. Revest, O. Pavlou, D. Karagogeos, A. Furley, G. Rougon, and C. Faivre-Sarrailh. 1998. A functional interaction between the neuronal adhesion molecules TAG-1 and F3 modulates neurite outgrowth and fasciculation of cerebellar granule cells. *J Neurosci.* 18:6853-6870.

Charles, P., S. Tait, C. Faivre-Sarrailh, G. Barbin, F. Gunn-Moore, N. Denisenko-Nehrbass, A. M. Guennoc, J. A. Girault, P. J. Brophy, and C. Lubetzki. 2002. Neurofascin is a glial receptor for the paranodin/Caspr-contactin axonal complex at the axoglial junction. *Curr. Biol.* 12:217-220.

Chen, M. S., A. B. Huber, M. E. van der Haar, M. Frank, L. Schnell, A. A. Spillmann, F. Christ, and M. E. Schwab. 2000. Nogo-A is a myelin-associated neurite outgrowth inhibitor and an antigen for monoclonal antibody IN-1. *Nature.* 403:434-439.

Coetzee, T., Fujita, N., Dupree, J., Shi, R., Blight, A., Suzuki, K., Suzuki, K., Popko, B. 1996. Myelination in the absence of galactocerebroside and sulfatide: normal structure with abnormal function and regional instability. *Cell.* 86(2):209-219.

Dawson, M. R., Levine, J. M., and Reynolds, R. 2000. NG2-expressing cells in the central nervous system: are they oligodendroglial progenitors? *J. Neurosci. Res.* 61, 471-479.

Dupree, J. L., J. A. Girault, and B. Popko. 1999. Axo-glial interactions regulate the localization of axonal paranodal proteins. *J. Cell Biol.* 147:1145-1152.

Einheber, S., G. Zanazzi, W. Ching, S. Scherer, T. A. Milner, E. Peles, and J. L. Salzer. 1997. The axonal membrane protein Caspr, a homologue of neurexin IV, is a component of the septate-like paranodal junctions that assemble during myelination. *J. Cell Biol.* 139:1495-1506.

Faivre-Sarrailh, C., F. Gauthier, N. Denisenko-Nehrbass, A. Le Bivic, G. Rougon, and J A. Girault. 2000. The glycosylphosphatidyl inositol-anchored adhesion molecule F3/contactin is required for surface transport of paranodin/contactin-associated protein (caspr). *J. Cell Biol.* 149:491-502.

Fournier, A. E., T. GrandPre, and S. M. Strittmatter. 2001. Identification of a receptor mediating Nogo-66 inhibition of axonal regeneration. *Nature.* 409:341-346.

Gennarini, G., P. Durbec, A. Boned, G. Rougon, and C. Goridis. 1991. Transfected F3/F11 neuronal cell surface protein mediates intercellular adhesion and promotes neurite outgrowth. *Neuron.* 6:595-606.

Girault, J. A., and Peles, E. 2002. Development of nodes of Ranvier. *Curr Opin Neurobiol.* 12(5):476-485.

Gollan, L., H. Sabanay, S. Poliak, E. O. Berglund, B. Ranscht, and E. Peles. 2002. Retention of a cell adhesion complex at the paranodal junction requires the cytoplasmic region of Caspr. *J. Cell Bio.* 157:1247-1256

GrandPre, T., F. Nakamura, T. Vartanian, and S. M. Strittmatter. 2000. Identification of the Nogo inhibitor of axon regeneration as a reticulon protein. *Nature.* 403:439-444.

Guan, K. L., and J. E. Dixon. 1991. Eukaryotic proteins expressed in *Escheridhia coli*: an improved thrombin cleavage and purification procedure of fusion proteins with glutathione S-transferase. *Anal. Biochem.* 192:262-267.

Hu, W. H., O. N. Hausmann, M. S. Yan, W. M. Walters, P. K. Wong, and J. R. Bethea. 2002. Identification and characterization of a novel Nogo-interacting mitochondrial protein (NIMP). *J. Neurochem.* 81:36-45.

Huber, A. B., O. Weinmann, C. Brosamle, T. Oertle, and M. E. Schwab. 2002. Pattern of Nogo mRNA and protein expression in the developing and adult rat and after CNS lesions. *J. Neurosci.* 22:3553-3567.

Hunt, D., M. Mason, G. Campbell, R. Coffin, and P. Anderson. 2002. Nogo receptor mRNA expression in intact and regenerating CNS neurons. *Mol. Cell. Neurosci.* 20:537.

Ishibashi, T., J. L. Dupree, K. Ikenaka, Y. Hirahara, K. Honke, E. Peles, B. Popko, K. Suzuki, H. Nishino, and H. Baba. 2002. A myelin galactolipid, sulfatide, is essential for maintenance of ion channels on myelinated axon but not essential for initial cluster formation. *J. Neurosci.* 22:6507-6514.

Kazarinova-Noyes, K., J. D. Malhotra, D. P. McEwen, L. N. Mattei, E. O. Berglund, B. Ranscht, S. R. Levinson, M. Schachner, P. Shrager, L. L. Isom, and Z. C. Xiao. 2001. Contactin associates with Na+ channels and increases their functional expression. *J. Neurosci.* 21:7517-7525.

Krämer, E. M., C. Klein, T. Koch, M. Boytinck, and J. Trotter. 1999. Compartmentation of Fyn kinase with glycosylphosphatidylinositol-anchored molecules in oligodendrocytes facilitates kinase activation during myelination. *J. Biol. Chem.* 274:29042-29049.

Lee, S., Y. Takeda, H. Kawano, H. Hosoya, M. Nomoto, D. Fujimoto, N. Takahashi, and K. Watanabe. 2000. Expression and regulation of a gene encoding neural recognition molecule NB-3 of the contactin/F3 subgroup in mouse brain. *Gene.* 245:253-66.

Lei, G., Xue, S., Chery, N., Liu, Q., Xu, J., Kwan, C. L., Fu, Y. P., Lu, Y. M., Liu, M., Harder, K. W., Yu, X. M. 2002. Gain control of N-methyl-D-aspartate receptor activity by receptor-like protein tyrosine phosphatase α. *EMBO J.* 21(12): 2977-2989.

Liu, H., C. E. Ng, and B. L. Tang. 2002. Nogo-A expression in mouse central nervous system neurons. *Neurosci. Lett.* 328:257-260.

Marcus, J., J. L. Dupree, and B. Popko. 2000. Effects of galactolipid elimination on oligodendrocyte development and myelination. *Glia.* 30:319-328.

Menegoz, M., P. Gaspar, M. Le Bert, T. Galvez, F. Burgaya, C. Palfrey, P. Ezan, F. Arnos, and J. A. Girault. 1997. Paranodin, a glycoprotein of neuronal paranodal membranes. *Neuron.* 19:319-331.

Nakahira, K., Shi, G., Rhodes, K. J., Trimmer, J. S. 1996. Selective interaction of voltage-gated $K^+$ channel β-subunits with α-subunits. *J. Bio. Chem.* 271(12): 7084-7089.

Pedraza, L., J. K. Huang, and D. R. Colman. 2001. Organizing principles of the axoglial apparatus. *Neuron.* 30:335-344.

Peles, E., K. Joho, G. D. Plowman, and J. Schlessinger. 1997. Close similarity between *Drosophila* neurexin IV and mammalian Caspr protein suggests a conserved mechanism for cellular interactions. *Cell.* 88:745-746.

Poliak, S., L. Gollan, R. Martinez, A. Custer, S. Einheber, J. L. Salzer, J. S. Trimmer, P. Shrager, and E. Peles. 1999. Caspr2, a new member of the neurexin superfamily, is localized at the juxtaparanodes of myelinated axons and associates with $K^+$ channels. *Neuron.* 24:1037-47.

Poliak, S., Gollan, L., Salomon, D., Berglund, E. O., Ohara, R., Ranscht, B., Peles, E. 2001. Localization of Caspr2 in myelinated nerves depends on axon-glia interactions and the generation of barriers along the axon. *J Neurosci.* 21(19):7568-7575.

Popko B. 2000. Myelin galactolipids: mediators of axon-glial interactions? *Glia.* 29:149-153.

Prinjha, R., S. E. Moore, M. Vinson, S. Blake, R. Morrow, G. Christie, D. Michalovich, D. L. Simmons, and F. S. Walsh. 2000. Inhibitor of neurite outgrowth in humans. *Nature.* 403:383-384.

Rasband, M. N., and P. Shrager. 2000. Ion channel sequestration in central nervous system axons. *J. Physio.* 525:63-73.

Rasband, M. N., and J. S. Trimmer. 2001a. Developmental clustering of ion channels at and near the Node of Ranvier. *Dev. Biol.* 236:5-16.

Rasband, M. N., and J. S. Trimmer. 2001b. Subunit composition and novel localization of $K^+$ channels in spinal cord. *J. Comp. Neurol.* 429: 166-176.

Rasband, M. N., J. S. Trimmer, E. Peles, S. R. Levinson, and P. Shrager. 1999. $K^+$ channel distribution and clustering in developing and hypomyelinated axons of the optic nerve. *J. Neurocytol.* 28:319-331.

Rasband, M. N., J. S. Trimmer, T. L. Schwarz, S. R. Levinson, M. H. Ellisman, M. Schachner, and P. Shrager. 1998. Potassium channel distribution, clustering, and function in remyelinating rat axons. *J. Neurosci.* 18:36-47.

Scherer, S. S., and E. J. Arroyo. 2002. Recent progress on the molecular organization of myelinated axons. *J. Peripher. Nerv. Syst.* 7:1-12.

Spiegel, I., D. Salomon, B. Erne, N. Schaeren-Wiemers, and E. Peles. 2002. Caspr3 and caspr4, two novel members of the caspr family are expressed in the nervous system and interact with PDZ domains. *Mol. Cell. Neurosci.* 20:283-297.

Swanborg, R. H. 2001. Experimental autoimmune encephalomyelitis in the rat: lessons in T-cell immunology and autoreactivity. *Immunol Rev.* 184: 129-135.

Taketomi, M., N. Kinoshita, K. Kimura, M. Kitada, T. Noda, H. Asou, T. Nakamura, and C. Ide. 2002. Nogo-A expression in mature oligodendrocytes of rat spinal cord in association with specific molecules. *Neurosci. Lett.* 332:37.

Tait, S., F. Gunn-Moore, J. M. Collinson, J. Huang, C. Lubetzki, L. Pedraza, D. L. Sherman, D. R. Colman, and P. J. Brophy. 2000. An oligodendrocyte cell adhesion molecule at the site of assembly of the paranodal axo-glial junction. *J. Cell Biol.* 150:657-666.

Trimmer, J. S. 1991 Immunological identification and characterization of a delayed rectifier $K^+$ channel polypeptide in rat brain. *Proc Natl Acad Sci USA.* 88(23):10764-10768.

Vabnick, I., and Shrager, P. 1998. Ion channel redistribution and function during development of the myelinated axon, *J Neurobiol.* 37 (1) 280-96.

Vabnick, I., J. S. Trimmer, T. L. Schwarz, S. R. Levinson, D. Risal, and P. Shrager. 1999. Dynamic potassium channel distributions during axonal development prevent aberrant firing patterns. *J. Neurosci.* 19:747-758.

Wang, X., S. J. Chun, H. Treloar, T. Vartanian, C. A. Greer, and S. M. Strittmatter. 2002. Localization of Nogo-A and Nogo-66 receptor proteins at sites of axon-myelin and synaptic contact. *J. Neurosci.* 22:5505-5515.

Woolf, C. J. 2003. No Nogo: now where to go? *Neuron.* 38(2):153-156

Xiao, Z. C., J. Taylor, D. Montag, G. Rougon, and M. Schachner. 1996. Distinct effects of tenascin-R domains in neuronal cell functions and identification of the domain interacting with the neuronal recognition molecule F3/F11. *Eur. J. Neurosci.* 8:766-782.

REFERENCE FOR THE SECOND ASPECT OF THE INVENTION

Arsenijevic, Y., Weiss, S., Schneider, B. & Aebischer, P. 2001. *J. Neurosci.* 21, 7194-7202.

Artavanis-Tsakonas, S., Rand, M. D. and Lake, R. J. 1999. Notch signalling: cell fate control and signal integration in development. Science 284, 770-776.

Arroyo, E. J. and Scherer, S. S. 2000. On the molecular architecture of myelinated fibres. Histochem. Cell Biol. 113, 1-18.

Baker, N. E. 2000. Notch signalling in the nervous system. Pieces still missing from the puzzle. BioMssays 22, 264-273.

Barres, B. A. & Raff, M. C. 1999. Axonal control of oligodendrocyte development. *J. Cell Biol.* 147, 1123-1128

Baumgartner, S., Littleton, J. T., Broadie, K., Bhat, M. A., Harbecke, R., Lengyel, J. A., Chiquet-Ehrismann, R., Prokop, A. and Bellen, H. J. 1996. A *drosophila* neurexin is required for septate junction and blood-nerve barrier formation and function. Cell 87, 1059-1068.

Berglund, E. O., Murai, K. K., Fredette, B., Serkekova, G., Marturano, B., Weber, L., Mugnaini, E. and Ranscht, B. 1999 Ataxia and abnormal cerebellar microorganization in mice with ablated contactin gene expression. Neuron 24, 739-750.

Bogler, 0.1997. Isolation and purification of primary oligodendrocyte precursors. In *Current Protocols in Neuroscience.* 3.4.1-3.4.9 (John Wiley & Sons, Inc).

Bosio, A., Bussow, H., Adam, J. and Stoffel, W. 1998. Galactosphingolipids and axonal-glial interaction in myelin of the central nervous system. Cell Tissue Res. 292, 199-210.

Boyle, M. E. T., Berglund, E. O., Murai, K. K., Weber, L., Peles, E. and Ranscht, B. 2001. Contactin orchestrates assembly of the septate-like junctions at the paranode in myelinated peripheral nerve. Neuron 30, 385-387.

Brennan, K., and Gardner, P. 2002. Notching up another pathway. Bioessays 24, 405-410.

Coetzee, T., Fujita, N., Dupree, J., Shi, R., Blight, A., Suzuki, K. and Popko, B. 1996. Myelination in the absence of galactocerebroside and sulfatide: normal structure with abnormal function and regional instability. Cell 86, 209-219.

Colello, R. J. and Sato-Bigbee, C. 1998. Purification of oligodendrocytes and their progenitors using immunomagnetic separation and percoll gradient centrifugation. In: Current Protocols in Neuroscience (Crawley, J. N. et. al. eds.). John Wiley and Sons, Inc., pp. 3.12.7-3.12.10.

Dale, J. K., and Maroto, M. 2003. A HES1-based oscillator in cultured cells and its potential implications for the segmentation clock. Bioessays 25, 200-203.

Dawson, M. R., Levine, J. M., and Reynolds, R. 2000. NG2-expressing cells in the central nervous system: are they oligodendroglial progenitors? J. Neurosci. Res. 61, 471-479

Denisenko-Nehrbass, N., Faivre-Sarrailh, C., Goutebroze, L. and Girault, J.-A. 2002. A molecular view on paranodal junctions of myelinated fibres. J. Physiology (Paris) 96, 99-103.

Dugas, J. C., Milligan, B. D. and Barres, B. A. 2001. Onset of myelination is triggered by target innervation. Soc. Neurosci. Abst. 900.4.

Ebinu, J. O., and Yankner, B. A. 2002. A RIP tide in neuronal signal transduction. Neuron 34, 499-502.

Einheber, S., Zanazzi, G., Ching, W., Scherer, S., Milner, T. A., Peles, E. and Salzer, J. L. 1997. The axonal membrane protein Caspr, a homologue of neurexin IV, is a component of the septate-like paranodal junctions that assemble during myelination. J. Cell Biol. 139, 1495-1506.

Ellisen, L. W., Bird, J., West, D. C., Soreng, A. L., Reynolds, T. C., Smith, S. D. and Sklar, J. 1991. TAN-1, the human homolog of the drosophila Notch gene, is broken by chromosomal translocations in T lymphoblastic neoplasms. Cell 66, 649-661.

Faivre-Sarrailh, C., Gauthier, F., Denisenko-Nehrbass, N., Le Bivic, A., Rougon, G. and Girault, J. A. 2000. The glycosylphosphatidyl inositol-anchored adhesion molecule F3/contactin is required for surface transport of paranodin/contactin-associated protein (caspr). J. Cell Biol. 149, 491-502.

Furley, A. J., Morton, S. B., Manalo, D., Karagogeos, D., Dodd, J. and Jessell, T. M. 1990. The axonal glycoprotein TAG-1 is an immunoglobulin superfamily member with neurite outgrowth-promoting activity. Cell 61, 157-170.

Furukawa, T., Mukherjee, S., Bao, Z. Z., Morrow, E. M., and Cepko, C. L. 2000. rax, HES1, and Notch1 promote the formation of Muller glia by postnatal retinal progenitor cells. Neuron 26, 383-394.

Gaiano, N., Nye, J. S. and Fischell, G. 2000. Radial glial identitiy is promoted by Notch1 signalling in the murine forebrain, Neuron 26, 395-404.

Gennarini, G., Cibelli, G., Rougon, G., Mattei, M. G. and Gorodis, C. 1989. The mouse neuronal cell surface protein F3: a phosphatidyl-inositol anchored member of the immunoglobulin superfamily related to chicken contactin. J. Cell Biol. 109, 775-788.

Gennarini, G., Durbec, P., Boned, A., Rougon, G. and Goridis, C. 1991. Transfected F3/F11 neuronal cell surface protein mediates intercellular adhesion and promotes neurite outgrowth. Neuron 6, 595-606.

Genoud, S., Lappe-Siefke, C., Goebbels, S., Radtke, F., Aguet, M., Scherer, S. S., Suter, U., Nave, K. A., and Mantei, N. 2002. Notch1 control of oligodendrocyte differentiation in the spinal cord. J. Cell Biol. 158, 709-18.

Girault, J. A., and Peles, E. 2002. Development of nodes of Ranvier. Curr. Opin. Neurobiol. 12, 476-485.

Guan, K. L. and Dixon, J. E. 1991. Eukaryotic proteins expressed in *Escherichia coli*: an improved thrombin cleavage and purification procedure of fusion proteins with glutathione-S-transferase. Anal. Biochem. 192, 262-267.

Harlow, Ed., David, L. 1998. Immunizations. In *Antibodies A Laboratory Manual.* 53-244 (Cold Spring Harbor Laboratory).

Hemann, C., Gartner, E., Weidle, U. H. and Grummt, F. 1994. High-copy expression vector based on amplification-promoting sequences. DNA Cell Biol. 13, 437-445.

Hirata, H., Yoshiura, S., Ohtsuka, T., Bessho, Y., Harada, T., Yoshikawa, K., and Kageyama, R. 2002. Oscillatory expression of the bHLH factor Hes1 regulated by a negative feedback loop. Science 298, 840-843.

Hojo, M., Ohtsuka, T., Hashimoto, N., Gradwohl, G., Guillemot, F., and Kageyama, R. 2000. Glial cell fate specification modulated by the hHLH gene HES5 in mouse retina. Development 127, 2515-2522.

Holm, J., Hillenbrand, R., Steuber, V., Bartsch, U., Moos, M., Lubbert, H., Montag, D. and, Schachner, M. 1996. Structural features of a close homologue of L1 (CHL1) in the mouse: a new member of the L1 family of neural recognition molecules. Eur. J. Neurosci. 8, 1613-29.

Hoover, K. B. and Bryant, P. J. 2000. The genetics of the protein 4.1 family: organizers of the membrane and cytoskeleton. Curr. Opin. Cell Biol. 12, 229-234.

Hu, Q. D., Ang, B. T., Karsak, M., Hu, W. P., Cui, X. Y., Duka, T., Takeda, Y., Chia, W., Natesan, S., Ng, Y. K., Ling, E. A., Maciag, T., Small, D., Trifonova, R., Kopan, R., Okano, H., Nakafuku, M., Chiba, S., Hirai, H., Aster, J. C., Schachner, M., Pallen, C. J., Watanabe, K., and Xiao, Z. C. 2003. F3/Contactin acts as a functional ligand for Notch during oligodendrocyte differentiation. Cell (in press).

Huppert, S. S., Le, A., Schroeter, E. H., Mumm, J. S., Saxena, M. T., Milner, L. A., and Kopan, R. 2000. Embryonic lethality in mice homozygous for a processing-deficient allele of Notch1. Nature 405, 966-970.

Isom, L. L., Ragsdale, D. S., De Jongh, K. S., Westenbroek, R. E., Reber, B. F., Scheuer, T. and Catterall, W. A. 1995. Structure and function of the beta 2 subunit of brain sodium channels, a transmembrane glycoprotein with a CAM motif. Cell 83, 433-442.

Itoh, K. 2002. Culture of oligodendrocyte precursor cells (NG2+/O1−) and oligodendrocytes (NG2−/O1+) from embryonic rat cerebrum. *Brain Res. Brain Res. Protoc.* 10, 23-30.

Izon, D. J., Aster, J. C., He, Y., Weng, A., Karnell, F. G., Patriub, V., Xu, L., Bakkour, S., Rodriguez, C., Allman, D., and Pear, W. S. 2002. Deltex1 redirects lymphoid progenitors to the B cell lineage by antagonizing Notch1. Immunity 16, 231-243.

Jack, C., Berezovska, O., Wolfe, M. S., and Hyman, B. T. 2001. Effect of PS1 deficiency and an APP gamma-secretase inhibitor on Notch1 signaling in primary mammalian neurons. Brain Res. Mol. Brain. Res. 87, 166-174.

John, G. R., Shankar, S. L., Shafit-Zagardo, B., Massimi, A., Lee, S. C., Raine, C. S., and Brosnan, C. F. 2002. Multiple sclerosis: Re-expression of a developmental pathway that restricts oligodendrocyte maturation. Nat. Med18, 1115-1121.

Joutel, A., Vahedi, K., Corpechot, C., Troesch, A., Chabriat, H., Vayssiere, C., Cruaud, C., Maciazek, J., Weissenbach, J., Bousser, M. G., Bach, J. F. and Tournier-Lasserve, E. 1997 Strong clustering and stereotyped nature of Notch3 mutations in CADASIL patients. Lancet 350, 1511-1515.

Jung, M., Sommer, I., Schachner, M. and Nave, K. A. 1996. Monoclonal antibody 010 defines a conformationally sensitive cell-surface epitope of proteolipid protein (PLP): evidence that PLP misfolding underlies dysmyelination in mutant mice. J. Neurosci. 16, 7920-7929.

Kabos, P., Kabosova, A., and Neuman, T. 2002. Blocking HES1 expression initiates GABAergic differentiation and induces the expression of p21 (CIP1/WAF1) in human neural stem cells. J. Biol. Chem. 277, 8763-8766.

Kaneta, M., Osawa, M., Sudo, K., Nakauchi, H., Farr, A. G., and Takahama, Y. 2000. A role for pref-1 and HES-1 in thymocyte development. J. Immunol. 164, 256-264.

Kato, H., Taniguchi, Y., Kurooka, H., Minoguchi, S., Sakai, T., Nomura-Okazaki, S., Tamura, K., and Honjo, T. 1997. Involvement of RBP-J in biological functions of mouse Notch1 and its derivatives. Development 124, 4133-4141.

Kazarinova-Noyes, K., Malhotra, J. D., McEwen, D. P., Mattei, L. N., Berglund, E. O., Ranscht, B., Levinson, S. R., Schachner, M., Shrager, P., Isom, L. L., and Xiao, Z. C. 2001. Contactin associates with Na+ channels and increase their functional expression. J. Neurosci. 21, 7517-7525.

Kishi, N., Tang, Z., Maeda, Y., Hirai, A., Mo, R., Ito, M., Suzuki, S., Nakao, K., Kinoshita, T., Kadesch, T., Hui, C., Artavanis-Tsakonas, S., Okano, H., and Matsuno, K. 2001. Murine homologs of deltex define a novel gene family involved in vertebrate Notch signaling and neurogenesis. Int. J. Dev. Neurosci. 19, 21-35.

Klein, C., Kramer, E. M., Cardine, A. M., Schraven, B., Brandt, R., and Trotter, J. 2002. Process outgrowth of oligodendrocytes is promoted by interaction of fyn kinase with the cytoskeletal protein tau. J. Neurosci. 22, 698-707.

Koch, T., Brugger, T., Bach, A., Gennarini, G. and Trotter, J. 1997. Expression of the immunoglobulin superfamily cell adhesion molecule F3 by oligodendrocyte-lineage cells. Glia 19, 199-212.

Kramer, E. M., Klein, C., Koch, T., Boytinck, M., and Trotter, J. 1999. Compartmentation of Fyn kinase with glycosylphosphatidylinositol-anchored molecules in oligodendrocytes facilitates kinase activation during myelination. J Biol Chem. 274, 29042-29049.

Laemmli, U. K. 1970. Cleavage of structural proteins during the assembly of the head of bacteriophage T4. Nature 277, 680-685.

Lagenaur, C. and Lemmon, V. 1987. An L1-like molecule, the 8D9 antigen, is a potent substrate for neurite extension. Proc. Natl. Acad. Sci. USA 84, 7753-7757.

Lardelli, M., Dahlstrand, J., and Lendahl, U. 1994. The novel Notch homologue mouse Notch3 lacks specific epidermal growth factor-repeats and is expressed in proliferating neuroepithelium. Mech. Dev. 46, 123-136.

Lee, S., Takeda, Y., Kawano, H., Hosoya, H., Nomoto, M., Fujimoto, D., Takahashi, N. and Watanabe, K. 2000. Expression and regulation of a gene encoding neural recognition molecule NB-3 of the contactin/F3 subgroup in mouse brain. Gene 245, 253-266.

Logeat, F., Bessia, C., Brou, C., LeBail, O., Jarriault, S., Seidah, N. G. and Israel, A. 1998. The Notch1 receptor is cleaved constitutively by a furin-like convertase. Proc. Natl. Acad. Sci. USA 95, 8108-8112.

Martin-Collinson, J., Marshall, D., Stewart Gillespie, C. and Brophy, P. J. 1998. Transient expression of neurofascin by oligodendrocytes at the onset of myelinogenesis: Implications for mechanisms of axon-glial interaction. Glia 23, 11-23.

Martinez Arias, A., Zecchini, V., and Brennan, K. 2002. CSL-independent Notch signaling: a checkpoint in cell fate decisions during development? Curr. Opin. Genet. Dev. 12, 524-533.

Mathis, C., Denisenko-Nehrbass, N., Girault, J. A. and Borrelli, E. 2001. Essential role of oligodendrocytes in the formation and maintenance of central nervous system nodal regions. Development. 128, 4881-90.

Matsuno, K., Ito, M., Hori, K., Miyashita, F., Suzuki, S., Kishi, N., Artavanis-Tsakonas, S., Okano, H.2002. Involvement of a proline-rich motif and RING-H2 finger of Deltex in the regulation of Notch signaling. Development 129, 1049-1059.

Menegoz, M., Gaspar, P., Le Bert, M., Galvez, T., Burgaya, F., Palfrey, C., Ezan, P., Arnos, F. and Girault, J. A. 1997. Paranodin, a glycoprotein of neuronal paranodal membranes. Neuron 19, 319-331.

Mitsiadis, T. A., Lardelli, M., Lendahl, U. and Thesleff, I. 1995. Expression of Notch 1, 2 and 3 is regulated by epithelial-mesenchymal interactions and retinoic acid in the developing mouse tooth and associated with determination of ameloblast cell fate. J. Cell Biol. 130, 407-18.

Morell, P. and Quarles, R. H.1999. Myelin formation, structure and biochemistry. In: Basic Neurochemistry—molecular, cellular and biochemical aspects, $6^{th}$ edition (Siegel, G. J. et. al. eds.). Lippincott-Raven Publishers, Philadelphia, pp. 69-93.

Morrison, S. J., Perez, S. E., Qiao, Z., Verdi, J. M., Hicks, C., Weinmaster, G. and Anderson, D. J. 2000. Transient Notch activation initiates an irreversible switch from neurogenesis to gliogenesis by neural crest stem cells. Cell 101, 499-510.

Musm. J. S. and Kopan, R. 2000. Notch signalling: From the outside in. Dev. Biol. 228, 151-165.

Pedraza, L., Huang, J. K. and Colman, D. R. (2001) Organizing principles of the axoglial apparatus. Neuron 30, 335-344.

Peles, E. and Salzer, J. 2000. Molecular domains of myelinated axons. Curr. Opinion Cell Biol. 10, 558-565.

Pluchino, S. et al. 2003. *Nature* 422, 688-694.

Rand, M. D., Grimm, L. M., Artavanis-Tsakonas, S., Patriub, V., Blacklow, S. C., Sklar, J., and Aster, J. C. 2000. Calcium depletion dissociates and activates heterodimeric Notch receptors. Mol. Cell. Biol. 20, 1825-1835.

Rebay, R. J., Fleming, R. G., Fehon, R. G., Cherbas, L., Cherbas, P. and Artavanis-Tsakanos, S. 1991. Specific EGF repeats of Notch mediated interactions with Serrate: Implications for Notch as a multifunctional receptor. Cell 67, 687-699.

Revest, J. M., Faivre-Sarrailh, C., Schachner, M., and Rougon, G. 1999. Bidirectional signaling between neurons and glial cells via the F3 neuronal adhesion molecule. Adv. Exp. Med. Biol. 468, 309-318.

Richter-Landsberg, C. and Heinrich, M. 1996. OLN-93: A new permanent oligodendroglia cell line derived from primary rat brain glial cultures. J. Neurosci. Res. 45, 161-173.

Rios, J. C., Melendez-Vasquez, C. V., Einheber, S., Lustig, M., Grumet, M., Hemperly, J., Peles, E. and Salzer, J. L.

2000. Contactin-associated protein (Caspr) and contactin form a complex that is targeted to the paranodal junctions during myelination. J. Neurosci. 20, 8354-8364.

Robey, E., Chang, D., Itano, A., Cado, D., Alexander, H., Lans, D., Weinmaster, G. and Salmon, P. 1996. An activated form of Notch influences the choice between CD4 and CD8 T cell lineages. Cell 87, 483-492.

Roserbluth, J. 1995. Glial membranes and axoglial junctions. In: Neuroglia (Kettenmann, H. and Ransom, B. R. eds). Oxford University Press, New York. pp 613-633.

Sakurai, T., Lustig, M., Nativ, M., Hemperly, J. J., Schlessinger, J., Peles, E., and Grumet, M. 1997. Induction of neurite outgrowth through contactin and Nr-CAM by extracellular regions of glial receptor tyrosine phosphatase beta. J. Cell Biol. 136, 907-918.

Salzer, J. L. 1997. Clustering sodium channels at the node of Ranvier: Close encounters of the axon-glia kind. Neuron 18, 843-846.

Sauvageot, C. M. & Stiles, C. D. 2002. Curr. Opin. Neurobiol. 12, 244-249.

Schnaldelbach, O., Ozen, I., Blashuk, O. W., Gour, B. J., Meyer, R. L. and Fawcett, J. W. 2001. N-Cadherin is involved in axon-oligodendrocyte contact and myelination. Mol. Cell. Neurosci. 17, 1084-1093.

Schroeter, E. H., Kisslinger, J. A., and Kopan, R. 1998. Notch-1 signalling requires ligand-induced proteolytic release of intracellular domain. Nature 393, 382-386.

Schwab, M. E. and Schnell, L. 1989. Region-specific appearance of myelin constituents in the developing rat spinal cord. J. Neurocytol. 18, 161-169.

Shimazaki, K., Hosoya, H., Takeda, Y., Kobayashi, S., and Watanabe, K. 1998. Age-related decline of F3/contactin in rat hippocampus. Neurosci. Lett. 245, 117-20.

Shimizu, K., Chiba, S., Kumano, K., Hosoya, N., Takahashi, T., Kanda, Y., Hamada, Y., Yazaki, Y., and Hirai, H. 1999. Mouse jagged1 physically interacts with notch2 and other notch receptors. Assessment by quantitative methods. J. Biol. Chem. 274, 32961-32969.

Small, D., Kovalenko, D., Kacer, D., Liaw, L., Landriscina, M., Di Serio, C., Prudovsky, I., and Maciag, T. 2001. Soluble Jagged 1 represses the function of its transmembrane form to induce the formation of the Src-dependent chord-like phenotype. J. Biol. Chem. 276, 32022-32030.

Tait, S., Gunn-Moore, F., Collinson, J. M., Huang, J., Lubetzki, C., Pedraza, L., Sherman, D. L., Colman, D. R. and Brophy P. J. 2000. An oligodendrocyte cell adhesion molecule at the site of assembly of the paranodal axo-glial junction. J. Cell Biol. 150, 657-666.

Tanigaki, K., Nogaki, F., Takahashi, J., Tashiro, K., Kurooka, H., and Honjo, T. 2001. Notch1 and Notch3 instructively restrict bFGF-responsive multipotent neural progenitor cells to an astroglial fate. Neuron 29, 45-55.

Towbin, H., Staehelin, T. and Gordon, J. 1979. Electrophoretic transfer of proteins from polyacrylamide gels to nitrocellulose sheets: procedure and some applications. Proc. Natl. Acad. Sci. USA 76, 4350-4354.

Tsiotra, P. C., Karagogeos, D., Theodorakis, K., Michaelidis, T. M., Modi, W. S., Furley, A. J., Jessel, T. M. and Papamatheakis, J. 1993. Isolation of the cDNA and chromosomal localization of the gene (TAX1) encoding the human axonal glycoprotein TAG-1. Genomics 18, 562-567.

Umemori, H., Sato, S., Yagi, T., Aizawa, S., and Yamamoto, T. 1994. Initial events of myelination involve Fyn tyrosine kinase signalling. Nature 367, 572-576.

Wakamatsu, Y., Maynard, T. M., and Weston, J. A. 2000. Fate determination of neural crest cells by NOTCH-mediated lateral inhibition and asymmetrical cell division during gangliogenesis. Development 127, 2811-2821.

Wang, S., Sdrulla, A. D., diSibio, G., Bush, G., Nofziger, D., Hicks, C., Weinmaster, G. and Barres, B. A. 1998. Notch receptor activation inhibits oligodendrocyte differentiation. Neuron 21, 63-75.

Ward, R. E., Lamb, R. S. and Fehon, R. G. 1998. A conserved functional domain of *drosophila* coracle is required for localization at the septate junction and has membrane-organizing activity. J. Cell Biol. 140, 1463-1473.

Weinmaster, G. 2000. Notch signal transduction: a real rip and more. Curr. Opin. Gen. Dev. 10, 363-369.

Wintergerst, E. S., Fuss, B. and Bartsch, U. 1993. Localization of janusin mRNA in the central nervous system of the developing and adult mouse. Eur. J. Neurosci. 5, 299-310.

Xiao, Z. C., Taylor, J., Montag, D., Rougon, G. and Schachner, M. 1996. Distinct effects of tenascin-R domains in neuronal cell functions and identification of the domain interacting with the neuronal recognition molecule F3/11. Eur. J. Neurosci. 8, 766-782.

Xiao, Z. C., Bartsch, U., Margolis, R. K., Rougon, G., Montag, D., and Schachner M. 1997. Isolation of a tenascin-R binding protein from mouse brain membranes. A phosphacan-related chondroitin sulfate proteoglycan. J. Biol. Chem. 272, 32092-32101.

Xiao, Z. C., Hillenbrand, R., Schachner, M., Thermes, S., Rougon, G. and Gomez, S. 1997. Signalling events following the interaction of the neuronal adhesion molecule F3 with the N-terminal domain of tenascin-R. J. Neurosci. Res. 49, 698-709.

Xiao, Z. C., Revest, J. M., Laeng, P., Rougon, G., Schachner, M. and Montag, D. 1998. Defasciculation of neurites is mediated by tenascin-R and its neuronal receptor F3/11. J. Neurosci. Res. 52, 390-404.

Yamamoto, N., Yamamoto, S., Inagaki, F., Kawaichi, M., Fukamizu, A., Kishi, N., Matsuno, K., Nakamura, K., Weinmaster, G., Okano, H., and Nakafuku, M. 2001. Role of Deltex-1 as a transcriptional regulator downstream of the Notch receptor. J. Biol. Chem. 276, 45031-45040.

Yang, H., Xiao, Z. C., Becker, B., Hillenbrand, R., Rougon, G. and Schachner, M. 1999. Role for myelin-associated glycoprotein as a functional tenascin-R receptor. J. Neurosci. Res. 55, 687-701.

Zeng, L., D'Alessandri, L., Kalousek, M. B., Vaughan, L. and Pallen, C. J. 1999. Protein tyrosine phosphatase alpha (PTPA) and contactin form a novel neuronal receptor complex linked to the intracellular tyrosine kinase fyn. J. Cell Biol. 147, 707-714.

The invention claimed is:

1. A composition comprising isolated F3 and isolated NB-3, in combination with a carrier, wherein the F3 is a protein having greater than 90% sequence identity with the amino acid sequence of SEQ ID NO: 13, the NB-3 is a protein having greater than 90% sequence identity with the amino acid sequence of SEQ ID NO: 14.

2. A composition according to claim 1 wherein said carrier is a pharmaceutically acceptable carrier.

3. A composition according to claim 2 which is formulated for injection in vivo.

4. A composition according to claim 3 which is formulated for direct injection into the CNS.

* * * * *